US012508226B2

(12) United States Patent
Endo et al.

(10) Patent No.: US 12,508,226 B2

(45) **Date of Patent: *Dec. 30, 2025**

(54) LIPID COMPOSITION

(71) Applicant: FUJIFILM Corporation, Tokyo (JP)

(72) Inventors: Taisuke Endo, Ashigarakami-gun (JP); Shun Kaneumi, Ashigarakami-gun (JP); Masaki Noro, Ashigarakami-gun (JP); Shintaro Tanabe, Ashigarakami-gun (JP); Masahiko Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 724 days.

This patent is subject to a terminal disclaimer.

(21) Appl. No.: 17/457,793

(22) Filed: Dec. 6, 2021

(65) Prior Publication Data

US 2022/0096381 A1 Mar. 31, 2022

Related U.S. Application Data

(63) Continuation of application No. PCT/JP2020/022279, filed on Jun. 5, 2020.

(30) Foreign Application Priority Data

Jun. 7, 2019 (JP) ................................ 2019-107457
Nov. 15, 2019 (JP) ................................ 2019-207117

(51) Int. Cl.
*A61K 9/1272* (2025.01)
*A61K 31/7105* (2006.01)
(Continued)

(52) U.S. Cl.
CPC ........ *A61K 9/1272* (2013.01); *A61K 31/7105* (2013.01); *A61K 47/10* (2013.01);
(Continued)

(58) Field of Classification Search
CPC .. A61K 9/1272; A61K 31/7105; A61K 47/10; A61K 47/183; A61K 47/24;
(Continued)

(56) References Cited

U.S. PATENT DOCUMENTS

| | | | |
|---|---|---|---|
| 5,047,540 | A | 9/1991 | Kamata et al. |
| 2010/0324120 | A1 | 12/2010 | Chen et al. |
| 2011/0311582 | A1 | 12/2011 | Manoharan et al. |
| 2013/0245107 | A1 | 9/2013 | de Fougerolles et al. |
| 2014/0045913 | A1 | 2/2014 | Kuboyama et al. |
| 2014/0371293 | A1 | 12/2014 | Brown et al. |
| 2015/0174261 | A1 | 6/2015 | Kuboyama et al. |
| 2016/0257951 | A1 | 9/2016 | Koizumi et al. |
| 2016/0317458 | A1 | 11/2016 | Brito et al. |
| 2017/0137409 | A1 | 5/2017 | Brown |
| 2017/0157268 | A1 | 6/2017 | Ansell et al. |
| 2018/0051285 | A1 | 2/2018 | Koizumi et al. |
| 2021/0085604 | A1 | 3/2021 | Tanabe et al. |
| 2022/0273817 | A1 | 9/2022 | Sekiguchi et al. |
| 2024/0315970 | A1 | 9/2024 | Tanabe et al. |

FOREIGN PATENT DOCUMENTS

| | | |
|---|---|---|
| CA | 3 102 985 A1 | 12/2019 |
| CA | 3 143 865 A1 | 12/2020 |

(Continued)

OTHER PUBLICATIONS

Office Action issued Jun. 27, 2023 in Canadian Application No. 3,158,293, corresponding to U.S. Appl. No. 17/743,584.

(Continued)

*Primary Examiner* — Robert A Wax
*Assistant Examiner* — Ngoc-Anh Thi Nguyen
(74) *Attorney, Agent, or Firm* — Sughrue Mion, PLLC

(57) ABSTRACT

An object of the present invention is to provide a lipid composition making it possible to achieve excellent delivery of nucleic acids. According to the present invention, there is provided a lipid composition containing a lipid represented by Formula (1) or a salt thereof, a nonionic lipid, a lipid having a nonionic hydrophilic polymer structure, and a nucleic acid, in which the lipid composition contains or does not contain a zwitterionic lipid, and in a case where (A) represents a molar ratio in percentage of the lipid represented by Formula (1) or a salt thereof to total lipids constituting the lipid composition and (B) represents a molar ratio in percentage of the zwitterionic lipid to total lipids constituting the lipid composition, (A) and (B) satisfy 40<(A)−(B)≤90.

(1)

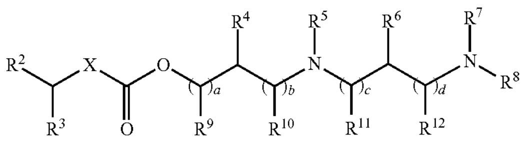

In the formula, X represents —$NR^1$— or —O—, $R^1$ represents a hydrogen atom, a hydrocarbon group, or the like, $R^2$ and $R^3$ each independently represent a hydrogen atom, a hydrocarbon group, or the like, $R^4$, $R^5$, $R^6$, $R^7$, $R^8$, $R^9$, $R^{10}$, $R^{11}$, and $R^{12}$ each independently represent a hydrogen atom or an alkyl group, groups in any one or more pairs among $R^4$ and $R^5$, $R^{10}$ and $R^5$, $R^5$ and $R^{12}$, $R^4$ and $R^6$, $R^5$ and $R^6$, $R^6$ and $R^7$, $R^6$ and $R^{10}$, $R^{12}$ and $R^7$, and $R^7$ and $R^8$ may be linked to each other to form a 4- to 7-membered ring which may contain an O atom, a, b, c, and d are each independently represent an integer of 0 to 3, a+b is 1 or more, and c+d is 1 or more.

13 Claims, No Drawings

Specification includes a Sequence Listing.

(51) Int. Cl.
*A61K 47/10* (2017.01)
*A61K 47/18* (2017.01)
*A61K 47/24* (2006.01)
*A61K 47/28* (2006.01)

(52) U.S. Cl.
CPC ............ *A61K 47/183* (2013.01); *A61K 47/24* (2013.01); *A61K 47/28* (2013.01)

(58) Field of Classification Search
CPC .. A61K 47/28; A61K 9/5123; A61K 31/7088; A61K 31/713; A61K 9/10; A61K 47/14; A61K 47/18; A61K 47/34; A61K 48/0016; C12N 2310/14; C12N 15/113; C12N 15/88; A61P 7/02
See application file for complete search history.

(56) References Cited

FOREIGN PATENT DOCUMENTS

| | | | | |
|---|---|---|---|---|
| CN | 102625696 | A | 8/2012 | |
| CN | 104159615 | A | 11/2014 | |
| CN | 104873464 | A | 9/2015 | |
| CN | 106008272 | A | 10/2016 | |
| CN | 107207428 | A | 9/2017 | |
| CN | 112262122 | A | 1/2021 | |
| JP | 6-298712 | A | 10/1994 | |
| JP | 2012-530059 | A | 11/2012 | |
| JP | 5288254 | B2 | 6/2013 | |
| JP | 2014-529328 | A | 11/2014 | |
| JP | 2015-501309 | A | 1/2015 | |
| JP | 2017-522376 | A | 8/2017 | |
| JP | 7178409 | B2 | 11/2022 | |
| TW | 201813632 | A | 4/2018 | |
| WO | 2007/130073 | A2 | 11/2007 | |
| WO | 2009/127060 | A1 | 10/2009 | |
| WO | 2010/054401 | A1 | 5/2010 | |
| WO | 2010/054405 | A1 | 5/2010 | |
| WO | 2010/144740 | A1 | 12/2010 | |
| WO | 2012/170952 | A2 | 12/2012 | |
| WO | 2013/059496 | A1 | 4/2013 | |
| WO | 2014/007398 | A1 | 1/2014 | |
| WO | WO-2015005253 | A1 * | 1/2015 | ......... A61K 31/7088 |
| WO | 2015/095340 | A1 | 6/2015 | |
| WO | 2015/095346 | A1 | 6/2015 | |
| WO | 2016/081029 | A1 | 5/2016 | |
| WO | 2018/078053 | A1 | 5/2018 | |
| WO | WO-2018087753 | A1 * | 5/2018 | ............. A61K 47/18 |
| WO | 2019/235635 | A1 | 12/2019 | |

OTHER PUBLICATIONS

Office Action issued Jul. 1, 2023 in Chinese Application No. 202080079111.X, corresponding to U.S. Appl. No. 17/743,584.
Office Action issued Oct. 18, 2022 in Japanese Application No. 2021-524926, corresponds to U.S. Appl. No. 17/457,793.
Office Action issued Nov. 1, 2022 in Chinese Application No. 201980038935.X, corresponds to U.S. Appl. No. 17/112,239.
RN 2155113-73-6, Dec. 10, 2017, Registry [online], American Chemical Society, Retrieved from STN (7 pages).
International Search Report dated Jul. 28, 2020 in Application No. PCT/JP2020/022279.
Written Opinion of the International Searching Authority dated Jul. 28, 2020 in Application No. PCT/JP 2020/022279.
International Preliminary Report on Patentability dated Dec. 7, 2021 in Application No. PCT/JP 2020/022279.
T.W. Green et al., "Protective Groups in Organic Synthesis", John Wiley & Sons, Inc., 4th Edition, 2007, pp. 696-926 (118 pages total).
Akin Akinc et al., "Development of Lipidoid-siRNA Formulations for Systemic Delivery to the Liver", Molecular Therapy, 2009, vol. 17, No. 5, pp. 872-879 (8 pages total).
Sean C. Semple et al., "Rational design of cationic lipids for siRNA delivery", Nature Biotechnology, Feb. 2010, vol. 28, No. 2, pp. 172-176 (9 pages total).
Vudhgiri Srikanth et al., "Synthesis of dihydrosterculic acid-based monoglucosyl diacylglycerol and its analogues and their biological evaluation", European Journal of Medicinal Chemistry, 2016, vol. 109, pp. 134-145 (12 pages total).
Office Action dated Nov. 17, 2023 in U.S. Appl. No. 17/112,239.
Office Action issued Jul. 26, 2023 in Chinese Application No. 202080041980.3.
Extended European Search Report dated Jul. 21, 2022 in corresponding European Application No. 20818988.6.
Office Action dated Mar. 21, 2023 issued in Korean Patent Application No. 10-2020-7037881, corresponding to U.S. Appl. No. 17/112,239.
Office Action dated Apr. 11, 2023 issued in Japanese Patent Application No. 2021-556193, corresponding to U.S. Appl. No. 17/743,584.
International Search Report issued Aug. 27, 2019 in International Application No. PCT/JP2019/022833, corresponds to U.S. Appl. No. 17/112,239.
Written Opinion of the International Searching Authority issued Aug. 27, 2019 in International Application No. PCT/JP2019/022833, corresponds to U.S. Appl. No. 17/112,239.
International Preliminary Report on Patentability issued Dec. 8, 2020 in International Application No. PCT/JP2019/022833, corresponds to U.S. Appl. No. 17/112,239.
RN 2001907-05-5, Sep. 29, 2016, Registry [online], American Chemical Society, [retrieved on Aug. 14, 2019], Retrieved from STN (1 page).
RN 2001651-45-0, Sep. 28, 2016, Registry [online], American Chemical Society, [retrieved on Aug. 14, 2019], Retrieved from STN (1 page).
RN 2001788-05-0, Sep. 29, 2016, Registry [online], American Chemical Society, [retrieved on Aug. 14, 2019], Retrieved from STN (1 page).
RN 2003930-61-6, Oct. 2, 2016, Registry [online], American Chemical Society, [retrieved on Aug. 14, 2019], Retrieved from STN (1 page).
RN 2012853-22-2, Oct. 16, 2016, Registry [online], American Chemical Society, [retrieved on Aug. 14, 2019], Retrieved from STN (1 page).
RN 2005720-56-7, Oct. 5, 2016, Registry [online], American Chemical Society, [retrieved on Aug. 14, 2019], Retrieved from STN (1 page).
RN 2024626-33-1, Nov. 3, 2016, Registry [online], American Chemical Society, [retrieved on Aug. 14, 2019], Retrieved from STN (1 page).
RN 2030447-26-6, Nov. 13, 2016, Registry [online], American Chemical Society, [retrieved on Aug. 14, 2019], Retrieved from STN (1 page).
RN 2169605-81-4, Jan. 4, 2018, Registry [online], American Chemical Society, [retrieved on Aug. 14, 2019], Retrieved from STN (1 page).
RN 2016779-95-4, Oct. 21, 2016, Registry [online], American Chemical Society, [retrieved on Aug. 14, 2019], Retrieved from STN (1 page).
RN 2155113-73-6, Dec. 10, 2017, Registry [online], American Chemical Society, [retrieved on Aug. 14, 2019], Retrieved from STN (1 page).
Extended European Search Report dated Jun. 16, 2021, issued by the European Patent Office in EP Application No. 19814985.8, corresponds to U.S. Appl. No. 17/112,239.
Office Action dated Nov. 30, 2021 issued in Japanese Patent Application No. 2020-523214, corresponds to U.S. Appl. No. 17/112,239.
Office Action dated Feb. 17, 2022, issued by the Canadian Patent Office in application No. 3,102,985, corresponds to U.S. Appl. No. 17/112,239.
International Search Report issued Jan. 26, 2021 in International Application No. PCT/JP2020/042513, corresponds to U.S. Appl. No. 17/743,584.

(56) References Cited

OTHER PUBLICATIONS

Written Opinion of the International Searching Authority issued Jan. 26, 2021 in International Application No. PCT/JP2020/042513, corresponds to U.S. Appl. No. 17/743,584.
U.S. Appl. No. 17/743,584, filed May 13, 2022 (Sekiguchi et al.).
U.S. Appl. No. 17/112,239, filed Dec. 4, 2020 (Tanabe et al.).
Canadian Office Action dated Jan. 14, 2023, in corresponding Canadian Application No. 3,143,865.
Office Action issued Mar. 7, 2023 in Japanese Application No. 2022-011921, corresponding to U.S. Appl. No. 17/112,239.
Office Action dated May 24, 2022 from the Japanese Patent Office in JP Application No. 2020-523214, corresponds to U.S. Appl. No. 17/112,239.
Xue et al., "Highlighting the Role of Polymer Length, Carbohydrate Size, and Nucleic Acid Type in Potency of Glycopolycation Agents for pDNA and siRNA Delivery", Biomacromolecules, 2013, vol. 14, pp. 3903-3915 (13 pages).
International Preliminary Report on Patentability issued May 17, 2022 in International Application No. PCT/JP2020/042513, corresponds to U.S. Appl. No. 17/743,584.
Office Action issued Jun. 4, 2024 in Japanese Application No. 2023-094459, corresponding to U.S. Appl. No. 17/743,584.
Office Action issued May 7, 2024 in U.S. Appl. No. 17/112,239.
Advisory Action dated Aug. 22, 2024, issued by the United States Patent and Trademark Office in U.S. Appl. No. 17/112,239.
Extended European Search Report dated Aug. 22, 2024 issued by the European Patent Office in application No. 24150973.6, corresponding to U.S. Appl. No. 17/743,584.
Notice of Allowance dated Mar. 13, 2025 issued by USPTO in U.S. Appl. No. 18/443,959.

* cited by examiner

LIPID COMPOSITION

CROSS-REFERENCE TO RELATED APPLICATIONS

This application is a Continuation of PCT International Application No. PCT/JP2020/022279 filed on Jun. 5, 2020, which claims priority under 35 U.S.C § 119(a) to Japanese Patent Application No. 2019-107457 filed on Jun. 7, 2019 and Japanese Patent Application No. 2019-207117 filed on Nov. 15, 2019. Each of the above application(s) is hereby expressly incorporated by reference, in its entirety, into the present application.

BACKGROUND OF THE INVENTION

1. Field of the Invention

The present invention relates to a lipid composition containing lipids and a nucleic acid.

2. Description of the Related Art

With the development of techniques enabling the delivery of nucleic acids to cells, nucleic acid drugs have been actively developed. As one of the nucleic acid delivery techniques, a method of administering nucleic acid-containing particles consisting of particles (liposomes or lipid particles) encapsulating nucleic acids is known. In this technique, the nucleic acid-containing particles are prepared using lipids that have an amino group or the like and turn into cations at a low pH, and appropriate charge is applied to the particles for the delivery of nucleic acids. For example, as a compound to be incorporated into the lipid particles, WO2010/054401A discloses a compound having an ester group, an acetal group, or the like as a linking group that links an aliphatic group to an amino group. WO2010/054405A discloses a compound having a vinyloxy group, an amide group, an oxime group, or the like as a linking group that links an aliphatic group to an amino group. In the present specification, the aforementioned lipids that have an amino group or the like and turn into a cation at a low pH are called a cationic lipid in some cases.

There are studies on changing type and compositional ratio of lipid compounds used for manufacturing nucleic acid-containing particles. WO2009/127060A describes nucleic acid-liquid particles containing (a) nucleic acid; (b) cationic lipid that accounts for about 50 mol % to about 85 mol % of the total lipids present in the particles; (c) non-cationic lipid that accounts for about 13 mol % to about 49.5 mol % of the total lipids present in the particles; and (d) composite lipid that accounts for about 0.5 mol % to about 2 mol % of the total lipids present in the particles and inhibit the aggregation of particles. WO2010/144740A describes a lipid preparation containing 40% to 65% of a cationic lipid having a specific structure, 5% to 10% of a neutral lipid, 25% to 40% of a sterol, and 0.5% to 10% of PEG or a PEG-modified lipid.

SUMMARY OF THE INVENTION

Because the lipids having an amino group are known to have toxicity, there is a demand for a technique enabling more efficient delivery of nucleic acids.

The present invention has been made in consideration of the above circumstances, and an object thereof is to provide a lipid composition enabling excellent delivery of nucleic acids.

In order to achieve the above object, the inventors of the present invention conducted intensive studies. As a result, the inventors have accomplished the present invention by finding that excellent delivery of nucleic acids can be achieved using a lipid composition which contains a lipid represented by Formula (1) or a salt thereof, a nonionic lipid, a lipid having a nonionic hydrophilic polymer structure, and a nucleic acid and contains or does not contain a zwitterionic lipid, in which in a case where (A) represents a molar ratio in percentage of the lipid represented by Formula (1) or a salt thereof to total lipids constituting the lipid composition and (B) represents a molar ratio in percentage of the zwitterionic lipid to the total lipids constituting the lipid composition, (A) and (B) satisfy $40<(A)-(B)\leq 90$. According to the present invention, the following inventions are provided.

<1> A lipid composition containing a lipid represented by Formula (1) or a salt thereof, a nonionic lipid, a lipid having a nonionic hydrophilic polymer structure, and a nucleic acid, in which the lipid composition contains or does not contain a zwitterionic lipid, and in a case where (A) represents a molar ratio in percentage of the lipid represented by Formula (1) or a salt thereof to total lipids constituting the lipid composition and (B) represents a molar ratio in percentage of the zwitterionic lipid to the total lipids constituting the lipid composition, (A) and (B) satisfy $40<(A)-(B)\leq 90$.

(1)

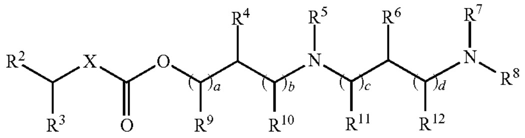

In the formula, X represents —$NR^1$— or —O—, $R^1$ represents a hydrogen atom, a hydrocarbon group having 6 to 24 carbon atoms, or a group represented by $R^{21}$-$L^1$-$R^{22}$—, $R^{21}$ represents a hydrocarbon group having 1 to 24 carbon atoms, $L^1$ represents —O(CO)O—, —O(CO)—, —(CO)O—, —O—, or a group represented by the following formula,

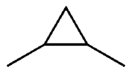

$R^{22}$ represents a divalent hydrocarbon linking group having 1 to 18 carbon atoms, $R^2$ and $R^3$ each independently represent a hydrogen atom, a hydrocarbon group having 3 to 24 carbon atoms, or a group represented by $R^{31}$-$L^2$-$R^{32}$—, $R^{31}$ represents a hydrocarbon group having 1 to 24 carbon atoms, $L^2$ represents —O(CO)O—, —O(CO)—, —(CO)O—, —O—, or a group represented by the following formula,

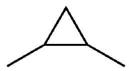

$R^{32}$ represents a divalent hydrocarbon linking group having 1 to 18 carbon atoms, $R^4$, $R^5$, $R^6$, $R^7$, $R^8$, $R^9$, $R^{10}$, $R^{11}$, and $R^{12}$ each independently represent a hydrogen atom or an alkyl group having 1 to 18 carbon atoms that may be substituted, groups in any one or more pairs among $R^4$ and $R^5$, $R^{10}$ and $R^5$, $R^5$ and $R^{12}$, $R^4$ and $R^6$, $R^5$ and $R^6$, $R^6$ and $R^7$, $R^6$ and $R^{10}$, $R^{12}$ and $R^7$, and $R^7$ and $R^8$ may be linked to each other to form a 4- to 7-membered ring which may contain an O atom, a substituent on the alkyl group having 1 to 18 carbon atoms that may be substituted is a hydroxyl group, a carboxyl group, an amino group represented by $—NR^{45}R^{46}$, a substituted or unsubstituted aryl group, a substituted or unsubstituted heteroaryl group, or a group represented by $—O(CO)O—R^{41}$, $—O(CO)—R^{42}$, $—(CO)O—R^{43}$, or $—O—R^{44}$, $R^{41}$, $R^{42}$, $R^{43}$, $R^{44}$, $R^{45}$, and $R^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by $—NR^{45}R^{46}$, or a group represented by $—O(CO)O—R^{41}$, $—O(CO)—R^{42}$, $—(CO)O—R^{43}$, or $—O—R^{44}$, and $R^{41}$, $R^{42}$, $R^{43}$, $R^{44}$, $R^{45}$, and $R^{46}$ each independently represent a hydrocarbon group having 1 to 18 carbon atoms, and a, b, c, and d each independently represent an integer of 0 to 3, a+b is 1 or more, and c+d is 1 or more.

<2> The lipid composition described in <1>, in which the nonionic lipid is sterols.

<3> The lipid composition described in <2>, in which the sterols are cholesterol.

<4> The lipid composition described in any one of <1> to <3>, in which the zwitterionic lipid is a phospholipid.

<5> The lipid composition described in any one of <1> to <4>, in which the lipid having a nonionic hydrophilic polymer structure is a lipid having a polyethylene glycol structure.

<6> The lipid composition described in <5>, in which the lipid having a polyethylene glycol structure is a lipid having a diacylglycerol structure and a polyethylene glycol structure.

<7> The lipid composition described in any one of <1> to <6>, in which a content of the lipid represented by Formula (1) or a salt thereof is more than 40 mol % and 90 mol % or less, a content of the nonionic lipid is 20 to 60 mol %, a content of the lipid having a nonionic hydrophilic polymer structure is 0.5 to 10 mol %, and a content of the zwitterionic lipid is 0 to 30 mol %.

<8> The lipid composition described in any one of <1> to <7>, in which the compound represented by Formula (1) is a compound represented by Formula (2).

(2)

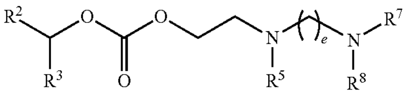

in the formula, $R^2$ and $R^3$ each independently represent a hydrogen atom, a hydrocarbon group having 3 to 24 carbon atoms, or a group represented by $R^{31}$-$L^2$-$R^{32}$—, $R^{31}$ represents a hydrocarbon group having 1 to 24 carbon atoms, $L^2$ represents —O(CO)O—, —O(CO)—, —(CO)O—, —O—, or a group represented by the following formula,

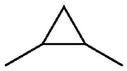

$R^{32}$ represents a divalent hydrocarbon linking group having 1 to 18 carbon atoms, $R^5$ represents a hydrogen atom or an alkyl group having 1 to 18 carbon atoms that may be substituted, $R^7$ and $R^8$ each independently represent a hydrogen atom or an alkyl group having 1 to 18 carbon atoms that may be substituted, a substituent on the alkyl group having 1 to 18 carbon atoms that may be substituted is a hydroxyl group, a carboxyl group, an amino group represented by $—NR^{45}R^{46}$, a substituted or unsubstituted aryl group, a substituted or unsubstituted heteroaryl group, or a group represented by $—O(CO)O—R^{41}$, $—O(CO)—R^{42}$, $—(CO)O—R^{43}$, or $—O—R^{44}$, $R^{41}$, $R^{42}$, $R^{43}$, $R^{44}$, $R^{45}$, and $R^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by $—NR^{45}R^{46}$, or a group represented by $—O(CO)O—R^{41}$, $—O(CO)—R^{42}$, $—(CO)O—R^{43}$, or $—O—R^{44}$, and $R^{41}$, $R^{42}$, $R^{43}$, $R^{44}$, $R^{45}$, and $R^{46}$ each independently represent a hydrocarbon group having 1 to 18 carbon atoms, and e represents 2 or 3.

<9> The lipid composition described in <8>, in which in Formula (2), at least one of $R^2$ or $R^3$ represents a hydrocarbon group having 3 to 24 carbon atoms containing one or more unsaturated bonds; $R^2$ and $R^3$ each independently represent a group represented by $R^{31}$-$L^2$-$R^{32}$—: or one of $R^2$ and $R^3$ represents a group represented by $R^{31}$-$L^2$-$R^{32}$— and the other represents a hydrocarbon group having 3 to 24 carbon atoms, $R^5$ represents an unsubstituted alkyl group having 1 to 18 carbon atoms or an alkyl group having 1 to 18 carbon atoms substituted with $—O(CO)—R^{42}$ or $—(CO)O—R^{43}$, $R^7$ and $R^8$ each independently represent an alkyl group having 1 to 4 carbon atoms, and $R^{31}$, $L^2$, $R^{32}$, $R^{42}$, and $R^{43}$ have the same definitions as $R^{31}$, $L^2$, $R^{32}$, $R^{42}$, and $R^{43}$ in <8>.

<10> The lipid composition described in any one of <1> to <9>, in which a content of the nucleic acid with respect to the total lipids is 1% to 25% by mass.

<11> The lipid composition described in any one of <1> to <10>, further containing a pharmaceutically acceptable carrier.

<12> The lipid composition described in any one of <1> to <11>, which is a composition for introducing nucleic acids into cells.

<13> The lipid composition described in any one of <1> to <11>, which is a composition for in vivo delivery of nucleic acids.

The lipid composition according to the embodiment of the present invention can achieve excellent nucleic acid delivery.

DESCRIPTION OF THE PREFERRED EMBODIMENTS

Hereinafter, the present invention will be specifically described.

In the present specification, "to" shows a range including numerical values described before and after "to" as a minimum value and a maximum value respectively.

The lipid composition according to the embodiment of the present invention contains a lipid represented by Formula (1) or a salt thereof, a nonionic lipid, a lipid having a nonionic hydrophilic polymer structure, and a nucleic acid and contains or does not contain a zwitterionic lipid.

<Content of Lipid Represented by Formula (1) or Salt Thereof and Zwitterionic Lipid>

In the lipid composition according to the embodiment of the present invention, in a case where (A) represents a molar ratio in percentage of the lipid represented by Formula (1) or a salt thereof to the total lipids constituting the lipid composition, and (B) represents a molar ratio in percentage of the zwitterionic lipid to the total lipids constituting the lipid composition, (A) and (B) satisfy $40<(A)-(B)\leq 90$, preferably satisfy $40<(A)-(B)\leq 80$, more preferably satisfy $45<(A)-(B)\leq 80$, and even more preferably satisfy $45<(A)-(B)\leq 70$. For example, (A) and (B) satisfy $50<(A)-(B)\leq 65$. In a case where (A)−(B) is set within the above range, the lipid composition according to the embodiment of the present invention can achieve excellent nucleic acid delivery.

<Lipid Represented by Formula (1) or Salt Thereof>

The lipid composition according to an embodiment of the present invention contains a lipid represented by Formula (1) or a salt thereof.

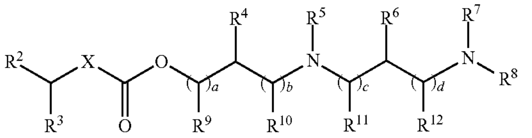

(1)

In the formula, X represents —$NR^1$— or —O—, $R^1$ represents a hydrogen atom, a hydrocarbon group having 6 to 24 carbon atoms, or a group represented by $R^{21}$-$L^1$-$R^{22}$—, $R^{21}$ represents a hydrocarbon group having 1 to 24 carbon atoms, $L^1$ represents —O(CO)O—, —O(CO)—, —(CO)O—, —O—, or a group represented by the following formula,

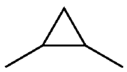

$R^{22}$ represents a divalent hydrocarbon linking group having 1 to 18 carbon atoms, $R^2$ and $R^3$ each independently represent a hydrogen atom, a hydrocarbon group having 3 to 24 carbon atoms, or a group represented by $R^{31}$-$L^2$-$R^{32}$—, $R^{31}$ represents a hydrocarbon group having 1 to 24 carbon atoms, $L^2$ represents —O(CO)O—, —O(CO)—, —(CO)O—, —O—, or a group represented by the following formula,

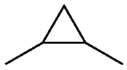

$R^{32}$ represents a divalent hydrocarbon linking group having 1 to 18 carbon atoms, $R^4$, $R^5$, $R^6$, $R^7$, $R^8$, $R^9$, $R^{10}$, $R^{11}$, and $R^{12}$ each independently represent a hydrogen atom or an alkyl group having 1 to 18 carbon atoms that may be substituted, groups in any one or more pairs among $R^4$ and $R^5$, $R^{10}$ and $R^5$, $R^5$ and $R^{12}$, $R^4$ and $R^6$, $R^5$ and $R^6$, $R^6$ and $R^7$, $R^6$ and $R^{10}$, $R^{12}$ and $R^7$, and $R^7$ and $R^8$ may be linked to each other to form a 4- to 7-membered ring which may contain an O atom, the substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, the substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, a, b, c, and d each independently represent an integer of 0 to 3, a+b is 1 or more, and c+d is 1 or more.

As the hydrocarbon group having 6 to 24 carbon atoms that is represented by $R^1$ and the hydrocarbon group having 3 to 24 carbon atoms that is represented by $R^2$ and $R^3$, an alkyl group, an alkenyl group, or an alkynyl group is preferable, and an alkyl group or an alkenyl group is more preferable. The alkyl group having 6 to 24 carbon atoms and the alkyl group having 3 to 24 carbon atoms may be linear or branched or may be chainlike or cyclic. The alkyl group having 6 to 24 carbon atoms is preferably an alkyl group having 6 to 20 carbon atoms, and the alkyl group having 3 to 24 carbon atoms is more preferably an alkyl group having 6 to 20 carbon atoms. Specifically, examples thereof include a hexyl group, a heptyl group, an octyl group, a nonyl group, a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a tetramethylhexadecyl group (preferably a 3,7,11,15-tetramethylhexadecyl group), a heptadecyl group, an octadecyl group, a nonadecyl group, an icosyl group, and the like. The alkenyl group having 6 to 24 carbon atoms and the alkenyl group having 3 to 24 carbon atoms may be linear or branched or may be chainlike or cyclic. The alkenyl group having 6 to 24 carbon atoms is preferably an alkenyl group having 6 to 20 carbon atoms, and the alkenyl group having 3 to 24 carbon atoms is more preferably an alkenyl group having 6 to 20 carbon atoms. Specifically, examples thereof include a hexenyl group, a heptenyl group, an octenyl group, a nonenyl group, a decenyl group, an undecenyl group, a dodecenyl group, a dodecadienyl group, a tridecenyl group, a tetradecenyl group, a pentadecenyl group, a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), a nonadecenyl group, an icosenyl group (preferably a (Z)-icos-11-enyl group), an icosadienyl group (preferably a (11,14)-icosa-11,14-dienyl group), and the like. The alkynyl group having 6 to 24 carbon atoms is preferably an alkynyl group having 6 to 20 carbon atoms, and the alkynyl group having 3 to 24 carbon atoms is more preferably an alkynyl group having 6 to 20 carbon atoms. Specifically, examples thereof include a hexynyl group, a heptynyl group, an octynyl group, a nonynyl group, a decynyl group, an undecynyl group, a dodecynyl group, a tetradecynyl group, a pentadecynyl group, a hexadecynyl group, a heptadecynyl group, an octadecynyl group, and the like. All of the above alkenyl groups preferably have one double bond or two double bonds. All of the above alkynyl groups preferably have one triple bond or two triple bonds.

The hydrocarbon group having 1 to 24 carbon atoms that is represented by $R^{21}$ and $R^{31}$ is preferably an alkyl group having 10 to 24 carbon atoms, an alkenyl group having 10 to 24 carbon atoms, or an alkynyl group having 10 to 24 carbon atoms. The alkyl group having 10 to 24 carbon atoms may be linear or branched or may be chainlike or cyclic. The alkyl group having 10 to 24 carbon atoms is preferably an alkyl group having 12 to 24 carbon atoms. Specifically, examples thereof include a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a tetramethylhexadecyl group (preferably a 3,7,11,15-tetramethylhexadecyl group), a heptadecyl group, an octadecyl group, a 2-butylhexyl group, a 2-butyloctyl group, a 1-pentylhexyl group, a 2-pentylheptyl group, a 3-pentyloctyl group, a 1-hexylheptyl group, a 1-hexylnonyl group, a 2-hexyloctyl group, a 2-hexyldecyl group, a 3-hexylnonyl group, a 1-heptyloctyl group, a 2-heptylnonyl group, a 2-heptylundecyl group, a 3-heptyldecyl group, a 1-octylnonyl group, a 2-octyldecyl group, a 2-octyldodecyl group, a 3-octylundecyl group, a 2-nonylundecyl group, a 3-nonyldodecyl group, a 2-decyldodecyl group, a 2-decyltetradecyl group, a 3-decyltridecyl group, a 2-(4,4-dimethylpentan-2-yl)-5,7,7-trimethyloctyl group, and the like. The alkenyl group having 10 to 24 carbon atoms may be linear or branched or may be chainlike or cyclic. Specifically, examples thereof include a decenyl group, an undecenyl group, a dodecenyl group, a dodecadienyl group, tridecenyl group (preferably a (Z)-tridec-8-enyl group), a tetradecenyl group (preferably a tetradec-9-enyl group), a pentadecenyl group (preferably a (Z)-pentadec-8-enyl group), a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), and the like. The alkynyl group having 10 to 24 carbon atoms may be linear or branched or may be chainlike or cyclic. Specifically, examples thereof include a decynyl group, an undecynyl group, a dodecynyl group, a tetradecynyl group, a pentadecynyl group, a hexadecynyl group, a heptadecynyl group, an octadecynyl group, and the like. All of the above alkenyl groups preferably have one double bond or two double bonds. All of the above alkynyl groups preferably have one triple bond or two triple bonds.

The divalent hydrocarbon linking group having 1 to 18 carbon atoms that is represented by $R^{22}$ and $R^{32}$ is preferably an alkylene group having 1 to 18 carbon atoms or an alkenylene group having 2 to 18 carbon atoms. The alkylene group having 1 to 18 carbon atoms may be linear or branched or may be chainlike or cyclic. The number of carbon atoms in the alkylene group is preferably 1 to 12, more preferably 1 to 10, and even more preferably 2 to 10. Specifically, examples thereof include a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, and the like. The alkenylene group having 2 to 18 carbon atoms may be linear or branched or may be chainlike or cyclic. The number of carbon atoms in the alkenylene group is preferably 1 to 12, and more preferably 2 to 10.

—O(CO)O—, —O(CO)—, and —(CO)O— are in a preferred range of $L^1$, and —O(CO)— and —(CO)O— are in a more preferred range of $L^1$.

—O(CO)O—, —O(CO)—, and —(CO)O— are in a preferred range of $L^2$, and —O(CO)— and —(CO)O— are in a more preferred range of $L^2$.

The alkyl group which is represented by $R^4$, $R^6$, $R^9$, $R^{10}$, $R^{11}$, and $R^{12}$ and has 1 to 18 carbon atoms that may be substituted may be linear or branched or may be chainlike or cyclic. The number of carbon atoms in the alkyl group is preferably 1 to 12. Specifically, examples thereof include a methyl group, an ethyl group, a propyl group, an isopropyl group, a cyclopropyl group, a butyl group, an isobutyl group, a tert-butyl group, a cyclobutyl group, a pentyl group, a cyclopentyl group, a hexyl group, a cyclohexyl group, a heptyl group, an octyl group, a nonyl group, a decyl group, an undecyl group, a dodecyl group, and the like. In a case where the alkyl group has a substituent, as the substituent, a hydroxyl group, a carboxyl group, or a group represented by —O(CO)O—$R^{41}$, —O(CO)—$R^{42}$, —(CO)O—$R^{43}$, or —O—$R^{44}$ is preferable, and a group represented by —O(CO)—$R^{42}$ or —(CO)O—$R^{43}$ is more preferable.

The alkyl group which is represented by $R^5$, $R^7$, and $R^8$ and has 1 to 18 carbon atoms that may be substituted may be linear or branched or may be chainlike or cyclic. The number of carbon atoms in the alkyl group is preferably 1 to 12, and more preferably 1 to 8. Specifically, examples thereof include a methyl group, an ethyl group, a propyl group, an isopropyl group, a cyclopropyl group, a butyl group, an isobutyl group, a tert-butyl group, a cyclobutyl group, a pentyl group, a cyclopentyl group, a hexyl group, a cyclohexyl group, a heptyl group, an octyl group, a nonyl group, a decyl group, an undecyl group, a dodecyl group, and the like. In a case where the alkyl group has a substituent, as the substituent, a hydroxyl group, a carboxyl group, or a group represented by —O(CO)O—$R^{41}$, —O(CO)—$R^{42}$, —(CO)O—$R^{43}$, or —O—$R^{44}$ is preferable, and a group represented by —O(CO)—$R^{42}$, —(CO)O—$R^{43}$, or —O—$R^{44}$ is more preferable.

Examples of the 4- to 7-membered ring which may contain an O atom include an azetidine ring, a pyrrolidine ring, a piperidine ring, a morpholine ring, and an azepane ring. The 4- to 7-membered ring is preferably a 6-membered ring which is preferably a piperidine ring or a morpholine ring.

In a case where the alkyl group which is represented by $R^4$, $R^5$, $R^6$, $R^7$, $R^8$, $R^9$, $R^{10}$, $R^{11}$, and $R^{12}$ and has 1 to 18 carbon atoms that may be substituted has a substituted or unsubstituted aryl group as a substituent, the number of carbon atoms in the aryl group is preferably 6 to 22, more preferably 6 to 18, and even more preferably 6 to 10. Specifically, examples of the aryl group include a phenyl group, a naphthyl group, an anthracenyl group, a phenanthrenyl group, and the like. As the substituent on the aryl group, an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$ is preferable, and a hydroxyl group or a carboxyl group is more preferable. Specifically, examples of the substituted aryl group include a hydroxyphenyl group, a carboxyphenyl group, and the like.

In a case where the alkyl group which is represented by $R^4$, $R^5$, $R^6$, $R^7$, $R^8$, $R^9$, $R^{10}$, $R^{11}$, and $R^{12}$ and has 1 to 18 carbon atoms that may be substituted has a substituted or unsubstituted heteroaryl group as a substituent, the number of carbon atoms in the heteroaryl group is preferably 1 to 12, and more preferably 1 to 6. Specifically, examples of the heteroaryl group include a pyridyl group, a pyrazolyl group, an imidazolyl group, a benzimidazolyl group, a thiazolyl group, an oxazolyl group, and the like. As the substituent on the heteroaryl group, an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$ is preferable, and a hydroxyl group or a carboxyl group is more preferable. Specifically, examples of the substituted or unsubstituted heteroaryl group include a hydroxypyridyl group, a carboxypyridyl group, a pyridonyl group, and the like.

As hydrocarbon group having 1 to 18 carbon atoms that is represented by $R^{41}$, $R^{42}$, $R^{43}$, $R^{44}$, $R^{45}$, and $R^{46}$, an alkyl group having 1 to 18 carbon atoms, an alkenyl group having 2 to 18 carbon atoms, or an alkynyl group having 2 to 18 carbon atoms is preferable, and an alkyl group having 1 to 18 carbon atoms or an alkenyl group having 2 to 18 carbon atoms is more preferable. The alkyl group having 1 to 18 carbon atoms may be linear or branched or may be chainlike or cyclic. The number of carbon atoms in the alkyl group is preferably 3 to 18, and more preferably 5 to 18. Specifically, examples thereof include a propyl group, an isopropyl group, a cyclopropyl group, a butyl group, an isobutyl group, a tert-butyl group, a cyclobutyl group, a pentyl group, a cyclopentyl group, a hexyl group, a cyclohexyl group, a heptyl group, an octyl group, a nonyl group, a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a heptadecyl group, an octadecyl group, and the like. The alkenyl group having 2 to 18 carbon atoms may be linear or branched or may be chainlike or cyclic. The number of carbon atoms in the alkyl group is preferably 3 to 18, and more preferably 5 to 18. Specifically, examples thereof include an allyl group, a prenyl group, a pentenyl group, a hexenyl group, a heptenyl group, an octenyl group, a nonenyl group (preferably a (Z)-2-nonenyl group or an (E)-2-nonenyl group), a decenyl group, an undecenyl group, a dodecenyl group, a dodecadienyl group, a tridecenyl group (preferably a (Z)-tridec-8-enyl group), a tetradecenyl group (preferably a tetradec-9-enyl group), a pentadecenyl group (preferably a (Z)-pentadec-8-enyl group), a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), and the like. The alkynyl group having 2 to 18 carbon atoms may be linear or branched or may be chainlike or cyclic. The number of carbon atoms in the alkynyl group is preferably 3 to 18, and more preferably 5 to 18. Specifically, examples thereof include a propargyl group, a butynyl group, a pentynyl group, a hexynyl group, a heptynyl group, an octynyl group, a nonynyl group, a decynyl group, an undecynyl group, a dodecynyl group, a tetradecynyl group, a pentadecynyl group, a hexadecynyl group, a heptadecynyl group, an octadecynyl group, and the like.

In a case where X represents —$NR^1$—, $R^1$ preferably represents a hydrocarbon group having 6 to 24 carbon atoms or a group represented by $R^{21}$-$L^1$-$R^{22}$—. In this case, it is preferable that one of $R^2$ and $R^3$ represent a hydrogen atom and the other represent a hydrocarbon group having 6 to 24 carbon atoms or a group represented by $R^{31}$-$L^2$-$R^{32}$—.

In a case where X represents —O—, it is preferable that $R^2$ and $R^3$ each independently represent a hydrocarbon group having 6 to 24 carbon atoms or a group represented by $R^{31}$-$L^2$-$R^{32}$—.

It is preferable that $R^4$, $R^6$, $R^9$, $R^{10}$, $R^{11}$, and $R^{12}$ each represent a hydrogen atom.

$R^5$ is preferably a hydrogen atom, an alkyl group having 1 to 18 carbon atoms, an alkyl group having 1 to 18 carbon atoms that may be substituted with —O(CO)—$R^{42}$ or —(CO)O—$R^{43}$, an alkyl group having 1 to 18 carbon atoms that may be substituted with an aryl group, or an alkyl group having 1 to 18 carbon atoms that may be substituted with a hydroxyl group. In a case where $R^5$ is an alkyl group, $R^5$ may be linked to $R^4$, $R^6$, $R^{10}$, and $R^{12}$ so as to form a ring which may contain an O atom. Particularly, $R^5$ is preferably an alkyl group having 1 to 18 carbon atoms, an alkyl group having 1 to 18 carbon atoms that may be substituted with —O(CO)—$R^{42}$ or —(CO)O—$R^{43}$, an alkyl group having 1 to 12 carbon atoms that may be substituted with an aryl group, or an alkyl group having 1 to 8 carbon atoms that may be substituted with a hydroxyl group, and more preferably an alkyl group having 1 to 18 carbon atoms or an alkyl group having 1 to 18 carbon atoms that may be substituted with —O(CO)—$R^{42}$ or —(CO)O—$R^{43}$.

$R^7$ and $R^8$ preferably each independently represent a hydrogen atom, a hydrocarbon group having 1 to 18 carbon atoms, an alkyl group having 1 to 18 carbon atoms that may be substituted with —O(CO)—$R^{42}$ or —(CO)O—$R^{43}$, an alkyl group having 1 to 8 carbon atoms that may be substituted with an aryl group, or an alkyl group having 1 to 8 carbon atoms that may be substituted with a hydroxyl group. Alternatively, it is preferable that $R^7$ and $R^8$ be linked to each other so as to form a 4- to 7-membered ring which may contain an O atom.

$R^5$ is not linked to $R^7$ or $R^8$ and does not form a ring with $R^7$ or $R^8$.

a+b is preferably 1 or 2, and more preferably 1. c+d is preferably 1 or 2, and more preferably 1.

The compound represented by Formula (1) is preferably a compound represented by Formula (1-1).

(1-1)

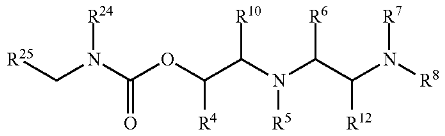

$R^{24}$ represents a hydrogen atom, a hydrocarbon group having 6 to 24 carbon atoms, or a group represented by $R^{21}$-$L^1$-$R^{22}$—, $R^{21}$ represents a hydrocarbon group having 1 to 24 carbon atoms, $L^1$ represents —O(CO)O—, —O(CO)—, —(CO)O—, —O—, or a group represented by the following formula,

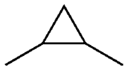

$R^{22}$ represents a divalent hydrocarbon linking group having 1 to 18 carbon atoms.

$R^{25}$ represents a hydrogen atom, a hydrocarbon group having 3 to 24 carbon atoms, or a group represented by $R^{31}$-$L^2$-$R^{32}$—, $R^{31}$ represents a hydrocarbon group having 1 to 24 carbon atoms, $L^2$ represents —O(CO)O—, —O(CO)—, —(CO)O—, —O—, or a group represented by the following formula,

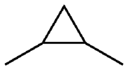

$R^{32}$ represents a divalent hydrocarbon linking group having 1 to 18 carbon atoms.

$R^4$, $R^5$, $R^6$, $R^7$, $R^8$, $R^{10}$, and $R^{12}$ each independently represent a hydrogen atom or an alkyl group having 1 to 18 carbon atoms that may be substituted, and groups in any one or more pairs among $R^4$ and $R^5$, $R^{10}$ and $R^5$, $R^5$ and $R^{12}$, $R^4$ and $R^6$, $R^5$ and $R^6$, $R^6$ and $R^7$, $R^6$ and $R^{10}$, $R^{12}$ and $R^7$, and $R^7$ and $R^8$ may be linked to each other so as to form a 4- to 7-membered ring which may contain an O atom. However, it is preferable that $R^5$ be not linked to $R^7$ or $R^8$ and do not form a ring with $R^7$ or $R^8$.

the substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, the substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$, and $R^{46}$ each independently represent a hydrocarbon group having 1 to 18 carbon atoms.

The definitions and preferred ranges of $R^4$, $R^5$, $R^6$, $R^7$, $R^8$, $R^{10}$, and $R^{12}$ in Formula (1-1) are the same as those of $R^4$, $R^5$, $R^6$, $R^7$, $R^8$, $R^{10}$, and $R^{12}$ in Formula (1).

$R^{24}$ in Formula (1-1) is preferably an alkyl group or an alkenyl group having 6 to 24 carbon atoms. The alkyl group having 6 to 24 carbon atoms may be linear or branched or may be chainlike or cyclic. The alkyl group having 6 to 24 carbon atoms is preferably an alkyl group having 8 to 20 carbon atoms. Specifically, examples thereof include an octyl group, a nonyl group, a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a tetramethylhexadecyl group (preferably a 3,7,11,15-tetramethylhexadecyl group), a heptadecyl group, an octadecyl group, a nonadecyl group, an icosyl group, and the like. The alkenyl group having 6 to 24 carbon atoms may be linear or branched or may be chainlike or cyclic. The alkenyl group having 6 to 24 carbon atoms is preferably an alkenyl group having 8 to 20 carbon atoms. Specifically, examples thereof include an octenyl group, a nonenyl group, a decenyl group, an undecenyl group, a dodecenyl group, a dodecadienyl group, a tridecenyl group, a tetradecenyl group, a pentadecenyl group, a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), a nonadecenyl group, an icosenyl group (preferably a (Z)-icos-11-enyl group), an icosadienyl group (preferably a (11,14)-icosa-11,14-dienyl group), and the like.

It is preferable that all of the above alkenyl groups have one double bond or two double bonds.

$R^{25}$ in Formula (1-1) is preferably an alkyl group or an alkenyl group having 6 to 24 carbon atoms. The alkyl group having 6 to 24 carbon atoms may be linear or branched or may be chainlike or cyclic. The alkyl group having 6 to 24 carbon atoms is preferably an alkyl group having 7 to 20 carbon atoms. Specifically, examples thereof include a hexyl group, a heptyl group, an octyl group, a nonyl group, a decyl group, an undecyl group, a dodecyl group, a tridecyl group, a trimethyldodecyl group (preferably a 3,7,11-trimethyldodecyl group), a tetradecyl group, a pentadecyl group, a hexadecyl group, a tetramethylhexadecyl group (preferably a 3,7,11,15-tetramethylhexadecyl group), a heptadecyl group, an octadecyl group, and the like. The alkenyl group having 6 to 24 carbon atoms may be linear or branched or may be chainlike or cyclic. The alkenyl group having 6 to 24 carbon atoms is preferably an alkenyl group having 8 to 20 carbon atoms. Specifically, examples thereof include an octenyl group, a nonenyl group, a decenyl group, an undecenyl group, a dodecenyl group, a dodecadienyl group, a tridecenyl group, a tetradecenyl group, a pentadecenyl group, a hexadecenyl group (preferably a (Z)-hexadec-9-enyl group), a hexadecadienyl group, a heptadecenyl group (preferably a (Z)-heptadec-8-enyl group), a heptadecadienyl group (preferably a (8Z,11Z)-heptadeca-8,11-dienyl group), an octadecenyl group (preferably a (Z)-octadec-9-enyl group), an octadecadienyl group (preferably a (9Z,12Z)-octadeca-9,12-dienyl group), a nonadecenyl group, an icosenyl group (preferably a (Z)-icos-11-enyl group), an icosadienyl group (preferably a (11,14)-icosa-11,14-dienyl group), and the like.

It is preferable that all of the above alkenyl groups have one double bond or two double bonds.

In a preferred embodiment,

X represents —O—;

$R^2$, $R^3$, $R^{31}$, $L^2$, and $R^{32}$ have the same definitions as $R^2$, $R^3$, $R^{31}$, $L^2$, and $R^{32}$ in Formula (1), $R^4$, $R^5$, $R^6$, $R^7$, $R^8$, $R^9$, $R^{10}$, $R^{11}$, and $R^{12}$ each independently represent a hydrogen atom or an alkyl group having 1 to 18 carbon atoms that may be substituted, the substituent on the alkyl group having 1 to 18 carbon atoms that may be substituted and the substituent on the substituted or unsubstituted aryl group and on the substituted or unsubstituted heteroaryl group have the same definitions as those in Formula (1), a+b is 1, and c+d is 1 or 2.

In a more preferred embodiment, the compound represented by Formula (1) is a compound represented by Formula (2).

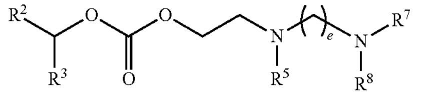

(2)

In the formula, $R^2$ and $R^3$ each independently represent a hydrogen atom, a hydrocarbon group having 3 to 24 carbon atoms, or a group represented by $R^{31}$-$L^2$-$R^{32}$—, $R^{31}$ represents a hydrocarbon group having 1 to 24 carbon atoms, $L^2$ represents —O(CO)O—, —O(CO)—, —(CO)O—, —O—, or a group represented by the following formula,

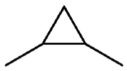

$R^{32}$ represents a divalent hydrocarbon linking group having 1 to 18 carbon atoms, $R^5$ represents a hydrogen atom or an alkyl group having 1 to 18 carbon atoms that may be substituted, $R^7$ and $R^8$ each independently represent a hydrogen atom or an alkyl group having 1 to 18 carbon atoms that may be substituted, the substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, the substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$, and $R^{46}$ each independently represent a hydrocarbon group having 1 to 18 carbon atoms, and e represents 2 or 3.

$R^2$, $R^3$, $R^5$, $R^7$, and $R^8$ have the same definitions as $R^2$, $R^3$, $R^5$, $R^7$, and $R^8$ in Formula (1).

Formula (2) preferably represents a compound in which $R^7$ and $R^8$ each independently represent a hydrogen atom or an alkyl group having 1 to 18 carbon atoms, the substituent on the alkyl group which is represented by $R^5$ and has 1 to 18 carbon atoms that may be substituted is a hydroxyl group, a substituted or unsubstituted aryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, the substituent on the substituted or unsubstituted aryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$, and $R^{46}$ each independently represent a hydrocarbon group having 1 to 18 carbon atoms.

Formula (2) more preferably represents a compound in which $R^2$ and $R^3$ each independently represent a hydrocarbon group having 3 to 24 carbon atoms or a group represented by $R^{31}$-$L^2$-$R^{32}$—, $L^2$ represents —O(CO)— or —(CO)O—, $R^7$ and $R^8$ each independently represent a hydrogen atom or an alkyl group having 1 to 18 carbon atoms, the substituent on the alkyl group which has 1 to 18 carbon atoms and may be substituted is an unsubstituted aryl group, —O(CO)—$R^{42}$, or —(CO)O—$R^{43}$, and $R^{42}$ and $R^{43}$ each independently represent a hydrocarbon group having 1 to 18 carbon atoms.

Formula (2) even more preferably represents a compound in which $R^2$ and $R^3$ each independently represent a hydrogen atom or a hydrocarbon group having 3 to 24 carbon atoms, $R^7$ and $R^8$ each independently represent a hydrogen atom or an alkyl group having 1 to 18 carbon atoms, the substituent on the alkyl group which has 1 to 18 carbon atoms and may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) preferably represents a compound in which at least one of $R^2$ or $R^3$ represents a group represented by $R^{31}$-$L^2$-$R^{32}$—, $L^2$ represents —O(CO)— or —(CO)O—, $R^7$ and $R^8$ each independently represent a hydrogen atom or an alkyl group having 1 to 18 carbon atoms, the substituent on the alkyl group which has 1 to 18 carbon atoms and may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) more preferably represents a compound in which $R^2$ and $R^3$ each independently represent a group represented by $R^{31}$-$L^2$-$R^{32}$—, $L^2$ represents —O(CO)— or —(CO)O—, $R^7$ and $R^8$ each independently represent a hydrogen atom or an alkyl group having 1 to 18 carbon atoms, the substituent on the alkyl group which has 1 to 18 carbon atoms and may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) preferably represents a compound in which one of $R^2$ and $R^3$ represents a group represented by $R^{31}$-$L^2$-$R^{32}$— and the other represents a hydrocarbon group having 3 to 24 carbon atoms, $L^2$ represents —O(CO)— or —(CO)O—, $R^7$ and $R^8$ each independently represent a hydrogen atom or an alkyl group having 1 to 18 carbon atoms, the substituent on the alkyl group which has 1 to 18 carbon atoms and may be substituted is an unsubstituted aryl group or a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^7$ and $R^8$ each independently represent a hydrogen atom or an alkyl group having 1 to 18 carbon atoms, the substituent on the alkyl group which has 1 to 18 carbon atoms and may be substituted is a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) even more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or an alkyl group having 1 to 18 carbon atoms, and $R^7$ and $R^8$ each independently represent a hydrogen atom or an alkyl group having 1 to 18 carbon atoms.

Formula (2) still more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or an alkyl group having 1 to 18 carbon atoms, $R^7$ and $R^8$ each independently represent a hydrogen atom or an alkyl group having 1 to 18 carbon atoms, and e represents 2.

Formula (2) yet more preferably represents a compound in which one of $R^2$ and $R^3$ represents a group represented by $R^{31}$-$L^2$-$R^{32}$— and the other represents a hydrocarbon group having 3 to 5 carbon atoms, $L^2$ represents —O(CO)— or —(CO)O—, $R^5$ represents a hydrogen atom or an alkyl group having 1 to 18 carbon atoms, and $R^7$ and $R^8$ each independently represent a hydrogen atom or an alkyl group having 1 to 18 carbon atoms.

Formula (2) more preferably represents a compound in which one of $R^2$ and $R^3$ represents a group represented by $R^{31}$-$L^2$-$R^{32}$— and the other represents a hydrocarbon group having 3 to 5 carbon atoms, $L^2$ represents —O(CO)— or —(CO)O—, $R^5$ represents a hydrogen atom or an alkyl group having 1 to 18 carbon atoms, $R^7$ and $R^8$ each independently represent a hydrogen atom or an alkyl group having 1 to 18 carbon atoms, and e represents 2.

Formula (2) even more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or a substituted alkyl group having 1 to 18 carbon atoms, $R^7$ and $R^8$ each independently represent a hydrogen atom or an alkyl group having 1 to 18 carbon atoms, the substituent on the substituted alkyl group having 1 to 18 carbon atoms is a group represented by —O(CO)—$R^{42}$ or —(CO)O—$R^{43}$, and $R^{42}$ and $R^{43}$ each independently represent a hydrocarbon group having 1 to 18 carbon atoms.

Formula (2) still more preferably represents a compound in which one of $R^2$ and $R^3$ represents a group represented by $R^{31}$-$L^2$-$R^{32}$— and the other represents a hydrocarbon group having 6 carbon atoms, $L^2$ represents —O(CO)— or —(CO)O—, $R^5$ represents a hydrogen atom or a substituted alkyl group having 1 to 18 carbon atoms, $R^7$ and $R^8$ each independently represent a hydrogen atom or an alkyl group having 1 to 18 carbon atoms, the substituent on the substituted alkyl group having 1 to 18 carbon atoms is a group represented by —O(CO)—$R^{42}$ or —(CO)O—$R^{43}$, $R^{42}$ and $R^{43}$ each independently represent a hydrocarbon group having 1 to 18 carbon atoms, and e represents 2.

In a preferred aspect, Formula (2) represents a compound, at least one of $R^2$ or $R^3$ represents a hydrocarbon group having 3 to 24 carbon atoms containing one or more unsaturated bonds; $R^2$ and $R^3$ each independently represent a group represented by $R^{31}$-$L^2$-$R^{32}$—: or one of $R^2$ and $R^3$ represents a group represented by $R^{31}$-$L^2$-$R^{32}$— and the other represents a hydrocarbon group having 3 to 24 carbon atoms;

$R^5$ represents an unsubstituted alkyl group having 1 to 18 carbon atoms or an alkyl group having 1 to 18 carbon atoms substituted with —O(CO)—$R^{42}$ or —(CO)O—$R^{43}$;

$R^7$ and $R^8$ each independently represent an alkyl group having 1 to 4 carbon atoms;

($R^{31}$, $L^2$, $R^{32}$, $R^{42}$, and $R^{43}$ have the same definitions as $R^{31}$, $L^2$, $R^{32}$, $R^{42}$, and $R^{43}$ in Formula (2)).

The compound represented by Formula (1) may form a salt.

Examples of the salt in a basic group include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salt in an acidic group include salts with alkali metals such as sodium and potassium; salts with alkaline earth metals such as calcium and magnesium; ammonium salts; salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine, and the like.

Among the above salts, for example, pharmacologically acceptable salts are preferable.

Specifically, preferable examples of the compound represented by Formula (1) include the compounds described in Examples 1 to 133 which will be described later. However, the present invention is not limited thereto.

The compounds described in Examples 1 to 133 are called compounds 1 to 133 respectively.

Among the above compounds, the compounds 30, 56, 62, 70, 76, 77, 88, 89, 94, 100, 112, 124, 133, 134, 135, 136, 137, and 138 are particularly preferable.

The method for manufacturing the compound represented by Formula (1) will be described.

The compound represented by Formula (1) can be manufactured using known methods in combination. For example, the compound can be manufactured by the following manufacturing method.

[Manufacturing Method 1]

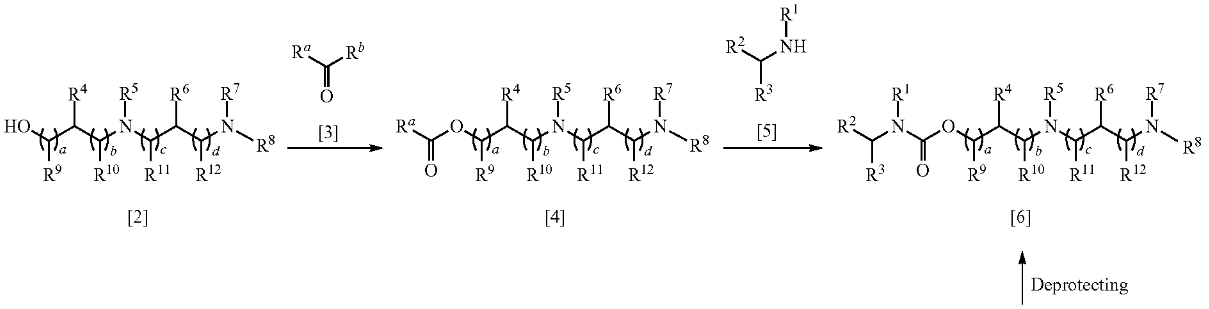

-continued

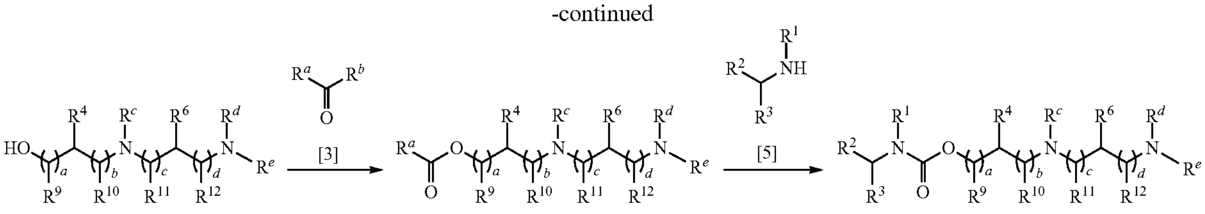

[2A] [4A] [6A]

"In the formula, $R^a$ and $R^b$ each represent a leaving group; $R^c$, $R^d$, and $R^e$ each represent an amino protecting group or an imino protecting group; and $R^1$, $R^2$, $R^3$, $R^4$, $R^5$, $R^6$, $R^7$, $R^8$, $R^9$, $R^{10}$, $R^{11}$, and $R^{12}$ have the same definitions as $R^1$, $R^2$, $R^3$, $R^4$, $R^5$, $R^6$, $R^7$, $R^8$, $R^9$, $R^{10}$, $R^{11}$, and $R^{12}$ described above." Examples of the leaving group include a chloro group, a fluoro group, a bromo group, a trichloromethoxy group, a 4-nitro-phenoxy group, a 2,4-dinitrophenoxy group, a 2,4,6-trichlorophenoxy group, a pentafluorophenoxy group, a 2,3,5,6-tetrafluorophenoxy group, an imidazolyl group, a triazolyl group, a 3,5-dioxo-4-methyl-1,2,4-oxadiazolidyl group, a N-hydroxysuccinimidyl group, and the like. Examples of the amino protecting group and the imino protecting group include a tert-butoxycarbonyl group, a benzyloxycarbonyl group, a 2-nitrobenzenesulfonyl group, a benzyl group, and the like.

(1-1)

As the compound represented by Formula [3], for example, 4-nitrophenyl chloroformate, 1,1'-carbonyldiimidazole, triphosgene, phosgene, and the like are known.

The compound represented by Formula [4] can be manufactured by reacting the compound represented by Formula [2] with the compound represented by Formula [3] in the presence of a base.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [2].

Examples of the base used in this reaction include an inorganic base and an organic base. As the base, an organic base is preferable. Specifically, examples thereof include triethylamine, N,N-diisopropylethylamine, 4-methylmorpholine, pyridine, N,N-dimethylaminopyridine, and the like.

The amount of the base used may be 1 to 50 times and preferably 1 to 10 times the molar amount of the compound represented by Formula [2].

The amount of the used compound represented by Formula [3] is not particularly limited, but may be 0.3 to 10 times (v/w) the amount of the compound represented by Formula [2].

This reaction may be carried out at −30° C. to 150° C. preferably at 0° C. to 100° C. for 5 minutes to 48 hours.

(1-2)

As the compound represented by Formula [5], for example, (9Z,12Z)-di((9Z,12Z)-octadeca-9,12-dien-1-yl) amine, dihexadecylamine, and the like are known.

The compound represented by Formula [6] can be manufactured by reacting the compound represented by Formula [4] with the compound represented by Formula [5] in the presence of a base.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [4].

Examples of the base used in this reaction include an inorganic base and an organic base. As the base, an organic base is preferable. Specifically, examples thereof include triethylamine, N,N-diisopropylethylamine, 4-methylmorpholine, pyridine, N,N-dimethylaminopyridine, and the like.

The amount of the base used may be 1 to 50 times and preferably 1 to 10 times the molar amount of the compound represented by Formula [4].

The amount of the used compound represented by Formula [5] is not particularly limited, but may be 1 to 10 times (v/w) the amount of the compound represented by Formula [4].

This reaction may be carried out at −30° C. to 150° C. preferably at 0° C. to 100° C. for 5 minutes to 48 hours.

(1-3)

As the compound represented by Formula [2A], for example, tert-butyl(2-((tert-butoxycarbonyl)amino)ethyl)(2-hydroxyethyl)carbamate, tert-butyl(2-((2-hydroxyethyl)(methyl)amino)ethyl)carbamate, and the like are known.

The compound represented by Formula [6A] can be manufactured by reacting the compound represented by Formula [2A] with the compound represented by Formula [3] in the presence of a base, and then reacting the compound represented by Formula [4A] with the compound represented by Formula [5] in the presence of a base.

This reaction may be performed based on the manufacturing methods (1-1) and (1-2).

(1-4)

The compound represented by Formula [6] can be manufactured by deprotecting the compound represented by Formula [6A].

This reaction may be performed, for example, based on the method described in "Protective Groups in Organic Synthesis, T. W. Greene et al., 4th Edition, pp. 696-926, 2007, John Wiley & Sons, INC".

[Manufacturing Method 2]

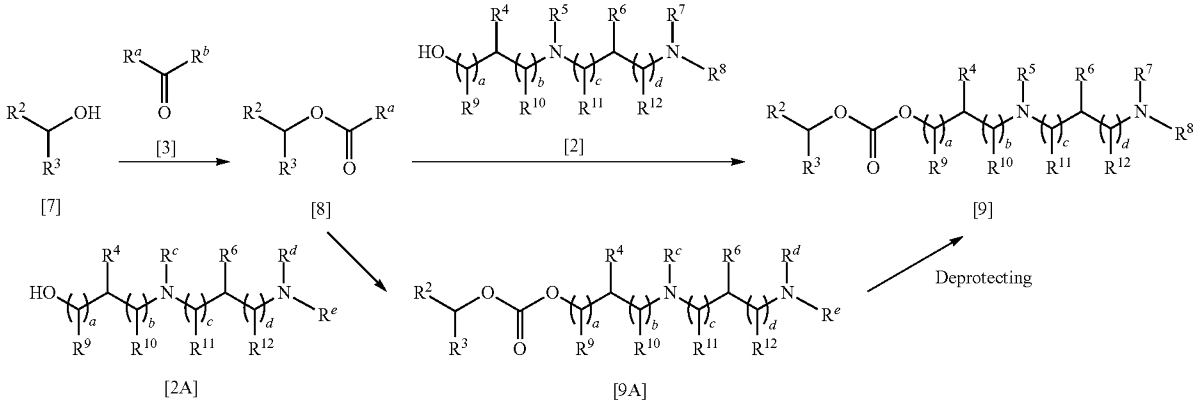

[7] [8] [9] [2A] [9A]

"In the formula, $R^a$ and $R^b$ each represent a leaving group; $R^c$, $R^d$, and $R^e$ each represent an amino protecting group or an imino protecting group; and $R^1$, $R^2$, $R^3$, $R^4$, $R^5$, $R^6$, $R^7$, $R^8$, $R^9$, $R^{10}$, $R^{11}$, and $R^{12}$ have the same definitions as $R^1$, $R^2$, $R^3$, $R^4$, $R^5$, $R^6$, $R^7$, $R^8$, $R^9$, $R^{10}$, $R^{11}$, and $R^{12}$ described above." Examples of the leaving group include a chloro group, a fluoro group, a bromo group, a trichloromethoxy group, a 4-nitro-phenoxy group, a 2,4-dinitrophenoxy group, a 2,4,6-trichlorophenoxy group, a pentafluorophenoxy group, a 2,3,5,6-tetrafluorophenoxy group, an imidazolyl group, a triazolyl group, a 3,5-dioxo-4-methyl-1,2,4-oxadiazolidyl group, a N-hydroxysuccinimidyl group, and the like. Examples of the amino protecting group and the imino protecting group include a tert-butoxycarbonyl group, a benzyloxycarbonyl group, a 2-nitrobenzenesulfonyl group, a benzyl group, and the like.

(2-1)

As the compound represented by Formula [3], for example, 4-nitrophenyl chloroformate, 1,1'-carbonyldiimidazole, triphosgene, phosgene, and the like are known.

The compound represented by Formula [8] can be manufactured by reacting the compound represented by Formula [7] with the compound represented by Formula [3] in the presence of a base.

This reaction may be performed based on the manufacturing method (1-1).

(2-2)

The compound represented by Formula [9] can be manufactured by reacting the compound represented by Formula [8] with the compound represented by Formula [2] in the presence of a base.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [8].

Examples of the base used in this reaction include an inorganic base and an organic base. As the base, an organic base is preferable. Specifically, examples thereof include triethylamine, N,N-diisopropylethylamine, 4-methylmorpholine, pyridine, N,N-dimethylaminopyridine, and the like.

The amount of the base used may be 1 to 50 times and preferably 1 to 10 times the molar amount of the compound represented by Formula [8].

The amount of the used compound represented by Formula [2] is not particularly limited, but may be 1 to 10 times (v/w) the amount of the compound represented by Formula [8].

This reaction may be carried out at −30° C. to 150° C. preferably at 0° C. to 100° C. for 5 minutes to 48 hours.

(2-3)

As the compound represented by Formula [2A], for example, tert-butyl(2-((tert-butoxycarbonyl)amino)ethyl)(2-hydroxyethyl)carbamate, tert-butyl(2-((2-hydroxyethyl)(methyl)amino)ethyl)carbamate, and the like are known.

The compound represented by Formula [9] can be manufactured by reacting the compound represented by Formula [8] with the compound represented by Formula [2A] in the presence of a base, and then deprotecting the compound represented by Formula [9A] in the presence of a base.

This reaction may be performed based on the manufacturing methods (2-2) and (1-4).

[Manufacturing Method 3]

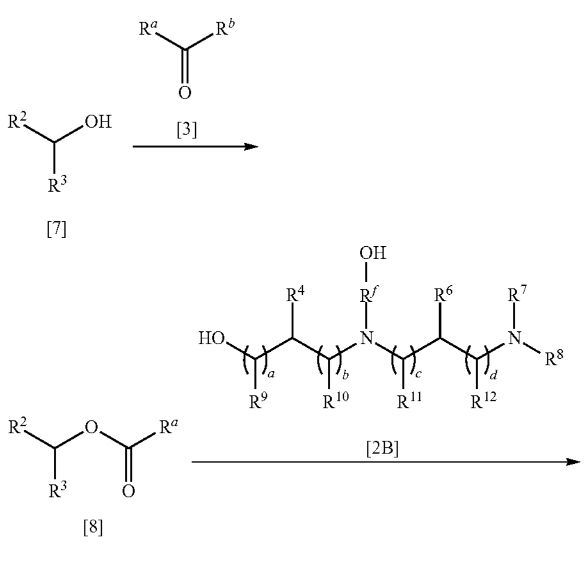

[7] [8]

-continued

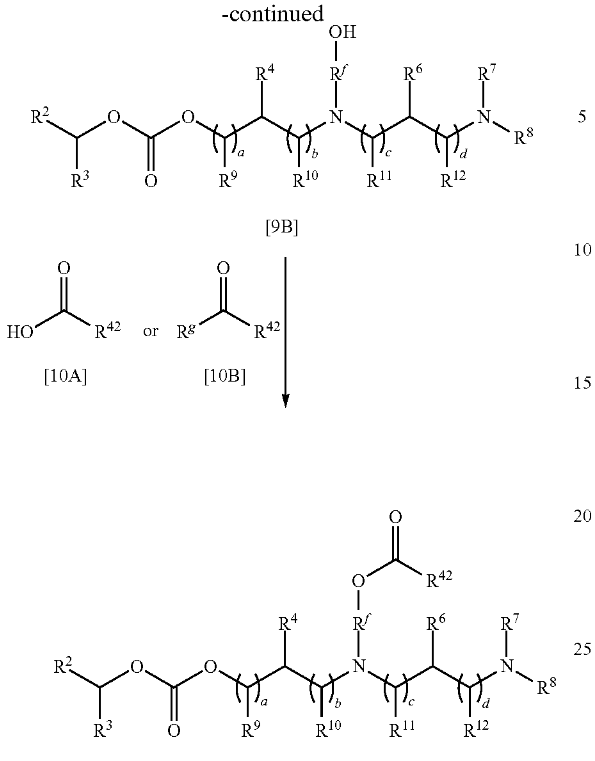

[9B]

[10A] or [10B]

[9C]

"In the formula, $R^a$, $R^b$, and $R^g$ each represent a leaving group; $R^f$ represents an alkyl group having 1 to 18 carbon atoms; and $R^1$, $R^2$, $R^3$, $R^4$, $R^5$, $R^6$, $R^7$, $R^8$, $R^9$, $R^{10}$, $R^{11}$, $R^{12}$, and $R^{42}$ have the same definitions as $R^1$, $R^2$, $R^3$, $R^4$, $R^5$, $R^6$, $R^7$, $R^8$, $R^9$, $R^{10}$, $R^{11}$, $R^{12}$, and $R^{42}$ described above." Examples of the leaving group include a chloro group, a fluoro group, a bromo group, a trichloromethoxy group, a 4-nitro-phenoxy group, a 2,4-dinitrophenoxy group, a 2,4,6-trichlorophenoxy group, a pentafluorophenoxy group, a 2,3,5,6-tetrafluorophenoxy group, an imidazolyl group, a triazolyl group, a 3,5-dioxo-4-methyl-1,2,4-oxadiazolidyl group, a N-hydroxysuccinimidyl group, and the like.

(3-1)

As the compound represented by Formula [3], for example, 4-nitrophenyl chloroformate, 1,1'-carbonyldiimidazole, triphosgene, phosgene, and the like are known.

The compound represented by Formula [8] can be manufactured by reacting the compound represented by Formula [7] with the compound represented by Formula [3] in the presence of a base.

This reaction may be performed based on the manufacturing method (1-1).

(3-2)

As the compound represented by Formula [2B], for example, 2,2'-((2-(diethylamino)ethyl)azanediyl)bis(ethan-1-ol), 2,2'-((3-(diethylamino)propyl)azanediyl)bis(ethan-1-ol), and the like are known.

The compound represented by Formula [9B] can be manufactured by reacting the compound represented by Formula [8] with the compound represented by Formula [2B] in the presence of a base.

This reaction may be performed based on the manufacturing method (2-2).

(3-3)

As the compound represented by Formula [10A], for example, dodecanoic acid, decanoic acid, nonanoic acid, octanoic acid, and the like are known.

The compound represented by Formula [9C] can be manufactured by reacting the compound represented by Formula [9B] with the compound represented by Formula [10A] in the presence of a condensing agent or an acid halide or in the presence of a base.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [9B].

Examples of the base used in this reaction include an inorganic base and an organic base. As the base, an organic base is preferable. Specifically, examples thereof include triethylamine, N,N-diisopropylethylamine, 4-methylmorpholine, pyridine, N,N-dimethylaminopyridine, and the like.

The amount of the base used may be 1 to 50 times and preferably 1 to 10 times the molar amount of the compound represented by Formula [9B].

Examples of the condensing agent used in this reaction include carbodiimides such as N,N'-dicyclohexylcarbodiimide and 1-ethyl-3-(3-dimethylaminopropyl)carbodiimide; carbonyls such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium=hexafluorophosphate, 0-(7-azabenzotriazol-1-yl)-1,1,3,3-tetramethyluronium=hexafluorophosphate, and the like.

Examples of the acid halide used in this reaction include carboxylic acid halides such as acetyl chloride and trifluoroacetyl chloride; sulfonic acid halides such as methanesulfonyl chloride and tosyl chloride; chloroformic acid esters such as ethyl chloroformate and isobutyl chloroformate, and the like.

The amount of the used compound represented by Formula [10A] is not particularly limited, but may be 1 to 10 times (v/w) the amount of the compound represented by Formula [9B].

This reaction may be carried out at −30° C. to 150° C. preferably at 0° C. to 100° C. for 5 minutes to 48 hours.

(3-4)

As the compound represented by Formula [10B], for example, dodecanoic acid chloride, decanoic acid chloride, nonanoic acid chloride, octanoic acid chloride, and the like are known.

The compound represented by Formula [9C] can be manufactured by reacting the compound represented by Formula [9B] with the compound represented by Formula [10B] in the presence of a base.

The compound represented by Formula [10B] can be manufactured by reacting the compound represented by Formula [10A] with thionyl chloride, oxalyl chloride, or the like.

The solvent used in this reaction is not particularly limited as long as the solvent does not affect the reaction. Examples of the solvent include halogenated hydrocarbons, ethers, esters, amides, nitriles, sulfoxides, and aromatic hydrocarbons. These solvents may be used by being mixed together.

As the solvent, for example, ethers are preferable, and tetrahydrofuran is more preferable.

The amount of the solvent used is not particularly limited, but may be 1 to 500 times (v/w) the amount of the compound represented by Formula [9B].

Examples of the base used in this reaction include an inorganic base and an organic base.

The amount of the base used may be 1 to 50 times and preferably 1 to 10 times the molar amount of the compound represented by Formula [9B].

The amount of the used compound represented by Formula [10B] is not particularly limited, but may be 1 to 10 times (v/w) the amount of the compound represented by Formula [2B].

This reaction may be carried out at −30° C. to 150° C. preferably at 0° C. to 100° C. for 5 minutes to 48 hours.

Next, the synthesis of the compound represented by Formula [2], which is a raw material for manufacturing the compound according to the embodiment of the present invention, will be described.

[Manufacturing Method 4]

The compound represented by Formula [2] can be manufactured by reacting the compound represented by Formula [11] with the compound represented by Formula [12] in the presence or absence of a base.

The solvent used in this reaction is not particularly limited as long as the solvent does not affect the reaction. Examples of the solvent include alcohols, halogenated hydrocarbons, ethers, esters, amides, nitriles, sulfoxides, aromatic hydrocarbons, and water. These solvents may be used by being mixed together.

The amount of the solvent used is not particularly limited, but may be 1 to 500 times (v/w) the amount of the compound represented by Formula [11].

Examples of the base used in this reaction include an inorganic base and an organic base. The amount of the base used may be 1 to 10,000 times and preferably 1 to 5,000 times the molar amount of the compound represented by Formula [11].

The amount of the used compound represented by Formula [12] is not particularly limited, but may be 1 to 10 times (v/w) the amount of the compound represented by Formula [11].

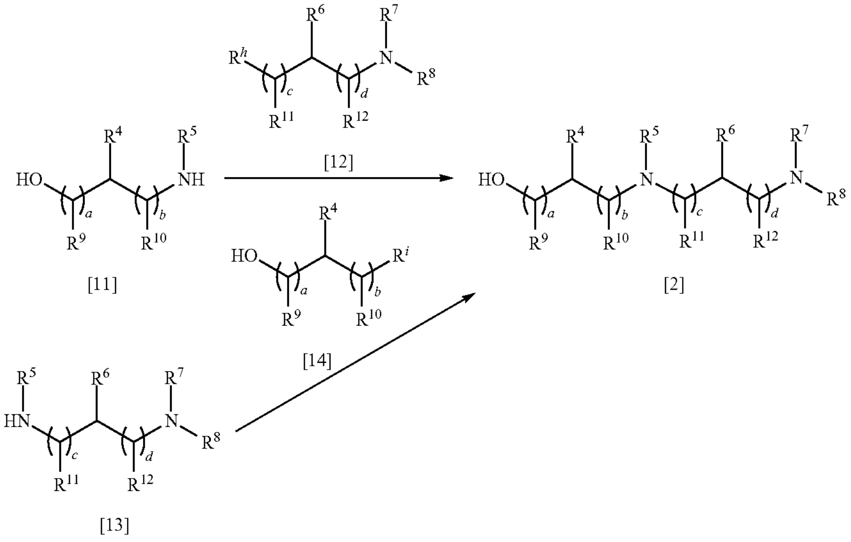

"In the formula, $R^h$ and $R^i$ each represent a leaving group; and $R^4$, $R^5$, $R^6$, $R^7$, $R^8$, $R^9$, $R^{10}$, $R^{11}$, and $R^{12}$ have the same definitions as $R^4$, $R^5$, $R^6$, $R^7$, $R^8$, $R^9$, $R^{10}$, $R^{11}$, and $R^{12}$ described above." Examples of the leaving group include a chloro group, a bromo group, an iodo group, a methanesulfonyl group, a 4-toluenesulfonyl group, a chloromethanesulfonyl group, a trifluoromethanesulfonyl group, and the like.

(4-1)

As the compound represented by Formula [12], for example, 2-chloro-N,N-dimethylethan-1-amine, 4-(2-chloroethyl)morpholine, 2-chloro-N,N-diethylethan-1-amine, 2-bromo-N,N-diethylethan-1-amine, 3-chloro-N,N-diethylethan-1-amine, and the like are known.

This reaction may be carried out at −30° C. to 150° C. preferably at 0° C. to 100° C. for 5 minutes to 48 hours.

(4-2)

As the compound represented by Formula [14], for example, 2-bromoethan-1-ol, 3-bromopropan-1-ol, and the like are known.

The compound represented by Formula [2] can be manufactured by reacting the compound represented by Formula [13] with the compound represented by Formula [14] in the presence or absence of a base.

This reaction may be performed based on the manufacturing method (4-1).

[Manufacturing Method 5]

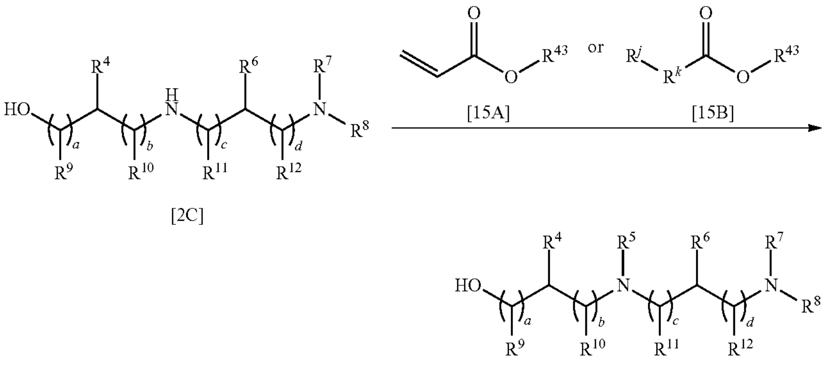

[2C] [15A] or [15B] [2]

"In the formula, $R^1$ represents a leaving group; $R^k$ represents an alkyl group having 1 to 18 carbon atoms; and $R^4$, $R^5$, $R^6$, $R^7$, $R^8$, $R^9$, $R^{10}$, $R^{11}$, $R^{12}$, and $R^{43}$ have the same definitions as $R^4$, $R^5$, $R^6$, $R^7$, $R^8$, $R^9$, $R^{10}$, $R^{11}$, $R^{12}$, and $R^{43}$ described above." Examples of the leaving group include a chloro group, a bromo group, an iodo group, a methanesulfonyl group, a 4-toluenesulfonyl group, a chloromethanesulfonyl group, a trifluoromethanesulfonyl group, and the like.

(5-1)

As the compound represented by Formula [15A], for example, heptyl acrylate and the like are known.

The compound represented by Formula [2] can be manufactured by reacting the compound represented by Formula [2C] with the compound represented by Formula [15A] in the presence or absence of a base.

The solvent used in this reaction is not particularly limited as long as the solvent does not affect the reaction. Examples of the solvent include alcohols, halogenated hydrocarbons, ethers, esters, amides, nitriles, sulfoxides, aromatic hydrocarbons, and water. These solvents may be used by being mixed together.

As the solvent, for example, ethers or nitriles are preferable. Among these, tetrahydrofuran or acetonitrile is more preferable.

The amount of the solvent used is not particularly limited, but may be 1 to 500 times (v/w) the amount of the compound represented by Formula [2C].

Examples of the base used in this reaction include an inorganic base and an organic base.

The amount of the base used may be 1 to 10,000 times and preferably 1 to 5,000 times the molar amount of the compound represented by Formula [2C].

The amount of the used compound represented by Formula [15A] is not particularly limited, but may be 1 to 10 times (v/w) the amount of the compound represented by Formula [13].

This reaction may be carried out at −30° C. to 150° C. preferably at 0° C. to 100° C. for 5 minutes to 48 hours.

(5-2)

As the compound represented by Formula [15B], for example, heptyl 3-chloropropanoate and the like are known.

The compound represented by Formula [2] can be manufactured by reacting the compound represented by Formula [2C] with the compound represented by Formula [15B] in the presence or absence of a base.

This reaction may be performed based on the manufacturing method (4-1).

[Manufacturing Method 6]

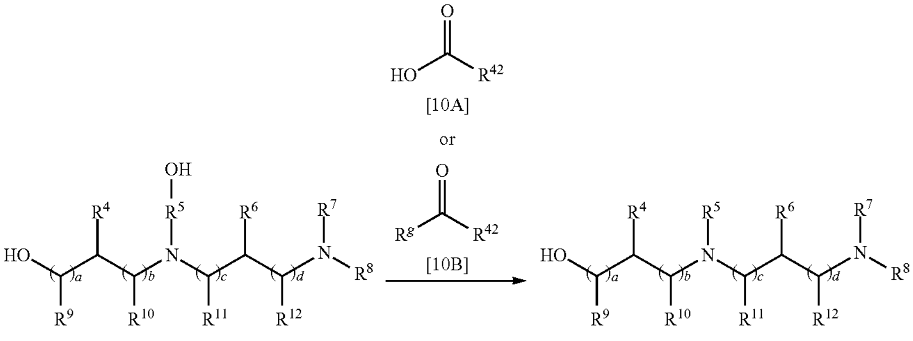

[10A] or [10B] [2B] [2]

-continued

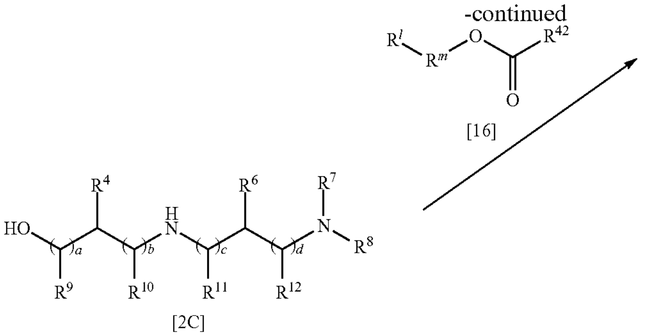

[16]

[2C]

"In the formula, $R^g$ and $R^l$ each represent a leaving group; $R^m$ represents an alkyl group having 1 to 18 carbon atoms; and $R^4$, $R^5$, $R^6$, $R^7$, $R^8$, $R^9$, $R^{10}$, $R^{11}$, $R^{12}$, and $R^{42}$ have the same definitions as $R^4$, $R^5$, $R^6$, $R^7$, $R^8$, $R^9$, $R^{10}$, $R^{11}$, $R^{12}$, and $R^{42}$ described above." Examples of the leaving group include a chloro group, a bromo group, an iodo group, a methanesulfonyl group, a 4-toluenesulfonyl group, a chloromethanesulfonyl group, a trifluoromethanesulfonyl group, a trichloromethoxy group, a 4-nitro-phenoxy group, a 2,4-dinitrophenoxy group, a 2,4,6-trichlorophenoxy group, a pentafluorophenoxy group, a 2,3,5,6-tetrafluorophenoxy group, an imidazolyl group, a triazolyl group, a 3,5-dioxo-4-methyl-1,2,4-oxadiazolidyl group, a N-hydroxysuccinimidyl group, and the like.

The compound represented by Formula [2] can be manufactured by reacting the compound represented by Formula [2B] with the compound represented by Formula [10B] in the presence of a base.

This reaction may be performed based on the manufacturing method (3-4).

(6-3)

As the compound represented by Formula [16], for example, heptyl 3-chloropropanoate and the like are known.

The compound represented by Formula [2] can be manufactured by reacting the compound represented by Formula [2C] with the compound represented by Formula [16] in the presence or absence of a base.

This reaction may be performed based on the manufacturing method (4-1).

[Manufacturing Method 7]

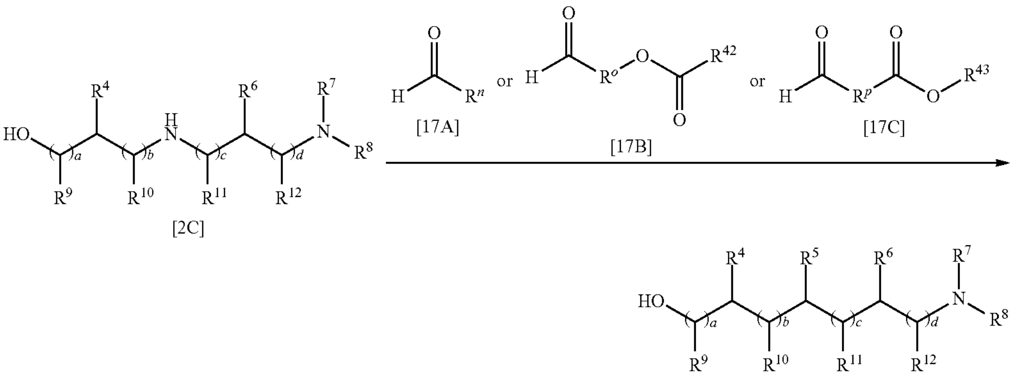

[2C]

[17A] or [17B] or [17C]

[2]

(6-1)

As the compound represented by Formula [10A], for example, dodecanoic acid, decanoic acid, nonanoic acid, octanoic acid, and the like are known.

The compound represented by Formula [2] can be manufactured by reacting the compound represented by Formula [2B] with the compound represented by Formula [10A] in the presence of a condensing agent or an acid halide or in the presence of a base.

This reaction may be performed based on the manufacturing method (3-3).

(6-2)

As the compound represented by Formula [10B], for example, dodecanoic acid chloride, decanoic acid chloride, nonanoic acid chloride, octanoic acid chloride, and the like are known.

"In the formula, $R^n$, $R^o$, and $R^p$ each represent an alkyl group having 1 to 17 carbon atoms; and $R^4$, $R^5$, $R^6$, $R^7$, $R^8$, $R^9$, $R^{10}$, $R^{11}$, $R^{12}$, $R^{42}$, and $R^{43}$ have the same definitions as $R^4$, $R^5$, $R^6$, $R^7$, $R^8$, $R^9$, $R^{10}$, $R^{11}$, $R^{12}$, $R^{42}$, and $R^{43}$ described above."

(7-1)

As the compound represented by Formula [17A], for example, formaldehyde, acetaldehyde, propanal, butanal, pentanal, hexanal, heptanal, octanal, and the like are known.

The compound represented by Formula [2] can be manufactured by reacting the compound represented by Formula [2C] with the compound represented by Formula [17A] in the presence of a reducing agent, in the presence or absence of a reducing catalyst, or in the presence or absence of an acid.

The solvent used in this reaction is not particularly limited as long as the solvent does not affect the reaction. Examples of the solvent include alcohols, halogenated hydrocarbons, ethers, esters, amides, nitriles, sulfoxides, aromatic hydrocarbons, and water. These solvents may be used by being mixed together.

The amount of the solvent used is not particularly limited, but may be 1 to 500 times (v/w) the amount of the compound represented by Formula [2C].

Examples of the acid used in this reaction include an inorganic acid and an organic acid.

The amount of the acid used may be 0.01 to 10,000 times and preferably 0.05 to 100 times the molar amount of the compound represented by Formula [2C].

Examples of the reducing agent used in this reaction include sodium triacetoxyborohydride, sodium cyanoborohydride, 2-picolineborane, formic acid, hydrogen, and the like.

Examples of the reducing catalyst used in this reaction include palladium-carbon, palladium hydroxide-carbon, platinum-carbon, rhodium-carbon, ruthenium-carbon, and the like.

The amount of the used compound represented by Formula [17A] is not particularly limited, but may be 1 to 10 times (v/w) the amount of the compound represented by Formula [13].

This reaction may be carried out at −30° C. to 150° C. preferably at 0° C. to 100° C. for 5 minutes to 48 hours.

(7-2)

As the compound represented by Formula [17B], for example, 2-oxoethyloctanoate, 2-oxoethylnonanoate, and the like are known.

The compound represented by Formula [2] can be manufactured by reacting the compound represented by Formula [2C] with the compound represented by Formula [17B] in the presence of a reducing agent, in the presence or absence of a reducing catalyst, or in the presence or absence of an acid.

This reaction may be performed based on the manufacturing method (7-1).

(7-3)

As the compound represented by Formula [17C], for example, heptyl 3-oxopropanoate, octyl 3-oxopropanoate, and the like are known.

The compound represented by Formula [2] can be manufactured by reacting the compound represented by Formula [2C] with the compound represented by Formula [17C] in the presence of a reducing agent, in the presence or absence of a reducing catalyst, or in the presence or absence of an acid.

This reaction may be performed based on the manufacturing method (7-1).

In a case where the compounds used in the above manufacturing methods have isomers (for example, an optical isomer, a geometric isomer, a tautomer, and the like), these isomers can also be used.

Furthermore, in a case where the compounds are in the form of solvates, hydrates, and crystals of various shapes, these solvates, hydrates, and crystals of various shapes can also be used.

Among the compounds used in the aforementioned manufacturing methods, for example, for the compounds having an amino group, a hydroxyl group, or a carboxyl group, these groups can be protected in advance with general protecting groups, and the protecting groups can be eliminated by known methods after the reaction.

The compounds obtained by the aforementioned manufacturing methods can be induced into other compounds by being subjected to known reactions such as condensation, addition, oxidation, reduction, transition, substitution, halogenation, dehydration, and hydrolysis or subjected to these reactions that are appropriately combined.

In the lipid composition according to the embodiment of the present invention, the content of the lipid represented by Formula (1) or a salt thereof with respect to the total lipids is more preferably more than 40 mol % and 90 mol % or less, and more preferably 45 mol % or more and 80 mol % or less, and particularly preferably 45 mol % or more and 70 mol % or less.

<Nonionic Lipid>

The lipid composition according to the embodiment of the present invention contains a nonionic lipid.

As the nonionic lipid, sterols are preferable. In a case where the oil phase contains sterols, the fluidity of the membrane can be reduced, and hence the lipid particles can be effectively stabilized.

The sterols are not particularly limited, and examples thereof include cholesterol, phytosterol (sitosterol, stigmasterol, fucosterol, spinasterol, brassicasterol and the like), ergosterol, cholestanone, cholestenone, coprostanol, cholesteryl-2'-hydroxy ethyl ether, cholesteryl-4'-hydroxybutyl ether, and the like. Among these, cholesterol is preferable.

In the lipid composition according to the embodiment of the present invention, the content of the nonionic lipid with respect to the total lipids is preferably 20 mol % to 60 mol %, even more preferably 25 mol % to 60 mol %, still more preferably 25 mol % to 55 mol %, and particularly preferably 25 mol % to 50 mol %.

<Lipid Having Nonionic Hydrophilic Polymer Structure>

The lipid composition according to the embodiment of the present invention contains a lipid having a nonionic hydrophilic polymer structure.

In a case where the oil phase contains the lipid having a nonionic hydrophilic polymer structure, the dispersion of the lipid particles can be effectively stabilized.

The nonionic hydrophilic polymer is not particularly limited, and examples thereof include a nonionic vinyl-based polymer, a nonionic polyamino acid, a nonionic polyester, a nonionic polyether, a nonionic natural polymer, a nonionic modified natural polymer, and a block polymer or a graft copolymer having two or more kinds of these polymers as constitutional units.

Among these nonionic hydrophilic polymers, a nonionic polyether, a nonionic polyester, a nonionic polyamino acid, or a nonionic synthetic polypeptide is preferable, a nonionic polyether or a nonionic polyester is more preferable, a nonionic polyether or a nonionic monoalkoxy polyether is even more preferable, and polyethylene glycol (hereinafter, polyethylene glycol will be also called PEG) is particularly preferable. That is, as the lipid having a nonionic hydrophilic polymer structure, a lipid having a polyethylene glycol structure is preferable.

The lipid having a nonionic hydrophilic polymer is not particularly limited, and examples thereof include PEG-modified phosphoethanolamine, a diacylglycerol PEG derivative, a dialkylglycerol PEG derivative, a cholesterol PEG derivative, a ceramide PEG derivative, and the like. Among these, diacylglycerol PEG is preferable. That is, as the lipid having a polyethylene glycol structure, a lipid having a diacylglycerol structure and a polyethylene glycol structure is preferable. The acyl group of the diacylglycerol moiety is more preferably an acyl group having 12 to 22 carbon atoms.

In a case where the lipid having a nonionic hydrophilic polymer has a PEG chain, the weight-average molecular weight of the PEG chain is preferably 500 to 5,000, and more preferably 750 to 3,000.

The nonionic hydrophilic polymer chain may be branched or may have a substituent such as a hydroxymethyl group.

In the lipid composition according to the embodiment of the present invention, the content of the lipid having a nonionic hydrophilic polymer structure with respect to the total lipids is more preferably 0.5 mol % to 10 mol %, even more preferably 0.5 mol % to 5 mol %, and particularly preferably 0.5 mol % to 3 mol %.

<Zwitterionic Lipid>

The lipid composition according to the embodiment of the present invention may or may not contain a zwitterionic lipid.

As the zwitterionic lipid, phospholipid is preferable. The phospholipid is not particularly limited, and examples thereof include phosphatidylcholine, phosphatidylethanolamine, sphingomyelin, and the like. Among these, phosphatidylcholine and phosphatidylethanolamine are preferable. One zwitterionic lipid may be used alone, or two or more different zwitterionic lipids may be used in combination.

The phosphatidylcholine is not particularly limited, and examples thereof include soybean lecithin (SPC), hydrogenated soybean lecithin (HSPC), egg yolk lecithin (EPC), hydrogenated egg yolk lecithin (EPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), l-palmitoyl-2-oleoyl-sn-glycero-3-phosphocholine (POPC), 1,2-dioleoyl-sn-glycero-3-phosphocholine (DOPC), and the like.

Among the above, 1,2-dimyristoyl-sn-glycero-3-phosphocholine (DMPC), 1,2-dipalmitoyl-sn-glycero-3-phosphocholine (DPPC), and 1,2-distearoyl-sn-glycero-3-phosphocholine (DSPC) are more preferable.

The phosphatidylethanolamine is not particularly limited, and examples thereof include 1,2-dimyristoyl-sn-glycero-3-phosphoethanolamine (DMPE), 1,2-dipalmitoyl-sn-glycero-3-phosphoethanolamine (DPPE), 1,2-distearoyl-sn-glycero-3-phosphoethanolamine (DSPE), 1,2-dioleoyl-sn-glycero-3-phosphoethanolamine (DOPE), 1,2-dilinoleoyl-sn-glycero-3-phosphoethanolamine (DLoPE), 1,2-diphytanoyl-sn-glycero-3-phosphoethanolamine (D(Phy)PE), 1-palmitoyl-2-oleoyl-sn-glycero-3-phosphoethanolamine (POPE), 1,2-ditetradecyl-sn-glycero-3-phosphoethanolamine, 1,2-dihexadecyl-sn-glycero-3-phosphoethanolamine, 1,2-dioctadecyl-sn-glycero-3-phosphoethanolamine, 1,2-diphytanyl-sn-glycero-3-phosphoethanolamine, and the like.

Among the above, 1,2-dioleoyl-sn-glycero-3-phosphoethanolamine (DOPE) is more preferable.

The sphingomyelin is not particularly limited, and examples thereof include egg yolk-derived sphingomyelin, milk-derived sphingomyelin, and the like.

In the lipid composition according to the embodiment of the present invention, the content of the zwitterionic lipid with respect to the total lipids is preferably 0 mol % to 30 mol %, more preferably 0 mol % to 20 mol %, and even more preferably 0 mol % to 15 mol %.

In a case where the lipid composition according to the embodiment of the present invention contains a zwitterionic lipid, the lower limit of the content of the zwitterionic lipid with respect to the total lipids is not particularly limited. The lower limit is generally 0.5 mol % or more, preferably 1 mol % or more, and more preferably 2 mol % or more.

<Nucleic Acid>

The lipid composition according to the embodiment of the present invention contains a nucleic acid. Examples of the nucleic acid include a plasmid, single-stranded DNA, double-stranded DNA, small interfering RNA (siRNA), micro RNA (miRNA), mRNA, an antisense nucleic acid, ribozyme, and the like. The lipid particles may contain any of these. In addition, the lipid particles may contain a modified nucleic acid.

In the lipid composition according to the embodiment of the present invention, the content of the nucleic acid with respect to the total lipids is preferably 0.5% to 50% by mass, more preferably 1% to 25% by mass, even more preferably 1.5% to 20% by mass, and particularly preferably 2% to 15% by mass.

<Method for Manufacturing Lipid Composition>

The method for manufacturing the lipid composition according to the embodiment of the present invention will be described.

The method for manufacturing the lipid composition is not limited. For example, the lipid composition can be manufactured by a method in which all of the constituent components of the lipid composition or some of oil-soluble components of the lipid composition are dissolved in an organic solvent or the like so that an oil phase is formed, water-soluble components of the lipid composition are dissolved in water so that a water phase is formed, and the oil phase and the water phase are mixed together. A micromixer may be used for mixing, or an emulsifying machine such as a homogenizer, an ultrasonic emulsifying machine, or a high-pressure injection emulsifying machine may be used for emulsification.

Alternatively, the lipid composition can also be manufactured by a method in which a lipid-containing solution is subjected to evaporation to dryness using an evaporator under reduced pressure or subjected to spray drying using a spray drier so that a dried mixture containing a lipid is prepared, and the mixture is added to an aqueous solvent and further emulsified using the aforementioned emulsifying machine or the like.

One of the examples of the method for manufacturing the lipid composition containing a nucleic acid is a method including Step (a) of dissolving the constituent components of the lipid composition in an organic solvent so as to obtain an oil phase;

Step (b) of mixing the oil phase obtained in Step (a) with a water phase containing a water-soluble component such as a nucleic acid;

Step (c) of diluting the mixed solution containing the oil phase and the water phase obtained in Step (b) so as to obtain a dispersion liquid of lipid particles; and Step (d) of removing the organic solvent from the dispersion liquid of lipid particles obtained in Step (c); and Step (e) of adjusting the concentration of the dispersion liquid of lipid particles obtained in Step (d).

Step (a) includes a process of dissolving the constituent components classified as lipids in an organic solvent (an alcohol such as ethanol, an ester, or the like). The total lipid concentration after the dissolution of lipids in an organic solvent is not particularly limited, but is generally 1 mmol/L to 100 mmol/L, preferably 5 mmol/L to 50 mmol/L, and more preferably 10 mmol/L to 30 mmol/L.

In Step (b), the water phase can be obtained by dissolving a nucleic acid (for example, siRNA, an antisense nucleic acid, miRNA (micro RNA), mRNA, or the like) in water or a buffer solution. If necessary, a component such as an antioxidant can be added. The mixing ratio (mass ratio) of water phase:oil phase is preferably 5:1 to 1:1 and more preferably 4:1 to 2:1.

In Step (d), as the method of removing the organic solvent from the dispersion liquid of lipid particles, a general method can be used without particular limitation. For example, by dialyzing the dispersion liquid with the phosphate buffered saline, the organic solvent can be removed.

In Step (e), the concentration of the dispersion liquid obtained in Step (d) can be adjusted. In a case where dilution is used, it is possible to dilute the dispersion liquid to an appropriate concentration by using phosphate buffered saline, physiological saline, or the like as a diluent. In a case where concentration is used, it is possible to concentrate the dispersion liquid obtained in Step (d) by ultrafiltration using an ultrafiltration membrane or the like. It is preferable to use the concentrated dispersion as it is. Alternatively, it is preferable to concentrate the dispersion liquid and then adjust the concentration to a desired value by using the aforementioned diluent.

In order to make the dispersion liquid of lipid particles of the present invention into a pharmaceutical composition, it is preferable to perform sterile filtration. As a filtration method, a hollow fiber membrane, a reverse osmosis membrane, a membrane filter, or the like can be used to remove unnecessary substances from the dispersion liquid of lipid particles. In the present invention, the filtration method is not limited. However, it is preferable to filter the dispersion liquid through a filter having a pore diameter capable of sterilization (preferably a filtration sterilization filter with a pore diameter of 0.2 μm). Furthermore, it is preferable that the sterile filtration be performed after Step (c) or Step (d).

If necessary, the dispersion liquid of lipid particles of the present invention can be freeze-dried.

<Lipid Composition>

It is preferable that the composition according to the embodiment of the present invention be composed of lipid particles. Lipid particles mean particles composed of a lipid, and include a composition having any structure selected from a lipid aggregate composed of aggregated lipids, a micelle, and a liposome. The structure of the lipid particles is not limited to these as long as the lipid particles are a composition containing a lipid. The liposome includes a liposome which has a lipid bilayer structure, contains an internal water phase, and has a single bilayer membrane, and a multiphase liposome which has multiple layers stacked together. The present invention may include any of these liposomes.

The form of the lipid particles can be checked by electron microscopy, structural analysis using X-rays, and the like. For example, by a method using Cryo transmission electron microscopy (CryoTEM method), it is possible to check, for example, whether a lipid particle such as a liposome has a structure composed of a bimolecular lipid membrane structure (lamella structure) and an inner water layer or a structure composed of an inner core with a high electron density and packed with constituent components including a lipid. The X-ray small angle scattering (SAXS) analysis also makes it possible to check whether or not a lipid particle has a bimolecular lipid membrane structure (lamella structure).

The particle size of the lipid particles is not particularly limited, but is preferably 10 to 1,000 nm, more preferably 30 to 500 nm, even more preferably 50 to 250 nm, particularly preferably 50 to 200 nm, and most preferably 50 to 150 nm. The particle size of the lipid particles can be measured by a general method (for example, a dynamic light scattering method, a laser diffraction method, or the like).

<Use of Lipid Composition>

For example, the lipid composition according to the embodiment of the present invention can be used to introduce a nucleic acid (for example, a gene) into a cell by introducing the lipid composition containing the nucleic acid into the cell. Furthermore, in a case where the lipid composition according to the embodiment of the present invention contains a nucleic acid for a pharmaceutical use, the lipid composition can be administered to a living body as a nucleic acid drug. That is, the lipid composition according to the embodiment of the present invention is preferably a composition for introducing nucleic acids into cells.

In a case where the lipid composition according to the embodiment of the present invention is used as a nucleic acid drug, the lipid composition according to the embodiment of the present invention can be administered alone to a living body or administered to a living body by being mixed with a pharmaceutically acceptable carrier (also called dosing medium, such as physiological saline or a phosphate buffer solution).

The concentration of the lipid composition (lipid particles) in the mixture with a pharmaceutically acceptable carrier is not particularly limited, and can be set to 0.05% by mass to 90% by mass in general. Furthermore, other pharmaceutically acceptable additives, for example, a pH adjusting buffer and an osmotic pressure adjusting agent, may be added to the nucleic acid drug containing the lipid composition according to the embodiment of the present invention.

The route of administration for administering the nucleic acid drug containing the lipid composition according to the embodiment of the present invention is not particularly limited. The nucleic acid drug can be administered by any method. Examples of the administration method include oral administration and parenteral administration (intra-articular administration, intravenous administration, intra-arterial administration, subcutaneous administration, intracutaneous administration, intravitreal administration, intraperitoneal administration, intramuscular administration, intravaginal administration, intravesical administration, intrathecal administration, pulmonary administration, rectal administration, colonic administration, buccal administration, nasal administration, intracisternal administration, inhalation, and the like). Among these, parenteral administration is preferable. As the method of administration, intravenous injection, subcutaneous injection, intracutaneous injection, or intramuscular injection is preferable. The nucleic acid drug containing the lipid composition according to the embodiment of the present invention can also be administered by being directly injected into the affected area.

The dosage form of the lipid composition according to the embodiment of the present invention is not particularly limited. For oral administration, the lipid composition according to the embodiment of the present invention can be used in the form of tablets, troches, capsules, pills, suspension, syrup, and the like by being combined with an appropriate excipient. In addition, in a case where the lipid composition according to the embodiment of the present invention is to be given by parenteral administration, additives such as an antioxidant, a buffer, a bacteriostat, an isotonic sterile injection, a suspending agent, a solubilizer, a thickener, a stabilizer, and a preservative can be appropriately combined with the lipid composition.

<Nucleic Acid Delivery Carrier>

The lipid composition according to the embodiment of the present invention can retain a nucleic acid at a high encapsulation rate. Therefore, the lipid composition is extremely useful as a nucleic acid delivery carrier. According to the nucleic acid delivery carrier using the present invention, for example, by transfecting cells with the lipid composition in vitro or in vivo, the nucleic acid and the like can be introduced into the cells. Furthermore, the nucleic acid delivery carrier using the present invention is also useful as a nucleic acid delivery carrier in nucleic acid drugs. That is, the lipid composition according to the embodiment of the present invention is useful as a composition for in vitro or in vivo (preferably in vivo) delivery of nucleic acids.

Next, the present invention will be described based on examples, but the present invention is not limited thereto.

EXAMPLES

Unless otherwise specified, for the purification by column chromatography, an automatic purification device ISOLERA (Biotage) or a medium pressure liquid chromatograph YFLC W-prep 2XY (Yamazen Corporation) was used.

Unless otherwise specified, as a carrier for silica gel column chromatography, Chromatorex Q-Pack SI 50 (FUJI SILYSIA CHEMICAL LTD.) or HIGH FLASH COLUMN W001, W002, W003, W004, or W005 (Yamazen Corporation) was used.

As an NH silica gel, Chromatorex Q-Pack NH 60 (FUJI SILYSIA CHEMICAL LTD.) was used.

NMR spectra were measured using tetramethylsilane as an internal standard and using Bruker AV300 (manufactured by Bruker Corporation) or Bruker AV400 (manufactured by Bruker Corporation), and all 8 scales are expressed as ppm.

MS spectra were measured using an ACQUITY SQD LC/MS System (manufactured by WATERS).

Synthesis of Compound

Example 1

(1)

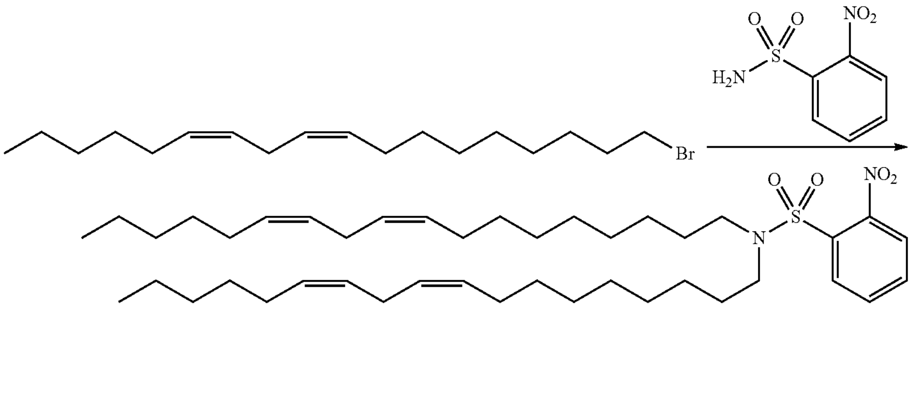

Potassium carbonate (70.4 g) and sodium iodide (2.54 g) were added to a N,N-dimethylformamide (830 mL) solution of (6Z,9Z)-18-bromooctadeca-6,9-diene (131 g) and 2-nitrobenzenesulfonamide (34.4 g), and the mixture was stirred at 80° C. for 5 hours. The reaction mixture was cooled to room temperature, and hexane (300 mL) and water (600 mL) were added thereto. The organic layer was separated, and then the obtained mixture was purified by silica gel column chromatography (ethyl acetate-hexane), thereby obtaining 2-nitro-N,N-di((9Z,12Z)-octadeca-9,12-dien-1-yl)benzenesulfonamide (96.7 g).

$^1$H-NMR ($CDCl_3$) δ: 8.03-7.99 (1H, m), 7.69-7.58 (3H, m), 5.43-5.28 (8H, m), 3.26 (4H, t, J=6.0 Hz), 2.77 (4H, t, J=6.0 Hz), 2.09-2.00 (8H, m), 1.56-1.45 (4H, m), 1.40-1.19 (32H, m), 0.89 (6H, t, J=6.0 Hz).

(2)

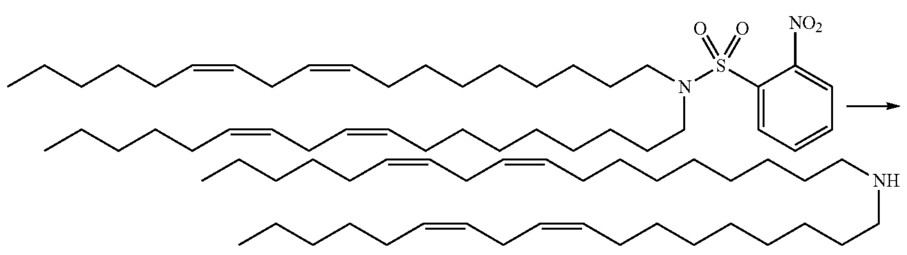

A 10.0 mol/L aqueous potassium hydroxide solution (47.5 mL) was added to a mixture of 2-nitro-N,N-di((9Z,12Z)-octadeca-9,12-dien-1-yl)benzenesulfonamide (96.7 g), dodecanethiol (54.9 mL), acetonitrile (400 mL), and tetrahydrofuran (400 mL), and the mixture was stirred at 40° C. for 2 hours. The reaction mixture was cooled to room temperature, hexane (400 mL), tert-butyl methyl ether (100 mL), and water (200 mL) were added thereto, the organic layer was separated and then dried over anhydrous magnesium sulfate, and the solvent was distilled away under reduced pressure. The obtained residue was purified by silica gel column chromatography (ethyl acetate-hexane), thereby obtaining (9Z,12Z)-di((9Z,12Z)-octadeca-9,12-dien-1-yl) amine (57.7 g).

$^1$H-NMR ($CDCl_3$) δ: 5.43-5.28 (8H, m), 2.77 (4H, t, J=6.0 Hz), 2.58 (4H, t, J=6.0 Hz), 2.09-1.99 (8H, m), 1.56-1.45 (4H, m), 1.40-1.19 (32H, m), 0.89 (6H, t, J=6.0 Hz).

MS m/z (M+H): 514.

(3)

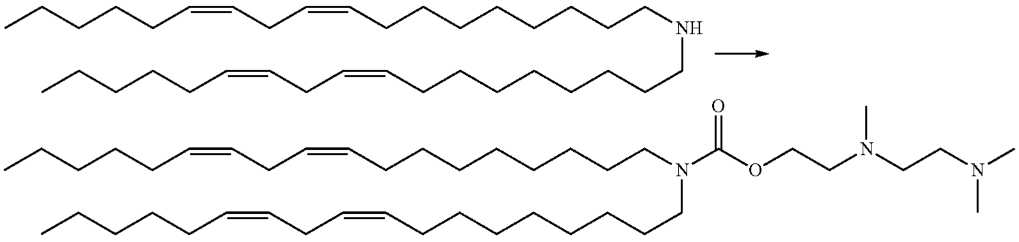

2-((2-(Dimethylamino)ethyl)(methyl)amino)ethan-1-ol (9.36 mL) was added to a tetrahydrofuran (150 mL) solution of 4-nitrophenyl chloroformate (11.7 g), and the mixture was stirred at room temperature for 1 hour. (9Z,12Z9-di((9Z, 12Z)-octadeca-9,12-dien-1-yl)amine (15.0 g) and triethylamine (16.3 mL) were added to the reaction mixture, and the reaction mixture was stirred at 50° C. for 4 hours. The reaction mixture was cooled to room temperature, ethyl acetate (150 mL) and water (100 mL) were added thereto, the organic layer was separated and then dried over anhydrous magnesium sulfate, the solvent was distilled away under reduced pressure, and the obtained residue was purified by a silica gel column chromatography (methanol-chloroform). The obtained oily substance was purified by silica gel column chromatography (ethyl acetate-hexane, NH silica gel), thereby obtaining 2-((2-(dimethylamino) ethyl)(methyl)amino)ethyl di((9Z,12Z)-octadeca-9,12-dien-1-yl)carbamate (11.2 g).

$^1$H-NMR ($CDCl_3$) δ: 5.42-5.23 (8H, m), 4.17 (2H, t, J=6.0 Hz), 3.26-3.08 (4H, m), 2.77 (4H, t, J=6.0 Hz), 2.67 (2H, t, 6.0 Hz), 2.54 (2H, t, J=6.0 Hz), 2.39 (2H, t, J=6.0), 2.32 (3H, s), 2.24 (6H, s), 2.12-1.97 (8H, m), 1.57-1.43 (4H, m), 1.42-1.18 (32H, m), 0.89 (6H, t, J=6.0 Hz).

MS m/z (M+H): 687.

Example 2

(1)

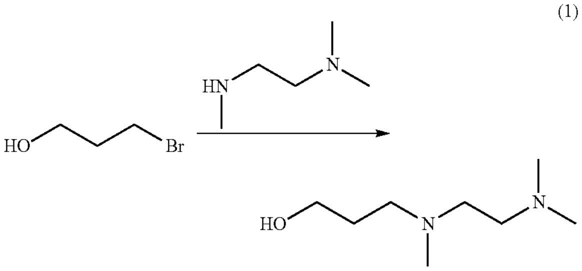

N,N,N'-trimethylethane-1,2-diamine (5 mL) was added to an ethanol (10 mL) solution of 3-bromopropan-1-ol (1.67 mL), and the mixture was stirred at 60° C. for 8 hours. The solvent of the reaction mixture was distilled away under reduced pressure, and the obtained residue was purified by silica gel column chromatography (ethyl acetate-hexane, NH silica gel), thereby obtaining 3-((2-(dimethylamino) ethyl)(methyl)amino)propan-1-ol (1.2 g).

MS m/z (M+H): 161.

(2)

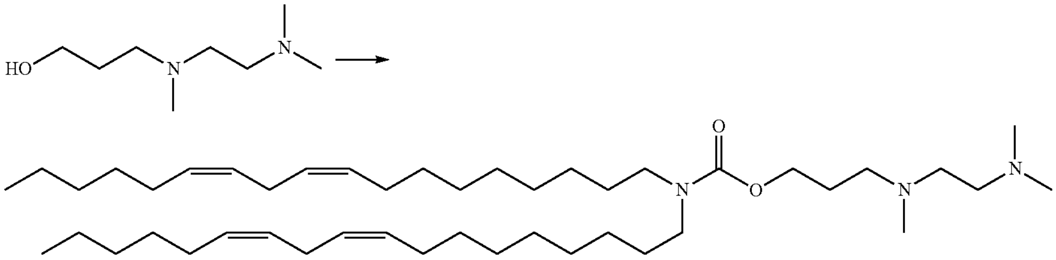

3-((2-(Dimethylamino)ethyl)(methyl)amino)propyl di((9Z,12Z)-octadeca-9,12-dien-1-yl)carbamate was obtained by the same method as that in (3) of Example 1, except that 3-((2-(dimethylamino)ethyl)(methyl)amino)propan-1-ol was used instead of 2-((2-(dimethylamino)ethyl) (methyl)amino)ethan-1-ol in (3) of Example 1.

$^1$H-NMR ($CDCl_3$) δ:5.44-5.27 (8H, m), 4.09 (2H, t, J=6.0 Hz), 3.25-3.09 (4H, m), 2.77 (4H, t, J=6.0 Hz), 2.50-2.34 (6H, m), 2.25 (3H, s), 2.24 (6H, s), 2.10-1.99 (8H, m), 1.86-1.74 (2H, m), 1.58-1.43 (4H, m), 1.42-1.18 (32H, m), 0.89 (6H, t, J=6.0 Hz)

MS m/z (M+H): 701.

Example 3

(1)

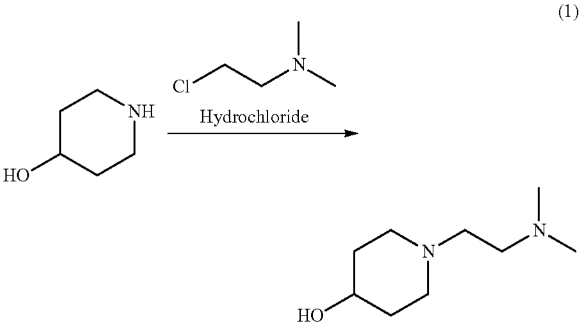

A 12.0 mol/L aqueous sodium hydroxide solution (5 mL) was added to an aqueous solution (5 mL) of piperidin-4-ol (2.0 g) and 2-chloro-N,N-dimethylethan-1-amine hydrochloride (5.69 g), and the mixture was stirred at room temperature for 9 hours. Dichloromethane and water were added to the reaction mixture, the organic layer was separated, and the aqueous layer was extracted using dichloromethane. The organic layer and the extract were combined and dried over anhydrous sodium sulfate, and the solvent was distilled away under reduced pressure. The obtained residue was purified by silica gel column chromatography (ethyl acetate-hexane, NH silica gel), thereby obtaining 1-(2-(dimethylamino)ethyl)piperidin-4-ol (1.3 g).

MS m/z (M+H): 173.

(2)

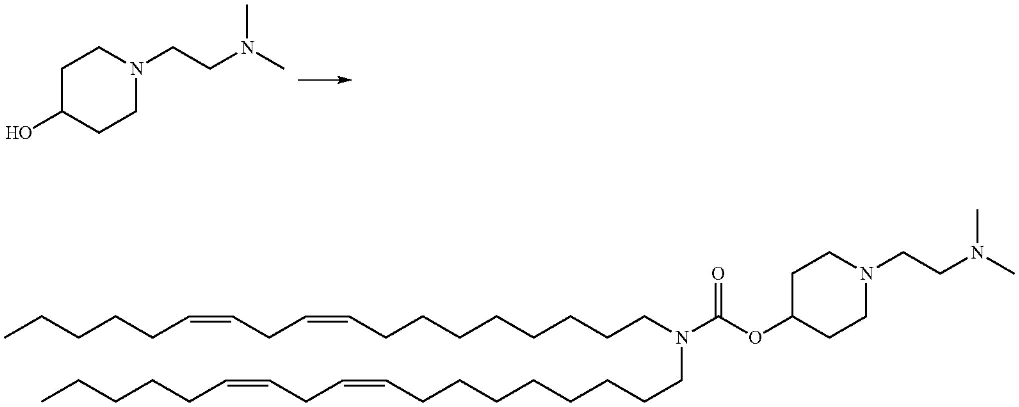

1-(2-(Dimethylamino)ethyl)piperidin-4-yl di((9Z,12Z)-octadeca-9,12-dien-1-yl)carbamate was obtained by the same method as that in (3) of Example 1, except that 1-(2-(dimethylamino)ethyl)piperidin-4-ol was used instead of 2-((2-(dimethylamino)ethyl)(methyl)amino)ethan-1-ol in (3) of Example 1.

$^1$H-NMR ($CDCl_3$) δ:5.43-5.28 (8H, m), 4.75-4.66 (1H, m), 3.24-3.10 (4H, m), 2.77 (4H, t, J=6.0 Hz), 2.72-2.60 (2H, m), 2.50-2.39 (4H, m), 2.37-2.27 (2H, m), 2.24 (6H, s), 2.09-1.99 (8H, m), 1.97-1.85 (2H, m), 1.76-1.65 (2H, m), 1.66-1.58 (8H, m), 1.56-1.43 (4H, m), 1.41-1.19 (32H, m), 0.89 (6H, t, J=6.0 Hz).

MS m/z (M+H): 713.

Example 4

(1)

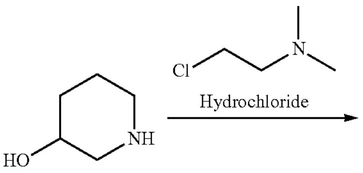

-continued

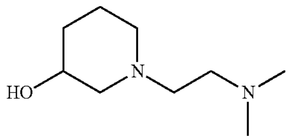

1-(2-(Dimethylamino)ethyl)piperidin-3-ol was obtained by the same method as that in (1) of Example 3, except that piperidin-3-ol was used instead of piperidin-4-ol in (1) of Example 3.

MS m/z (M+H): 173.

(2)

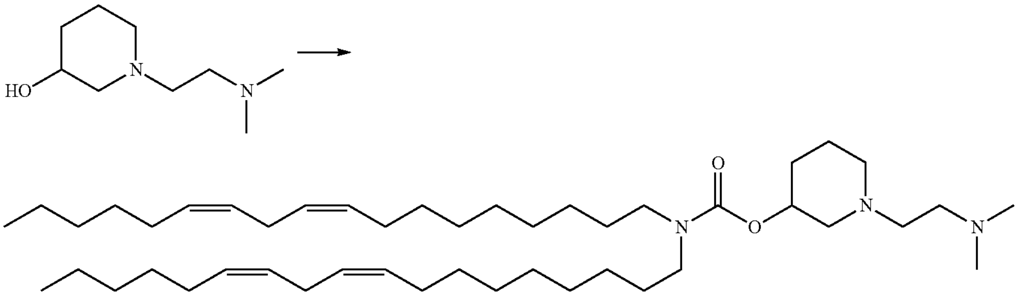

1-(2-(Dimethylamino)ethyl)piperidin-3-yl di((9Z,12Z)-octadeca-9,12-dien-1-yl)carbamate was obtained by the same method as that in (3) of Example 1, except that 1-(2-(dimethylamino)ethyl)piperidin-3-ol was used instead of 2-((2-(dimethylamino)ethyl)(methyl)amino)ethan-1-ol in (3) of Example 1.

$^1$H-NMR ($CDCl_3$) δ:5.43-5.28 (8H, m), 4.78-4.68 (1H, m), 3.26-3.06 (4H, m), 2.94-2.87 (1H, m), 2.77 (4H, t, J=6.0 Hz), 2.70-2.61 (1H, m), 2.52-2.38 (4H, m), 2.24 (6H, s), 2.16-1.99 (10H, m), 1.97-1.87 (1H, m), 1.77-1.43 (7H, m), 1.41-1.19 (32H, m), 0.89 (6H, t, J=6.0 Hz).

MS m/z (M+H): 713.

Example 5

(1)

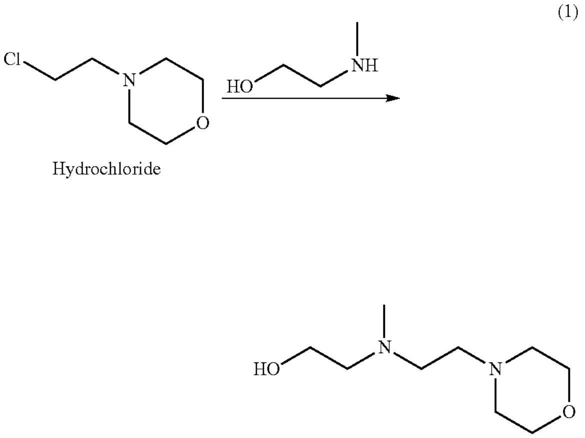

4-(2-Chloroethyl)morpholine hydrochloride (14.9 g) was added to an ethanol (60 mL) suspension of 2-(methylamino)ethan-1-ol (3.0 g) and potassium carbonate (22.1 g), and the mixture was stirred at 60° C. for 4 hours and stirred under reflux for 3 hours. The reaction mixture was cooled to room temperature, insoluble matters were then filtered off, and the solvent was distilled away under reduced pressure. The obtained residue was purified by silica gel column chromatography (ethyl acetate-hexane, NH silica gel), thereby obtaining 2-(methyl(2-morpholinoethyl)amino)ethan-1-ol (5.5 g).

MS m/z (M+H): 189.

2-(Methyl(2-morpholinoethyl)amino)ethyl di((9Z,12Z)-octadeca-9,12-diene-1-yl)carbamate was obtained by the same method as that in (3) of Example 1, except that 2-(methyl(2-morpholinoethyl)amino)ethan-1-ol was used instead of 2-((2-(dimethylamino)ethyl)(methyl)amino)ethan-1-ol in (3) of Example 1.

$^1$H-NMR ($CDCl_3$) δ: 5.46-5.25 (8H, m), 4.16 (2H, t, J=6.0 Hz), 3.71 (4H, t, J=6.0 Hz), 3.25-3.09 (4H, m), 2.27 (4H, t, J=6.0 Hz), 2.67 (2H, t, J=6.0 Hz), 2.62-2.53 (2H, m), 2.52-2.42 (6H, m), 2.32 (3H, s), 2.11-1.97 (8H, m), 1.55-1.44 (4H, m), 1.42-1.17 (32H, m), 0.89 (6H, t, J=6.0 Hz).

MS m/z (M+H): 729.

Example 6

(1)

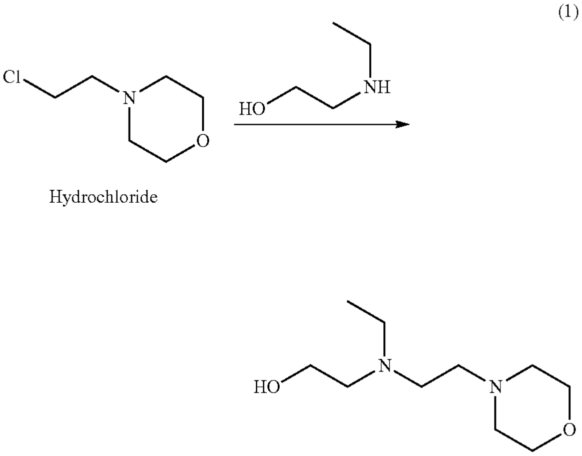

2-(Ethyl(2-morpholinoethyl)amino)ethan-1-ol was obtained by the same method as that in (1) of Example 5, except that 2-(ethylamino)ethan-1-ol was used instead of 2-(methylamino)ethan-1-ol in (1) of Example 5.

MS m/z (M+H): 203.

(2)

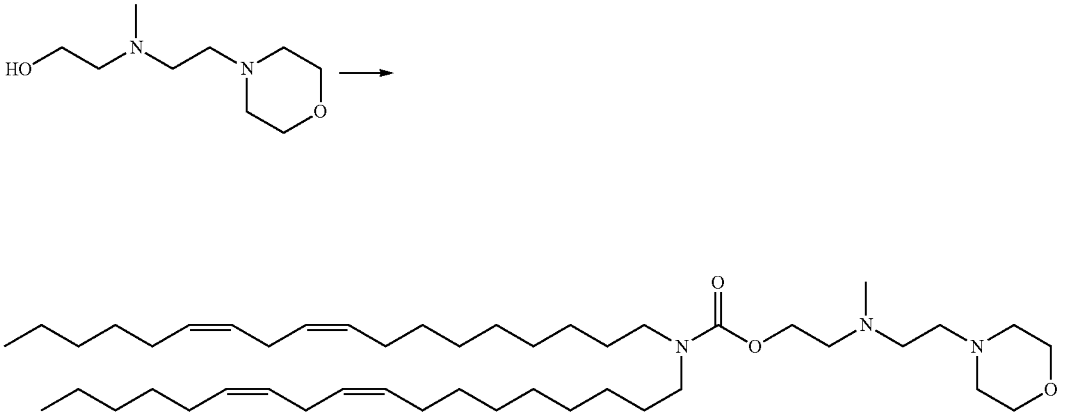

(2)

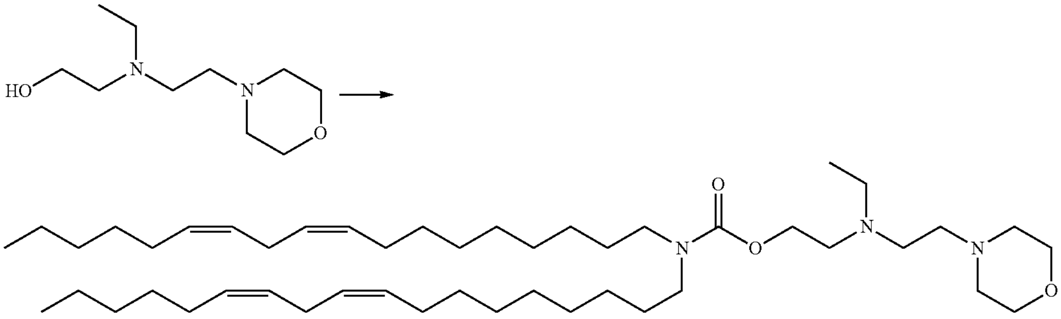

2-(Ethyl(2-morpholinoethyl)amino)ethyl di((9Z,12Z)-octadeca-9,12-dien-1-yl)carbamate was obtained by the same method as that In (3) of Example 1, except that 2-(ethyl(2-morpholinoethyl)amino)ethan-1-ol was used instead of 2-((2-(dimethylamino)ethyl)(methyl)amino)ethan-1-ol in (3) of Example 1.

$^1$H-NMR ($CDCl_3$) δ:5.45-5.24 (8H, m), 4.12 (2H, t, J=6.0 Hz), 3.70 (4H, t, J=6.0 Hz), 3.27-3.06 (4H, m), 2.82-2.69 (6H, m), 2.69-2.54 (4H, m), 2.52-2.39 (6H, m), 2.12-1.97 (8H, m), 1.55-1.42 (4H, m), 1.41-1.17 (32H, m), 1.03 (3H, t, J=6.0 Hz), 0.89 (6H, t, J=6.0 Hz).

MS m/z (M+H): 743.

Example 7

(1)

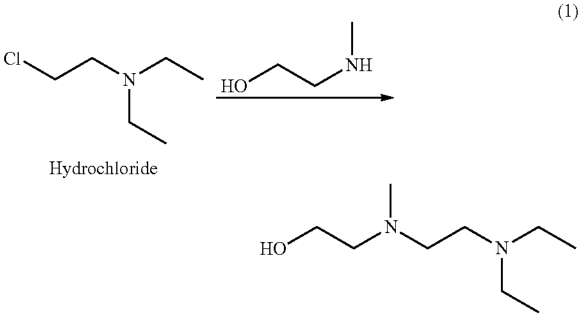

2-((2-(Diethylamino)ethyl)(methyl)amino)ethan-1-ol was obtained by the same method as that in (1) of Example 5, except that 2-chloro-N,N-diethylethan-1-amine hydrochloride was used instead of 4-(2-chloroethyl)morpholine hydrochloride in (1) of Example 5.

MS m/z (M+H): 175.

2-((2-(Diethylamino)ethyl)(methyl)amino)ethyl di((9Z,12Z)-octadeca-9,12-dien-1-yl)carbamate was obtained by the same method as that in (3) of Example 1, except that 2-((2-(diethylamino)ethyl)(methyl)amino)ethan-1-ol was used instead of 2-((2-(dimethylamino)ethyl)(methyl)amino)ethan-1-ol in (3) of Example 1.

$^1$H-NMR ($CDCl_3$) δ: 5.45-5.26 (8H, m), 4.16 (2H, t, J=6.0 Hz), 3.25-3.09 (4H, m), 2.77 (4H, t, J=6.0 Hz), 2.67 (2H, t, J=6.0 Hz), 2.60-2.49 (8H, m), 2.32 (3H, s), 2.12-1.96 (8H, m), 1.56-1.44 (4H, m), 1.42-1.17 (32H, m), 1.02 (6H, t, J=6.0 Hz), 0.89 (6H, t, J=6.0 Hz).

MS m/z (M+H): 715.

Example 8

(1)

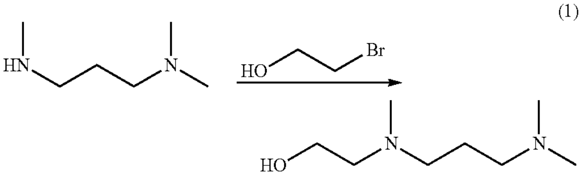

2-((3-(Dimethylamino)propyl)(methyl)amino)ethan-1-ol was obtained by the same method as that in (1) of Example 2, except that in (1) of Example 2, 2-bromoethan-1-ol was used instead of 3-bromopropan-1-ol, and N,N,N'-trimethylpropane-1,3-diamine was used instead of N,N,N'-trimethylethane-1,2-diamine.

MS m/z (M+H): 161.

(2)

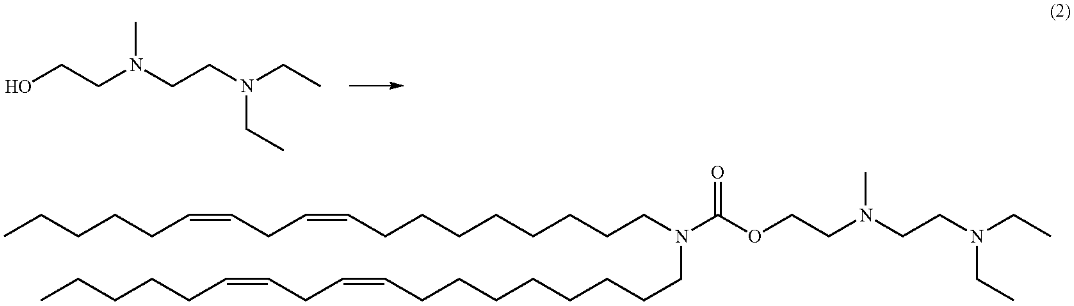

(2)

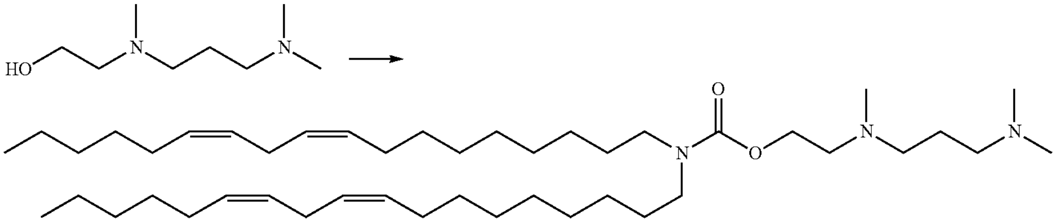

2-((3-(Dimethylamino)propyl)(methyl)amino)ethyl di((9Z,12Z)-octadeca-9,12-dien-1-yl)carbamate was obtained by the same method as that in (3) of Example 1, except that 2-((3-(dimethylamino)propyl)(methyl)amino) ethan-1-ol was used instead of 2-((2-(dimethylamino)ethyl) (methyl)amino)ethan-1-ol in (3) of Example 1.

$^1$H-NMR ($CDCl_3$) δ:5.43-5.28 (8H, m), 4.16 (2H, t, J=6.0 Hz), 3.25-3.10 (4H, m), 2.77 (4H, t, J=6.0 Hz), 2.63 (2H, t, J=6.0 Hz), 2.42 (2H, t, J=6.0 Hz), 2.28 (3H, s), 2.27 (2H, t, J=6.0 Hz), 2.21 (6H, s), 2.04 (8H, q, J=6.0 Ha), 1.67-1.58 (2H, m), 1.56-1.43 (4H, m), 1.40-1.19 (32H, m), 0.89 (6H, t, J=6.0 Hz).

MS m/z (M+H): 701.

Example 9

(1)

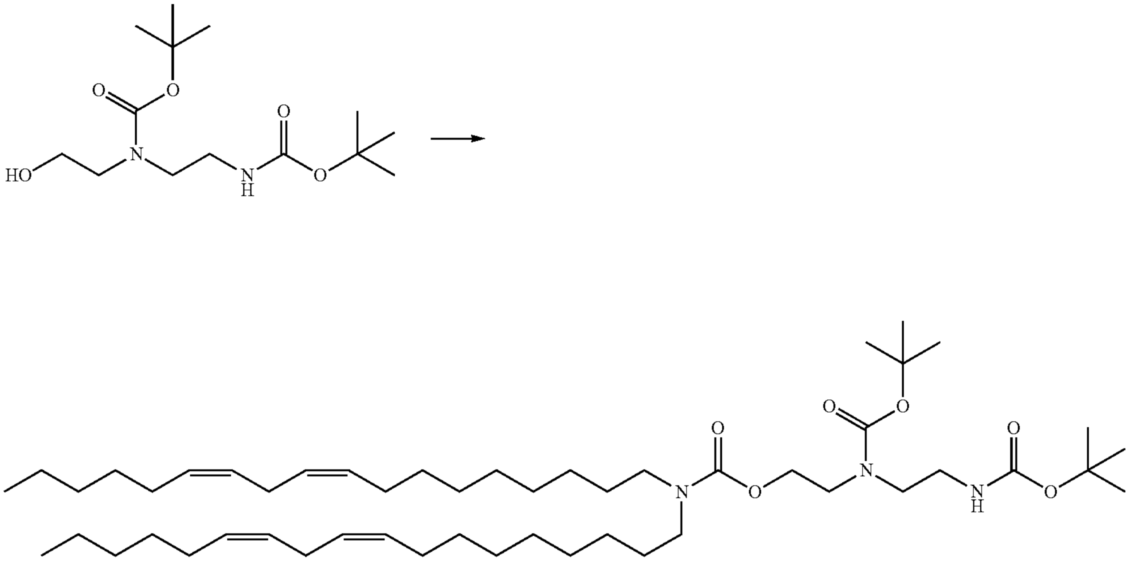

2-((tert-Butoxycarbonyl)(2-((tert-butoxycarbonyl)amino) ethyl)amino)ethyl)di((9Z,12Z)-octadeca-9,12-dien-1-yl) carbamate was obtained by the same method as that in (3) of Example 1, except that tert-butyl(2-((tert-butoxycarbonyl) amino)ethyl)(2-hydroxyethyl)carbamate was used instead of 2-((2-(dimethylamino)ethyl)(methyl)amino)ethan-1-ol in (3) of Example 1.

$^1$H-NMR ($CDCl_3$) δ:5.44-5.27 (8H, m), 4.20-4.09 (1H, m), 3.51-3.10 (10H, m), 2.77 (4H, t, J=6.0 Hz), 2.10-1.99 (8H, m), 1.64-1.48 (4H, m), 1.41-1.23 (32H, m), 0.89 (6H, t, J=6.0 Hz).

(2)

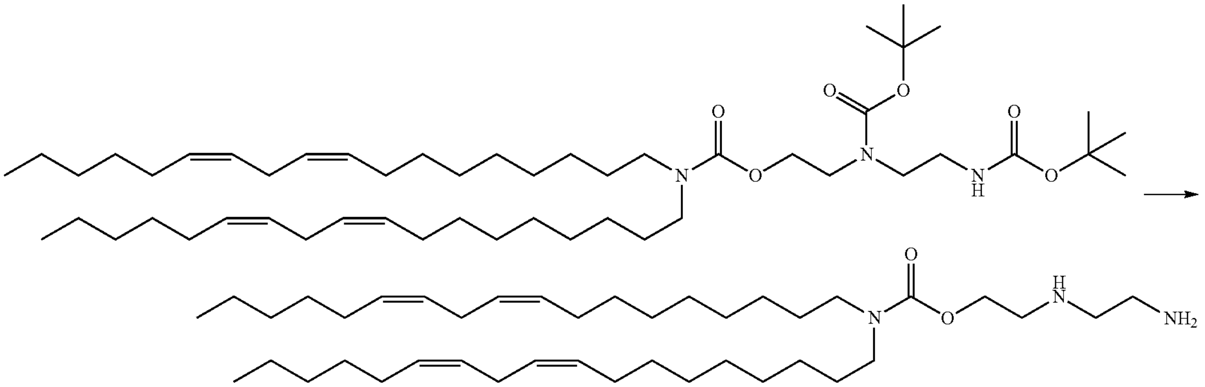

Trifluoroacctic acid (2 mL) was added to a mixture of 2-((tert-butoxycarbonyl)(2-((tert-butoxycarbonyl)amino) ethyl)amino)ethyl)di((9Z,12Z)-octade ca-9,12-dien-1-yl) carbamate (0.6 g), water (0.2 mL), and dichloromethane (0.5 mL), and the mixture was stirred at room temperature for 30 minutes. Toluene was added to the reaction mixture, and the solvent was distilled away under reduced pressure. The obtained residue was purified by silica gel column chromatography (methanol-chloroform, NH silica gel), thereby obtaining 2-((2-aminoethyl)amino)ethyl di((9Z,12Z)-octadeca-9,12-dien-1-yl)carbamate (0.3 g).

$^1$H-NMR ($CDCl_3$) δ: 5.43-5.28 (8H, m), 4.18 (2H, t, J=6.0 Hz), 3.24-3.11 (4H, m), 2.87 (2H, t, J=6.0 Hz), 2.80 (2H, t, J=6.0 Hz), 2.77 (4H, t, J=6.0 Hz), 2.70 (2H, t, J=6.0 Hz), 2.09-2.00 (8H, m), 1.59-1.44 (4H, m), 1.40-1.19 (32H, m), 0.89 (6H, t, J=6.0 Hz).

MS m/z (M+H): 645.

Example 10

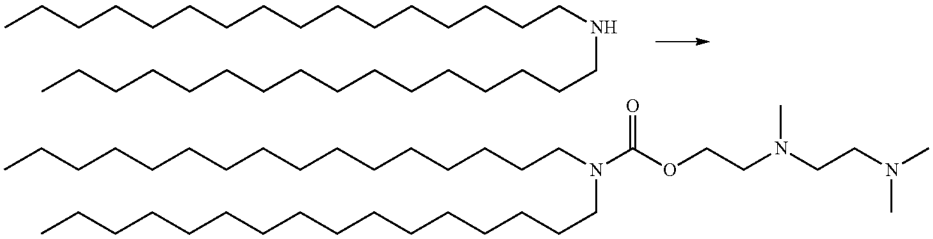

2-((2-(Dimethylamino)ethyl)(methyl)amino)ethyl dihexadecylcarbamate was obtained by the same method as that in (3) of Example 1, except that dihexadecylamine was used instead of (9Z,12Z9-di((9Z,12Z)-octadeca-9,12-dien-1-yl)amine in (3) of Example 1.

$^1$H-NMR ($CDCl_3$) δ:4.17 (2H, t, J=6.0 Hz), 3.23-3.12 (4H, m), 2.67 (2H, t, J=6.0 Hz), 2.54 (2H, t, J=6.0 Hz), 2.39 (2H, t, J=6.0 Hz), 2.32 (3H, s), 2.24 (6H, s), 1.55-1.38 (4H, m), 1.35-1.18 (52H, m), 0.88 (6H, t, J=6.0 Hz).

MS m/z (M+H): 639.

Example 11

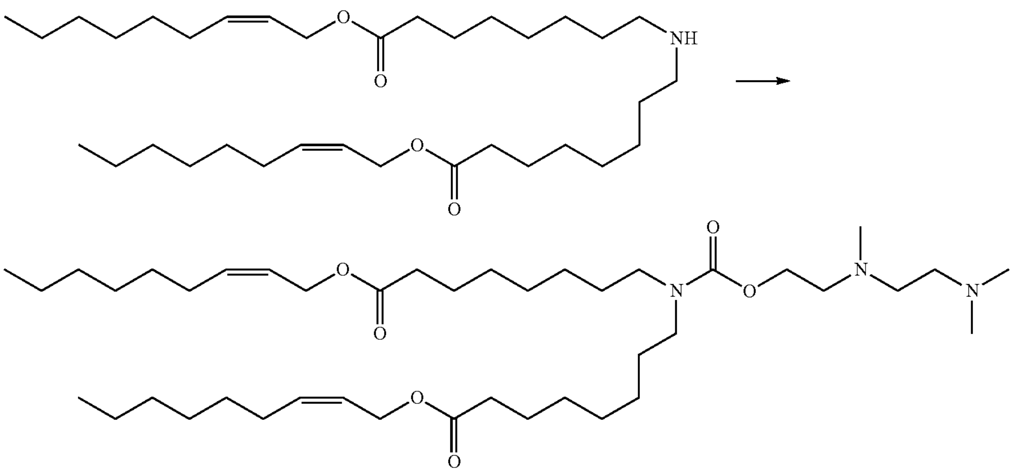

(Z)-non-2-en-1-yl 2,5-dimethyl-10-(8-(((Z)-non-2-en-1-yl)oxy)-8-oxooctyl)-9-oxo-8-oxa-2,5,10-triazaoctadecan-18-oate was obtained by the same method as that in (3) of Example 1, except that di((Z)-non-2-en-1-yl)8,8'-azanedyl dioctanoate synthesized according to the method described in WO2016/081029A1 was used instead of (9Z,12Z9-di ((9Z,12Z)-octadeca-9,12-dien-1-yl)amine in (3) of Example 1.

$^1$H-NMR ($CDCl_3$) δ:5.70-5.46 (4H, m), 4.61 (4H, d, J=6.0 Hz), 4.16 (2H, t, J=6.0 Hz), 3.23-3.09 (4H, m), 2.66 (2H, t, J=6.0 Hz), 2.61-2.45 (2H, m), 2.42-2.25 (2H, m), 2.31 (3H, s), 2.23 (6H, s), 2.15-2.05 (4H, m), 1.65-1.56 (4H, m), 1.55-1.43 (4H, m), 1.39-1.20 (32H, m), 0.88 (6H, t, J=6.0 Hz).

MS m/z (M+H): 723.

Example 12

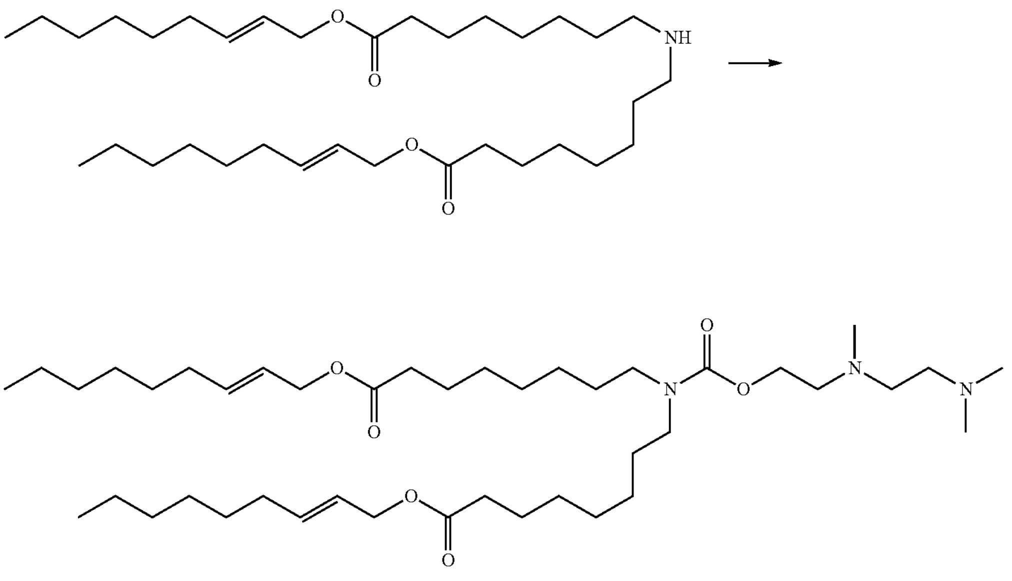

(E)-non-2-en-1-yl 2,5-dimethyl-10-(8-(((E)-non-2-en-1-yl)oxy)-8-oxooctyl)-9-oxo-8-oxa-2,5,10-triazaoctadecan-18-oate was obtained by the same method as that in (3) of Example 1, except that di((E)-non-2-en-1-yl)8,8'-azanedyl dioctanoate synthesized according to the method described in WO2016/081029A1 was used instead of (9Z,12Z9-di ((9Z,12Z)-octadeca-9,12-dien-1-yl)amine in (3) of Example 1.

$^1$H-NMR ($CDCl_3$) δ: 5.83-5.70 (2H, m), 5.61-5.49 (2H, m), 4.50 (4H, d, J=6.0 Hz), 4.16 (2H, t, J=6.0 Hz), 3.24-3.09 (4H, m), 2.67 (2H, t, J=6.0 Hz), 2.54 (2H, t, J=6.0 Hz), 2.38 (2H, t, J=6.0 Hz), 2.31 (3H, s), 2.24 (6H, s), 2.09-2.00 (4H, m), 1.65-1.56 (4H, m), 1.55-1.44 (4H, m), 1.41-1.23 (32H, m), 0.88 (6H, t, J=6.0 Hz).

MS m/z (M+H): 723.

Example 13
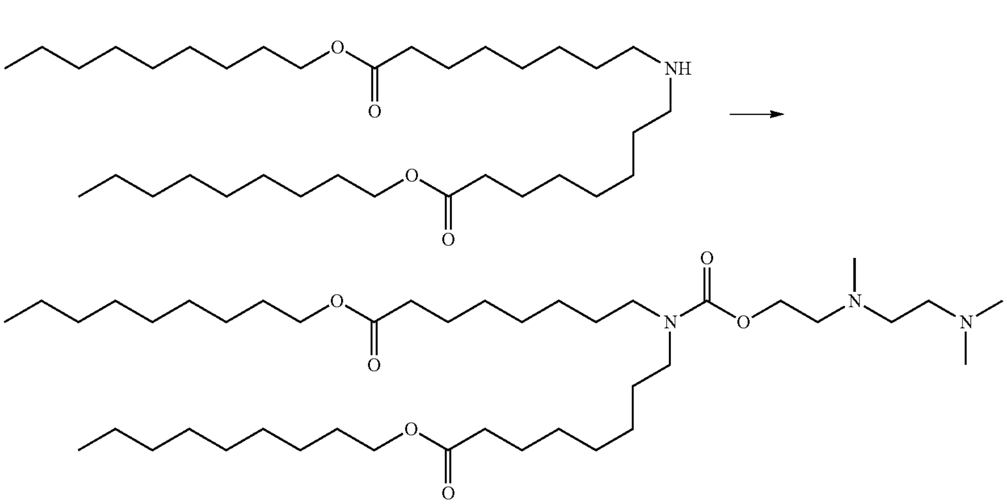
Nonyl 2,5-dimethyl-10-(8-(nonyloxy)-8-oxooctyl)-9-oxo-8-oxa-2,5,10-triazaoctadecan-18-oate was obtained by the same method as that in (3) of Example 1, except that dinonyl 8,8'-azanedyl dioctanoate synthesized according to the method described in WO2016/081029A1 was used instead of (9Z,12Z9-di((9Z,12Z)-octadeca-9,12-dien-1-yl) amine in (3) of Example 1.
$^1$H-NMR ($CDCl_3$) δ: 4.20-4.01 (6H, m), 3.24-3.09 (4H, m), 2.71-2.51 (4H, m), 2.44-2.38 (2H, m), 2.31 (3H, s), 2.26 (6H, s), 1.79-1.43 (12H, m), 1.37-1.23 (40H, m), 0.88 (6H, t, J=6.0 Hz).
MS m/z (M+H): 727.
Example 14
(1)
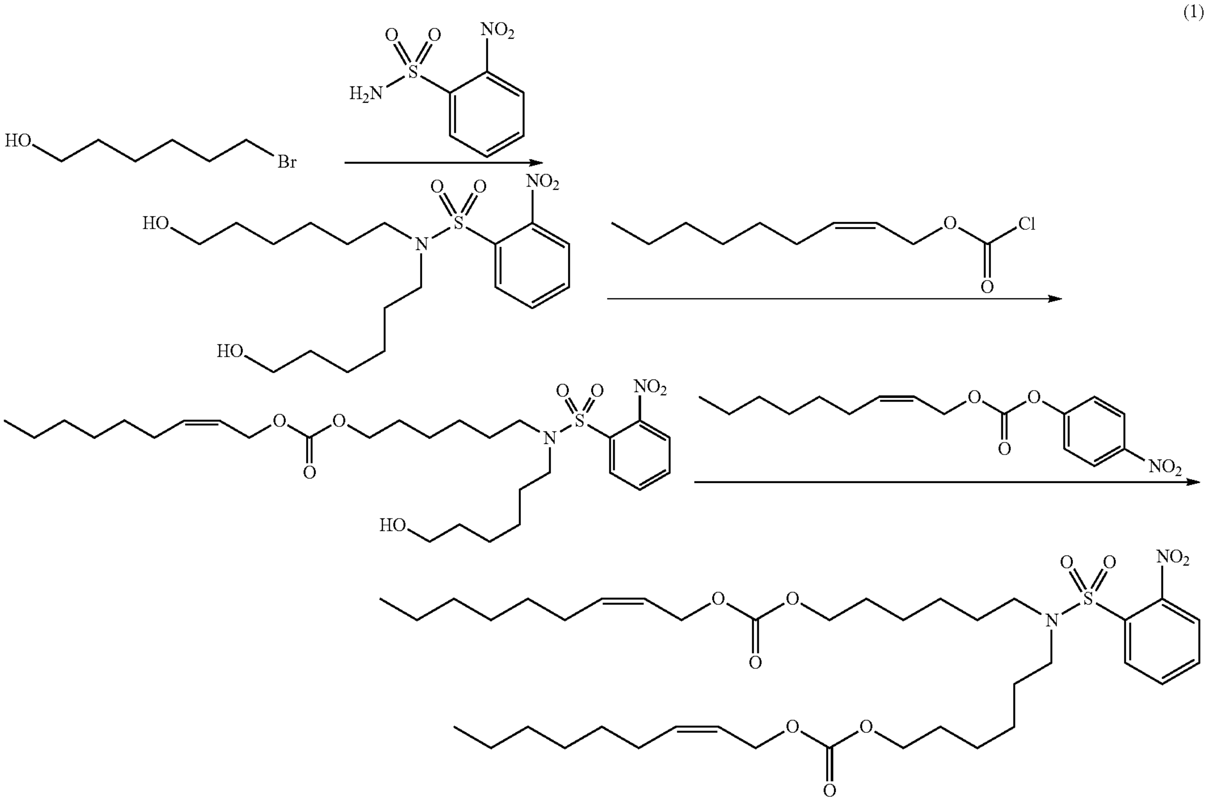

N,N-bis(6-hydroxyhexyl)-2-nitrobenzenesulfonamide was obtained by the same method as that in (1) of Example 1, except that 6-bromohexan-1-ol was used instead of (6Z, 9Z)-18-bromooctadeca-6,9-diene in (1) of Example 1.

(Z)-non-2-en-1-yl carbonochloridate (3.15 g) was added to a mixture of the obtained N,N-bis(6-hydroxyhexyl)-2-nitrobenzenesulfonamide (2.13 g), triethylamine (0.58 mL), and tetrahydrofuran (5 mL), and the mixture was stirred at room temperature for 1 hour. Water and ethyl acetate were added to the reaction mixture, the organic layer was separated, washed with water, and then dried over anhydrous sodium sulfate, and the solvent was distilled away under reduced pressure, thereby obtaining (Z)-6-((N-(6-hydroxyhexyl)-2-nitrophenyl)sulfonamido)hexyl non-2-en-1-yl carbonate (1.67 g).

$^1$H-NMR ($CDCl_3$) δ:8.04-7.97 (1H, m), 7.71-7.59 (3H, m), 5.72-5.51 (2H, m), 4.68 (2H, d, J=6.0 Hz), 4.12 (2H, t, J=6.0 Hz), 3.65-3.59 (2H, m), 3.30-3.24 (4H, m), 2.14-2.07 (2H, m), 1.66-1.48 (8H, m), 1.40-1.22 (16H, m), 0.88 (3H, t, J=6.0 Hz).

4-Dimethylaminopyridine (0.37 g) was added to a mixture of the obtained (Z)-6-((N-(6-hydroxyhexyl)-2-nitrophenyl)sulfonamido)hexyl non-2-en-1-yl carbonate (1.67 g), (Z)-4-nitrophenyl non-2-en-1-yl carbonate (1.84 g), triethylamine (1.7 mL), and tetrahydrofuran (17 mL), and the mixture was stirred at 50° C. for 6 hours. The reaction mixture was cooled to room temperature, and then the solvent was distilled away under reduced pressure. The obtained residue was purified by silica gel column chromatography (ethyl acetate-hexane), thereby obtaining (((2-nitrophenyl)sulfonyl)azanedyl)bis(hexane-6,1-diyl)di((Z)-non-2-en-1-yl)bis(carbonate) (1.96 g).

$^1$H-NMR ($CDCl_3$) δ: 8.04-7.97 (1H, m), 7.71-7.59 (3H, m), 5.72-5.51 (4H, m), 4.68 (4H, d, J=6.0 Hz), 4.12 (4H, t, J=6.0 Hz), 3.27 (4H, t, J=6.0 Hz), 2.14-2.07 (4H, m), 1.66-1.48 (8H, m), 1.40-1.22 (24H, m), 0.88 (6H, t, J=6.0 Hz).

(2)

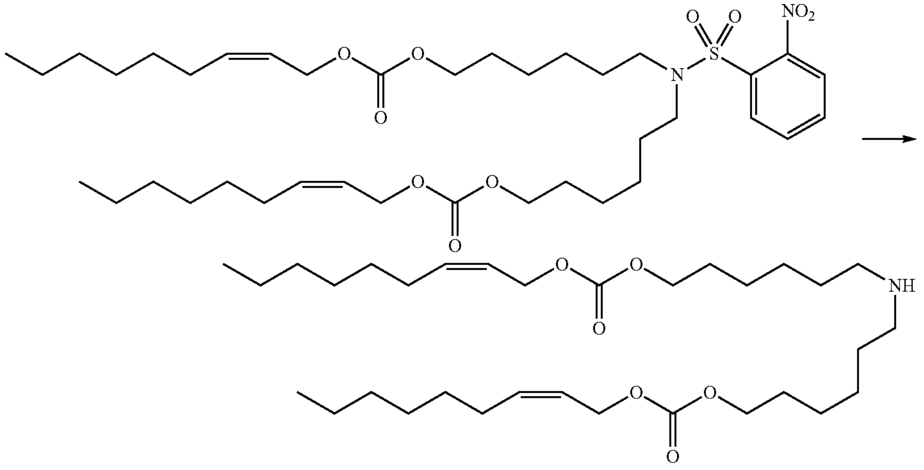

Cesium carbonate (2.51 g) was added to a mixture of (((2-nitrophenyl)sulfonyl)azanedyl)bis(hexane-6,1-diyl)di((Z)-non-2-en-1-yl)bis(carbonate) (1.01 g), dodecane-1-thiol (1.05 mL), and acetonitrile (10 mL), and the mixture was stirred at 50° C. for 10 hours. The reaction mixture was cooled to room temperature, water and ethyl acetate were added thereto, the organic layer was separated and dried over anhydrous sodium sulfate, and then the solvent was distilled away under reduced pressure. The obtained residue was purified by silica gel column chromatography (ethyl acetate-hexane), thereby obtaining azanedylbis(hexane-6,1-diyl)di((Z)-non-2-en-1-yl)bis(carbonate) (1.59 g).

$^1$H-NMR ($CDCl_3$) δ:5.73-5.50 (4H, m), 4.68 (4H, d, J=6.0 Hz), 4.12 (4H, t, J=6.0 Hz), 2.61 (4H, t, J=6.0 Hz), 2.15-2.05 (4H, m), 1.73-1.46 (8H, m), 1.42-1.24 (24H, m), 0.88 (6H, t, J=6.0 Hz).

(3)

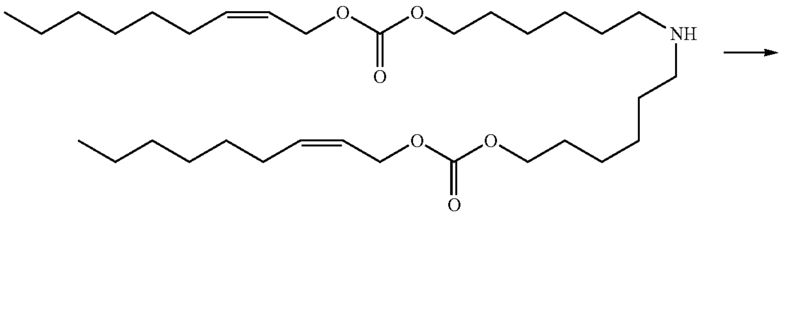

-continued

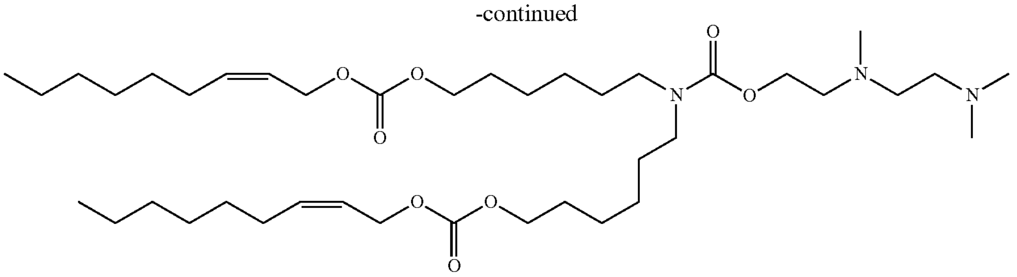

2-((2-(Dimethylamino)ethyl)(methyl)amino)ethyl bis(6-(((((Z)-non-2-en-1-yl)oxy)carbonyl)oxy)hexyl)carbamate was obtained by the same method as that in (3) of Example 1, except that azanedylbis(hexane-6,1-diyl)di((Z)-non-2-en-1-yl)bis(carbonate) was used instead of (9Z,12Z9-di((9Z,12Z)-octadeca-9,12-dien-1-yl)amine in (3) of Example 1.

$^1$H-NMR ($CDCl_3$) δ:5.73-5.50 (4H, m), 4.67 (4H, d, J=6.0 Hz), 4.20-4.08 (6H, m), 3.24-3.10 (4H, m), 2.66 (2H, d, J=6.0 Hz), 2.53 (2H, t, J=6.0 Hz), 2.38 (2H, t, J=6.0 Hz), 2.31 (3H, s), 2.24 (6H, s), 2.15-2.06 (4H, m), 1.72-1.45 (8H, m), 1.42-1.23 (24H, m), 0.88 (6H, t, J=6.0 Hz).

MS m/z (M+H): 727.

Example 15

(1)

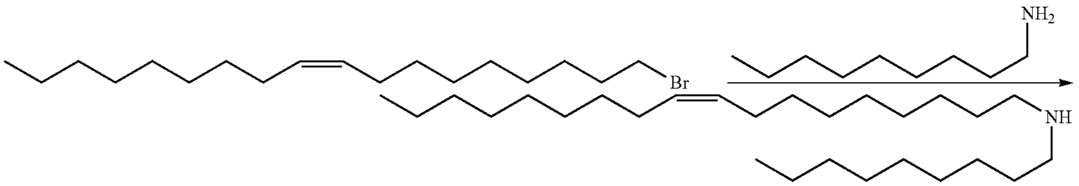

(Z)-1-bromooctadec-9-ene (4.53 g) was added to a N,N-dimethylformamide (20 mL) suspension of nonan-1-amine (1.95 g) and potassium carbonate (1.87 g), and the mixture was stirred at 80° C. for 9 hours. The reaction mixture was cooled to room temperature, and water (40 mL) and hexane (40 mL) were added thereto. The organic layer was separated, the solvent was then distilled away under reduced pressure, and the obtained residue was purified by silica gel column chromatography (ethyl acetate-hexane), thereby obtaining (Z)—N-nonyloctadec-9-en-1-amine (1.72 g).

MS m/z (M+H): 394.

(2)

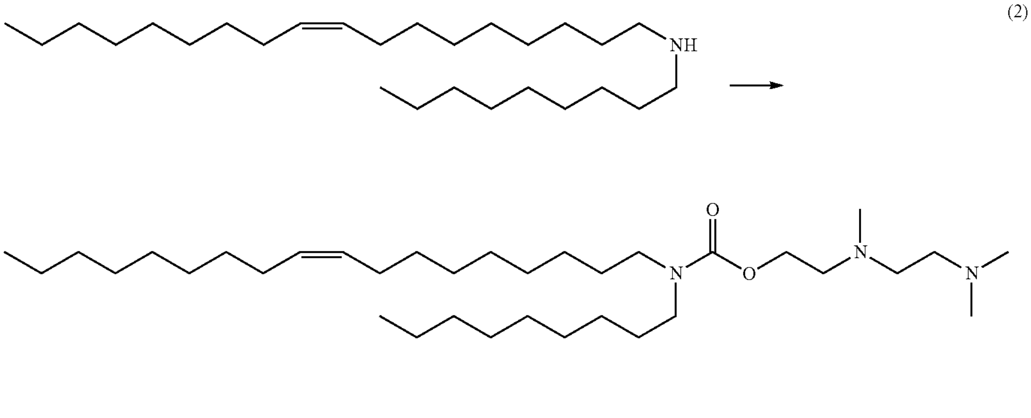 [SMILES: CCCCCCCC/C=C\CCCCCCCCNCCCCCCCCC ; CCCCCCCC/C=C\CCCCCCCCN(CCCCCCCCC)C(=O)OCCN(C)CCN(C)C]

2-((2-(Dimethylamino)ethyl)(methyl)amino)ethyl(Z)-nonyl(octadec-9-en-1-yl)carbamate was obtained by the same method as that in (3) of Example 1, except that (Z)—N-nonyloctadec-9-en-1-amine was used instead of (9Z,12Z9-di((9Z,12Z)-octadeca-9,12-dien-1-yl)amine in (3) of Example 1.

$^1$H-NMR ($CDCl_3$) δ:5.41-5.29 (2H, m), 4.17 (2H, t, J=6.0 Hz), 3.24-3.11 (4H, m), 2.68 (2H, t, J=6.0 Hz), 2.54 (2H, t, J=6.0 Hz), 2.38 (2H, t, J=6.0 Hz), 2.32 (3H, s), 2.24 (6H, s), 2.08-1.93 (4H, m), 1.56-1.43 (4H, m), 1.38-1.18 (34H, m), 0.89 (6H, t, J=6.0 Hz).

MS m/z (M+H): 567.

Example 16

(1)

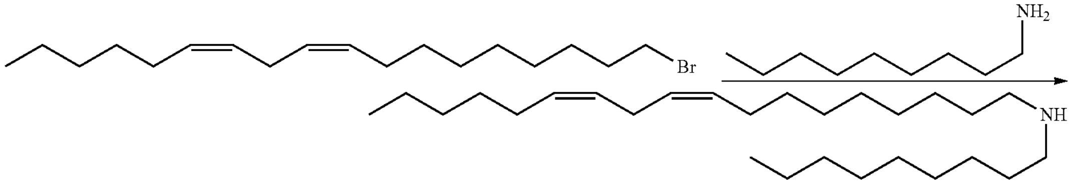

(9Z,12Z)—N-nonyloctadeca-9,12-dien-1-amine was obtained by the same method as that in (1) of Example 15, except that (6Z,9Z)-18-bromooctadeca-6,9-diene was used instead of (Z)-1-bromooctadec-9-ene in (1) of Example 15.

MS m/z (M+H): 392.

(2)

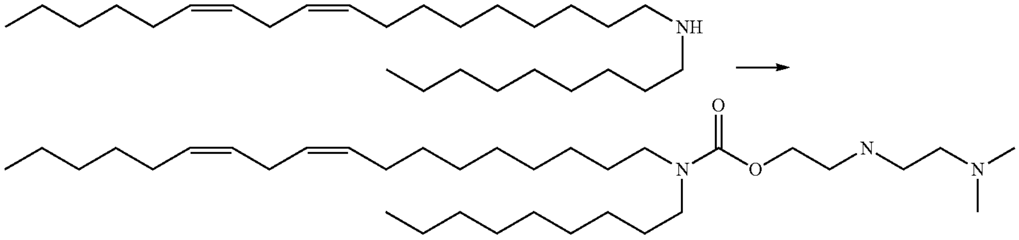

2-((2-(Dimethylamino)ethyl)(methyl)amino)ethyl nonyl((9Z,12Z)-octadeca-9,12-dien-1-yl)carbamate was obtained by the same method as that in (3) of Example 1, except that (9Z,12Z)—N-nonyloctadeca-9,12-dien-1-amine was used instead of (9Z,12Z9-di((9Z,12Z)-octadeca-9,12-dien-1-yl)amine in (3) of Example 1.

$^1$H-NMR ($CDCl_3$) δ:5.43-5.29 (4H, m), 4.17 (2H, t, J=6.0 Hz), 3.25-3.11 (4H, m), 2.77 (2H, t, J=6.0 Hz), 2.68 (2H, t, J=6.0 Hz), 2.54 (2H, t, J=6.0 Hz), 2.38 (2H, t, J=6.0 Hz), 2.32 (3H, s), 2.24 (6H, s), 2.10-1.99 (4H, m), 1.56-1.43 (4H, m), 1.41-1.19 (28H, m), 0.92-0.85 (6H, m).

MS m/z (M+H): 565.

Example 17

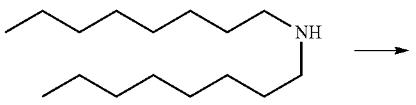

-continued

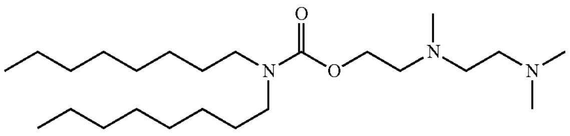

2-((2-(Dimethylamino)ethyl)(methyl)amino)ethyl dioctylcarbamate was obtained by the same method as that in (3) of Example 1, except that dioctylamine was used instead of (9Z,12Z9-di((9Z,12Z)-octadeca-9,12-dien-1-yl)amine in (3) of Example 1.

$^1$H-NMR ($CDCl_3$) δ:4.17 (2H, t, J=6.0 Hz), 3.24-3.12 (4H, m), 2.68 (2H, t, J=6.0 Hz), 2.54 (2H, t, J=6.0 Hz), 2.39 (2H, t, J=6.0 Hz), 2.32 (3H, s), 2.24 (6H, s), 1.55-1.43 (4H, m), 1.34-1.19 (20H, m), 0.88 (6H, t, J=6.0 Hz).

MS m/z (M+H): 414.

Example 18

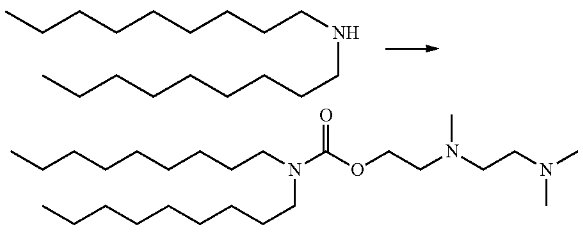

2-((2-(Dimethylamino)ethyl)(methyl)amino)ethyl dinonylcarbamate was obtained by the same method as that in (3) of Example 1, except that dinonylamine was used instead of (9Z,12Z9-di((9Z,12Z)-octadeca-9,12-dien-1-yl)amine in (3) of Example 1.

$^1$H-NMR ($CDCl_3$) δ:4.17 (2H, t, J=6.0 Hz), 3.24-3.12 (4H, m), 2.68 (2H, t, J=6.0 Hz), 2.54 (2H, t, J=6.0 Hz), 2.39

(2H, t, J=6.0 Hz), 2.32 (3H, s), 2.24 (6H, s), 1.55-1.43 (4H, m), 1.34-1.19 (24H, m), 0.88 (6H, t, J=6.0 Hz).

MS m/z (M+H): 442.

Example 19

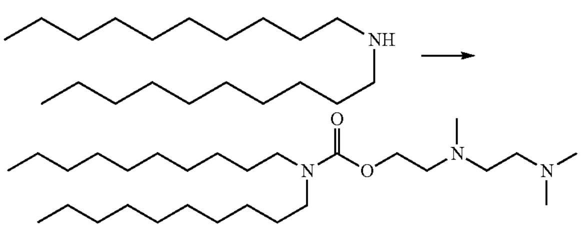

2-((2-(Dimethylamino)ethyl)(methyl)amino)ethyl didecylcarbamate was obtained by the same method as that in (3) of Example 1, except that didecylamine was used instead of (9Z,12Z9-di((9Z,12Z)-octadeca-9,12-dien-1-yl) amine in (3) of Example 1.

$^1$H-NMR ($CDCl_3$) δ:4.17 (2H, t, J=6.0 Hz), 3.23-3.12 (4H, m), 2.67 (2H, t, J=6.0 Hz), 2.54 (2H, t, J=6.0 Hz), 2.39 (2H, t, J=6.0 Hz), 2.32 (3H, s), 2.24 (6H, s), 1.55-1.38 (4H, m), 1.35-1.18 (28H, m), 0.88 (6H, t, J=6.0 Hz).

MS m/z (M+H): 470.

Example 20

(1)

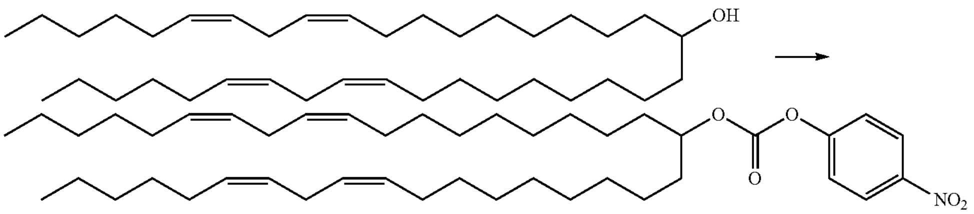

4-Nitrophenyl chloroformate (3.8 g) was added a mixture of (6Z,9Z,28Z,31Z)-heptatriaconta-6,9,28,31-tetraen-19-ol (5.0 g) synthesized according to the method described in WO2010/054401A1, triethylamine (4.0 mL), and tetrahydrofuran (25 mL), and the mixture was stirred at room temperature for 6 hours. Water and ethyl acetate were added to the reaction mixture, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining (6Z,9Z,28Z,31Z)-heptatriaconta-6,9,28,31-tetraen-19-yl(4-nitrophenyl)carbonate (6.25 g).

$^1$H-NMR ($CDCl_3$) δ:8.31-8.24 (2H, m), 7.42-7.35 (2H, m), 5.44-5.27 (8H, m), 4.87-4.76 (1H, m), 2.77 (4H, t, J=6.0 Hz), 2.11-1.99 (8H, m), 1.74-1.57 (4H, m), 1.44-1.21 (36H, m), 0.89 (6H, t, J=6.0 Hz).

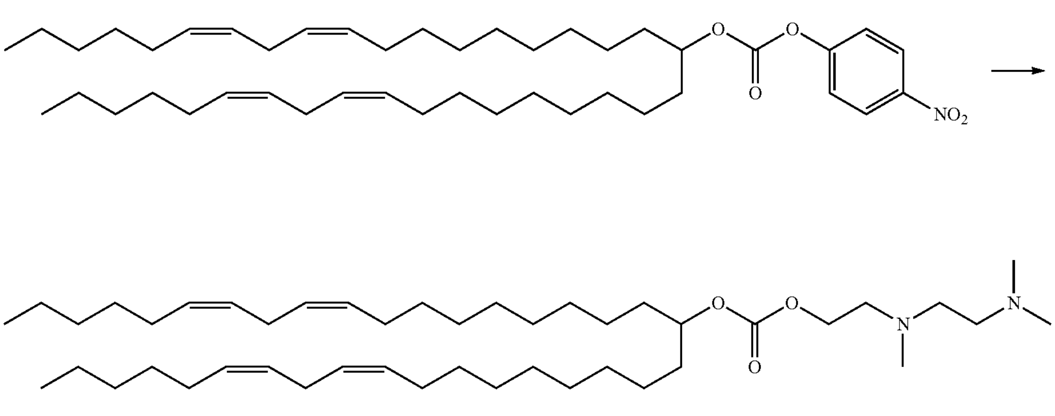

4-Dimethylaminopyridine (0.23 g) was added to a mixture of (6Z,9Z,28Z,31Z)-heptatriaconta-6,9,28,31-tetraen-19-yl(4-nitrophenyl)carbonate (0.89 g), 2-((2-(dimethylamino)ethyl)(methyl)amino)ethan-1-ol (0.30 mL), triethylamine (0.27 mL), and tetrahydrofuran (5 mL), and the mixture was stirred at 60° C. for 6 hours. The reaction mixture was cooled to room temperature, water and ethyl acetate were added thereto, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining 2-((2-(dimethylamino)ethyl)(methyl)amino)ethyl ((6Z,9Z,28Z,31Z)-heptatriaconta-6,9,28,31-tetraen-19-yl) carbonate (0.36 g).

$^1$H-NMR ($CDCl_3$) δ:5.44-5.27 (8H, m), 4.73-4.62 (1H, m), 4.22 (2H, t, J=6.0 Hz), 2.77 (4H, t, J=6.0 Hz), 2.71 (2H, t, J=6.0 Hz), 2.58-2.50 (2H, m), 2.43-2.35 (2H, m), 2.32 (3H, s), 2.24 (6H, s), 2.11-1.97 (8H, m), 1.63-1.48 (4H, m), 1.42-1.19 (36H, m), 0.89 (6H, t, J=6.0 Hz).

MS m/z (M+H): 702.

Example 21

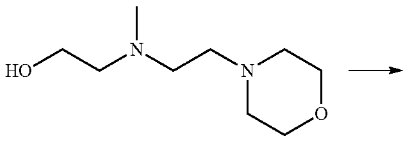

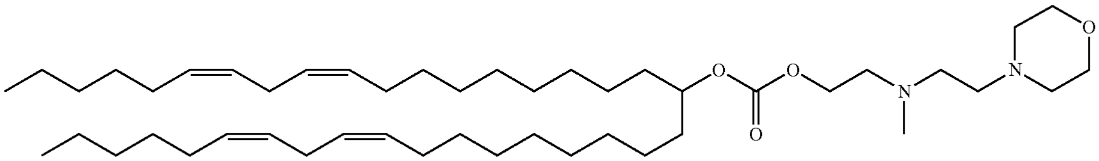

2-(Methyl(2-morpholinoethyl)amino)ethyl((6Z,9Z,28Z,31Z)-heptatriaconta-6,9,28,31-tetraen-19-yl)carbonate was obtained by the same method as that in (2) of Example 20, except that 2-(methyl(2-morpholinoethyl)amino)ethan-1-ol synthesized in (1) of Example 5 was used instead of 2-((2-(dimethylamino)ethyl)(methyl)amino)ethan-1-ol in (2) of Example 20.

$^1$H-NMR ($CDCl_3$) δ: 5.46-5.25 (8H, m), 4.73-4.61 (1H, m), 4.21 (2H, t, J=6.0 Hz), 3.71 (4H, t, J=6.0 Hz), 2.77 (4H, t, J=6.0 Hz), 2.71 (2H, t, J=6.0 Hz), 2.62-2.54 (2H, m), 2.51-2.43 (6H, m), 2.32 (3H, s), 2.13-1.98 (8H, m), 1.65-1.46 (4H, m), 1.43-1.20 (36H, m), 0.89 (6H, t, J=6.0 Hz).

MS m/z (M+H): 744.

Example 22

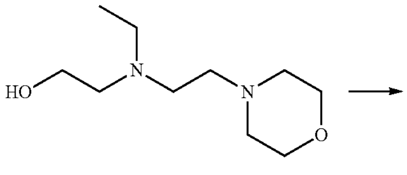

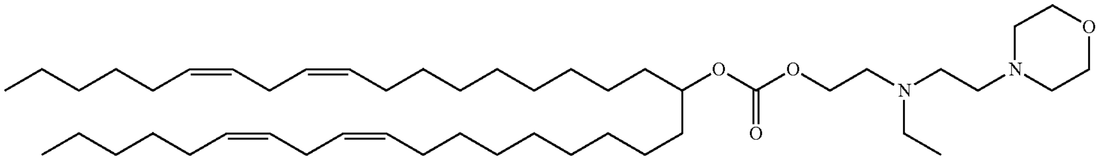

2-(Ethyl(2-morpholinoethyl)amino)ethyl((6Z,9Z,28Z,31Z)-heptatriaconta-6,9,28,31-tetraen-19-yl)carbonate was obtained by the same method as that in (2) of Example 20, except that 2-(ethyl(2-morpholinoethyl)amino)ethan-1-ol synthesized in (1) of Example 6 was used instead of 2-((2-(dimethylamino)ethyl)(methyl)amino)ethan-1-ol in (2) of Example 20.

$^1$H-NMR ($CDCl_3$) δ:5.45-5.26 (8H, m), 4.74-4.60 (1H, m), 4.17 (2H, t, J=6.0 Hz), 3.71 (4H, t, J=6.0 Hz), 2.84-2.72 (6H, m), 2.70-2.54 (4H, m), 2.52-2.39 (6H, m), 2.12-1.94 (8H, m), 1.66-1.47 (4H, m), 1.44-1.18 (36H, m), 1.03 (3H, t, J=6.0 Hz), 0.89 (6H, t, J=6.0 Hz).

MS m/z (M+H): 758.

Example 23

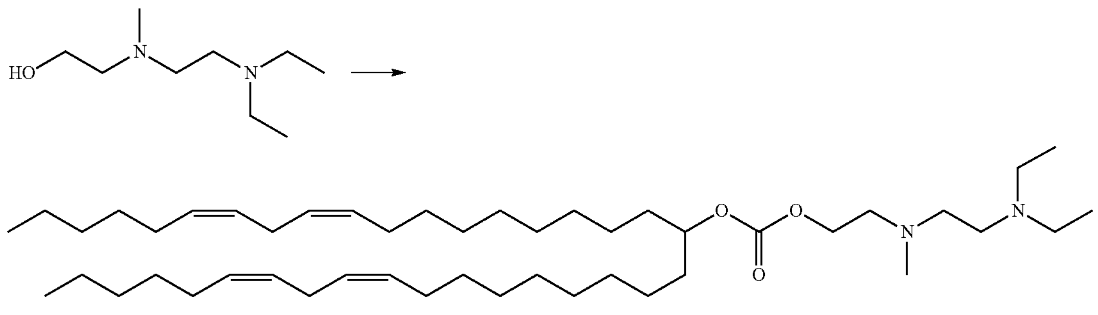

2-((2-(Diethylamino)ethyl)(methyl)amino)ethyl((6Z,9Z,28Z,31Z)-heptatriaconta-6,9, 28,31-tetraen-19-yl)carbonate was obtained by the same method as that in (2) of Example 20, except that 2-((2-(diethylamino)ethyl)(methyl)amino) ethan-1-ol synthesized in (1) of Example 7 was used instead of 2-((2-(dimethylamino)ethyl)(methyl)amino)ethan-1-ol in (2) of Example 20.

$^1$H-NMR ($CDCl_3$) δ: 5.44-5.27 (8H, m), 4.72-4.61 (1H, m), 4.21 (2H, t, J=6.0 Hz), 2.77 (4H, t, J=6.0), 2.70 (2H, t, J=6.0 Hz), 2.59-2.49 (8H, m), 2.31 (3H, s), 2.14-1.94 (8H, m), 1.64-1.47 (4H, m), 1.43-1.19 (36H, m), 1.02 (6H, t, J=6.0 Hz), 0.89 (6H, t, J=6.0 Hz).

MS m/z (M+H): 730.

Example 24

(1)

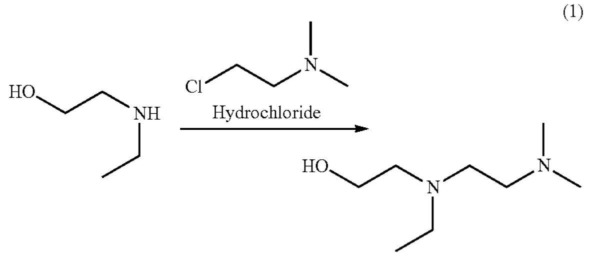

2-((2-(Dimethylamino)ethyl)(ethyl)amino)ethan-1-ol was obtained by the same method as that in (1) of Example 5, except that in (1) of Example 5, 2-chloro-N,N-dimethyl-ethan-1-amine hydrochloride was used instead of 4-(2-chloroethyl)morpholine hydrochloride, and 2-(ethylamino) ethan-1-ol was used instead of 2-(methylamino)ethan-1-ol.

MS m/z (M+H): 161.

(2)

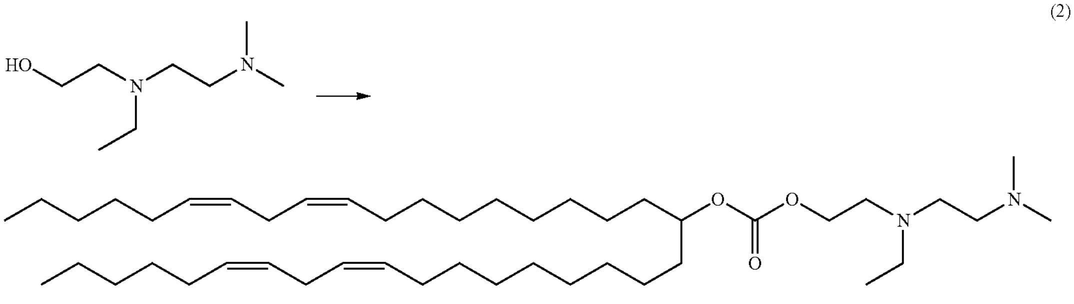

2-((2-(Dimethylamino)ethyl)(ethyl)amino)ethyl((6Z,9Z,28Z,31Z)-heptatriaconta-6,9, 28,31-tetraen-19-yl)carbonate was obtained by the same method as that in (2) of Example 20, except that 2-((2-(dimethylamino)ethyl)(ethyl)amino)ethan-1-ol was used instead of 2-((2-(dimethylamino)ethyl)(methyl)amino)ethan-1-ol in (2) of Example 20.

$^1$H-NMR ($CDCl_3$) δ:5.45-5.26 (8H, m), 4.73-4.61 (1H, m), 4.18 (2H, t, J=6.0 Hz), 2.83-2.71 (6H, m), 2.67-2.55 (4H, m), 2.42-2.33 (2H, m), 2.24 (6H, s), 2.12-1.98 (8H, m), 1.64-1.50 (4H, m), 1.45-1.19 (36H, m), 1.03 (3H, t, J=6.0 Hz), 0.89 (6H, t, J=6.0 Hz).

MS m/z (M+H): 716.

Example 25

(1)

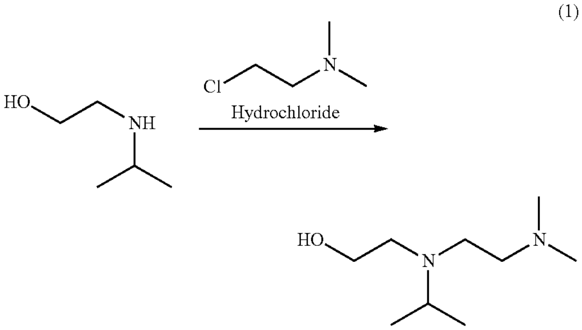

2-((2-(Dimethylamino)ethyl)(isopropyl)amino)ethan-1-ol was obtained by the same method as that in (1) of Example 5, except that in (1) of Example 5, 2-chloro-N,N-dimethylethan-1-amine hydrochloride was used instead of 4-(2-chloroethyl)morpholine hydrochloride, and 2-(isopropylamino)ethan-1-ol was used instead of 2-(methylamino)ethan-1-ol.

MS m/z (M+H): 175.

2-((2-(Dimethylamino)ethyl)(isopropyl)amino)ethyl((6Z,9Z,28Z,31Z)-heptatriaconta-6,9,28,31-tetraen-19-yl)carbonate was obtained by the same method as that in (2) of Example 20, except that 2-((2-(dimethylamino)ethyl)(isopropyl)amino)ethan-1-ol was used instead of 2-((2-(dimethylamino)ethyl)(methyl)amino)ethan-1-ol in (2) of Example 20.

$^1$H-NMR ($CDCl_3$) δ:5.46-5.26 (8H, m), 4.73-4.61 (1H, m), 4.10 (2H, t, J=6.0 Hz), 2.98-2.85 (1H, m), 2.77 (4H, t, J=6.0 Hz), 2.69 (2H, t, J=6.0 Hz), 2.60-2.52 (2H, m), 2.37-2.29 (2H, m), 2.24 (6H, s), 2.10-1.99 (8H, m), 1.58-1.49 (4H, m), 1.45-1.20 (36H, m), 0.99 (6H, d, J=6.0 Hz), 0.89 (6H, t, J=6.0 Hz).

MS m/z (M+H): 730.

Example 26

(1)

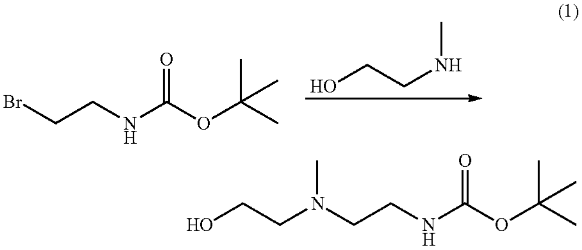

tert-Butyl(2-((2-hydroxyethyl)(methyl)amino)ethyl)carbamate was obtained by the same method as that in (1) of Example 5, except that tert-butyl(2-bromoethyl)carbamate was used instead of 4-(2-chloroethyl)morpholine hydrochloride in (1) of Example 5.

MS m/z (M+H): 219.

(2)

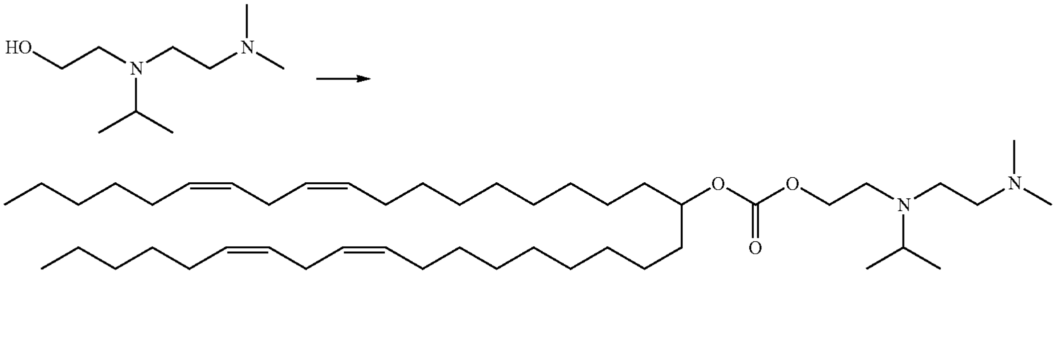

(2)

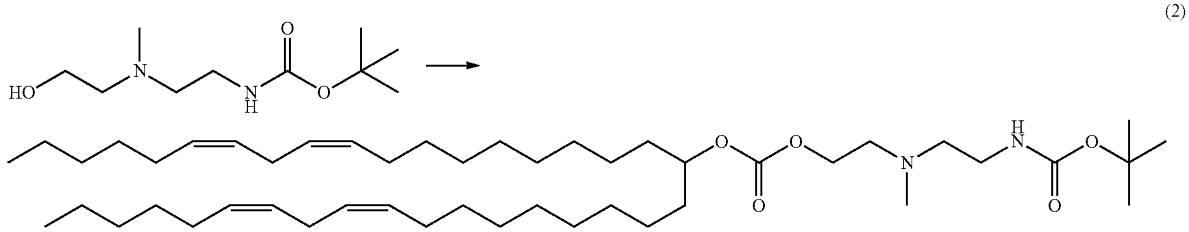

tert-Butyl(2-((2-(((((6Z,9Z,28Z,31Z)-heptatriaconta-6,9,28,31-tetraen-19-yl)oxy)ethyl)(methyl)amino)ethyl)carbamate was obtained by the same method as that in (2) of Example 20, except that tert-butyl(2-((2-hydroxyethyl)(methyl)amino)ethyl)carbamate was used instead of 2-((2-(dimethylamino)ethyl)(methyl)amino)ethan-1-ol in (2) of Example 20.

$^1$H-NMR ($CDCl_3$) δ:5.45-5.26 (8H, m), 5.04 (1H, bs), 4.76-4.62 (1H, m), 4.20 (2H, t, J=6.0 Hz), 3.25-3.12 (2H, m), 2.77 (4H, t, J=6.0 Hz), 2.68 (2H, t, J=6.0 Hz), 2.52 (2H, t, J=6.0 Hz), 2.28 (3H, s), 2.12-1.96 (8H, m), 1.62-1.50 (4H, m), 1.45 (9H, s), 1.62-1.50 (36H, m), 0.89 (6H, t, J=6.0 Hz).

MS m/z (M+H): 774.

Example 27

(1)

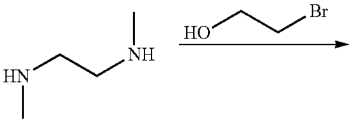

(3)

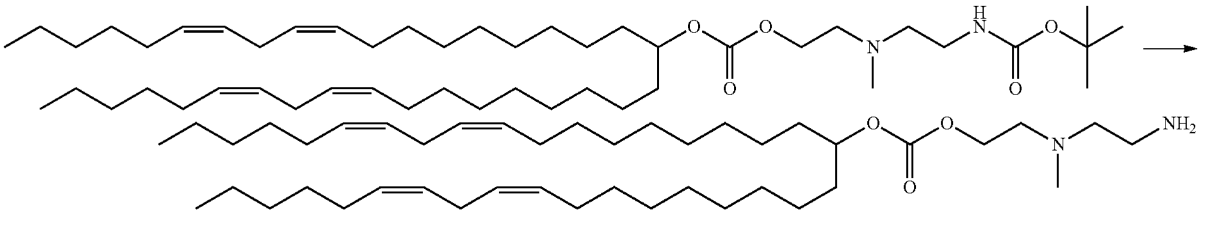

2-((2-Aminoethyl)(methyl)amino)ethyl((6Z,9Z,28Z,31Z)-heptatriaconta-6,9,28,31-tetraen-19-yl)carbonate was obtained by the same method as that in (2) of Example 9, except that tert-butyl (2-((2-(((((6Z,9Z,28Z,31Z)-heptatriaconta-6,9,28,31-tetraen-19-yl)oxy)ethyl)(methyl)amino)ethyl)carbamate synthesized in (2) of Example 26 was used instead of 2-((tert-butoxycarbonyl)(2-((tert-butoxycarbonyl)amino)ethyl)amino)ethyl)di((9Z,12Z)-octade ca-9,12-dien-1-yl)carbamate in (2) of Example 9.

$^1$H-NMR ($CDCl_3$) δ:5.45-5.26 (8H, m), 4.73-4.61 (1H, m), 4.22 (2H, t, J=6.0 Hz), 2.82-2.72 (6H, m), 2.68 (2H, t, J=6.0 Hz), 2.47 (2H, t, J=6.0 Hz), 2.29 (3H, s), 2.11-1.98 (8H, m), 1.62-1.44 (4H, m), 1.42-1.19 (36H, m), 0.89 (6H, t, J=6.0 Hz).

MS m/z (M+H): 674.

-continued

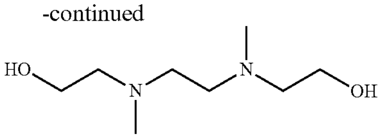

2-Bromoethan-1-ol (14.2 g) was added to an ethanol (50 mL) suspension of N,N'-dimethylethane-1,2-diamine (5.0 g) and potassium carbonate (17.2 g), and the mixture was stirred at 60° C. for 5 hours. The reaction mixture was cooled to room temperature, the insoluble matters were filtered off, and then the solvent was distilled away under reduced pressure, thereby obtaining 2,2'-(ethane-1,2-diylbis(methylazanedyl))bis(ethan-1-ol) (10.2 g).

MS m/z (M+H): 177.

(2)

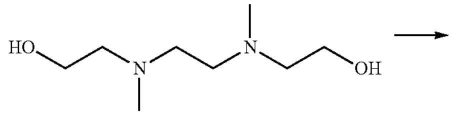

-continued

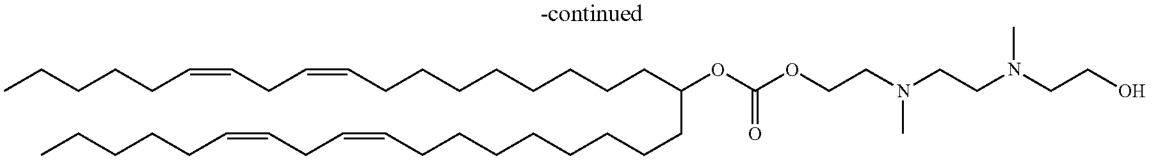

(6Z,9Z,28Z,31Z)-heptatriaconta-6,9,28,31-tetraen-19-yl (2-((2-((2-hydroxyethyl)(methyl)amino)ethyl)(methyl) amino)ethyl)carbonate was obtained by the same method as that in (2) of Example 20, except that 2,2'-(ethane-1,2-diylbis(methylazanedyl))bis(ethan-1-ol) was used instead of 2-((2-(dimethylamino)ethyl)(methyl)amino)ethan-1-ol in (2) of Example 20.

$^1$H-NMR ($CDCl_3$) δ:5.44-5.27 (8H, m), 4.73-4.61 (1H, m), 4.23 (2H, t, J=6.0 Hz), 3.56 (2H, t, J=6.0 Hz), 2.82-2.67 (6H, m), 2.58-2.52 (6H, m), 2.31 (6H, s), 2.11-1.99 (8H, m), 1.63-1.46 (4H, m), 1.42-1.20 (36H, m), 0.89 (6H, t, J=6.0 Hz).

MS m/z (M+H): 732.

Example 28

(1)

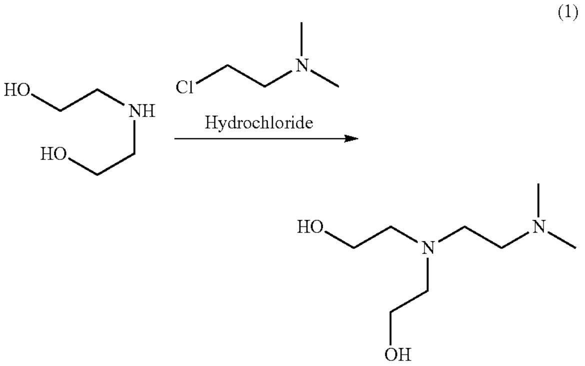

2,2'-((2-(Dimethylamino)ethyl)azanedyl)bis(ethan-1-ol) was obtained by the same method as that in (1) of Example 5, except that in (1) of Example 5, 2,2'-azanedylbis(ethan-1-ol) was used instead of 2-(methylamino)ethan-1-ol, and 2-chloro-N,N-dimethylethan-1-amine hydrochloride was used instead of 4-(2-chloroethyl)morpholine hydrochloride.

MS m/z (M+H): 177.

(2)

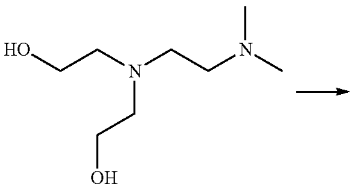

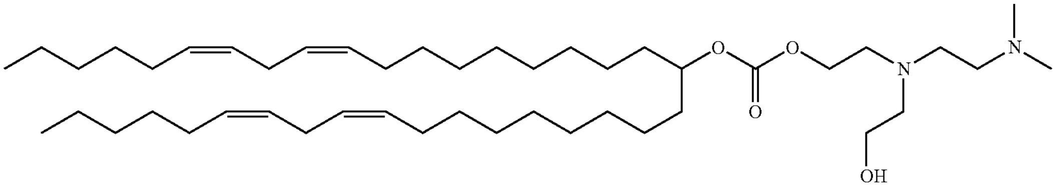

2-((2-(Dimethylamino)ethyl)(2-hydroxyethyl)amino) ethyl)((6Z,9Z,28Z,31Z)-heptatriaconta-6,9,28,31-tetraen-19-yl)carbonate was obtained by the same method as that in (2) of Example 20, except that 2,2'-((2-(dimethylamino) ethyl)azanedyl)bis(ethan-1-ol) was used instead of 2-((2-(dimethylamino)ethyl)(methyl)amino)ethan-1-ol in (2) of Example 20.

$^1$H-NMR ($CDCl_3$) δ: 5.45-5.25 (8H, m), 4.73-4.62 (1H, m), 4.21 (2H, t, J=6.0 Hz), 3.53 (2H, t, J=6.0 Hz), 2.89 (2H, t, J=6.0 Hz), 2.77 (4H, t, J=6.0 Hz), 2.73-2.64 (4H, m), 2.37 (2H, t, J=6.0 Hz), 2.23 (6H, s), 2.10-1.98 (8H, m), 1.65-1.46 (4H, m), 1.43-1.18 (36H, m), 0.89 (6H, t, J=6.0 Hz).

MS m/z (M+H): 732.

Example 29

(1)

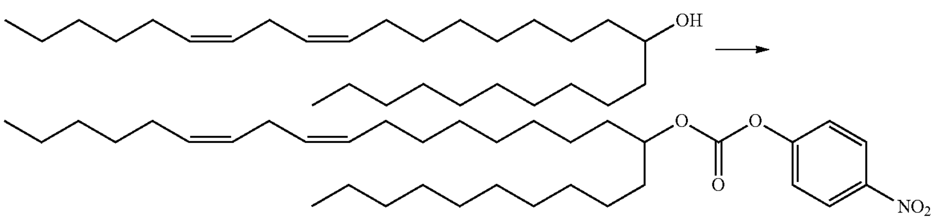

4-Nitrophenyl chloroformate (1.0 g) was added to a mixture of ((19Z,22Z)-octacosa-19,22-dien-11-ol (1.0 g) synthesized according to the method described in WO2015/005253A1, triethylamine (1.0 mL), and tetrahydrofuran (5.0 mL), and the mixture was stirred at room temperature for 2 hours. Water and ethyl acetate were added to the reaction mixture, the organic layer was separated and dried over anhydrous sodium sulfate, and then the solvent was distilled away under reduced pressure. The obtained residue was purified by silica gel column chromatography (ethyl acetate-hexane), thereby obtaining 4-nitrophenyl((19Z,22Z)-octacosa-19,22-dien-11-yl)carbonate (2.0 g).

$^1$H-NMR ($CDCl_3$) δ:8.28 (2H, d, J=9.0 Hz), 7.38 (2H, d, J=9.0 Hz), 5.43-5.28 (4H, m), 4.87-4.77 (1H, m), 2.77 (2H, t, J=6.0 Hz), 2.10-1.99 (4H, m), 1.76-1.60 (4H, m), 1.43-1.20 (32H, m), 0.92-0.83 (6H, m).

(2)

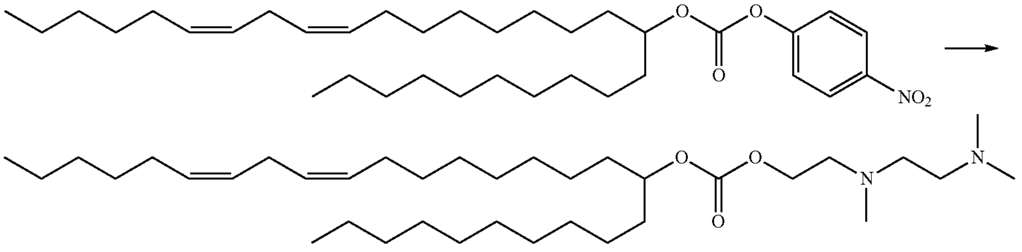

2-((2-(Dimethylamino)ethyl)(methyl)amino)ethyl((19Z,22Z)-octacosa-19,22-dien-11-yl)carbonate was obtained by the same method as that in (2) of Example 20, except that 4-nitrophenyl((19Z,22Z)-octacosa-19,22-dien-11-yl)carbonate was used instead of (6Z,9Z,28Z,31Z)-heptatriaconta-6,9,28,31-tetraen-19-yl(4-nitrophenyl)carbonate in (2) of Example 20.

$^1$H-NMR ($CDCl_3$) δ:5.44-5.26 (4H, m), 4.73-4.62 (1H, m), 4.22 (2H, t, J=6.0 Hz), 2.77 (2H, t, J=6.0 Hz), 2.71 (2H, t, J=6.0 Hz), 2.54 (2H, t, J=6.0 Hz), 2.39 (2H, t, J=6.0 Hz), 2.31 (3H, s), 2.24 (6H, s), 2.11-1.97 (4H, m), 1.65-1.45 (4H, m), 1.42-1.19 (32H, m), 0.93-0.84 (6H, m).

MS m/z (M+H): 580.

Example 30

(1)

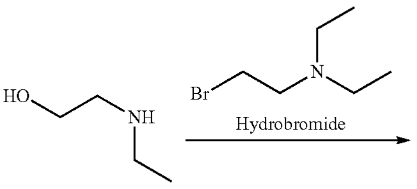

-continued

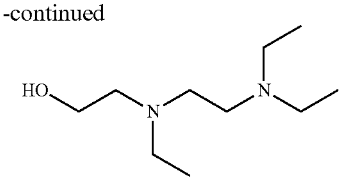

Potassium carbonate (18.6 g) was added to a mixture of 2-(ethylamino)ethan-1-ol (4.0 g), 2-bromo-N,N-diethylethan-1-amine hydrobromide (17.6 g), and ethanol (80 mL), and the mixture was stirred and heated under reflux for 7 hours. The reaction mixture was cooled to room temperature, the insoluble matters were filtered off, and the solvent was distilled away under reduced pressure. The obtained residue was purified by silica gel column chromatography (ethyl acetate-hexane, NH silica gel), thereby obtaining 2-((2-(diethylamino)ethyl)(ethyl)amino)ethan-1-ol (6.5 g) as a light yellow oily substance.

MS m/z (M+H): 189.

(2)

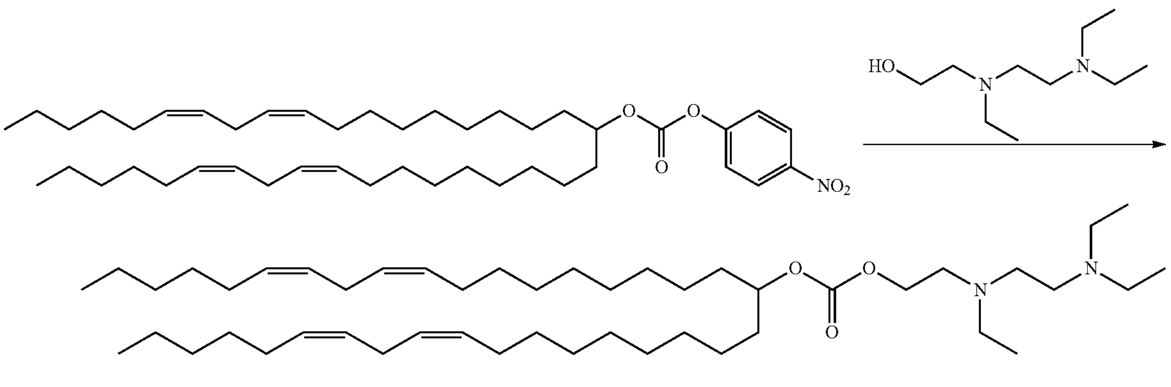

2-((2-(Diethylamino)ethyl)(ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(diethylamino)ethyl)(ethyl)amino)ethan-1-ol was used instead of 2-((2-(dimethylamino)ethyl)(methyl)amino)ethan-1-ol in (2) of Example 20.

$^1$H-NMR ($CDCl_3$) δ:5.45-5.26 (8H, m), 4.72-4.60 (1H, m), 4.17 (2H, t, J=6.6 Hz), 2.83-2.69 (6H, m), 2.65-2.46 (10H, m), 2.13-1.96 (8H, m), 1.65-1.47 (4H, m), 1.43-1.20 (36H, m), 1.09-0.98 (9H, m), 0.89 (6H, t, J=6.6 Hz).

MS m/z (M+H): 744.

Example 31

(1)

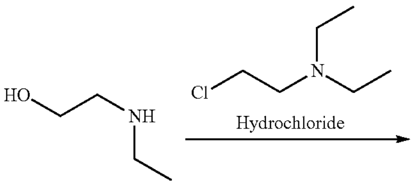

-continued

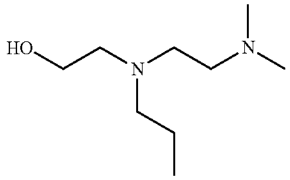

Potassium carbonate (8.0 g) was added to a mixture of 2-(propylamino)ethan-1-ol (2.0 g), 2-chloro-N,N-dimethylethan-1-amine hydrochloride (4.2 g), and ethanol (40 mL), and the mixture was stirred and heated under reflux for 9 hours. The reaction mixture was cooled to room temperature, the insoluble matters were filtered off, and the solvent was distilled away under reduced pressure. The obtained residue was purified by silica gel column chromatography (ethyl acetate-hexane, NH silica gel), thereby obtaining 2-((2-(dimethylamino)ethyl)(propyl)amino)ethan-1-ol (0.87 g) as a yellow oily substance.

MS m/z (M+H): 175.

(2)

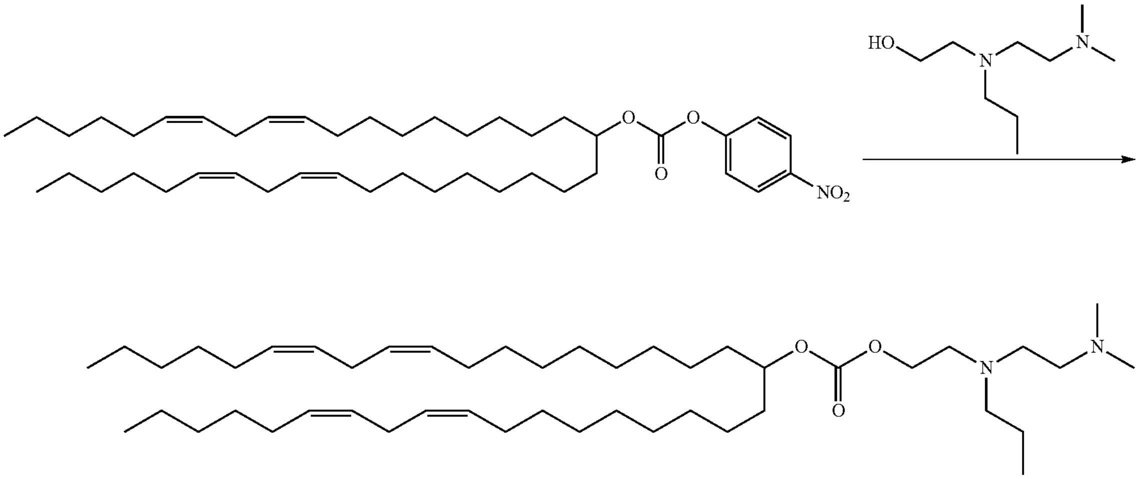

2-((2-(Dimethylamino)ethyl)(propyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(dimethylamino)ethyl)(propyl)amino)ethan-1-ol was used instead of 2-((2-(dimethylamino)ethyl)(methyl)amino)ethan-1-ol in (2) of Example 20.

$^1$H-NMR ($CDCl_3$) δ: 5.45-5.26 (8H, m), 4.73-4.61 (1H, m), 4.17 (2H, t, J=6.0 Hz), 2.85-2.70 (6H, m), 2.66-2.56 (2H, m), 2.51-2.41 (2H, m), 2.41-2.32 (2H, m), 2.24 (6H, s), 2.12-1.95 (8H, m), 1.66-1.18 (42H, m), 0.96-0.81 (9H, m).

MS m/z (M+H): 730.

Example 32

(1)

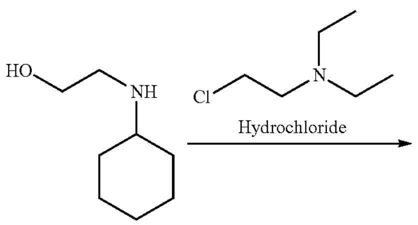

-continued

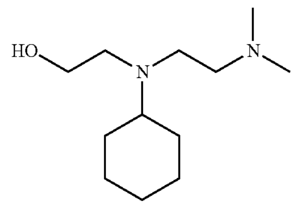

2-(Cyclohexyl(2-(dimethylamino)ethyl)amino)ethan-1-ol as a yellow oily substance was obtained by the same method as that in (1) of Example 31, except that 2-(cyclohexylamino)ethan-1-ol was used instead of 2-(propylamino)ethan-1-ol in (1) of Example 31.

MS m/z (M+H): 215.

(2)

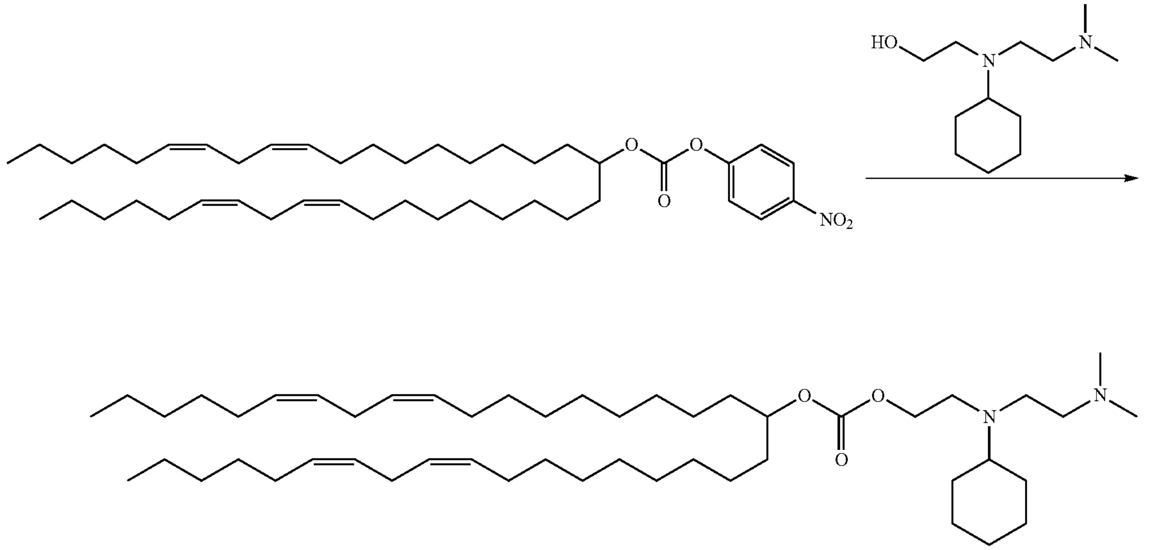

2-(Cyclohexyl(2-(dimethylamino)ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-(cyclohexyl(2-(dimethylamino)ethyl)amino)ethan-1-ol was used instead of 2-((2-(dimethylamino)ethyl)(methyl)amino)ethan-1-ol in (2) of Example 20.

$^1$H-NMR ($CDCl_3$) δ:5.45-5.25 (8H, m), 4.74-4.59 (1H, m), 4.08 (2H, t, J=6.6 Hz), 2.85-2.70 (6H, m), 2.68-2.57 (2H, m), 2.48-2.37 (1H, m), 2.37-2.29 (2H, m), 2.24 (6H, s), 2.13-1.94 (8H, m), 1.85-1.69 (4H, m), 1.66-1.49 (4H, m), 1.46-1.09 (42H, m), 0.89 (6H, t, J=6.6 Hz).

MS m/z (M+H): 770.

Example 33
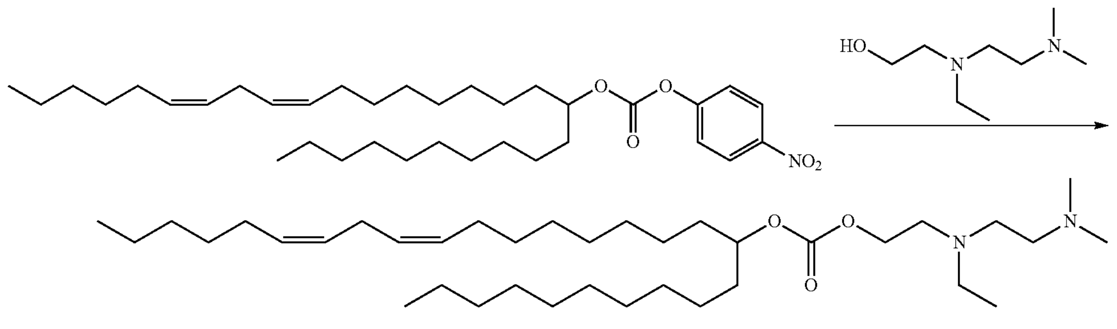
2-((2-(Dimethylamino)ethyl)(ethyl)amino)ethyl((19Z,22Z)-octacosa-19,22-dien-11-yl)carbonate as a colorless oily substance was obtained by the same method as that in (2) of Example 29, except that 2-((2-(dimethylamino)ethyl)(ethyl)amino)ethan-1-ol was used instead of 2-((2-(dimethylamino)ethyl)(methyl)amino)ethan-1-ol in (2) of Example 29.
$^1$H-NMR ($CDCl_3$) δ:5.45-5.27 (4H, m), 4.73-4.62 (1H, m), 4.18 (2H, t, J=4.8 Hz), 2.83-2.71 (4H, m), 2.67-2.55 (4H, m), 2.42-2.34 (2H, m), 2.24 (6H, s), 2.12-1.97 (4H, m), 1.67-1.47 (4H, m), 1.43-1.19 (32H, m), 1.03 (3H, t, J=5.4 Hz), 0.95-0.82 (6H, m).
MS m/z (M+H): 594.
Example 34
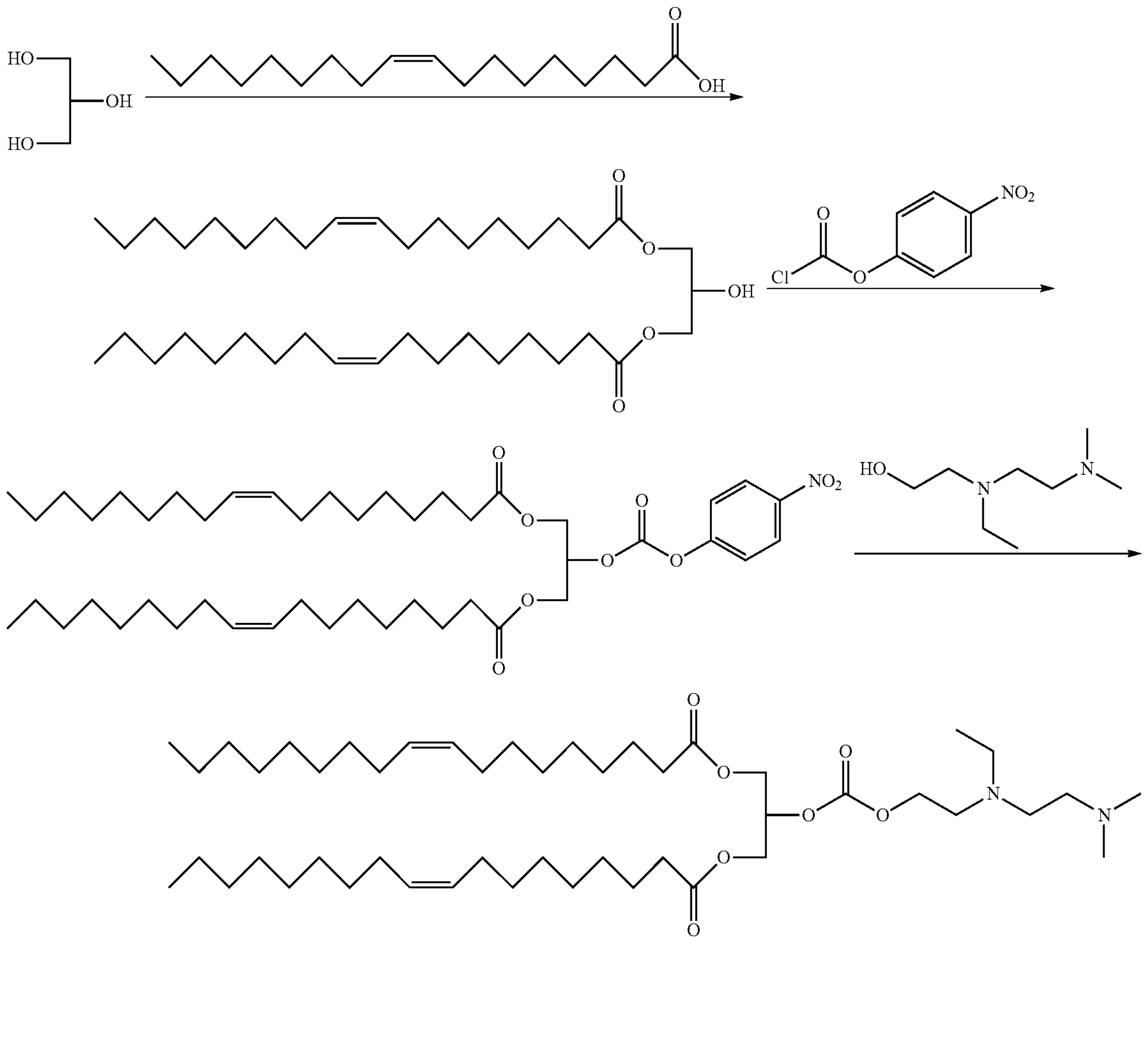

N,N'-dicyclohexylcarbodiimide (9.0 g) was added to a mixture of propane-1,2,3-triol (2.0 g), oleic acid (12.3 g), 4-dimethylaminopyridine (5.3 g), and tetrahydrofuran (100 mL), and the mixture was stirred at room temperature for 12 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 2-hydroxypropane-1,3-diyl-dioleate (2.5 g) as a colorless oily substance.

$^1$H-NMR ($CDCl_3$) δ:5.41-5.28 (4H, m), 4.22-4.04 (5H, m), 2.35 (4H, t, J=7.2 Hz), 2.05-1.97 (8H, m), 1.68-1.56 (4H, m), 1.40-1.23 (40H, m), 0.88 (6H, t, J=7.5 Hz).

4-Nitrophenyl chloroformate (246 mg) was added to a mixture of 2-hydroxypropane-1,3-diyldioleate (500 mg), triethylamine (0.34 mL), and tetrahydrofuran (5 mL), and the mixture was stirred at room temperature for 5 hours. 2-((2-(Diethylamino)ethyl)(ethyl)amino)ethan-1-ol (0.26 g), triethylamine (0.23 mL), and 4-dimethylaminopyridine (0.20 g) were added to the reaction mixture, and the reaction mixture was stirred at 70° C. for 5 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 2-(((2-((2-(dimethylamino)ethyl)(ethyl)amino)ethoxy)carbonyl)oxy)propane-1,3-diyl-dioleate (74 mg) as a colorless oily substance.

$^1$H-NMR ($CDCl_3$) δ:5.42-5.27 (4H, m), 5.13-5.04 (1H, m), 4.38-4.27 (2H, m), 4.25-4.10 (4H, m), 2.83-2.73 (2H, m), 2.67-2.54 (4H, m), 2.43-2.29 (6H, m), 2.24 (6H, s), 2.08-1.93 (8H, m), 1.68-1.46 (4H, m), 1.40-1.18 (40H, m), 1.03 (3H, t, J=5.1 Hz), 0.88 (6H, t, J=5.4 Hz).

MS m/z (M+H): 808.

Example 35

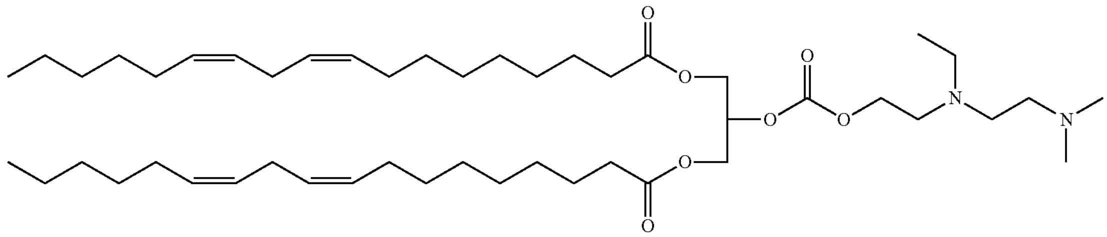 [SMILES: CCCCC/C=C\C/C=C\CCCCCCCC(=O)OCC(COC(=O)CCCCCCC/C=C\C/C=C\CCCCC)OC(=O)OCCN(CC)CCN(C)C]

2-(((2-((2-(Dimethylamino)ethyl)(ethyl)amino)ethoxy)carbonyl)oxy)propane-1,3-diyl (9Z,9'Z,12Z,12'Z)-bis(octadeca-9,12-dienoate) as a colorless oily substance was obtained by the same method as that in Example 34, except that (9Z,12Z)-octadeca-9,12-dienoic acid was used instead of oleic acid used in Example 34.

$^1$H-NMR ($CDCl_3$) δ:5.44-5.28 (8H, m), 5.13-5.03 (1H, m), 4.38-4.29 (2H, m), 4.25-4.13 (4H, m), 2.83-2.72 (6H, m), 2.66-2.55 (4H, m), 2.42-2.28 (6H, m), 2.24 (6H, s), 2.13-1.95 (8H, m), 1.68-1.50 (4H, m), 1.42-1.23 (28H, m), 1.03 (3H, t, J=5.4 Hz), 0.89 (6H, t, J=5.4 Hz).

MS m/z (M+H): 804.

Example 36

(1)

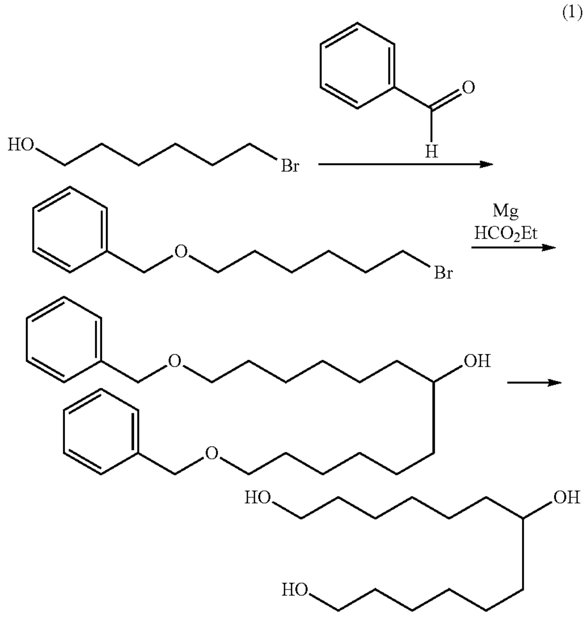

A boron trifluoride-diethyl ether complex (46.2 mL) was added to a mixture of benzaldehyde (30.0 g), 6-bromohexan-1-ol (56.1 g), triethylsilane (67.5 mL), and toluene (300 mL) under ice cooling, and the mixture was stirred at the same temperature for 40 minutes. Water was added to the reaction mixture, the organic layer was separated and washed with a saturated aqueous sodium hydrogen carbonate solution, and the solvent was distilled away under reduced pressure. The obtained residue was purified by silica gel column chromatography (ethyl acetate-hexane), thereby obtaining (((6-bromohexyl)oxy)methyl)benzene (73.5 g) as a colorless oily substance.

$^1$H-NMR ($CDCl_3$) δ:7.38-7.23 (5H, m), 4.50 (2H, s), 3.47 (2H, t, J=6.6 Hz), 3.40 (2H, t, J=6.6 Hz), 1.92-1.81 (2H, m), 1.68-1.58 (2H, m), 1.52-1.35 (4H, m).

A mixture of (((6-bromohexyl)oxy)methyl)benzene (66.7 g) and tetrahydrofuran (200 mL) was added dropwise to a mixture of magnesium (7.5 g) and tetrahydrofuran (40 mL), and the mixture was stirred at room temperature for 1 hour. A mixture of ethyl formate (8.3 g) and tetrahydrofuran (100 mL) was added to the reaction mixture under ice cooling, and the reaction mixture was stirred at the same temperature for 1 hour. The reaction mixture was poured into a 10% aqueous sulfuric acid solution (330 mL) under ice cooling, hexane (300 mL) was added thereto, the organic layer was separated and dried over anhydrous magnesium sulfate, and then the solvent was distilled away under reduced pressure. Tetrahydrofuran (200 mL), ethanol (100 mL), and a 10 mol/L aqueous potassium hydroxide solution were added to the obtained residue, and the mixture was stirred at 40° C. for 1 hour. Hexane (200 mL) and water (100 mL) were added to the reaction mixture, the organic layer was separated and then dried over anhydrous magnesium sulfate, and the solvent was distilled away under reduced pressure. The obtained residue was purified by silica gel column chromatography (ethyl acetate-hexane), thereby obtaining 1,13-bis(benzyloxy)tridecan-7-ol (25.3 g) as a colorless oily substance.

$^1$H-NMR ($CDCl_3$) δ:7.36-7.24 (10H, m), 4.50 (4H, s), 3.61-3.54 (1H, m), 3.46 (4H, t, J=6.6 Hz), 1.68-1.56 (4H, m), 1.48-1.26 (16H, m).

A mixture of 1,13-bis(benzyloxy)tridecan-7-ol (24.0 g), 10% palladium hydroxide-carbon (10.0 g), and methanol (240 mL) was stirred at 50° C. for 3 hours in a hydrogen atmosphere. The reaction mixture was cooled to room temperature, the insoluble matters were filtered off using celite, and then the solvent was distilled away under reduced pressure. Ethyl acetate (40 mL) was added to the obtained residue, and solids were collected by filtration, washed with ethyl acetate, and then dried under reduced pressure, thereby obtaining tridecane-1,7,13-triol (11.7 g) as white solids.

$^1$H-NMR ($CDCl_3$) δ:3.70-3.55 (5H, m), 1.64-1.24 (20H, m).

washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 7-hydroxytridecane-1,3-diyldioleate (3.6 g) as a colorless oily substance.

$^1$H-NMR ($CDCl_3$) δ:5.41-5.28 (4H, m), 4.06 (4H, t, J=6.6 Hz), 3.63-3.53 (1H, m), 2.29 (4H, t, J=7.2 Hz), 2.06-1.96 (8H, m), 1.68-1.20 (64H, m), 0.88 (6H, t, J=7.2 Hz).

4-Nitrophenyl chloroformate (161 mg) was added to a mixture of 7-hydroxytridecane-1,3-diyldioleate (400 mg), triethylamine (0.22 mL), and tetrahydrofuran (4 mL), and the mixture was stirred at room temperature for 5 hours. 2-((2-(Dimethylamino)ethyl)(ethyl)amino)ethan-1-ol (0.26 g), triethylamine (0.22 mL), and 4-dimethylaminopyridine (0.19 g) were added to the reaction mixture, and the reaction mixture was stirred at 70° C. for 4 hours. Water and ethyl acetate were added to the reaction mixture, the organic layer was separated and washed with a saturated aqueous sodium chloride solution, and then the solvent was distilled away under reduced pressure. The obtained residue was purified by silica gel column chromatography (methanol-ethyl acetate) and silica gel column chromatography (ethyl acetate-hexane, NH silica gel), thereby obtaining 7-(((2-((2-(dimethylamino)ethyl)(ethyl)amino)ethoxy)carbonyl)oxy)tridecane-1,13-diyldioleate (138 mg) as a colorless oily substance.

(2)

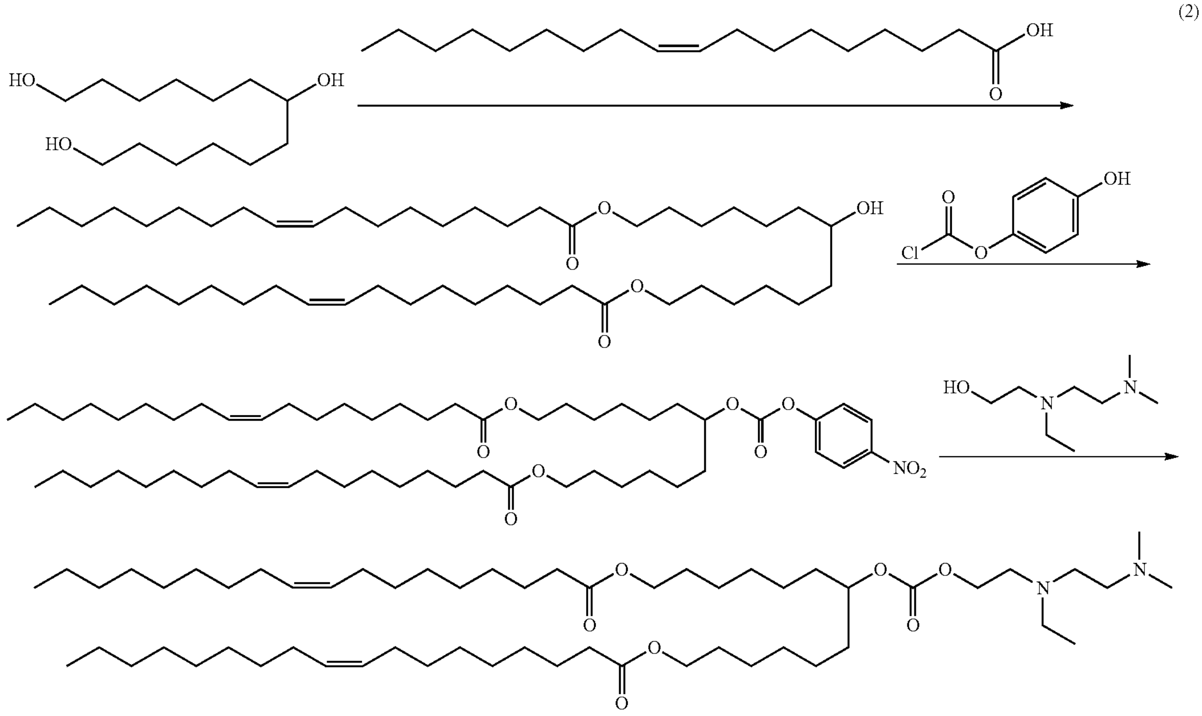

1-Ethyl-3-(3-dimethylaminopropyl)carbodiimide hydrochloride (10.3 g) was added to a mixture of tridecane-1,7,13-triol (5.0 g), oleic acid (13.4 g), triethylamine (18.2 mL), 4-dimethylaminopyridine (0.26 g), and N,N-dimethylformamide (25 mL), and the mixture was stirred at room temperature for 15 hours. Water and ethyl acetate were added to the reaction mixture, the organic layer was separated, $^1$H-NMR ($CDCl_3$) δ:5.41-5.26 (4H, m), 4.72-4.63 (1H, m), 4.18 (2H, t, J=6.4 Hz), 4.04 (4H, t, J=6.8 Hz), 2.77 (2H, t, J=6.8 Hz), 2.66-2.56 (4H, m), 2.43-2.34 (2H, m), 2.34-2.25 (4H, m), 2.24 (6H, s), 2.09-1.94 (8H, m), 1.70-1.47 (12H, m), 1.44-1.19 (52H, m), 1.03 (3H, t, J=7.2), 0.88 (6H, t, J=6.8 Hz).

MS m/z (M+H): 948.

Example 37

(1)

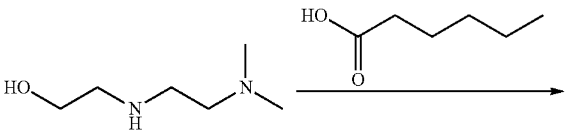

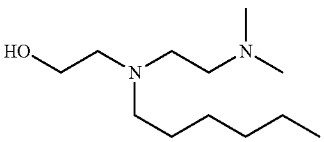

Sodium triacetoxyborohydride (1.8 g) was added to a mixture of 2-((2-(dimethylamino)ethyl)amino)ethan-1-ol (250 mg), hexanal (0.35 mL), acetic acid (0.16 mL), and tetrahydrofuran (2.5 mL), and the mixture was stirred at room temperature for 2 hours. Methanol was added to the reaction mixture under ice cooling, and the reaction mixture was purified by silica gel column chromatography (ethyl acetate-hexane, NH silica gel), thereby obtaining 2-((2-(dimethylamino)ethyl)(hexyl)amino)ethane-1-ol (400 mg) as a colorless oily substance.

MS m/z (M+H): 217.

(2)

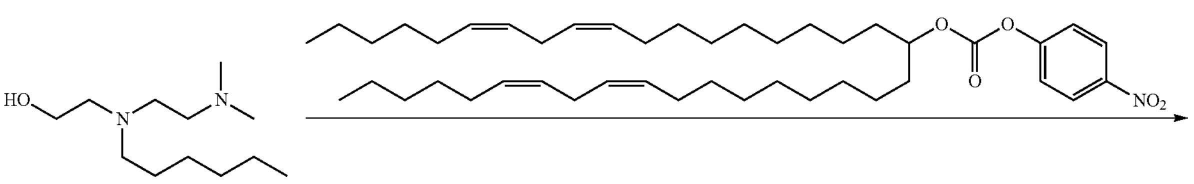

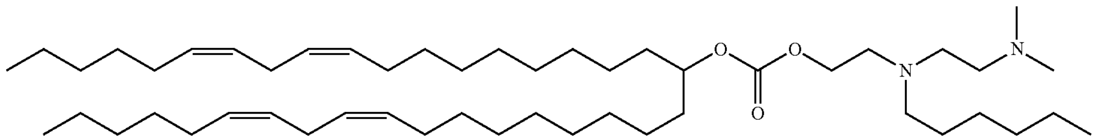

2-((2-(Dimethylamino)ethyl)(hexyl)amino)ethyl((6Z,9Z,28Z,31Z)-heptatriaconta-6,9, 28,31-tetraen-19-yl)carbonate as a colorless oily substance was obtained by the same method as that in (2) of Example 20, except that 2-((2-(dimethylamino)ethyl)(hexyl)amino)ethan-1-ol was used instead of 2-((2-(dimethylamino)ethyl)(methyl)amino) ethan-1-ol in (2) of Example 20.

$^1$H-NMR ($CDCl_3$) δ:5.45-5.27 (8H, m), 4.72-4.62 (1H, m), 4.17 (2H, t, J=6.4 Hz), 2.84-2.71 (6H, m), 2.65-2.57 (2H, m), 2.53-2.54 (2H, m), 2.41-2.32 (2H, m), 2.23 (6H, s), 2.12-1.97 (8H, m), 1.68-1.49 (4H, m), 1.48-1.20 (44H, m), 0.97-0.83 (9H, m).

MS m/z (M+H): 772.

Example 38

(1)

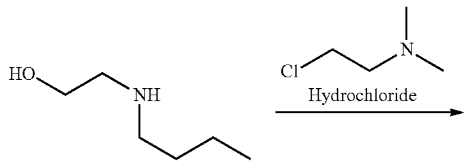

-continued

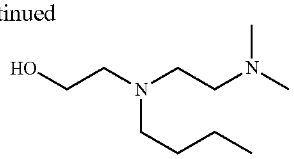

2-(Butyl(2-(dimethylamino)ethyl)amino)ethan-1-ol as a yellow oily substance was obtained by the same method as that in (1) of Example 31, except that 2-(butylamino)ethan-1-ol was used instead of 2-(propylamino)ethan-1-ol in (1) of Example 31.

MS m/z (M+H): 189.

(2)

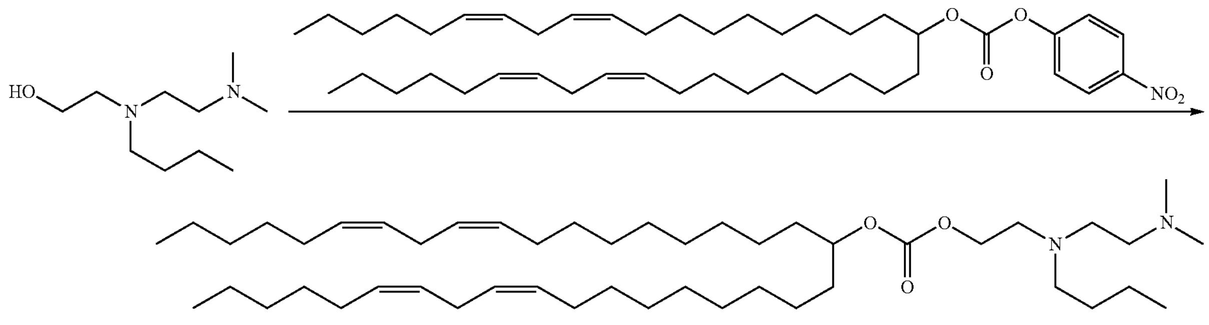

2-(Butyl(2-(dimethylamino)ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-(butyl(2-(dimethylamino)ethyl)amino)ethan-1-ol was used instead of 2-((2-(dimethylamino)ethyl)(methyl)amino)ethan-1-ol in (2) of Example 20.

$^1$H-NMR ($CDCl_3$) δ:5.44-5.26 (8H, m), 4.72-4.61 (1H, m), 4.17 (2H, t, J=6.4 Hz), 2.84-2.71 (6H, m), 2.67-2.57 (2H, m), 2.54-2.44 (2H, m), 2.42-2.33 (2H, m), 2.23 (6H, s), 2.12-1.96 (8H, m), 1.67-1.48 (4H, m), 1.48-1.19 (40H, m), 0.97-0.84 (9H, m).

MS m/z (M+H): 744.

Example 39

(1)

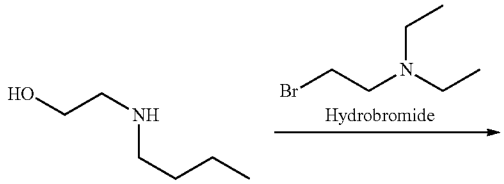

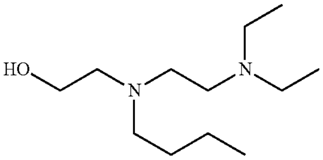

2-(Butyl(2-(diethylamino)ethyl)amino)ethan-1-ol as a light yellow oily substance was obtained by the same method as that in (1) of Example 30, except that 2-(butylamino)ethan-1-ol was used instead of 2-(ethylamino)ethan-1-ol in (1) of Example 30.

MS m/z (M+H): 217.

(2)

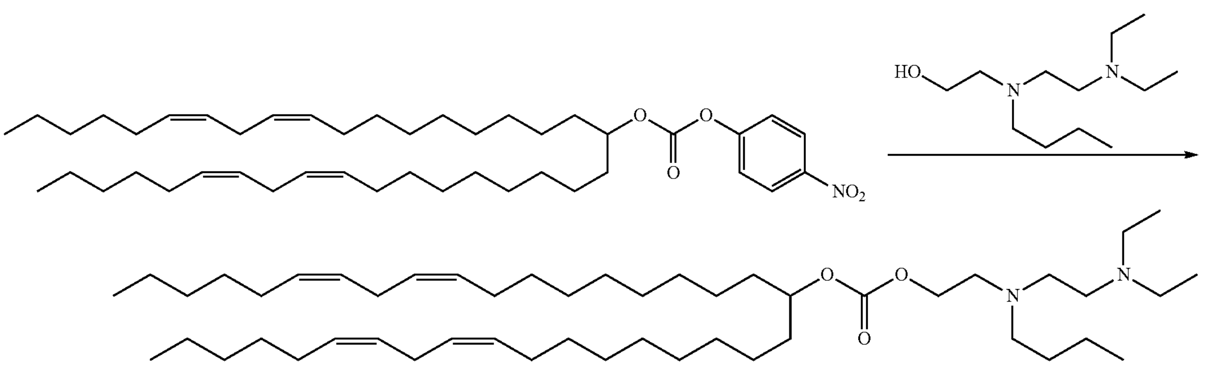

2-(Butyl(2-(diethylamino)ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-(butyl(2-(diethylamino)ethyl)amino)ethan-1-ol was used instead of 2-((2-(dimethylamino)ethyl)(methyl)amino)ethan-1-ol in (2) of Example 20.

$^1$H-NMR ($CDCl_3$) δ:5.43-5.28 (8H, m), 4.71-4.62 (1H, m), 4.16 (2H, t, J=6.4 Hz), 2.83-2.70 (6H, m), 2.65-2.43 (10H, m), 2.11-1.96 (8H, m), 1.65-1.49 (4H, m), 1.46-1.19 (40H, m), 1.02 (6H, t, J=7.2 Hz), 0.96-0.83 (9H, m).

MS m/z (M+H): 772.

Example 40

(1)

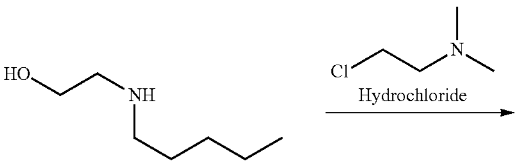

-continued

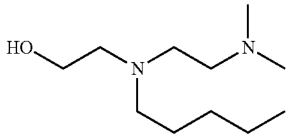

2-((2-(Dimethylamino)ethyl)(pentyl)amino)ethan-1-ol as a brown oily substance was obtained by the same method as that in (1) of Example 31, except that 2-(pentylamino)ethan-1-ol was used instead of 2-(propylamino)ethan-1-ol in (1) of Example 31.

MS m/z (M+H): 203.

(2)

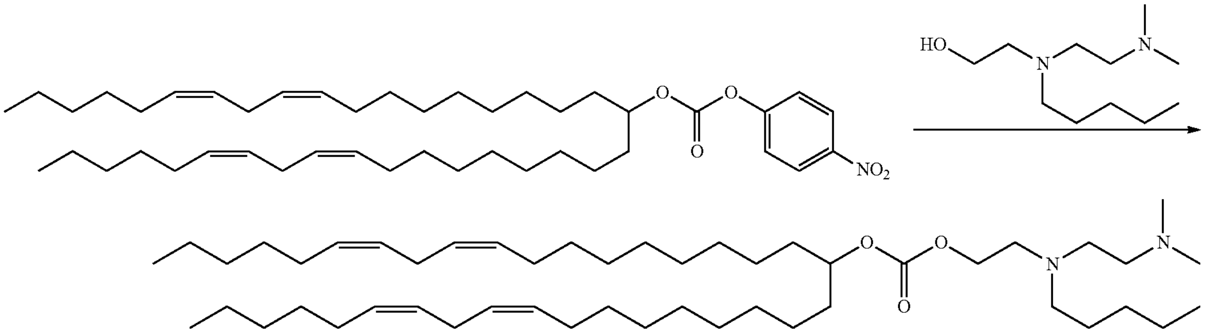

2-((2-(Dimethylamino)ethyl)(pentyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(dimethylamino)ethyl)(pentyl)amino)ethan-1-ol was used instead of 2-((2-(dimethylamino)ethyl)(methyl)amino)ethan-1-ol in (2) of Example 20.

$^1$H-NMR ($CDCl_3$) δ:5.43-5.26 (8H, m), 4.72-4.61 (1H, m), 4.17 (2H, t, J=6.0 Hz), 2.83-2.70 (6H, m), 2.65-2.57 (2H, m), 2.53-2.43 (2H, m), 2.41-2.32 (2H, m), 2.23 (6H, s), 2.11-1.97 (8H, m), 1.65-1.49 (4H, m), 1.48-1.19 (42H, m), 0.95-0.83 (9H, m).

MS m/z (M+H): 758.

Example 41

(1)

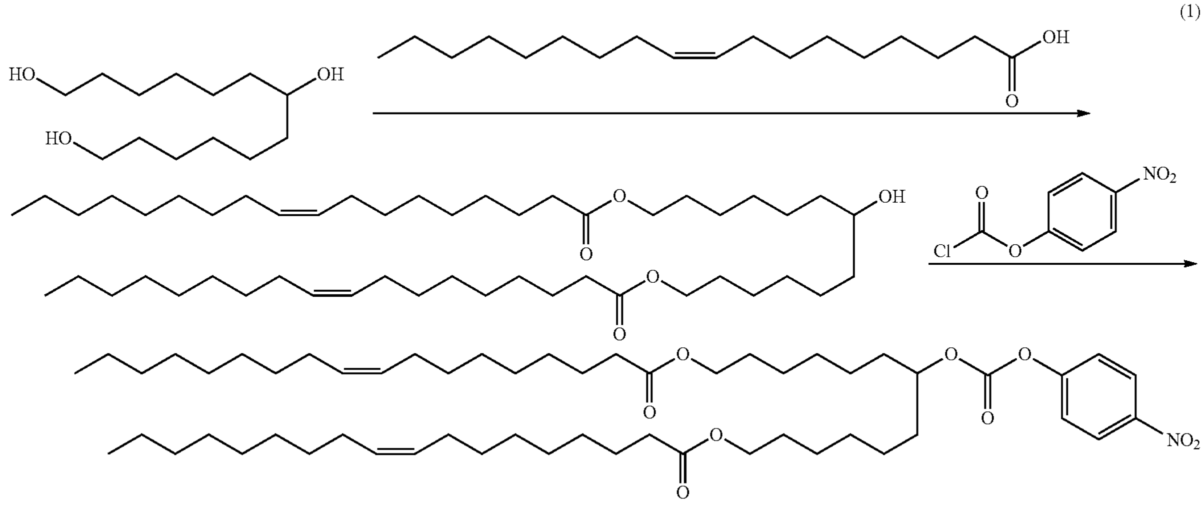

1-Ethyl-3-(3-dimethylaminopropyl)carbodiimide hydrochloride (10.3 g) was added to a mixture of tridecane-1,7,13-triol (5.0 g), oleic acid (13.4 g), triethylamine (18.2 mL), 4-dimethylaminopyridine (0.26 g), and N,N-dimethylformamide (25 mL), and the mixture was stirred at room temperature for 15 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 7-hydroxytridecane-1,3-diyldioleate (3.6 g) as a colorless oily substance.

$^1$H-NMR ($CDCl_3$) δ:5.41-5.28 (4H, m), 4.06 (4H, t, J=6.6 Hz), 3.63-3.53 (1H, m), 2.29 (4H, t, J=7.2 Hz), 2.06-1.96 (8H, m), 1.68-1.20 (64H, m), 0.88 (6H, t, J=7.2 Hz).

4-Nitrophenyl chloroformate (1.4 g) was added to a mixture of 7-hydroxytridecane-1,3-diyldioleate (3.6 g), triethylamine (2.0 mL), and tetrahydrofuran (36 mL), and the mixture was stirred at room temperature for 1 hour. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 7-(((4-nitrophenoxy)carbonyl)oxy)tridecane-1,13-diyldioleate (4.1 g) as a light yellow oily substance.

$^1$H-NMR ($CDCl_3$) δ:8.28 (2H, dd, J=7.2H, 2.1 Hz), 7.39 (2H, dd, J=7.2 Hz, 2.1 Hz), 5.40-5.28 (4H, m), 4.86-4.76 (1H, m), 4.06 (4H, t, J=6.6 Hz), 2.29 (4H, t, J=7.2 Hz), 2.05-1.96 (8H, m), 1.74-1.56 (12H, m), 1.42-1.21 (52H, m), 0.88 (6H, t, J=7.2 Hz).

(2)

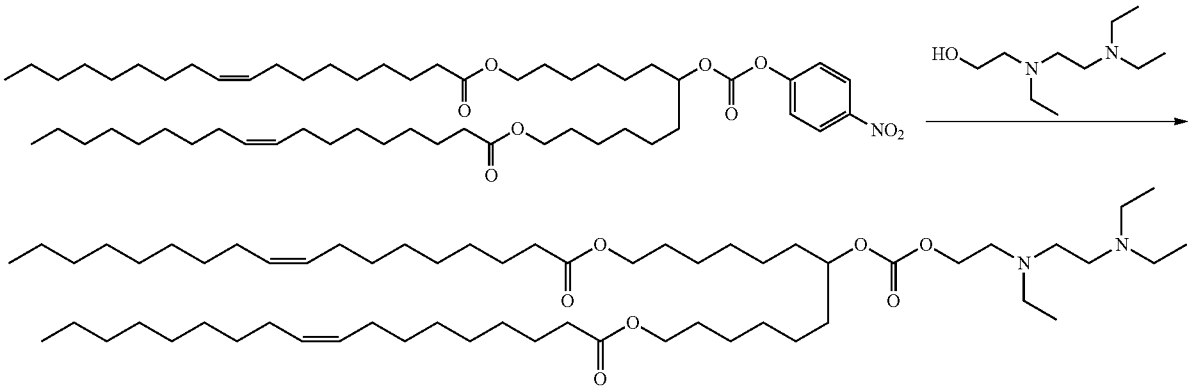

4-Dimethylaminopyridine (0.79 g) was added to a mixture of 7-(((4-nitrophenoxy)carbonyl)oxy)tridecane-1,13-diyldioleate (2.0 g), 2-((2-(diethylamino)ethyl)(ethyl)amino)ethan-1-ol (1.2 g), triethylamine (0.91 mL), and tetrahydrofuran (20 mL), and the mixture was stirred and heated under reflux for 8 hours. The reaction mixture was cooled to room temperature, water and ethyl acetate were added thereto, the organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 7-(((2-((2-(diethylamino)ethyl)(ethyl)amino)ethoxy)carbonyl)oxy)tridecane-1,13-diyldioleate (1.7 g) as a colorless oily substance.

$^{1}$H-NMR ($CDCl_3$) δ:5.39-5.27 (4H, m), 4.71-4.62 (1H, m), 4.17 (2H, t, J=6.4 Hz), 4.04 (4H, t, J=6.8 Hz), 2.76 (2H, t, J=6.0 Hz), 2.66-2.46 (10H, m), 2.29 (4H, t, J=7.6 Hz), 2.08-1.94 (8H, m), 1.69-1.48 (12H, m), 1.41-1.19 (52H, m), 1.07-0.97 (9H, m), 0.88 (6H, t, J=7.2 Hz).

MS m/z (M+H): 976.

Example 42

(1)

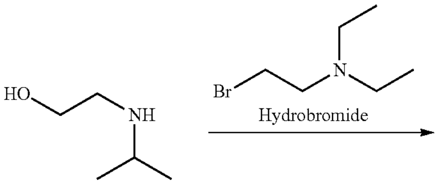

-continued

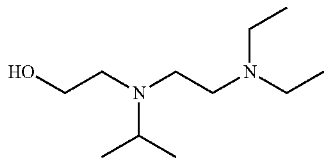

Potassium carbonate (8.0 g) was added to a mixture of 2-(isopropylamino)ethan-1-ol (2.0 g), 2-bromo-N,N-diethylethan-1-amine hydrobromide (7.6 g), and ethanol (20 mL), and the mixture was stirred and heated under reflux for 7 hours. The reaction mixture was cooled to room temperature, the insoluble matters were filtered off, and the solvent was distilled away under reduced pressure. The obtained residue was purified by silica gel column chromatography (ethyl acetate-hexane, NH silica gel), thereby obtaining 2-((2-(diethylamino)ethyl)(isopropyl)amino)ethan-1-ol (3.5 g) as a light yellow oily substance.

MS m/z (M+H): 203.

(2)

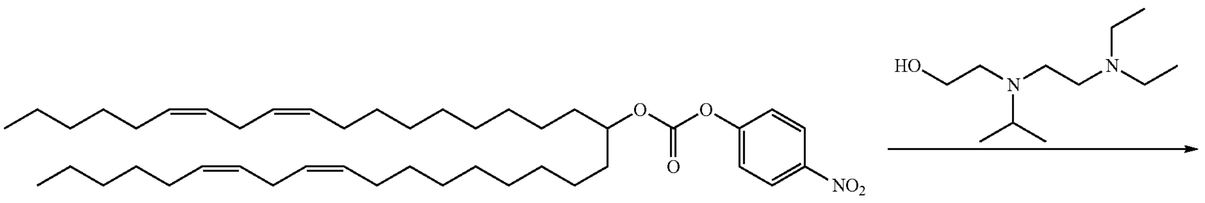

-continued

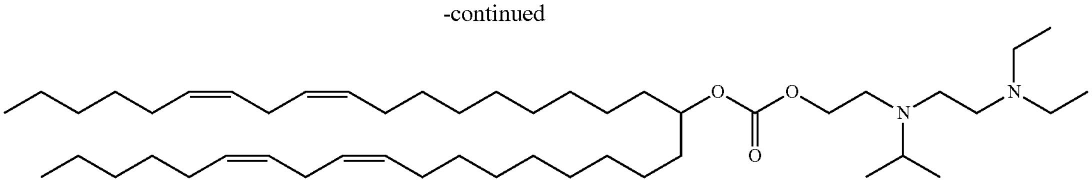

2-((2-(Diethylamino)ethyl)(isopropyl)amino)ethyl((6Z, 9Z,28Z,31Z)-heptatriaconta-6, 9,28,31-tetraen-19-yl)carbonate as a colorless oily substance was obtained by the same method as that in (2) of Example 20, except that 2-((2-(diethylamino)ethyl)(isopropyl)amino)ethan-1-ol was used instead of 2-((2-(dimethylamino)ethyl)(methyl)amino) ethan-1-ol in (2) of Example 20.

$^1$H-NMR ($CDCl_3$) δ:5.45-5.27 (8H, m), 4.72-4.61 (1H, m), 4.10 (2H, t, J=6.8 Hz), 2.96-2.85 (1H, m), 2.83-2.74 (4H, m), 2.68 (2H, t, J=6.8 Hz), 2.60-2.41 (8H, m), 2.12-1.96 (8H, m), 1.65-1.48 (4H, m), 1.45-1.19 (36H, m), 1.10-0.95 (12H, m), 0.89 (6H, t, J=6.8 Hz).

MS m/z (M+H): 758.

Example 43

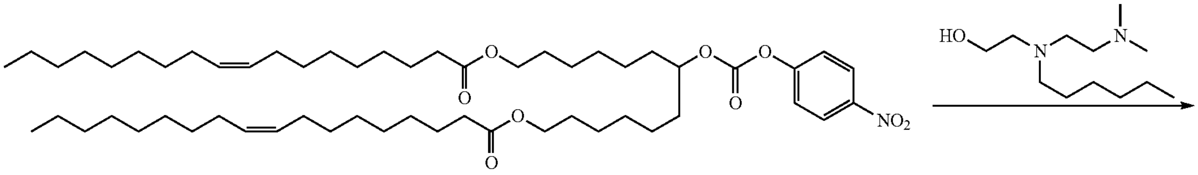

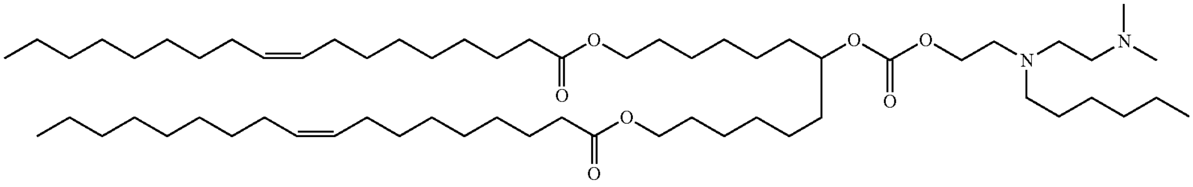

7-(((2-((2-(Dimethylamino)ethyl)(hexyl)amino)ethoxy) carbonyl)oxy)tridecane-1,13-diyldioleate) as a colorless oily substance was obtained by the same method as that in (2) of Example 41, except that 2-((2-(dimethylamino)ethyl)(hexyl) amino)ethan-1-ol was used instead of 2-((2-(diethylamino) ethyl)(ethyl)amino)ethan-1-ol in (2) of Example 41.

$^1$H-NMR ($CDCl_3$) δ:5.42-5.26 (4H, m), 4.73-4.60 (1H, m), 4.17 (2H, t, J=5.7 Hz), 4.04 (4H, t, J=6.6 Hz), 2.76 (2H, t, J=6.6 Hz), 2.67-2.56 (2H, m), 2.55-2.44 (2H, m), 2.42-2.34 (2H, m), 2.29 (4H, t, J=7.5 Hz), 2.23 (6H, s), 2.10-1.93 (8H, m), 1.69-1.49 (12H, m), 1.48-1.19 (60H, m), 0.95-0.81 (9H, m).

MS m/z (M+H): 1004.

Example 44

(1)

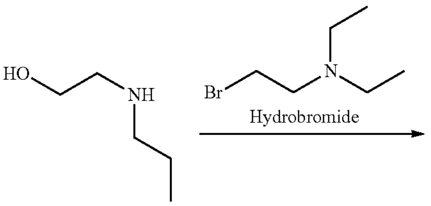

-continued

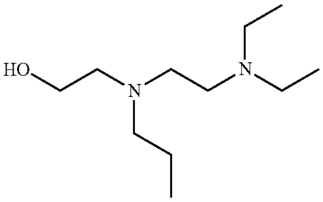

2-((2-(Diethylamino)ethyl)(propyl)amino)ethan-1-ol as a light yellow oily substance was obtained by the same method as that in (1) of Example 30, except that 2-(propylamino)ethan-1-ol was used instead of 2-(ethylamino)ethan-1-ol in (1) of Example 30.

MS m/z (M+H): 203.

(2)

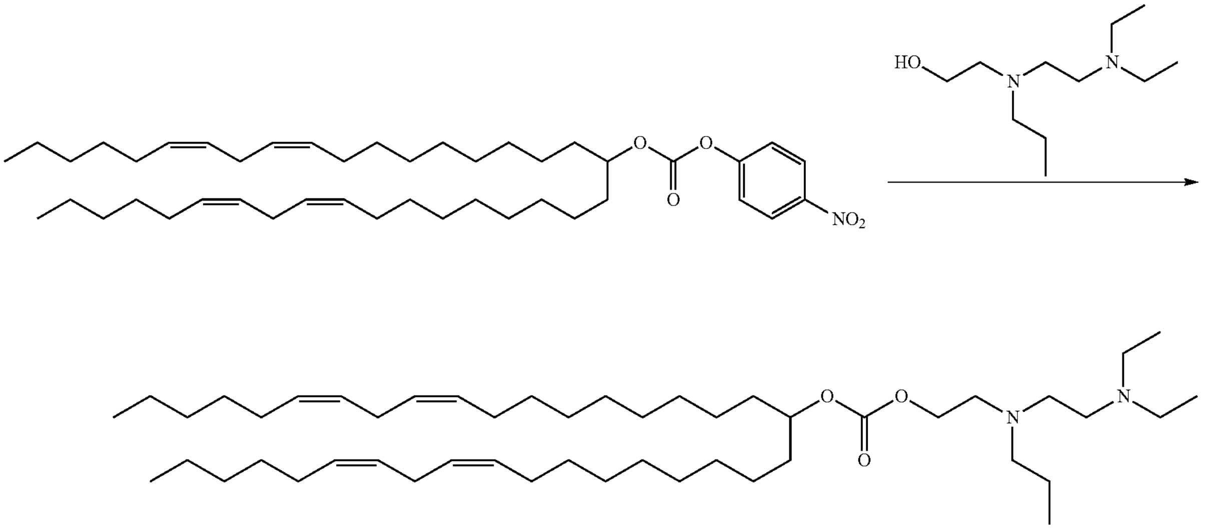

2-((2-(Diethylamino)ethyl)(propyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(diethylamino)ethyl)(propyl)amino)ethan-1-ol was used instead of 2-((2-(dimethylamino)ethyl)(methyl)amino)ethan-1-ol in (2) of Example 20.

$^1$H-NMR ($CDCl_3$) δ:5.46-5.24 (8H, m), 4.73-4.61 (1H, m), 4.16 (2H, t, J=6.6 Hz), 2.83-2.70 (6H, m), 2.65-2.41 (10H, m), 2.11-1.96 (8H, m), 1.64-1.51 (4H, m), 1.49-1.21 (38H, m), 1.02 (6H, t, J=7.2 Hz), 0.95-0.81 (9H, m).

MS m/z (M+H): 758.

Example 45

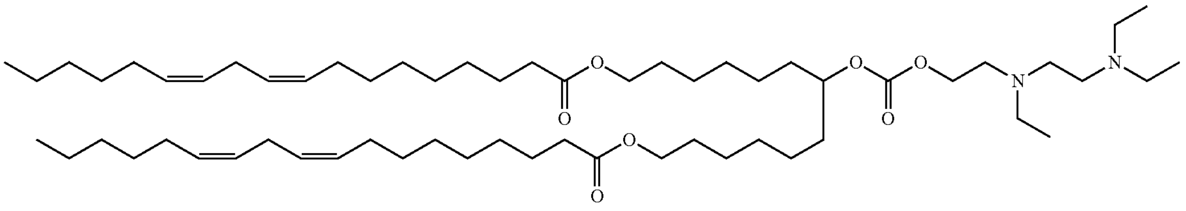 [SMILES: CCCCC/C=C\C/C=C\CCCCCCCC(=O)OCCCCCCC(CCCCCCOC(=O)CCCCCCC/C=C\C/C=C\CCCCC)OC(=O)OCCN(CC)CCN(CC)CC]

7-(((2-((2-(Diethylamino)ethyl)(ethyl)amino)ethoxy)carbonyl)oxy)tridecane-1,13-diyl (9Z,9'Z,12Z,12'Z)-bis(octadeca-9,12-dienoate) as a colorless oily substance was obtained by the same method as that in (1) and (2) of Example 41, except that (9Z,12Z)-octadeca-9,12-dienoic acid was used instead of oleic acid in (1) and (2) of Example 41.

$^1$H-NMR ($CDCl_3$) δ:5.46-5.24 (8H, m), 4.73-4.61 (1H, m), 4.17 (2H, t, J=6.6 Hz), 4.04 (4H, t, J=6.6 Hz), 2.83-2.71 (6H, m), 2.66-2.47 (10H, m), 2.29 (4H, t, J=8.1 Hz), 2.13-1.96 (8H, m), 1.69-1.50 (12H, m), 1.44-1.21 (40H, m), 1.08-0.97 (9H, m), 0.89 (6H, t, J=6.6 Hz).

MS m/z (M+H): 972.

Example 46

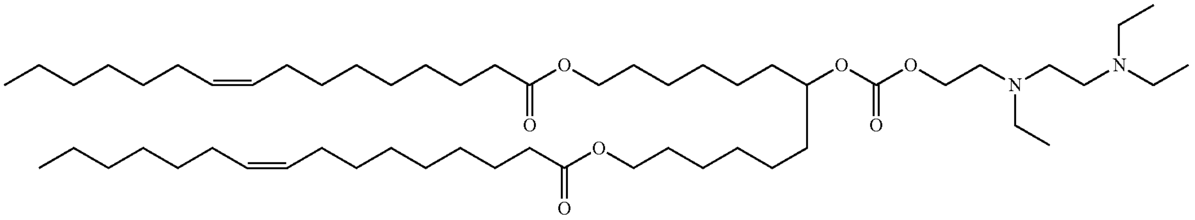 [SMILES: CCCCCC/C=C\CCCCCCCC(=O)OCCCCCCC(CCCCCCOC(=O)CCCCCCC/C=C\CCCCCC)OC(=O)OCCN(CC)CCN(CC)CC]

7-(((2-((2-(Diethylamino)ethyl)(ethyl)amino)ethoxy)carbonyl)oxy)tridecane-1,13-diyl (9Z,9'Z)-bis(hexadec-9-enoate) as a colorless oily substance was obtained by the same method as that in (1) and (2) of Example 41, except that (Z)-hexadec-9-enoic acid was used instead of oleic acid in (1) and (2) of Example 41.

$^1$H-NMR ($CDCl_3$) δ:5.40-5.27 (4H, m), 4.73-4.61 (1H, m), 4.17 (2H, t, J=6.6 Hz), 4.04 (4H, t, J=6.6 Hz), 2.76 (2H, t, J=6.6 Hz), 2.66-2.45 (10H, m), 2.29 (4H, t, J=7.2 Hz), 2.09-1.93 (8H, m), 1.70-1.48 (12H, m), 1.43-1.20 (44H, m), 1.11-0.97 (9H, m), 0.88 (6H, t, J=6.6 Hz).

MS m/z (M+H): 920.

Example 47

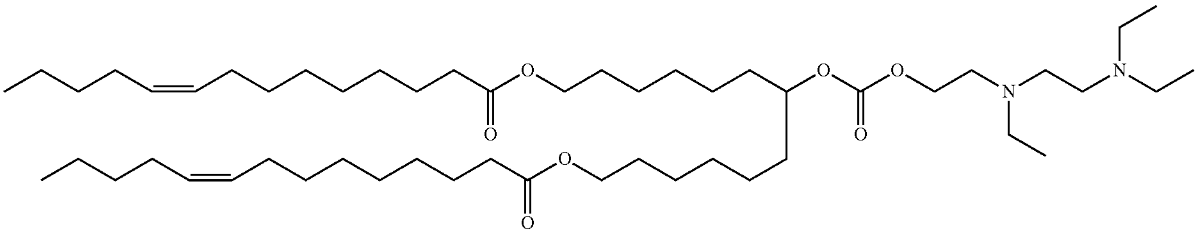 [SMILES: CCCC/C=C\CCCCCCCC(=O)OCCCCCCC(CCCCCCOC(=O)CCCCCCC/C=C\CCCC)OC(=O)OCCN(CC)CCN(CC)CC]

7-(((2-((2-(Diethylamino)ethyl)(ethyl)amino)ethoxy)carbonyl)oxy)tridecane-1,13-diyl (9Z,9'Z)-bis(tetradec-9-enoate) as a colorless oily substance was obtained by the same method as that in (1) and (2) of Example 41, except that (Z)-tetradec-9-enoic acid was used instead of oleic acid in (1) and (2) of Example 41.

$^1$H-NMR ($CDCl_3$) δ:5.44-5.24 (4H, m), 4.73-4.61 (1H, m), 4.17 (2H, t, J=6.0 Hz), 4.04 (4H, t, J=6.6 Hz), 2.76 (2H, t, J=6.6 Hz), 2.67-2.46 (10H, m), 2.29 (4H, t, J=7.8 Hz), 2.11-1.92 (8H, m), 1.71-1.47 (12H, m), 1.45-1.21 (36H, m), 1.09-0.96 (9H, m), 0.95-0.83 (6H, m).

MS m/z (M+H): 864.

Example 48

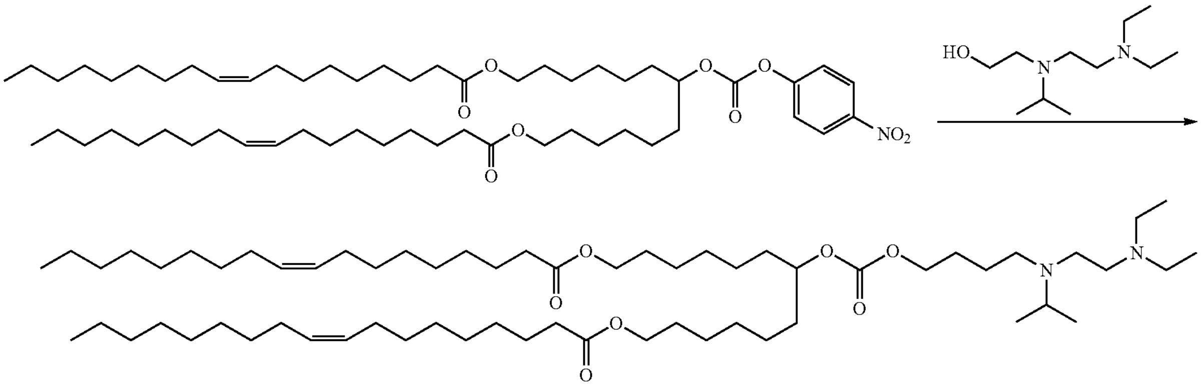

7-(((2-((2-(Diethylamino)ethyl)(isopropyl)amino)ethoxy)carbonyl)oxy)tridecane-1,13-diyldioleate as a colorless oily substance was obtained by the same method as that in (1) and (2) of Example 41, except that 2-((2-(diethylamino)ethyl)(isopropyl)amino)ethan-1-ol was used instead of 2-((2-(diethylamino)ethyl)(ethyl)amino)ethan-1-ol in (1) and (2) of Example 41.

$^1$H-NMR ($CDCl_3$) δ:5.41-5.27 (4H, m), 4.72-4.61 (1H, m), 4.17-3.99 (6H, m), 2.95-2.86 (1H, m), 2.68 (2H, t, J=6.4 Hz), 2.60-2.42 (8H, m), 2.28 (4H, t, J=8.0 Hz), 2.08-1.93 (8H, m), 1.69-1.48 (12H, m), 1.43-1.20 (52H, m), 1.09-0.95 (12H, m), 0.88 (6H, t, J=6.8 Hz).

MS m/z (M+H): 990.

Example 49

(1)

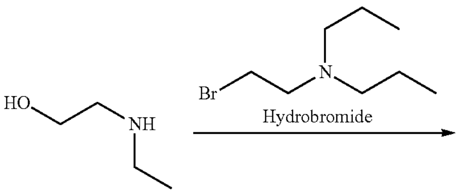

-continued

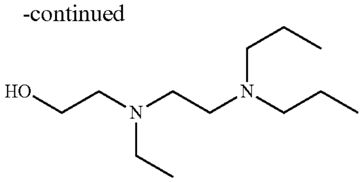

2-((2-(Dipropylamino)ethyl)(ethyl)amino)ethan-1-ol as a colorless oily substance was obtained by the same method as that in (1) of Example 30, except that N-(2-bromoethyl)-N-propylpropan-1-amine hydrobromide was used instead of 2-bromo-N,N-diethylethan-1-amine hydrobromide in (1) of Example 30.

MS m/z (M+H): 217.

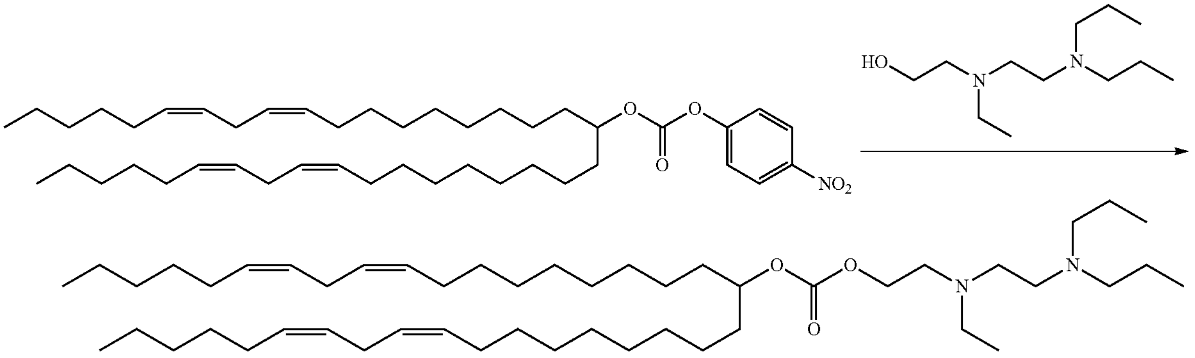

2-((2-(Dipropylamino)ethyl)(ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-((2-(dipropylamino)ethyl)(ethyl)amino)ethan-1-ol was used instead of 2-((2-(dimethylamino)ethyl)(methyl)amino)ethan-1-ol in (2) of Example 20.

$^1$H-NMR ($CDCl_3$) δ:5.45-5.26 (8H, m), 4.74-4.61 (1H, m), 4.17 (2H, t, J=6.0 Hz), 2.84-2.70 (6H, m), 2.65-2.46 (6H, m), 2.43-2.31 (4H, m), 2.13-1.97 (8H, m), 1.66-1.52 (4H, m), 1.50-1.21 (40H, m), 1.03 (3H, t, J=6.6 Hz), 0.95-0.80 (12H, m).

MS m/z (M+H): 772.

Example 50

(1)

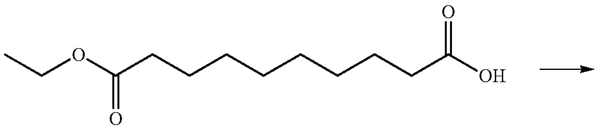

-continued

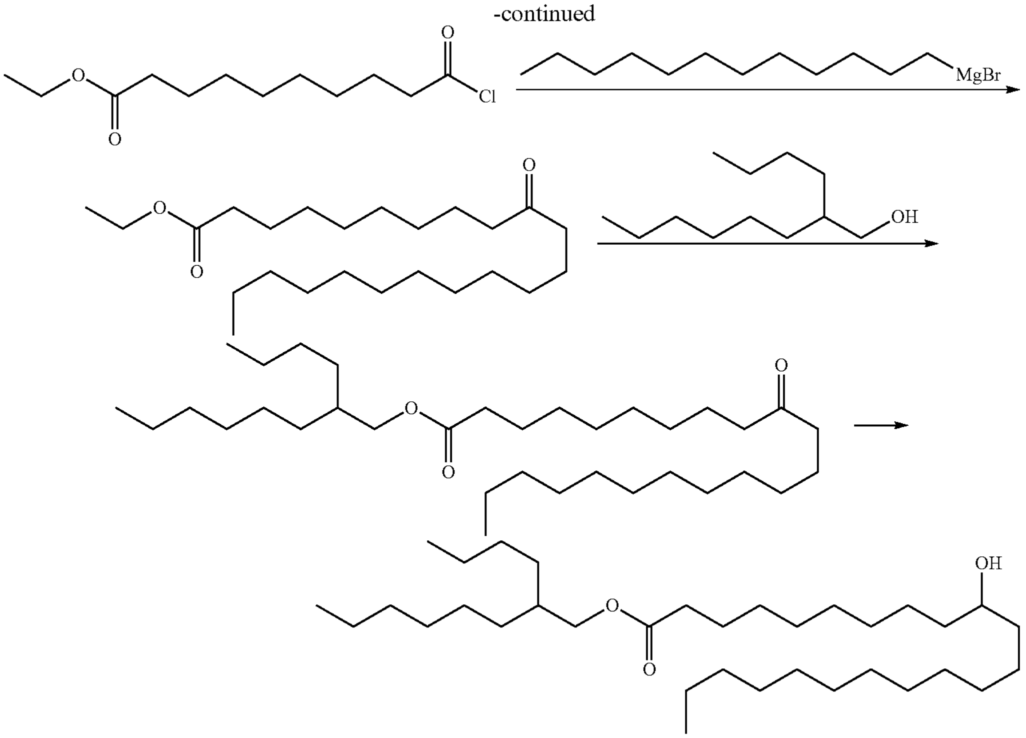

A mixture of 10-ethoxy-10-oxodecanoic acid (22.0 g), thionyl chloride (22.0 mL), and N,N-dimethylformamide (0.1 mL) was stirred and heated under reflux for 1 hour and 30 minutes. The solvent was distilled away under reduced pressure, thereby obtaining ethyl 10-chloro-10-oxodecanoate in the form of a light yellow oily substance as a crude product.

A 1.0 mol/L dodecyl magnesium bromide-diethyl ether solution (190 mL) was added dropwise to a tetrahydrofuran (284 mL) suspension of zinc (II) chloride (13.0 g) at −78° C., and the mixture was heated to 0° C. and then stirred at the same temperature for 30 minutes. Tetrakis(triphenylphosphine)palladium(0) (2.8 g) and ethyl 10-chloro-10-oxodecanoate were added to the reaction mixture, and the reaction mixture was stirred at 0° C. for 1 hour. A 1.0 mol/L aqueous hydrochloric acid solution (50 mL) and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining ethyl 10-oxodocosanoate (13.2 g) as a brown oily substance.

Tetraisopropyl orthotitanate (1.7 g) was added to a mixture of ethyl 10-oxodocosanoate (22.0 g) and 2-butyloctan-1-ol (31.9 g), and the mixture was stirred at 110° C. for 17 hours. Water and ethyl acetate were added to the reaction mixture, the organic layer was separated and dried over anhydrous sodium sulfate, and then the solvent was distilled away under reduced pressure. The obtained residue was purified by silica gel column chromatography (ethyl acetate-hexane), thereby obtaining 2-butyloctyl 10-oxodocosanoate (11.7 g) as light yellow solids.

Sodium borohydride (4.2 g) was added to a mixture of 2-butyloctyl 10-oxodocosanoate (11.7 g), methanol (47 mL), and tetrahydrofuran (47 mL) under ice cooling, and the mixture was stirred at room temperature for 1 hour. The reaction mixture was poured into a mixture of ice and water, a 1.0 mol/L aqueous hydrochloric acid solution (22 mL) was added thereto, the organic layer was separated and dried over anhydrous sodium sulfate, and then the solvent was distilled away under reduced pressure. The obtained residue was purified by silica gel column chromatography (ethyl acetate-hexane), thereby obtaining 2-butyloctyl 10-hydroxydocosanoate (7.8 g) as white solids.

$^{1}$H-NMR ($CDCl_3$) δ: 3.96-3.98 (2H, d), 3.58 (1H, s), 2.27-2.31 (2H, t), 1.60-1.63 (2H, t), 1.38-1.43 (6H, d), 1.26-1.29 (46H, m), 0.86-0.89 (9H, m).

(2)

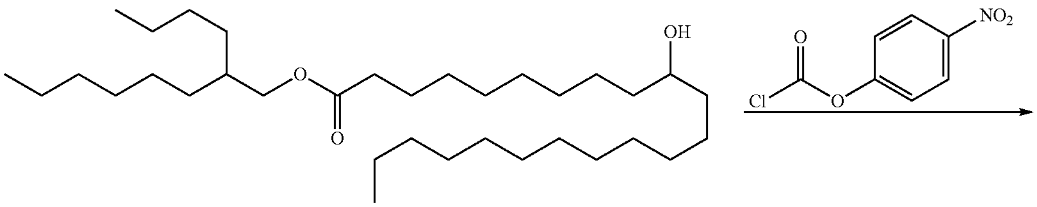

-continued

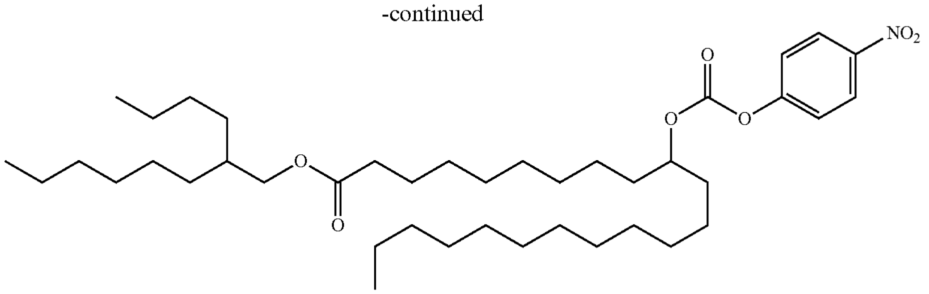

4-Nitrophenyl chloroformate (408 mg) was added to a mixture of 2-butyloctyl 10-hydroxydocosanoate (500 mg), triethylamine (0.43 mL), and tetrahydrofuran (5 mL), and the mixture was stirred at room temperature for 3 hours. Water and ethyl acetate were added to the reaction mixture, the organic layer was separated, washed with a saturated aqueous sodium chloride solution, and then dried over sodium sulfate, and the solvent was distilled away under reduced pressure. The obtained residue was purified by silica gel column chromatography (ethyl acetate-hexane), thereby obtaining 2-butyloctyl 10-(((4-nitrophenoxy)carbonyl)oxy)docosanoate (750 mg) as a colorless oily substance.

$^1$H-NMR ($CDCl_3$) δ:8.28 (2H, dd, J=7.2H, 2.1 Hz), 7.39 (2H, dd, J=7.2 Hz, 2.1 Hz), 4.86-4.77 (1H, m), 3.97 (2H, d, J=6.0 Hz), 2.30 (2H, t, J=7.2 Hz), 1.74-1.55 (7H, m), 1.40-1.21 (46H, m), 0.92-0.85 (9H, m).

Example 51

(1)

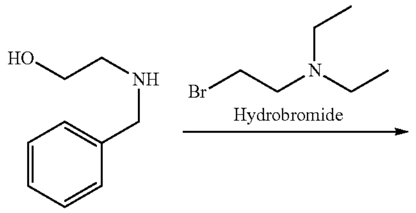

(3)

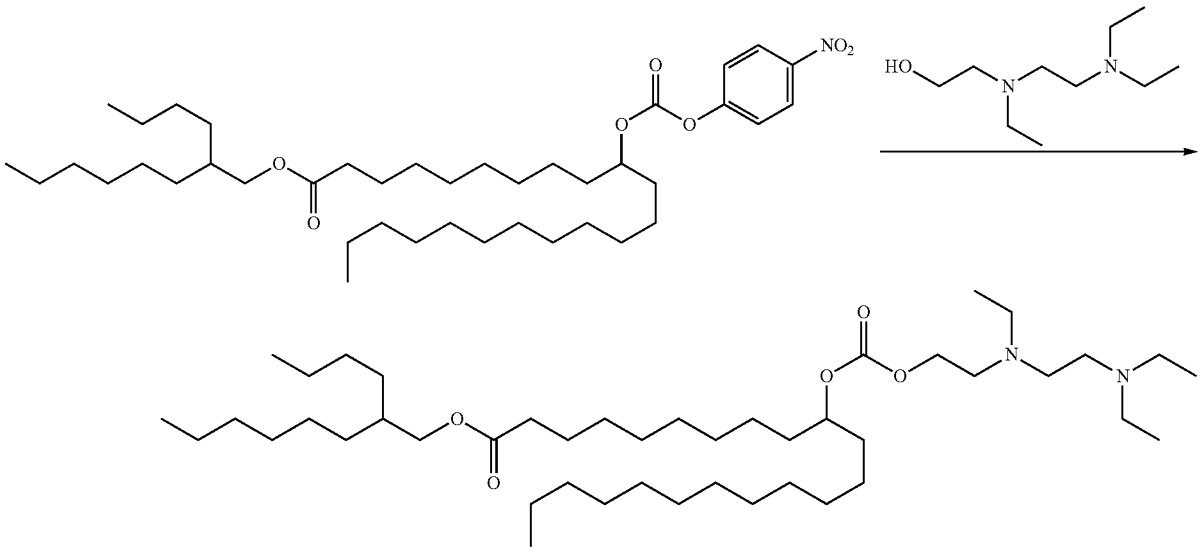

2-Butyloctyl 12-dodecyl-3,6-diethyl-10-oxo-9,11-dioxa-3,6-diazahenicosan-21-oate as a colorless oily substance was obtained by the same method as that in Example 41, except that 2-butyloctyl 10-(((4-nitrophenoxy)carbonyl)oxy)docosanoate was used instead of 7-(((4-nitrophenoxy)carbonyl)oxy)tridecane-1,13-diyldioleate in (2) of Example 41.

$^1$H-NMR ($CDCl_3$) δ:4.73-4.61 (1H, m), 4.17 (2H, t, J=6.6 Hz), 3.97 (2H, d, J=6.0 Hz), 2.76 (2H, t, J=6.6 Hz), 2.67-2.46 (10H, m), 2.29 (2H, t, J=7.8 Hz), 1.67-1.48 (7H, m), 1.39-1.18 (46H, m), 1.10-0.98 (9H, m), 0.96-0.82 (9H, m).

MS m/z (M+H): 740.

-continued

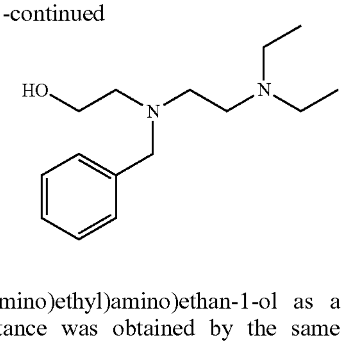

2-(Benzyl(2-(diethylamino)ethyl)amino)ethan-1-ol as a light yellow oily substance was obtained by the same method as that in (1) of Example 30, except that 2-(benzylamino)ethan-1-ol was used instead of 2-(ethylamino)ethan-1-ol in (1) of Example 30.

MS m/z (M+H): 251.

(2)

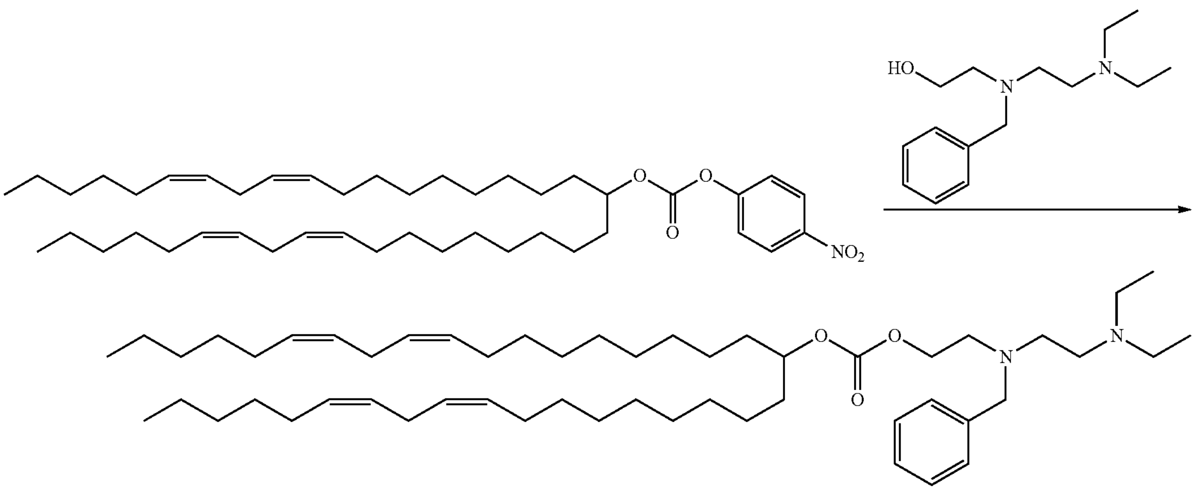

2-(Benzyl(2-(diethylamino)ethyl)amino)ethyl((6Z,9Z,28Z,31Z)-heptatriaconta-6,9,28,31-tetraen-19-yl)carbonate as a colorless oily substance was obtained by the same method as that in (2) of Example 20, except that 2-(benzyl(2-(diethylamino)ethyl)amino)ethan-1-ol was used instead of 2-((2-(dimethylamino)ethyl)(methyl)amino)ethan-1-ol in (2) of Example 20.

$^1$H-NMR ($CDCl_3$) δ:7.36-7.19 (5H, m), 5.46-5.27 (8H, m), 4.72-4.61 (1H, m), 4.18 (2H, t, J=6.0 Hz), 3.68 (2H, s), 2.84-2.73 (6H, m), 2.69-2.42 (8H, m), 2.13-1.97 (8H, m), 1.65-1.49 (4H, m), 1.42-1.19 (36H, m), 0.98 (6H, t, J=7.2 Hz), 0.89 (6H, t, J=6.6 Hz).

MS m/z (M+H): 806.

Example 52

(1)

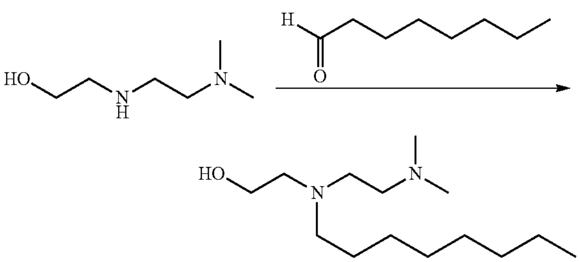

2-((2-Dimethylamino)ethyl)(octyl)amino)ethan-1-ol as a colorless oily substance was obtained by the same method as that in (1) of Example 37, except that octanal was used instead of hexanal in (1) of Example 37.

MS m/z (M+H): 245.

(2)

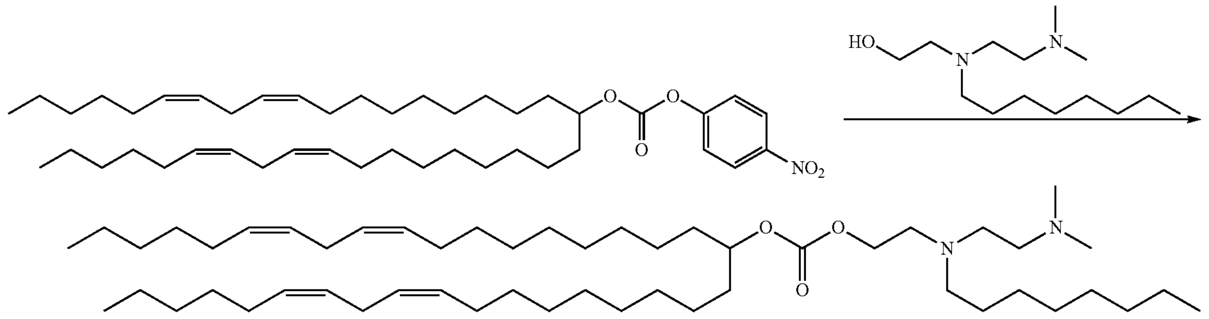

2-((2-(Dimethylamino)ethyl)(octyl)amino)ethyl((6Z,9Z,28Z,31Z)-heptatriaconta-6,9, 28,31-tetraen-19-yl)carbonate as a colorless oily substance was obtained by the same method as that in (2) of Example 20, except that 2-((2-dimethylamino)ethyl)(octyl)amino)ethan-1-ol was used instead of 2-((2-(dimethylamino)ethyl)(methyl)amino)ethan-1-ol in (2) of Example 20.

$^1$H-NMR ($CDCl_3$) δ:5.45-5.24 (8H, m), 4.73-4.62 (1H, m), 4.17 (2H, t, J=6.0 Hz), 2.84-2.71 (6H, m), 2.67-2.56 (2H, m), 2.53-2.43 (2H, m), 2.43-2.31 (2H, m), 2.23 (6H, s), 2.12-1.96 (8H, m), 1.66-1.51 (4H, m), 1.47-1.19 (48H, m), 0.96-0.80 (9H, m).

MS m/z (M+H): 800.

Example 53

(1)

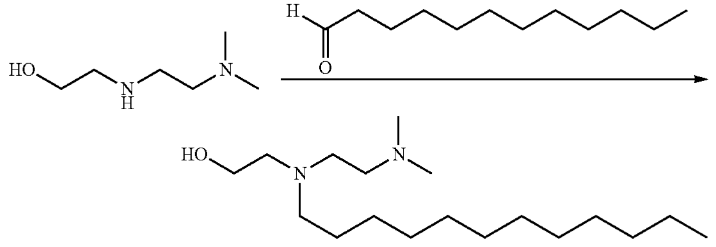

2-((2-(Dimethylamino)ethyl)(dodecyl)amino)ethan-1-ol as a colorless oily substance was obtained by the same method as that in (1) of Example 37, except that dodecanal was used instead of hexanal in (1) of Example 37.

MS m/z (M+H): 301.

(2)

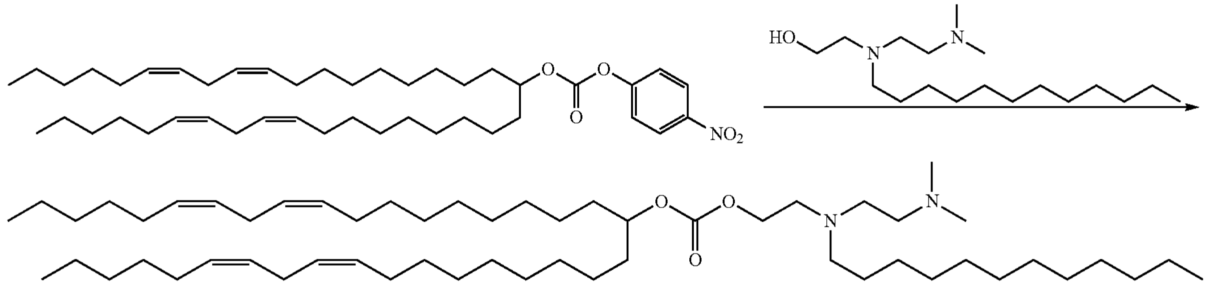

2-((2-(Dimethylamino)ethyl)(dodecyl)amino)ethyl)((6Z,9Z,28Z,31Z)-heptatriaconta-6,9,28,31-tetraen-19-yl)carbonate as a colorless oily substance was obtained by the same method as that in (2) of Example 20, except that 2-((2-(dimethylamino)ethyl)(dodecyl)amino)ethan-1-ol was used instead of 2-((2-(dimethylamino)ethyl)(methyl)amino)ethan-1-ol in (2) of Example 20.

$^1$H-NMR ($CDCl_3$) δ:5.46-5.25 (8H, m), 4.72-4.61 (1H, m), 4.17 (2H, t, J=6.6 Hz), 2.85-2.70 (6H, m), 2.66-2.57 (2H, m), 2.54-2.43 (2H, m), 2.42-2.32 (2H, m), 2.23 (6H, s), 2.11-1.97 (8H, m), 1.66-1.50 (4H, m), 1.47-1.17 (56H, m), 0.97-0.81 (9H, m).

MS m/z (M+H): 856.

Example 54

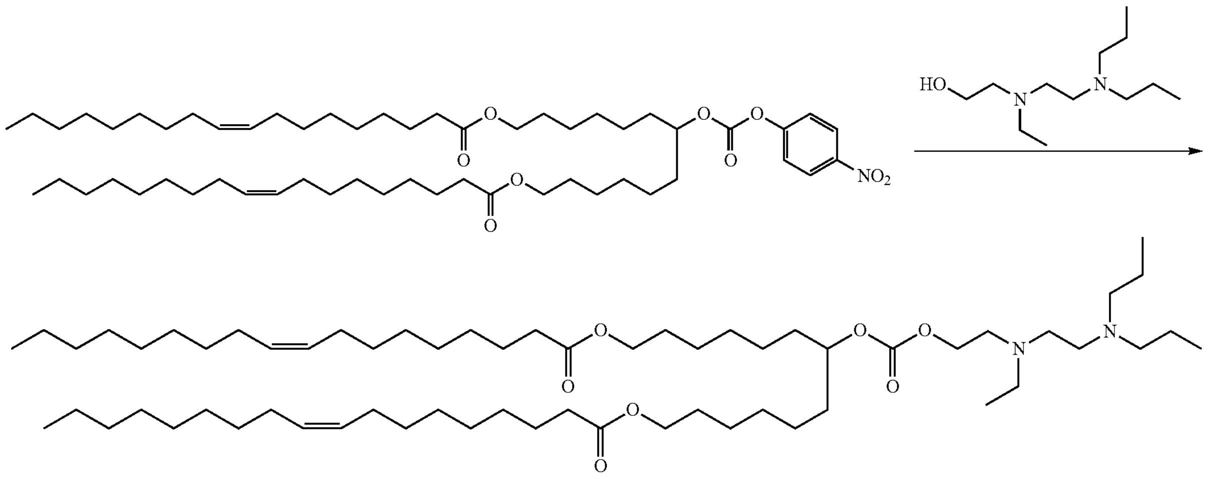

7-(((2-((2-(Dipropylamino)ethyl)(ethyl)amino)ethoxy)carbonyl)oxy)tridecane-1,13-diyldioleate as a colorless oily substance was obtained by the same method as that in (2) of Example 41, except that 2-((2-(dipropylamino)ethyl)(ethyl)amino)ethan-1-ol was used instead of 2-((2-(diethylamino)ethyl)(ethyl)amino)ethan-1-ol in (2) of Example 41.

$^1$H-NMR ($CDCl_3$) δ: 5.41-5.26 (4H, m), 4.73-4.60 (1H, m), 4.17 (2H, t, J=6.0 Hz), 4.04 (4H, t, J=6.6 Hz), 2.75 (2H, t, J=6.6 Hz), 2.65-2.46 (6H, m), 2.43-2.34 (4H, m), 2.28 (4H, t, J=7.2 Hz), 2.10-1.95 (8H, m), 1.69-1.51 (12H, m), 1.50-1.19 (56H, m), 1.03 (3H, t, J=7.5 Hz), 0.94-0.81 (12H, m).

MS m/z (M+H): 1004.

Example 55

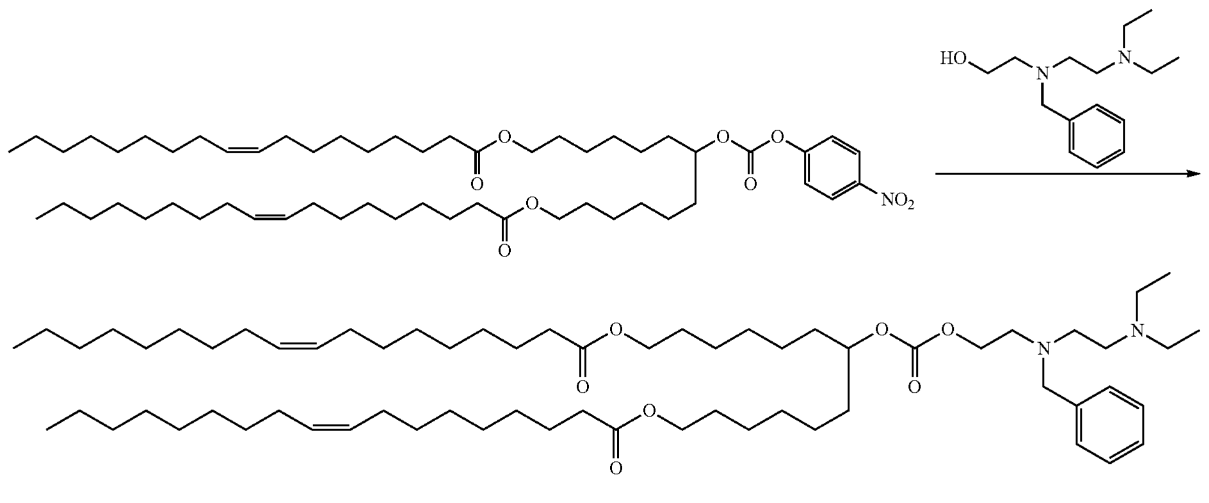

7-(((2-(Benzyl(2-(diethylamino)ethyl)amino)ethoxy)carbonyl)oxy)tridecane-1,13-diyl dioleate as a colorless oily substance was obtained by the same method as that in (2) of Example 41, except that 2-(benzyl(2-(diethylamino)ethyl)amino)ethan-1-ol was used instead of 2-((2-(diethylamino)ethyl)(ethyl)amino)ethan-1-ol in (2) of Example 41.

$^1$H-NMR ($CDCl_3$) δ:7.36-7.17 (5H, m), 5.42-5.27 (4H, m), 4.71-4.61 (1H, m), 4.19 (2H, t, J=6.6 Hz), 4.04 (4H, t, J=7.2 Hz), 3.68 (2H, s), 2.79 (2H, t, J=6.0 Hz), 2.67-2.42 (8H, m), 2.28 (4H, t, J=8.1 Hz), 2.08-1.93 (8H, m), 1.69-1.49 (12H, m), 1.42-1.20 (52H, m), 0.97 (6H, t, J=7.2 Hz), 0.88 (6H, t, J=6.6 Hz).

MS m/z (M+H): 1038.

Example 56

(1)

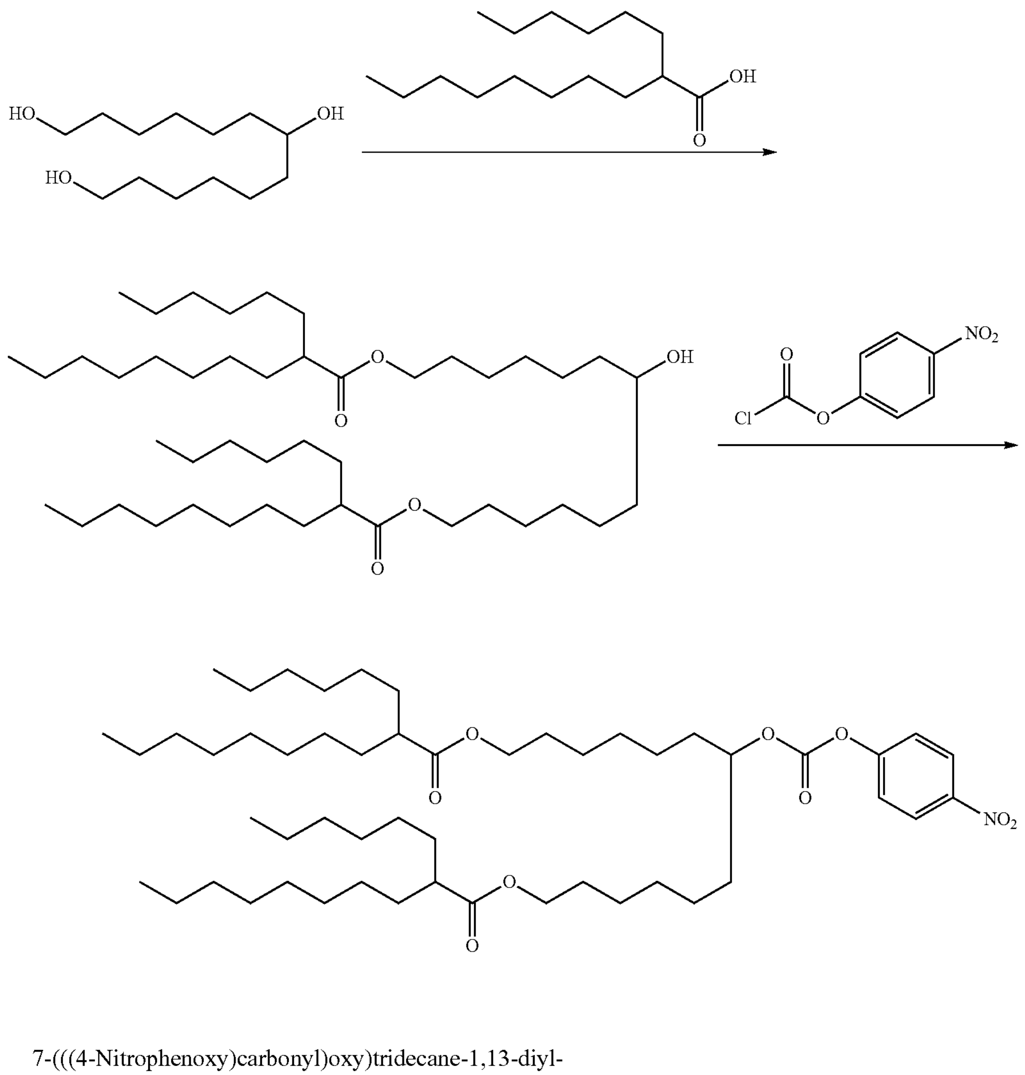

7-(((4-Nitrophenoxy)carbonyl)oxy)tridecane-1,13-diyl-bis(2-hexyldecanoate) as a colorless oily substance was obtained by the same method as that in (1) of Example 41, except that 2-hexyldecanoate was used instead of oleic acid in (1) of Example 41.

$^1$H-NMR ($CDCl_3$) δ: 8.28 (2H, dd, J=7.2H, 2.1 Hz), 7.39 (2H, dd, J=7.2 Hz, 2.1 Hz), 4.86-4.76 (1H, m), 4.07 (4H, t, J=6.6 Hz), 2.36-2.25 (2H, m), 1.72-1.20 (68H, m), 0.87 (12H, t, J=6.0 Hz).

(2)

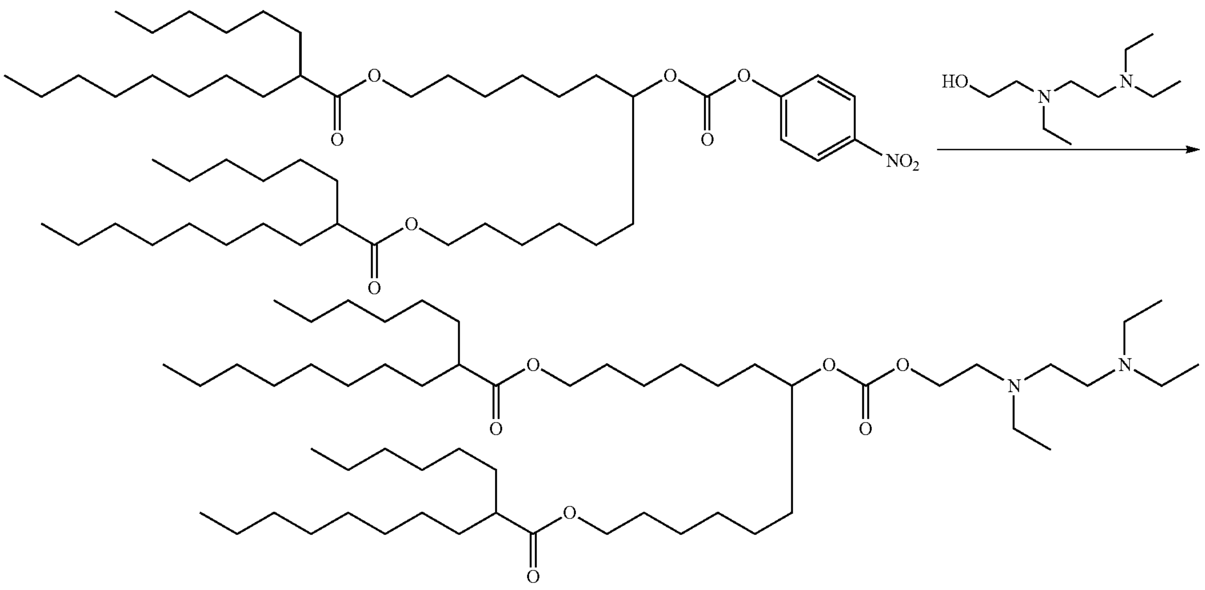

7-(((2-((2-(Diethylamino)ethyl)(ethyl)amino)ethoxy)carbonyl)oxy)tridecane-1,13-diyl bis(2-hexyldecanoate) as a colorless oily substance was obtained by the same method as that in (2) of Example 41, except that 7-(((4-nitrophenoxy)carbonyl)oxy)tridecane-1,13-diylbis(2-hexyldecanoate) was used instead of 7-(((4-nitrophenoxy)carbonyl)oxy)tridecane-1,13-diyldioleate in (2) of Example 41.

$^1$H-NMR ($CDCl_3$) δ:4.73-4.61 (1H, m), 4.17 (2H, t, J=6.6 Hz), 4.05 (4H, t, J=6.6 Hz), 2.76 (2H, t, J=6.6 Hz), 2.67-2.46 (10H, m), 2.36-2.23 (2H, m), 1.68-1.16 (68H, m), 1.09-0.97 (9H, m), 0.94-0.81 (12H, m).

MS m/z (M+H): 924.

Example 57

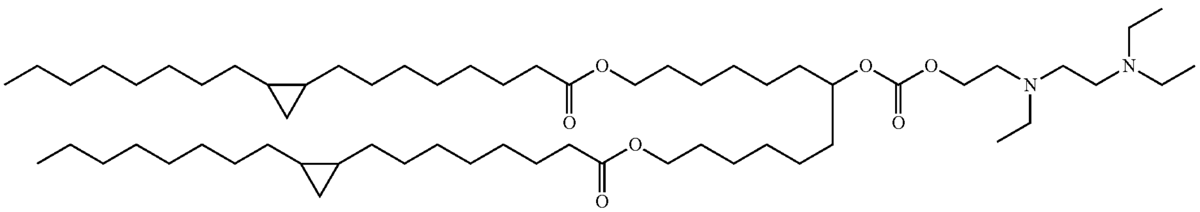 [SMILES: CCCCCCCCC1CC1CCCCCCCC(=O)OCCCCCCC(CCCCCCOC(=O)CCCCCCCC1CC1CCCCCCCC)OC(=O)OCCN(CC)CCN(CC)CC]

7-(((2-((2-(Diethylamino)ethyl)(ethyl)amino)ethoxy)carbonyl)oxy)tridecane-1,13-diyl bis(8-(2-octylcyclopropyl)octanoate)) as a colorless oily substance was obtained by the same method as that in (1) and (2) of Example 41, except that 8-(2-octylcyclopropyl)octanoate synthesized according to the method described in European Journal of Medicinal Chemistry, 2016, 109, p 134-145 was used instead of oleic acid in (1) and (2) of Example 41.

$^1$H-NMR ($CDCl_3$) δ:4.72-4.62 (1H, m), 4.18 (2H, t, J=6.6 Hz), 4.05 (4H, t, J=6.6 Hz), 2.76 (2H, t, J=6.6 Hz), 2.66-2.47 (10H, m), 2.29 (4H, t, J=8.1 Hz), 1.69-1.48 (12H, m), 1.45-1.08 (60H, m), 1.08-0.97 (9H, m), 0.88 (6H, t, J=7.2 Hz), 0.71-0.51 (6H, m), −0.29-−0.38 (2H, m).

MS m/z (M+H): 1004.

Example 58

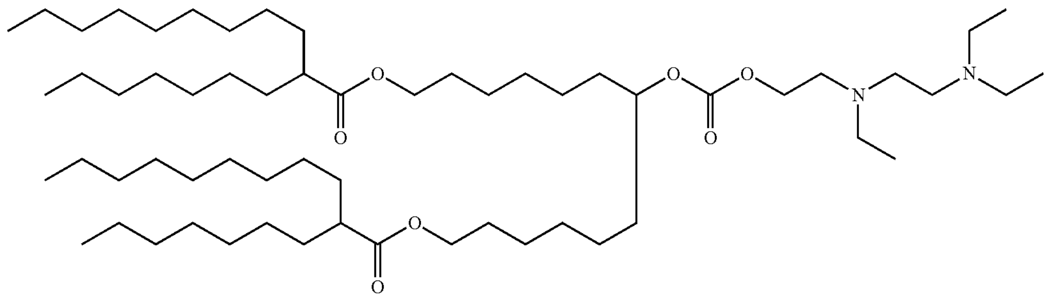 [SMILES: CCCCCCCCCC(CCCCCCC)C(=O)OCCCCCCC(CCCCCCOC(=O)C(CCCCCCC)CCCCCCCCC)OC(=O)OCCN(CC)CCN(CC)CC]

7-(((2-((2-(Diethylamino)ethyl)(ethyl)amino)ethoxy)carbonyl)oxy)tridecane-1,13-diyl bis(2-heptylundecanoate) as a colorless oily substance was obtained by the same method as that in (1) and (2) of Example 41, except that 2-heptylundecaonate was used instead of oleic acid in (1) and (2) of Example 41.

$^1$H-NMR ($CDCl_3$) δ:4.72-4.62 (1H, m), 4.17 (2H, t, J=6.6 Hz), 4.05 (4H, t, J=6.6 Hz), 2.76 (2H, t, J=5.7 Hz), 2.65-2.47 (10H, m), 2.36-2.24 (2H, m), 1.69-1.17 (76H, m), 1.08-0.98 (9H, m), 0.88 (12H, t, J=7.5 Hz).

MS m/z (M+H): 980.

Example 59

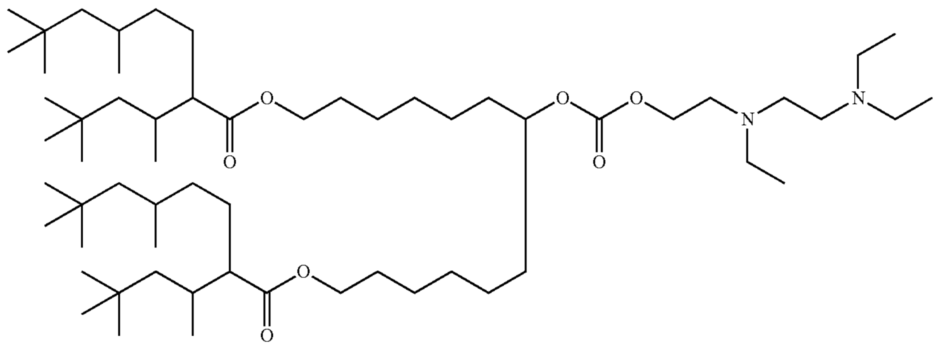 [SMILES: CCN(CC)CCN(CC)CCOC(=O)OC(CCCCCCOC(=O)C(CCC(C)CC(C)(C)C)C(C)CC(C)(C)C)CCCCCCOC(=O)C(CCC(C)CC(C)(C)C)C(C)CC(C)(C)C]

7-(((2-((2-(Diethylamino)ethyl)(ethyl)amino)ethoxy)carbonyl)oxy)tridecane-1,13-diyl bis(2-(4,4-dimethylpentan-2-yl)-5,7,7-trimethyloctanoate) as a colorless oily substance was obtained by the same method as that in (1) and (2) of Example 41, except that 2-(4,4-dimethylpentan-2-yl)-5,7,7-trimethyloctanoate was used instead of oleic acid in (1) and (2) of Example 41.

$^1$H-NMR ($CDCl_3$) δ:4.73-4.62 (1H, m), 4.17 (2H, t, J=6.6 Hz), 4.11-3.95 (4H, m), 2.76 (2H, t, J=6.0 Hz), 2.65-2.46 (10H, m), 2.19-2.06 (2H, m), 1.86-1.13 (40H, m), 1.10-0.79 (57H, m).

MS m/z (M+H): 980.

Example 60

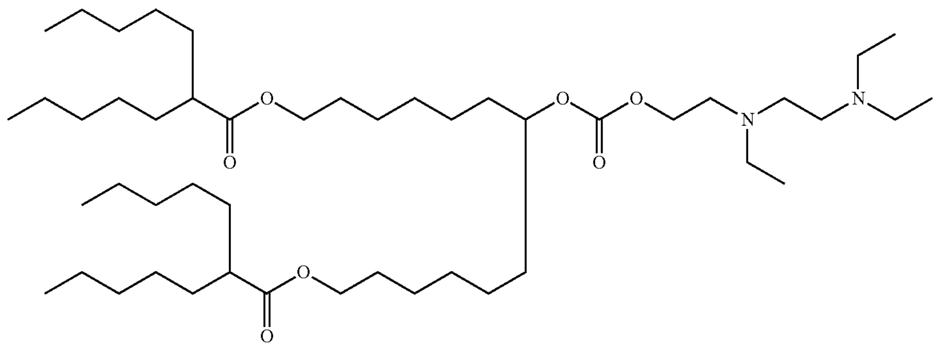 [SMILES: CCCCCC(CCCCC)C(=O)OCCCCCCC(CCCCCCOC(=O)C(CCCCC)CCCCC)OC(=O)OCCN(CC)CCN(CC)CC]

7-(((2-((2-(Diethylamino)ethyl)(ethyl)amino)ethoxy)carbonyl)oxy)tridecane-1,13-diyl bis(2-pentylheptanoate) as a colorless oily substance was obtained by the same method as that in (1) and (2) of Example 41, except that 2-pentylheptanoate was used instead of oleic acid in (1) and (2) of Example 41.

$^1$H-NMR ($CDCl_3$) δ:4.73-4.61 (1H, m), 4.17 (2H, t, J=6.6 Hz), 4.05 (4H, t, J=6.6 Hz), 2.76 (2H, t, J=6.0 Hz), 2.65-2.47 (10H, m), 2.37-2.25 (2H, m), 1.69-1.19 (52H, m), 1.07-0.98 (9H, m), 0.87 (12H, t, J=6.6 Hz).

MS m/z (M+H): 812.

Example 61

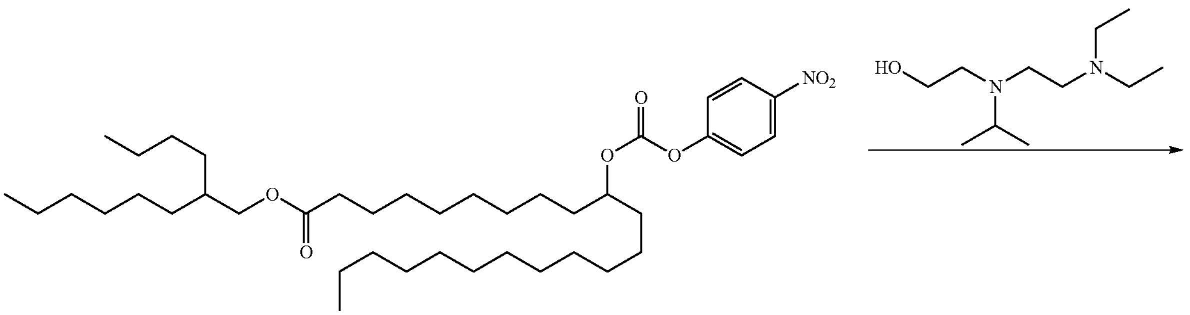

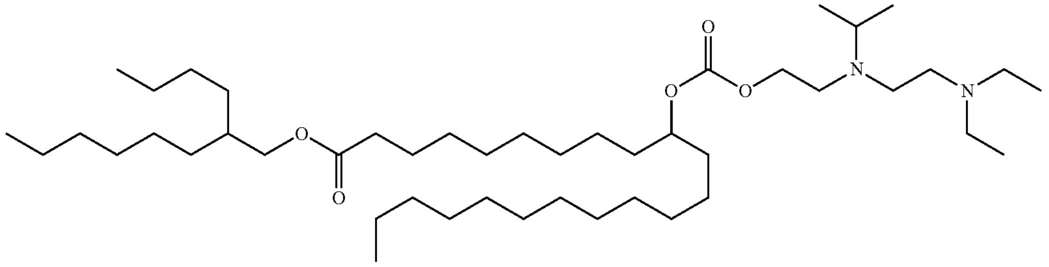

2-Butyloctyl 12-dodecyl-3-ethyl-6-isopropyl-10-oxo-9,11-dioxa-3,6-diazahenicosan-21-oate as a colorless oily substance was obtained by the same method as that in (3) of Example 50, except that 2-((2-(diethylamino)ethyl)(isopropyl)amino)ethan-1-ol was used instead of 2-((2-(diethylamino)ethyl)(ethyl)amino)ethan-1-ol in (3) of Example 50.

$^1$H-NMR ($CDCl_3$) δ:4.73-4.60 (1H, m), 4.10 (2H, t, J=6.6 Hz), 3.97 (2H, d, J=6.0 Hz), 2.97-2.85 (1H, m), 2.68 (2H, t, J=7.2 Hz), 2.60-2.41 (8H, m), 2.29 (2H, t, J=7.8 Hz), 1.66-1.48 (7H, m), 1.40-1.20 (46H, m), 1.07-0.95 (12H, m), 0.94-0.81 (9H, m).

MS m/z (M+H): 754.

Example 62

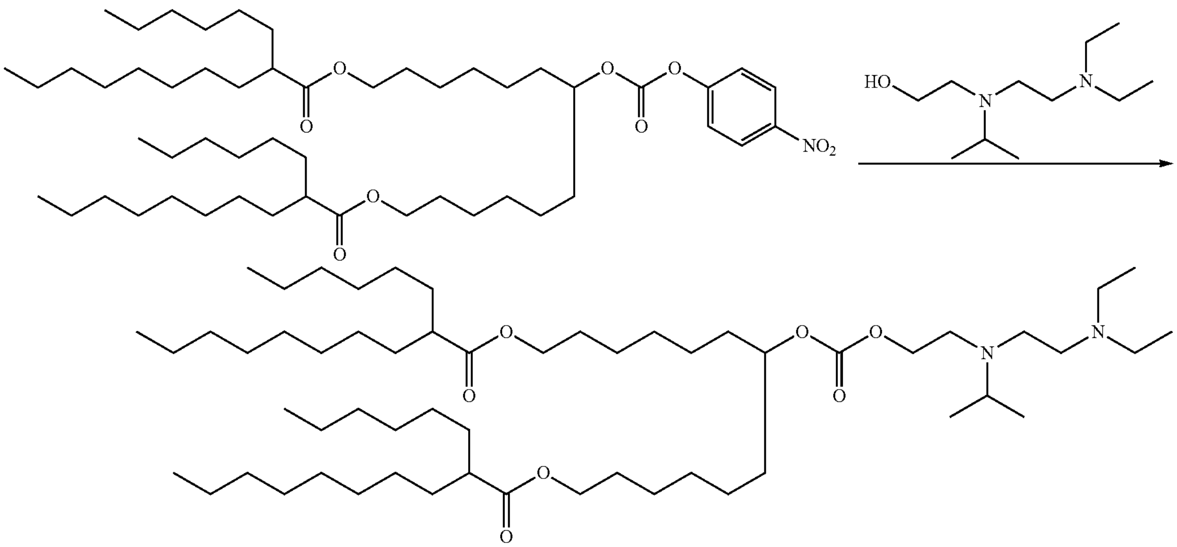

7-(((2-((2-(Diethylamino)ethyl)(isopropyl)amino)ethoxy) carbonyl)oxy)tridecane-1,13-diylbis(2-hexyldecanoate) as a colorless oily substance was obtained by the same method as that in (2) of Example 56, except that 2-((2-(diethylamino) ethyl)(isopropyl)amino)ethan-1-ol was used instead of 2-((2-(diethylamino)ethyl)(ethyl)amino)ethan-1-ol in (2) of Example 56.

$^1$H-NMR ($CDCl_3$) δ:4.73-4.61 (1H, m), 4.15-3.99 (6H, m), 2.97-2.84 (1H, m), 2.68 (2H, t, J=6.6 Hz), 2.60-2.41 (8H, m), 2.37-2.23 (2H, m), 1.69-1.16 (68H, m), 1.10-0.95 (12H, m), 0.87 (12H, t, J=6.6 Hz).

MS m/z (M+H): 938.

Example 63

(1)

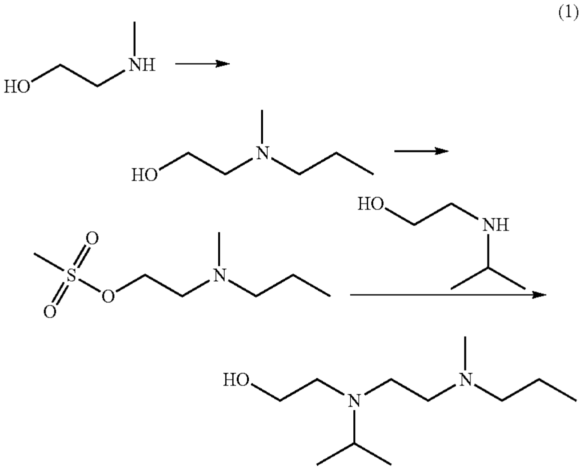

A mixture of 2-(methylamino)ethan-1-ol (3 g), potassium carbonate (6.6 g), 1-bromopropane (5.6 mL), and acetonitrile (30 mL) was stirred at 60° C. for 9 hours and 30 minutes. A saturated aqueous sodium hydrogen carbonate solution was added to the reaction mixture, and extraction was performed using chloroform. The organic layer was washed with saturated saline and dried over anhydrous sodium sulfate. The solvent was distilled away under reduced pressure, thereby obtaining 2-(methyl(propyl) amino)ethan-1-ol (4.3 g) as a colorless oily substance.

MS m/z (M+H): 118.

Methanesulfonic anhydride (1.9 g) was added dropwise to a mixture of 2-(methyl(propyl)amino)ethan-1-ol (1.2 g) and acetonitrile (10 mL) under ice cooling, and the mixture was stirred at 0° C. for 30 minutes and then stirred at room temperature for 30 minutes. 2-(Isopropylamino)ethan-1-ol (2.0 g) and N,N-diisopropylethylamine (2.0 mL) were added to the reaction mixture, and the reaction mixture was stirred at 70° C. for 25 hours and 30 minutes. The reaction mixture was cooled to room temperature, potassium carbonate and water were then added thereto, and extraction was performed using ethyl acetate. The organic layer was washed with saturated saline and dried over anhydrous sodium sulfate. The solvent was distilled away under reduced pressure, and the obtained residue was purified by silica gel column chromatography (methanol-chloroform), thereby obtaining 2-(isopropyl(2-(methyl(propyl)amino)ethyl) amino)ethan-1-ol (0.3 g) as a yellow oily substance.

MS m/z (M+H): 203.

(2)

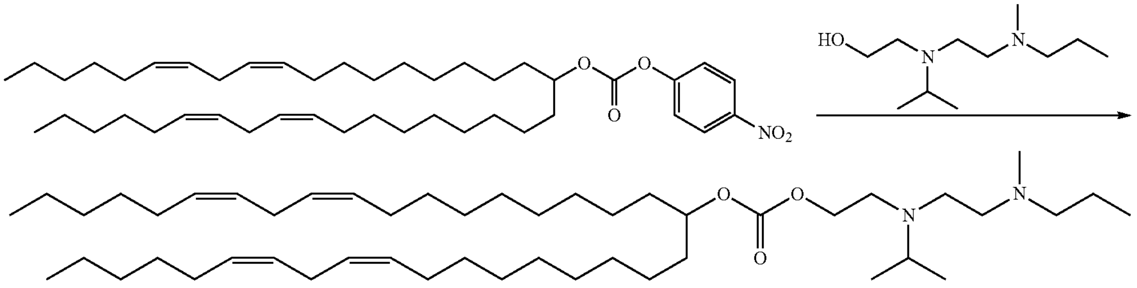

(6Z, 9Z, 28Z, 31Z)-heptatriaconta-6,9,28,31-tetraen-19-yl(2-(isopropyl(2-(methyl(propyl)amino)ethyl)amino)ethyl) carbonate as a colorless oily substance was obtained by the same method as that in (2) of Example 20, except that 2-(isopropyl(2-(methyl(propyl)amino)ethyl)amino)ethan-1-ol was used instead of 2-((2-(dimethylamino)ethyl)(methyl)amino)ethan-1-ol in (2) of Example 20.

$^1$H-NMR ($CDCl_3$) δ:5.45-5.26 (8H, m), 4.73-4.62 (1H, m), 4.09 (2H, t, J=6.6 Hz), 2.97-2.86 (1H, m), 2.77 (4H, t, J=6.0 Hz), 2.69 (2H, t, J=7.2 Hz), 2.62-2.51 (2H, m), 2.44-2.35 (2H, m), 2.35-2.27 (2H, m), 2.23 (3H, s), 2.11-1.96 (8H, m), 1.66-1.20 (42H, m), 0.98 (6H, d, J=6.6 Hz), 0.94-0.82 (9H, m).

MS m/z (M+H): 758.

Example 64

(1)

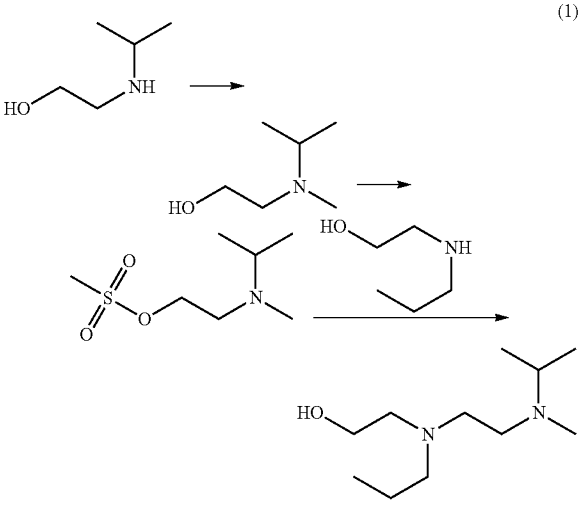

Methyl iodide (1.9 mL) was added dropwise to a dichloromethane (30 mL) solution of 2-(isopropylamino)ethan-1-ol (3 g) under ice cooling. The mixture was stirred at the same temperature for 1 hour and 15 minutes and then stirred at room temperature for 6 hours and 50 minutes. Potassium carbonate and water were added to the reaction mixture, and extraction was performed using chloroform. The organic layer was washed with saturated saline and dried over anhydrous sodium sulfate. The solvent was distilled away under reduced pressure, and the obtained residue was purified by silica gel column chromatography (methanol-chloroform, NH silica gel), thereby obtaining 2-(isopropyl(methyl)amino)ethan-1-ol (2.2 g) as a colorless oily substance.

MS m/z (M+H): 118.

Methanesulfonic anhydride (2.6 g) was added to a mixture of 2-(isopropyl(methyl)amino)ethan-1-ol (1.5 g), N,N-diisopropylethylamine (2.5 mL), and acetonitrile (15 mL) under ice cooling, and the mixture was stirred at room temperature for 4 hours and 50 minutes. 2-(Propylamino)ethan-1-ol (4.3 mL) was added to the reaction mixture, and the reaction mixture was stirred at 70° C. for 23 hours and 30 minutes. The reaction mixture was cooled to room temperature, a saturated aqueous sodium hydrogen carbonate solution was added thereto, and extraction was performed using ethyl acetate. The organic layer was washed with saturated saline and dried over anhydrous sodium sulfate. The solvent was distilled away under reduced pressure, and the obtained residue was purified by silica gel column chromatography (methanol-chloroform), thereby obtaining 2-((2-(isopropyl(methyl)amino)ethyl)(propyl)amino)ethan-1-ol (0.7 g) as a yellow oily substance.

MS m/z (M+H): 203.

(2)

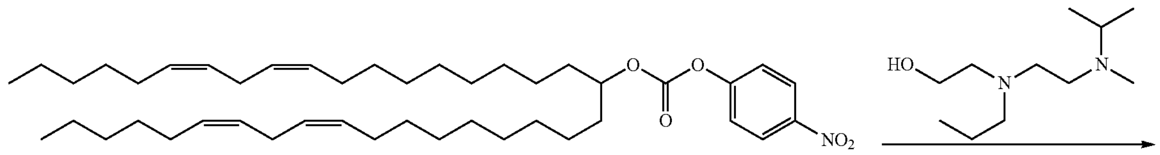

-continued

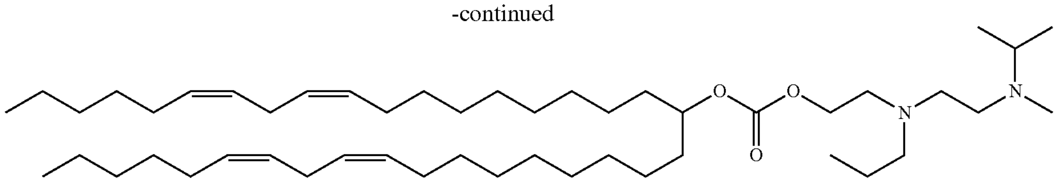

(6Z, 9Z, 28Z, 31Z)-heptatriaconta-6, 9, 28, 31-tetraen-19-yl(2-((2-isopropyl(methyl)amino)ethyl)(propyl)amino) ethyl)carbonate as a colorless oily substance was obtained by the same method as that in (2) of Example 20, except that 2-((2-(isopropyl(methyl)amino)ethyl)(propyl)amino)ethan-1-ol was used instead of 2-((2-(dimethylamino)ethyl) (methyl)amino)ethan-1-ol in (2) of Example 20.

$^1$H-NMR ($CDCl_3$) δ:5.46-5.26 (8H, m), 4.74-4.60 (1H, m), 4.17 (2H, t, J=6.6 Hz), 2.87-2.70 (7H, m), 2.65-2.54 (2H, m), 2.51-2.40 (4H, m), 2.21 (3H, s), 2.12-1.95 (8H, m), 1.64-1.20 (42H, m), 1.00 (6H, d, J=6.6 Hz), 0.94-0.81 (9H, m).

MS m/z (M+H): 758.

Example 65

(1)

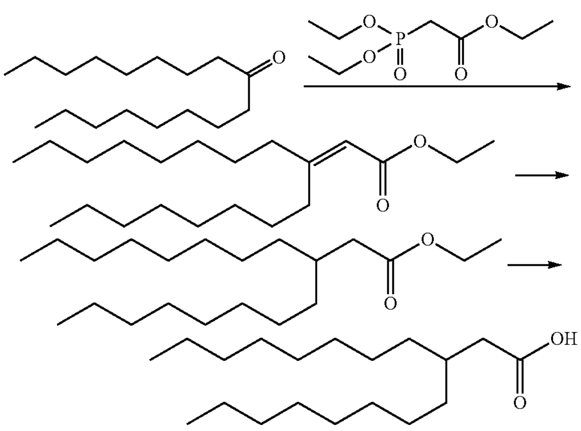

Ethyl 2-(diethoxyphosphoryl)acetate (9.4 mL) was added dropwise to a tetrahydrofuran (60 mL) suspension of 60 wt % sodium hydride (1.7 g) under ice cooling, and the mixture was stirred at the same temperature for 30 minutes. Heptadecan-9-one (1.5 g) was added to the reaction mixture, and the reaction mixture was stirred and heated under reflux for 16 hours. The reaction mixture was cooled to room temperature and poured into ice water, and then ethyl acetate was added thereto. The organic layer was separated and washed with a saturated aqueous sodium chloride solution, then the solvent was distilled away under reduced pressure, and the obtained residue was purified by silica gel column chromatography (ethyl acetate-hexane), thereby obtaining ethyl 3-octyl undec-2-enoate (1.2 g) as a colorless oily substance.

$^1$H-NMR ($CDCl_3$) δ:5.61 (1H, s), 4.14 (2H, q, J=6.6 Hz), 2.58 (2H, t, J=7.2 Hz), 2.12 (2H, t, J=7.2 Hz), 1.50-1.20 (27H, m), 0.91-0.85 (6H, m).

Ammonium formate (1.4 g) was added to a mixture of ethyl 3-octyl undec-2-enoate (1.2 g), 10% palladium-carbon (0.35 g), and methanol (24 mL), and the mixture was stirred and heated under reflux for 4 hours. The reaction mixture was cooled to room temperature, the insoluble matters were filtered off using celite, and then the solvent was distilled away under reduced pressure. The obtained residue was purified by silica gel column chromatography (ethyl acetate-hexane), thereby obtaining ethyl 3-octylundecanoate (1.1 g) as a colorless oily substance.

$^1$H-NMR ($CDCl_3$) δ: 4.12 (2H, q, J=7.2 Hz), 2.21 (2H, d, J=6.6 Hz), 2.05-2.04 (1H, m), 1.34-1.20 (31H, m), 0.88 (6H, 6.6 Hz).

A 5 mol/L aqueous sodium hydroxide solution (5 mL) was added to a mixture of ethyl 3-octylundecanoate (1.1 g) and ethanol (10 mL), and the mixture was stirred at 80° C. for 5 hours. The reaction mixture was cooled to room temperature, a 1 mol/L aqueous hydrochloric acid solution was added until the reaction mixture became acidic, and then ethyl acetate was added thereto. The organic layer was separated and washed with a saturated aqueous sodium chloride solution, the solvent was then distilled away under reduced pressure, and the obtained residue was purified by silica gel column chromatography (ethyl acetate-hexane), thereby obtaining 3-octylundecanoate (1.1 g) as a colorless oily substance.

$^1$H-NMR ($CDCl_3$) δ:2.28 (2H, d, J=6.6 Hz), 1.90-1.79 (1H, m), 1.35-1.19 (28H, m), 0.88 (6H, t, J=6.6 Hz).

(2)

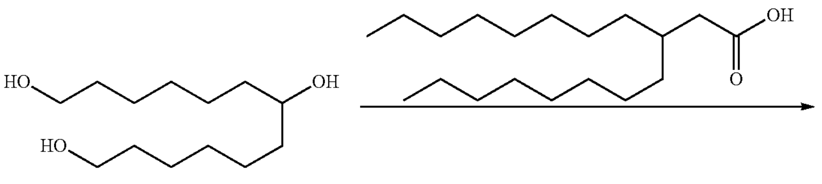

-continued

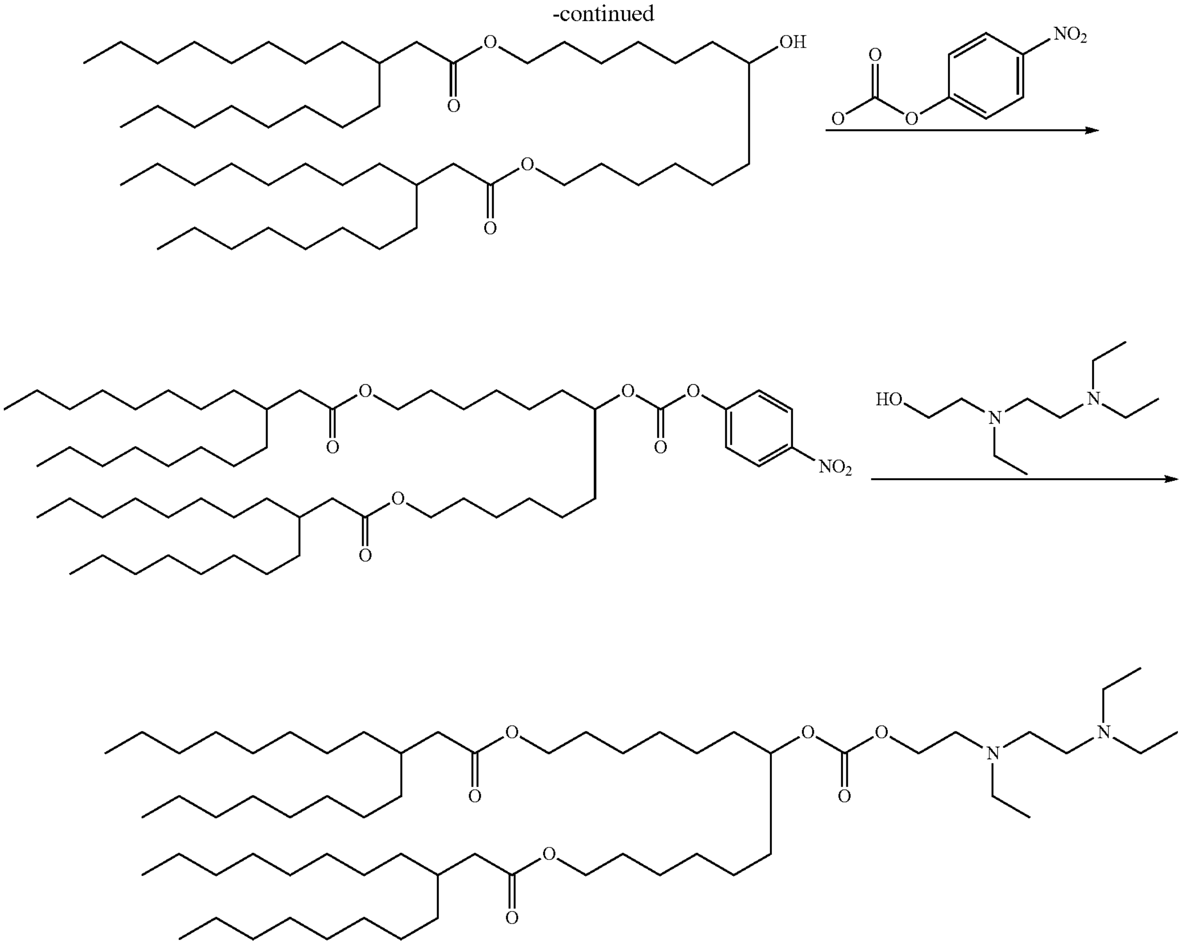

7-(((2-((2-(Diethylamino)ethyl)(ethyl)amino)ethoxy)carbonyl)oxy)tridecane-1,13-diyl bis(3-octylundecanoate) as a colorless oily substance was obtained by the same method as that in (1) and (2) of Example 41, except that 3-octylundecanoate was used instead of oleic acid in (1) and (2) of Example 41.

$^1$H-NMR ($CDCl_3$) δ:4.74-4.62 (1H, m), 4.17 (2H, t, J=6.6 Hz), 4.04 (4H, t, J=6.6 Hz), 2.76 (2H, t, J=6.6 Hz), 2.66-2.47 (10H, m), 2.22 (4H, d, J=6.6 Hz), 1.90-1.76 (2H, m), 1.70-1.17 (76H, m), 1.10-0.97 (9H, m), 0.88 (12H, t, J=6.6 Hz).

MS m/z (M+H): 1008

Example 66

2-Butyloctyl 12-decyl-3,6-diethyl-10-oxo-9,11-dioxa-3,6-diazatricosan-23-oate as a colorless oily substance was obtained by the same method as that in (1), (2), and (3) of Example 50, except that in (1), (2), and (3) of Example 50, 12-ethoxy-12-oxododecanoic acid was used instead of 10-ethoxy-10-oxodecanoic acid, and a 1.0 mol/L decyl magnesium bromide-diethyl ether solution was used instead of a 1.0 mol/L dodecyl magnesium bromide-diethyl ether solution.

$^1$H-NMR ($CDCl_3$) δ:4.73-4.61 (1H, m), 4.17 (2H, t, J=6.6 Hz), 3.97 (2H, d, J=5.7 Hz), 2.76 (2H, t, J=6.6 Hz), 2.66-2.46 (10H, m), 2.30 (2H, t, J=7.2 Hz), 1.70-1.47 (7H, m), 1.41-1.20 (46H, m), 1.11-0.98 (9H, m), 0.95-0.82 (9H, m).

MS m/z (M+H): 740.

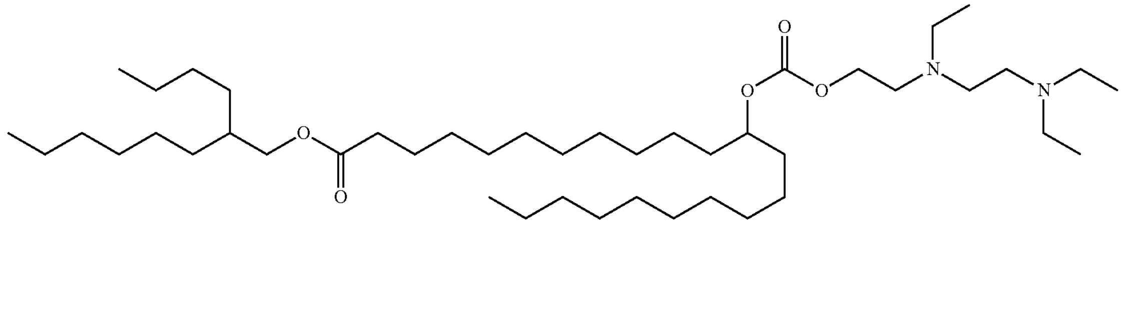 [SMILES: CCCCCCCCCCC(CCCCCCCCCCC(=O)OCC(CCCC)CCCCCC)OC(=O)OCCN(CC)CCN(CC)CC]

Example 67

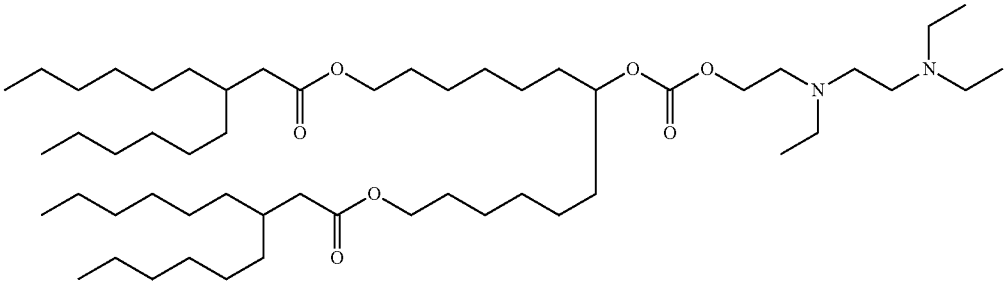 [SMILES: CCCCCCC(CCCCCC)CC(=O)OCCCCCCC(CCCCCCOC(=O)CC(CCCCCC)CCCCCC)OC(=O)OCCN(CC)CCN(CC)CC]

7-(((2-((2-(Diethylamino)ethyl)(ethyl)amino)ethoxy)carbonyl)oxy)tridecane-1,13-diyl bis(3-hexylnonanoate) as a colorless oily substance was obtained by the same method as that in (1) and (2) of Example 65, except that tridecan-7-one was used instead of heptadecan-9-one in (1) and (2) of Example 65.

$^1$H-NMR ($CDCl_3$) δ:4.73-4.62 (1H, m), 4.17 (2H, t, J=6.6 Hz), 4.04 (4H, t, J=6.6 Hz), 2.76 (2H, t, J=6.6 Hz), 2.67-2.45 (10H, m), 2.22 (4H, d, J=6.6 Hz), 1.89-1.77 (2H, m), 1.67-1.17 (60H, m), 1.08-0.98 (9H, m), 0.88 (12H, t, J=6.6 Hz).

MS m/z (M+H): 896.

Example 68

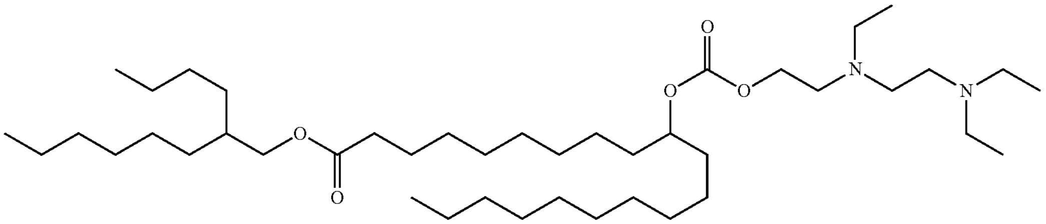 [SMILES: CCCCCCCCCCC(CCCCCCCCC(=O)OCC(CCCC)CCCCCC)OC(=O)OCCN(CC)CCN(CC)CC]

2-Butyloctyl 12-decyl-3,6-diethyl-10-oxo-9,11-dioxa-3,6-diazahenicosan-21-oate as a colorless oily substance was obtained by the same method as that in (1), (2), and (3) of Example 50, except that a 1.0 mol/L decyl magnesium bromide-diethyl ether solution was used instead of a 1.0 mol/L dodecyl magnesium bromide-diethyl ether solution in (1), (2), and (3) of Example 50.

$^1$H-NMR ($CDCl_3$) δ:4.73-4.60 (1H, m), 4.17 (2H, t, J=6.6 Hz), 3.97 (2H, J=5.4 Hz), 2.76 (2H, t, J=6.0 Hz), 2.67-2.46 (10H, m), 2.29 (2H, t, J=7.8 Hz), 1.68-1.50 (7H, m), 1.39-1.20 (42H, m), 1.07-0.98 (9H, m), 0.94-0.83 (9H, m).

MS m/z (M+H): 712.

Example 69

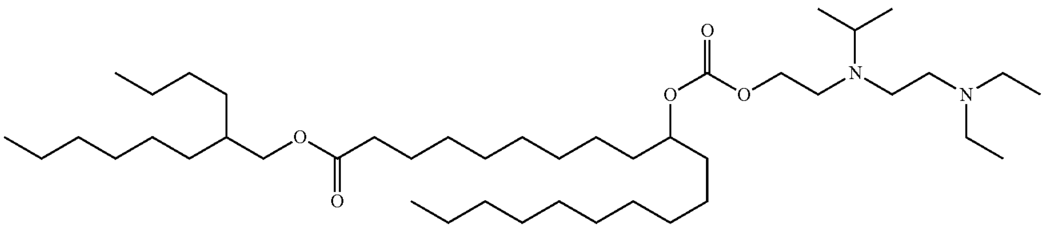 [SMILES: CCCCCCCCCCC(CCCCCCCCC(=O)OCC(CCCC)CCCCCC)OC(=O)OCCN(CCN(CC)CC)C(C)C]

2-Butyloctyl 12-decyl-3-ethyl-6-isopropyl-10-oxo-9,11-dioxa-3,6-diazahenicosan-21-oate as a colorless oily substance was obtained by the same method as that in Example 68, except that 2-((2-(diethylamino)ethyl)(isopropyl)amino)ethan-1-ol was used instead of 2-((2-(diethylamino)ethyl)(ethyl)amino)ethan-1-ol in Example 68.

$^1$H-NMR ($CDCl_3$) δ:4.73-4.61 (1H, m), 4.10 (2H, t, J=6.6 Hz), 3.97 (2H, d, J=6.0 Hz), 2.99-2.83 (1H, m), 2.68 (2H, t, J=6.6 Hz), 2.62-2.41 (8H, m), 2.29 (2H, t, J=7.2 Hz), 1.69-1.47 (7H, m), 1.40-1.19 (42H, m), 1.10-0.96 (12H, m), 0.94-0.83 (9H, m).

MS m/z (M+H): 726.

Example 70

(1)

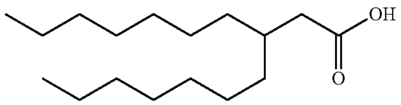

3-Heptyldecanoate as a colorless oily substance was obtained by the same method as that in (1) of Example 65, except that pentadecan-8-one was used instead of heptadecane-9-one in (1) of Example 65.

$^1$H-NMR ($CDCl_3$) δ:2.28 (2H, d, J=6.6 Hz), 1.90-1.79 (1H, m), 1.35-1.19 (24H, m), 0.88 (6H, t, J=6.6 Hz).

(2)

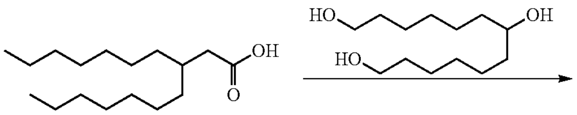

-continued

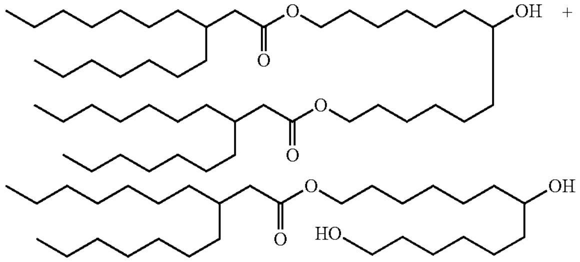

1-Ethyl-3-(3-dimethylaminopropyl)carbodiimide hydrochloride (1.07 g) was added to a mixture of 3-heptyldecanoate (974 mg), tridecane-1,7,13-triol (2.49 g), triethylamine (3.5 mL), 4-dimethylaminopyridine (51 mg), and dichloromethane (20 mL), and the mixture was stirred at room temperature for 4 days. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 7-hydroxytridecane-1,13-diylbis(3-heptyldecanoate) (1.03 g) as a colorless oily substance and 7,13-dihydroxytridecyl 3-heptyldecanoate (1.03 g) as a colorless oily substance.

7-Hydroxytridecane-1,13-diylbis(3-heptyldecanoate) $^1$H-NMR ($CDCl_3$) δ:4.05 (4H, t, J=6.6 Hz), 3.61-3.54 (1H, m), 2.22 (4H, d, J=7.2 Hz), 1.88-1.20 (70H, m), 0.88 (12H, t, J=6.6 Hz).

7,13-Dihydroxytridecyl 3-heptyldecanoate $^1$H-NMR ($CDCl_3$) δ:4.05 (2H, t, J=6.6 Hz), 3.68-3.55 (3H, m), 2.22 (2H, d, J=6.6 Hz), 1.88-1.77 (1H, m), 1.68-1.20 (44H, m), 0.88 (6H, t, J=6.6 Hz).

(3)

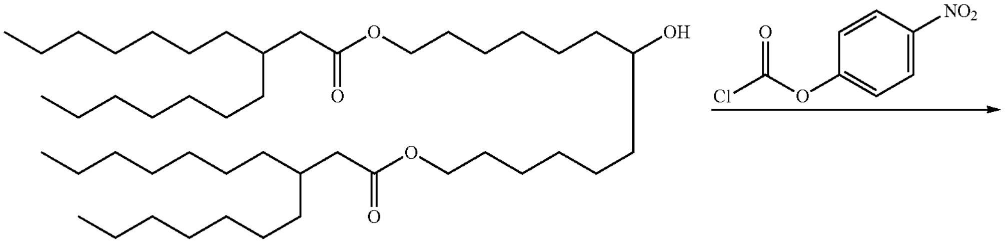

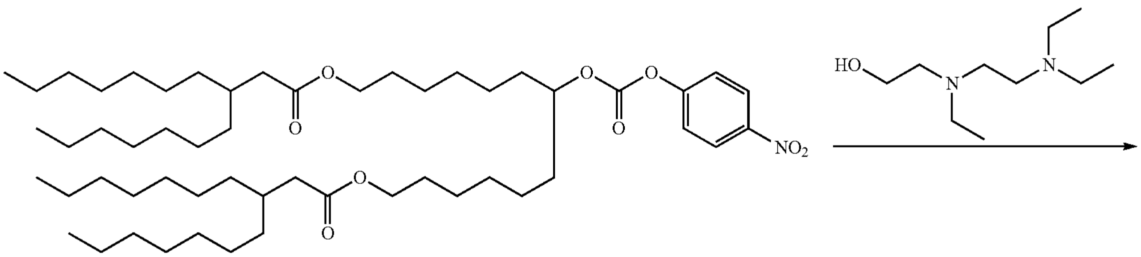

-continued

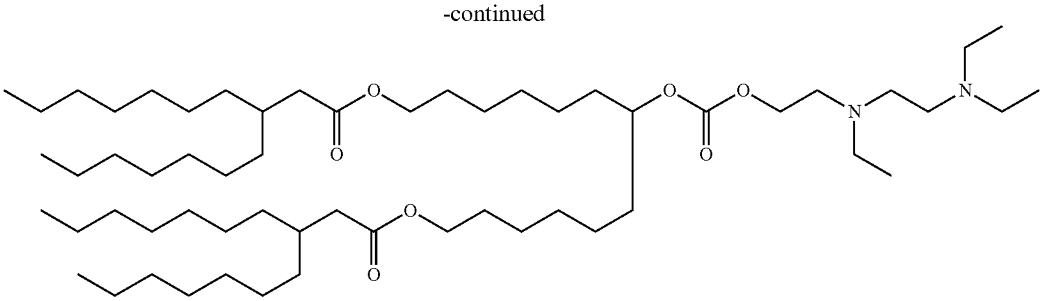

7-(((2-((2-(diethylamino)ethyl)(ethyl)amino)ethoxy)carbonyl)oxy)tridecane-1,13-diyl bis(3-heptyldecanoate) as a colorless oily substance was obtained by the same method as that in (1) and (2) of Example 20, except that in (1) and (2) of Example 20, 7-hydroxytridecane-1,13-diylbis(3-heptyldecanoate) was used instead of (6Z,9Z,28Z,31Z)-heptatriaconta-6,9,28,31-tetraen-19-ol, and 2-((2-(diethylamino)ethyl)(ethyl)amino)ethan-1-ol was used instead of 2-((2-(dimethylamino)ethyl)(methyl)amino)ethan-1-ol.

$^1$H-NMR ($CDCl_3$) δ:4.73-4.61 (1H, m), 4.17 (2H, t, J=6.6 Hz), 4.04 (4H, t, J=7.2 Hz), 2.76 (2H, t, J=6.0 Hz), 2.66-2.46 (10H, m), 2.22 (4H, d, J=7.2 Hz), 1.91-1.76 (2H, m), 1.67-1.15 (68H, m), 1.08-0.97 (9H, m), 0.88 (12H, t, J=6.6 Hz).

MS m/z (M+H): 952.

Example 71

(1)

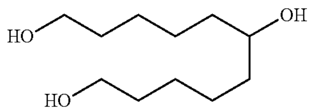

Undecane-1,6,11-triol as white solids was obtained by the same method as that in (1) of Example 36, except that 5-bromopentan-1-ol was used instead of 6-bromohexan-1-ol in (1) of Example 36.

$^1$H-NMR ($CDCl_3$) δ:3.70-3.55 (5H, m), 1.64-1.24 (16H, m).

(2)

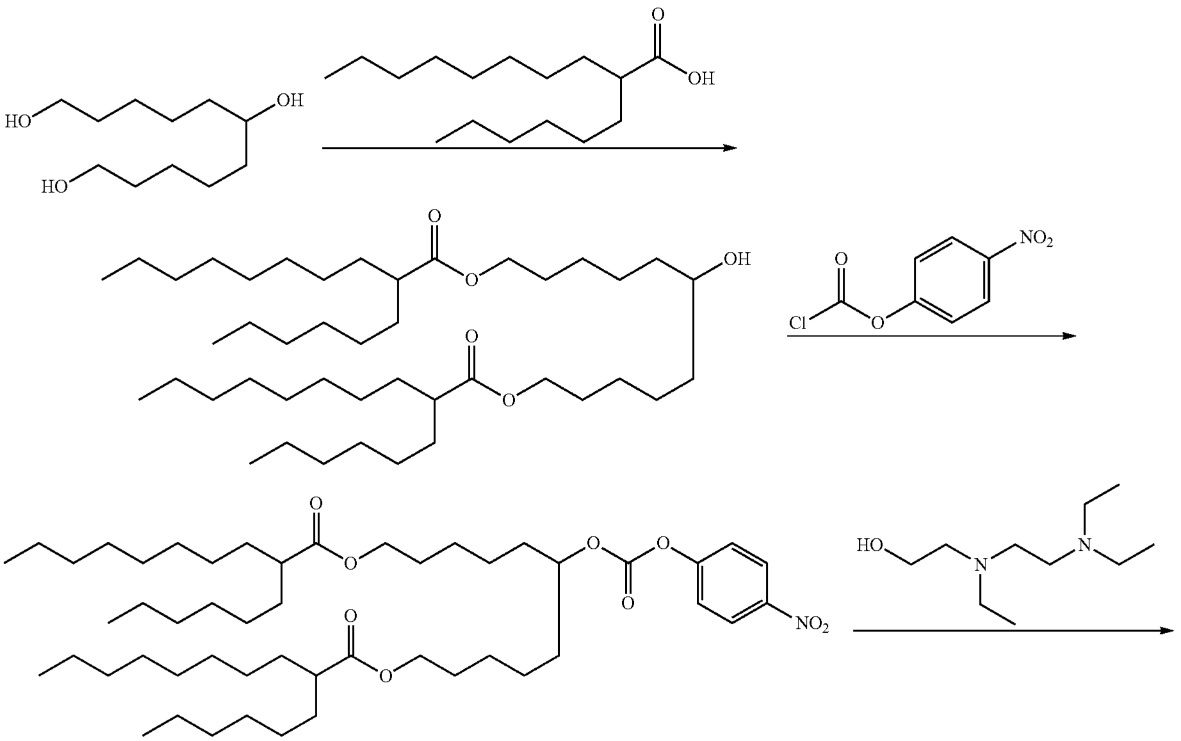

-continued
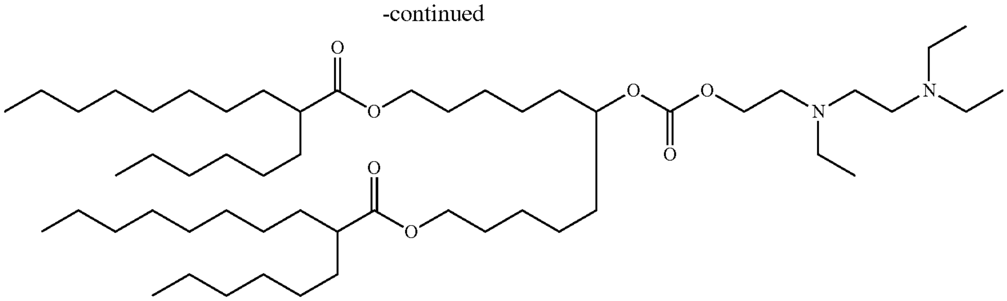
6-(((2-((2-(Diethylamino)ethyl)(ethyl)amino)ethoxy)carbonyl)oxy)undecane-1,11-diylbis(2-hexyldecanoate) as a colorless oily substance was obtained by the same method as that in (1) and (2) of Example 56, except that undecane-1,6,11-triol was used instead of tridecane-1,7,13-triol in (1) and (2) of Example 56.
$^1$H-NMR ($CDCl_3$) δ:4.72-4.63 (1H, m), 4.17 (2H, t, J=6.6 Hz), 4.05 (4H, t, J=6.6 Hz), 2.76 (2H, t, J=6.6 Hz), 2.66-2.47 (10H, m), 2.37-2.23 (2H, m), 1.71-1.18 (64H, m), 1.10-0.98 (9H, m), 0.88 (12H, t, J=7.2 Hz).
MS m/z (M+H): 896.
Example 72
(1)
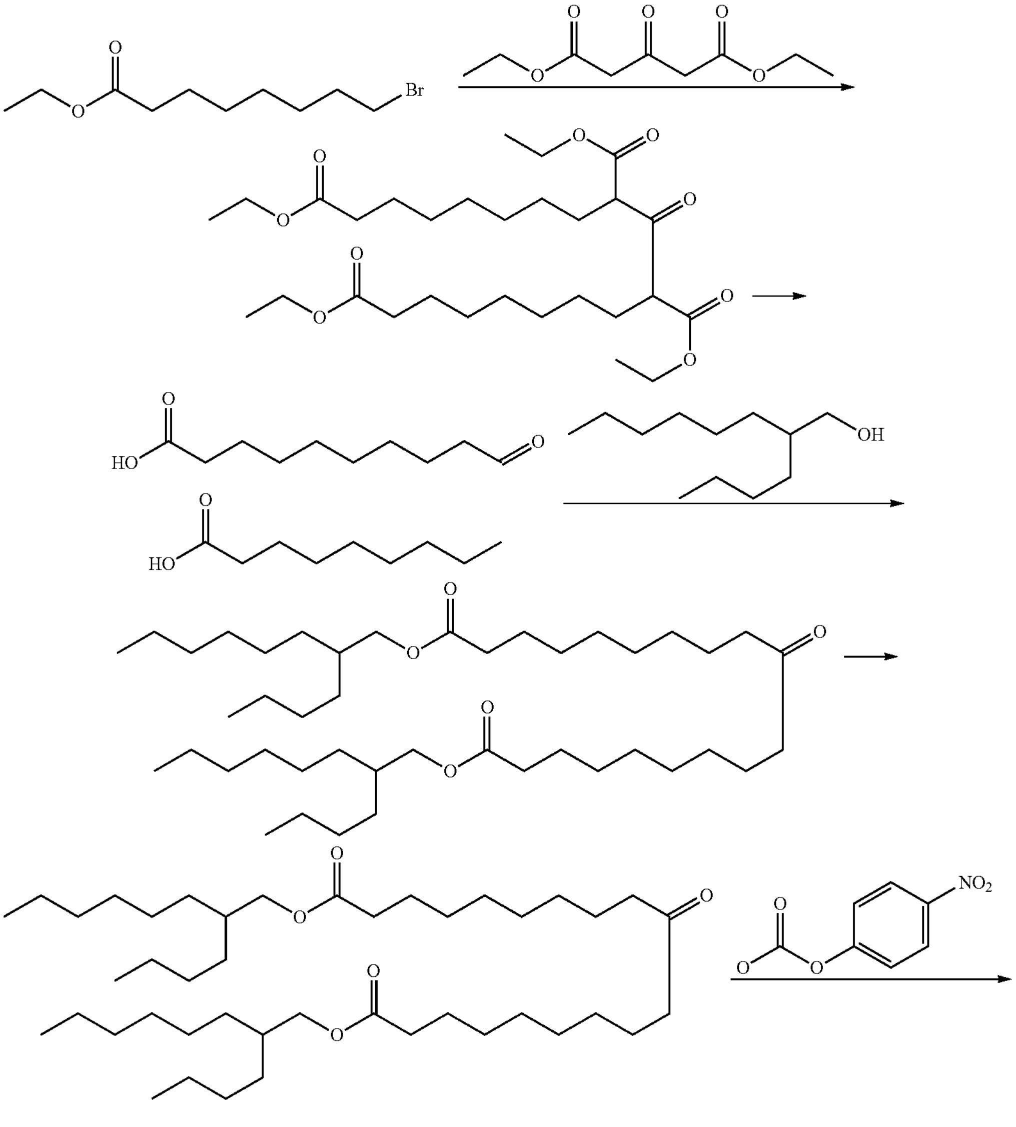

-continued

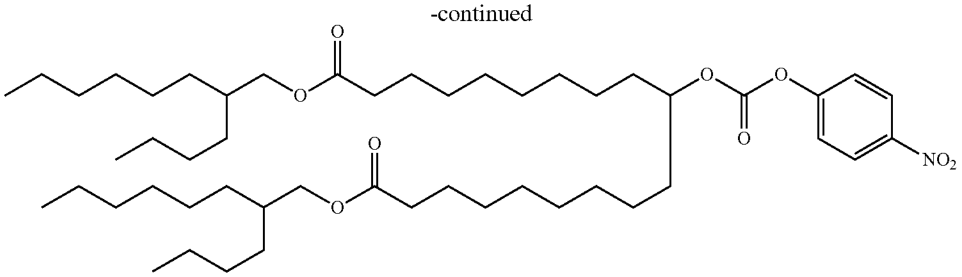

A mixture of diethyl 3-oxopentanedioate (4.0 g) and a 20% sodium ethoxide-ethanol solution (6.7 g) was stirred at 80° C. for 20 minutes, ethyl 8-bromooctanoate (5.0 g) was then added thereto, and the mixture was stirred for 4 hours. A 20% sodium ethoxide-ethanol solution (6.7 g) was added to the reaction mixture, the reaction mixture was stirred for 5 minutes, ethyl 8-bromooctanoate (5.0 g) was then added thereto, and the mixture was stirred for 3 hours. The reaction mixture was cooled to room temperature, hexane and a 20% aqueous ammonium chloride solution (10 mL) were then added thereto, the organic layer was separated, and the solvent was distilled away under reduced pressure, thereby obtaining tetraethyl 9-oxoheptadecane-1,8,10,17-tetracarboxylate (10.3 g) as a crude product.

A mixture of the obtained tetraethyl 9-oxoheptadecane-1,8,10,17-tetracarboxylate (2.5 g), acetic acid (4.0 mL), and a 30% aqueous hydrochloric acid solution (8.0 mL) was stirred at 115° C. for 6 hours. The reaction mixture was cooled to room temperature, the solvent was then distilled away under reduced pressure, and water and acetone were added to the residue. Solids were collected by filtration, washed with water and acetone, and then dried under reduced pressure, thereby obtaining 10-oxononane decanedioic acid (0.6 g) as white solids.

$^1$H-NMR (DMSO-$d_6$) δ: 2.38 (4H, t, J=7.2 Hz), 2.18 (4H, t, J=7.2 Hz), 1.54-1.38 (8H, m), 1.31-1.18 (16H, m).

1-Ethyl-3-(3-dimethylaminopropyl)carbodiimide hydrochloride (853 mg) was added to a mixture of 10-oxononane decanedioic acid (610 mg), 2-butyloctan-1-ol (663 mg), triethylamine (1.25 mL), 4-dimethylaminopyridine (217 mg), and dichloromethane (6 mL), and the mixture was stirred at room temperature for 2 days. A 10% aqueous potassium hydrogen sulfate solution (12 mL), hexane (6 mL), and ethyl acetate (6 mL) were added to the reaction mixture, the organic layer was separated and then dried over anhydrous sodium sulfate, and the solvent was distilled away under reduced pressure. The obtained residue was purified by silica gel column chromatography (ethyl acetate-hexane), thereby obtaining bis(2-butyloctyl) 10-oxononane decanedioate (612 mg) as a colorless oily substance.

$^1$H-NMR ($CDCl_3$) δ:3.97 (4H, d, J=6.0 Hz), 2.38 (4H, t, J=7.2 Hz), 2.30 (4H, t, J=7.2 Hz), 1.66-1.49 (10H, m), 1.36-1.23 (48H, m), 0.92-0.83 (12H, m).

Sodium borohydride (35 mg) was added to a mixture of bis(2-butyloctyl) 10-oxononane decanedioate (612 mg) and methanol (6 mL) under ice cooling, and the mixture was stirred at the same temperature for 1 hour. A 10% aqueous potassium hydrogen sulfate solution (6 mL) and hexane (6 mL) were added to the reaction mixture under ice cooling, the organic layer was separated and dried over anhydrous sodium sulfate, and the solvent was distilled away under reduced pressure. The obtained residue was purified by silica gel column chromatography (ethyl acetate-hexane), thereby obtaining bis(2-butyloctyl)10-hydroxynonadecanedioate (369 mg) as a colorless oily substance.

$^1$H-NMR ($CDCl_3$) δ:3.97 (4H, d, J=6.0 Hz), 3.62-3.52 (1H, m), 2.30 (4H, t, J=7.2 Hz), 1.66-1.53 (10H, m), 1.45-1.20 (52H, m), 0.92-0.83 (12H, m).

4-Nitrophenyl chloroformate (218 mg) was added to a mixture of bis(2-butyloctyl)10-hydroxynonadecanedioate (369 mg), triethylamine (0.30 mL), and tetrahydrofuran (2 mL), and the mixture was stirred at room temperature for 17 hours. Water and ethyl acetate were added to the reaction mixture, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining bis(2-butyloctyl)10-(((4-nitrophenoxy)carbonyl)oxy)nonadecanedioate (436 mg) as a colorless oily substance.

$^1$H-NMR ($CDCl_3$) δ:8.28 (2H, dd, J=7.2 Hz, 1.8 Hz), 7.38 (2H, dd, J=7.2 Hz, 1.8 Hz), 4.86-4.74 (1H, m), 3.97 (4H, d, J=6.0 Hz), 2.30 (4H, t, J=7.2 Hz), 1.66-1.53 (10H, m), 1.45-1.20 (52H, m), 0.92-0.83 (12H, m).

(2)

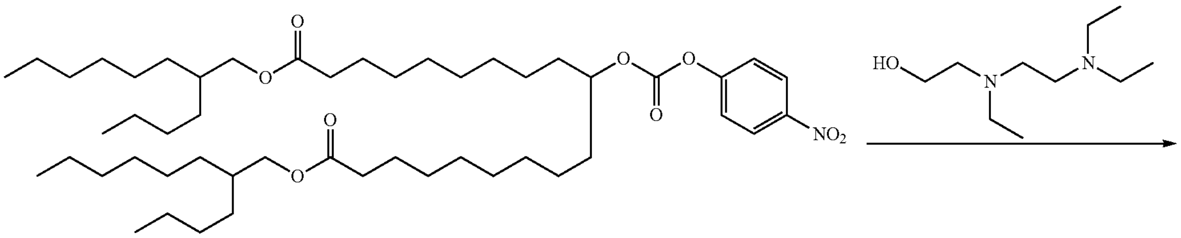

-continued

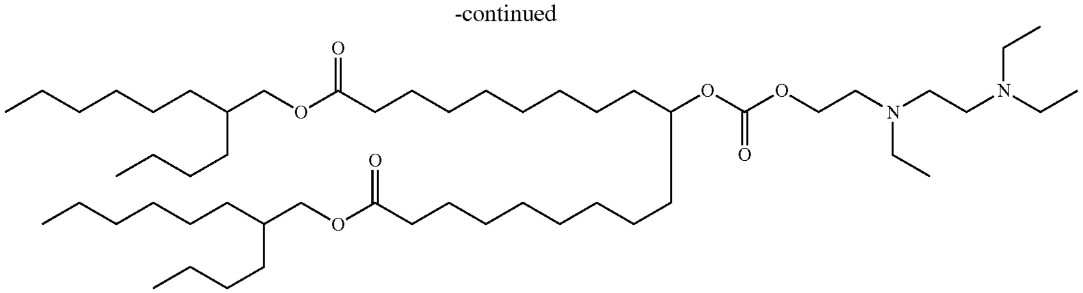

Bis(2-butyloctyl)10-(((2-((2-(diethylamino)ethyl)(ethyl)amino)ethoxy)carbonyl)oxy) nonadecanedioate as a colorless oily substance was obtained by the same method as that in (2) of Example 41, except that bis(2-butyloctyl)10-(((4-nitrophenoxy)carbonyl)oxy)nonadecanedioate was used instead of 7-(((4-nitrophenoxy)carbonyl)oxy)tridecane-1,13-diyldioleate in (2) of Example 41.

$^1$H-NMR ($CDCl_3$) δ:4.71-4.62 (1H, m), 4.17 (2H, t, J=6.6 Hz), 3.96 (4H, d, J=6.0 Hz), 2.76 (2H, t, J=6.6 Hz), 2.64-2.48 (10H, m), 2.29 (4H, t, J=7.2 Hz), 1.66-1.50 (10H, m), 1.36-1.20 (52H, m), 1.03 (3H, t, J=7.2 Hz), 1.02 (6H, t, J=7.2 Hz), 0.93-0.84 (12H, m).

MS m/z (M+H): 896.

Example 73

(1)

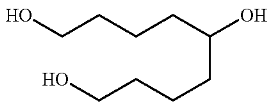

Nonane-1,5,9-triol as white solids was obtained by the same method as that in (1) of Example 36, except that 4-bromobutan-1-ol was used instead of 6-bromohexan-1-ol in (1) of Example 36.

$^1$H-NMR ($CDCl_3$) δ:3.70-3.55 (5H, m), 1.64-1.24 (12H, m).

(2)

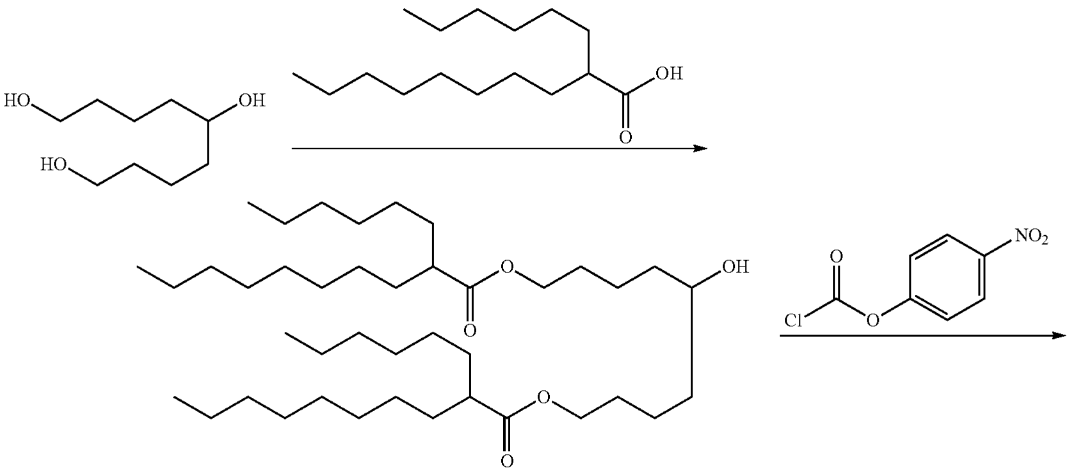

-continued

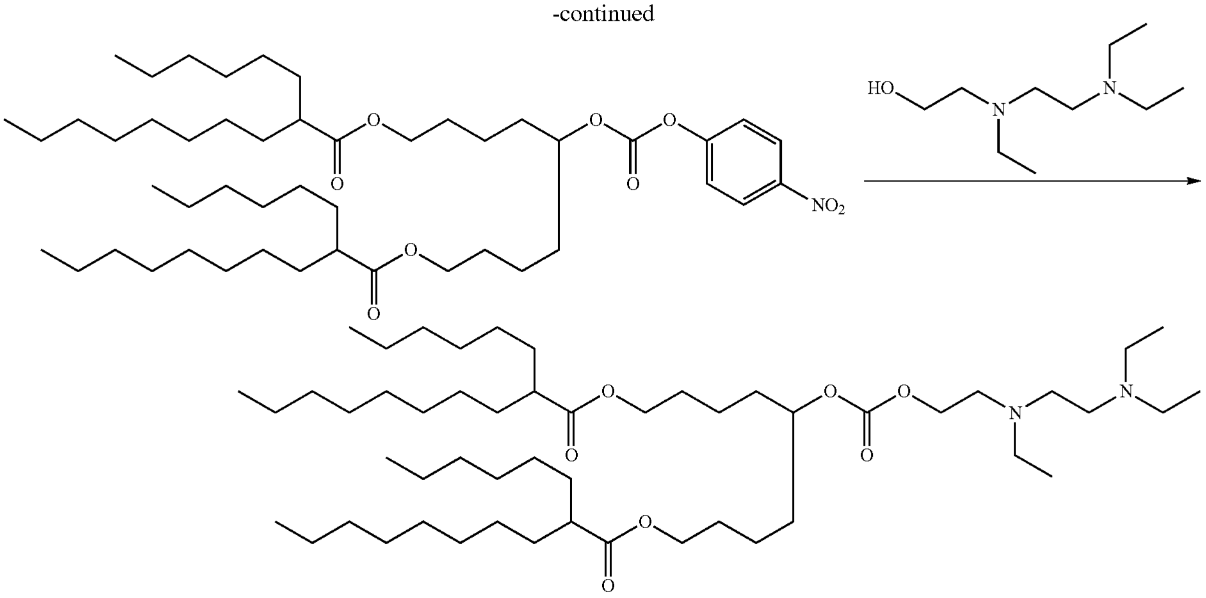

5-(((2-((2-(Diethylamino)ethyl)(ethyl)amino)ethoxy)carbonyl)oxy)nonane-1,9-diylbis (2-hexyldecanoate) as a colorless oily substance was obtained by the same method as that in (1) and (2) of Example 56, except that nonane-1,5,9-triol was used instead of tridecane-1,7,13-triol in (1) and (2) of Example 56.

$^1$H-NMR ($CDCl_3$) δ:4.74-4.63 (1H, m), 4.17 (2H, t, J=5.7 Hz), 4.05 (4H, t, J=6.6 Hz), 2.76 (2H, t, J=6.6 Hz), 2.66-2.48 (10H, m), 2.36-2.24 (2H, m), 1.70-1.16 (60H, m), 1.09-0.98 (9H, m), 0.88 (12H, t, J=6.6 Hz).

MS m/z (M+H): 868.

Example 74

(1)

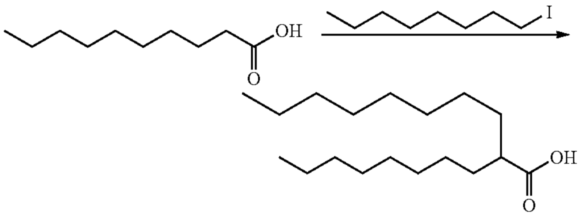

Decanoic acid (3.0 g) was added dropwise to a tetrahydrofuran (30 mL) suspension of 60 wt % sodium hydride under ice cooling, and the mixture was stirred at the same temperature for 30 minutes. A 1.5 mol/L lithium diisopropylamide-tetrahydrofuran-heptane-ethyl benzene solution (13.9 mL) was added to the reaction mixture at the same temperature, and the reaction mixture was stirred at room temperature for 30 minutes. Then, 1-iodooctane (3.8 mL) was added dropwise thereto, and the reaction mixture was stirred at 45° C. for 6 hours.

The reaction mixture was poured into a mixture of a 1 mol/L aqueous hydrochloric acid solution and ethyl acetate under ice cooling, the organic layer was then separated, washed with a saturated aqueous sodium chloride solution, and dried over anhydrous magnesium sulfate, and then the solvent was distilled away under reduced pressure. The obtained residue was purified by silica gel column chromatography (ethyl acetate-hexane), thereby obtaining 2-octyl decanoate (2.62 g) as a yellow oily substance.

$^1$H-NMR ($CDCl_3$) δ:2.43-2.30 (1H, m), 1.72-1.20 (28H, m), 0.88 (6H, t, J=6.6 Hz).

(2)

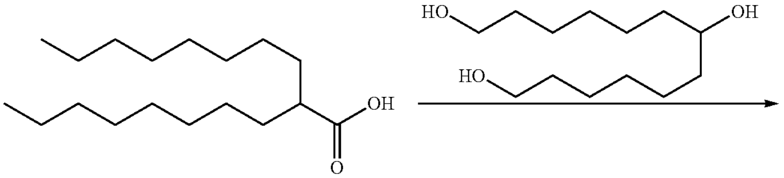

-continued

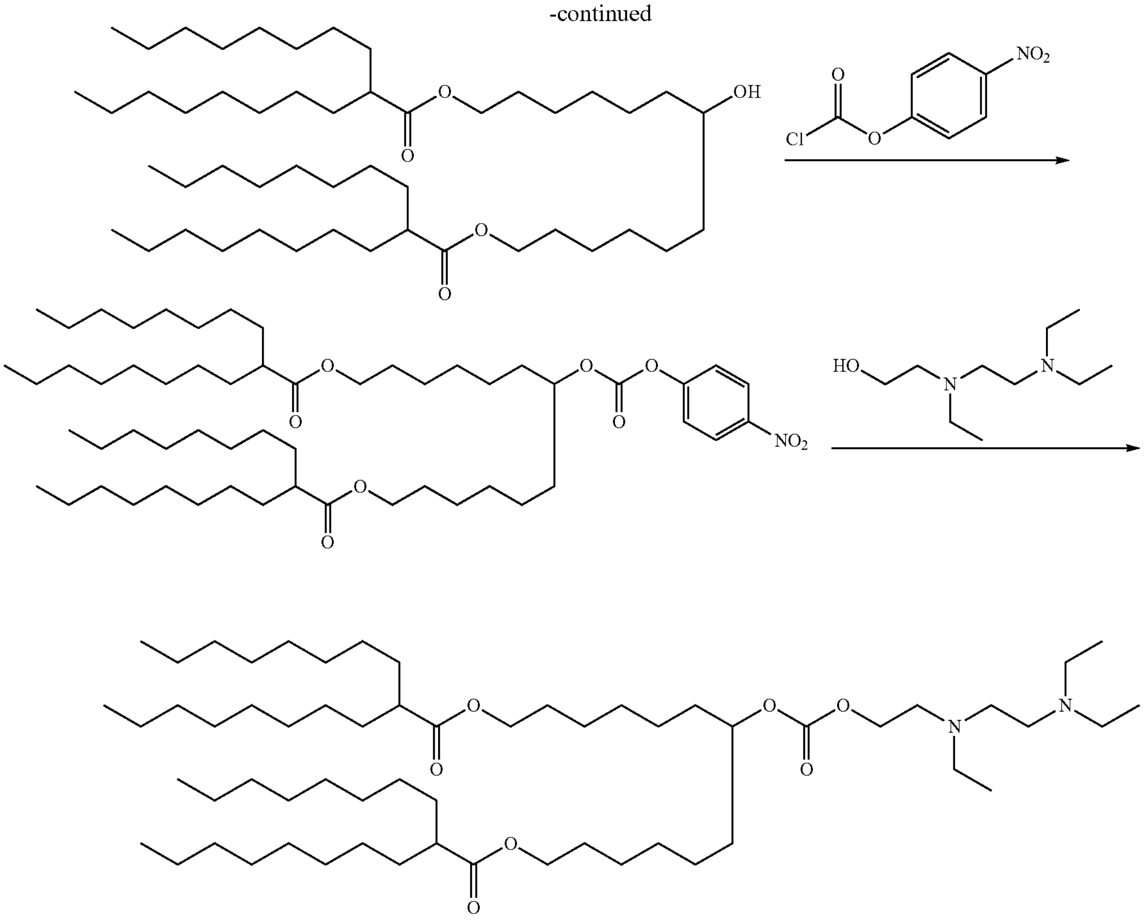

7-(((2-((2-(Diethylamino)ethyl)(ethyl)amino)ethoxy)carbonyl)oxy)tridecane-1,13-diyl bis(2-octyldecanoate) as a colorless oily substance was obtained by the same method as that in (1) and (2) of Example 41, except that 2-octyldecanoate was used instead of oleic acid in (1) and (2) of Example 41.

$^1$H-NMR ($CDCl_3$) δ:4.73-4.60 (1H, m), 4.17 (2H, t, J=6.6 Hz), 4.05 (4H, t, J=6.6 Hz), 2.76 (2H, t, J=6.0 Hz), 2.66-2.47 (10H, m), 2.37-2.24 (2H, m), 1.70-1.16 (76H, m), 1.11-0.98 (9H, m), 0.88 (12H, t, J=6.6 Hz).

MS m/z (M+H): 980.

Example 75

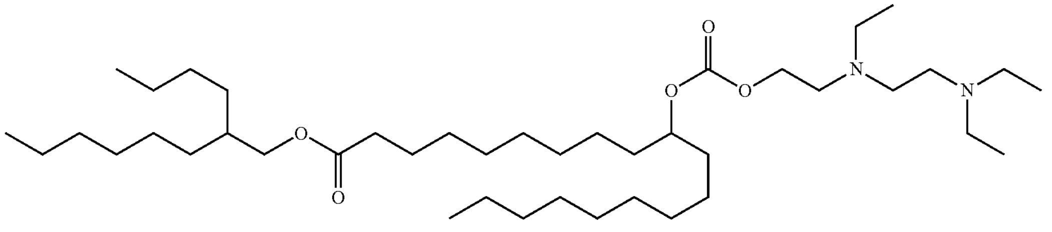 [SMILES: CCCCCCCCCC(CCCCCCCCC(=O)OCC(CCCC)CCCCCC)OC(=O)OCCN(CC)CCN(CC)CC]

2-Butyloctyl 3,6-diethyl-12-nonyl-10-oxo-9,11-dioxa-3,6-diazahenicosan-21-oate as a colorless oily substance was obtained by the same method as that in Example 50, except that a 1.0 mol/L nonyl magnesium bromide-diethyl ether solution was used instead of a 1.0 mol/L dodecyl magnesium bromide-diethyl ether solution in Example 50.

$^1$H-NMR ($CDCl_3$) δ:4.73-4.60 (1H, m), 4.18 (2H, t, J=6.6 Hz), 3.97 (2H, d, J=5.7 Hz), 2.76 (2H, t, J=6.6 Hz), 2.66-2.47 (10H, m), 2.30 (2H, t, J=7.8 Hz), 1.69-1.47 (7H, m), 1.41-1.19 (40H, m), 1.09-0.97 (9H, m), 0.94-0.83 (9H, m).

MS m/z (M+H): 698.

Example 76

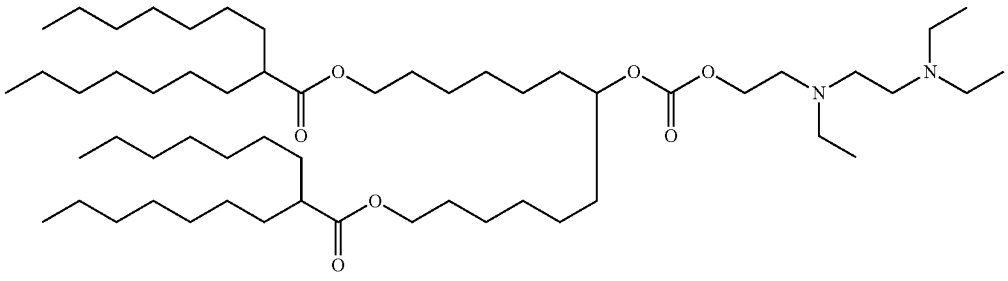 [SMILES: CCCCCCCC(CCCCCCC)C(=O)OCCCCCCC(CCCCCCOC(=O)C(CCCCCCC)CCCCCCC)OC(=O)OCCN(CC)CCN(CC)CC]

7-(((2-((2-(Diethylamino)ethyl)(ethyl)amino)ethoxy)carbonyl)oxy)tridecane-1,13-diyl bis(2-heptylnonanoate) as a colorless oily substance was obtained by the same method as that in (1) and (2) of Example 74, except that in (1) and (2) of Example 74, nonanoic acid was used instead of decanoic acid, and 1-iodoheptane was used instead of 1-iodooctane.

$^1$H-NMR ($CDCl_3$) δ:4.73-4.61 (1H, m), 4.18 (2H, t, J=6.6 Hz), 4.05 (4H, t, J=6.6 Hz), 2.76 (2H, t, J=6.6 Hz), 2.66-2.48 (10H, m), 2.37-2.23 (2H, m), 1.68-1.16 (68H, m), 1.08-0.97 (9H, m), 0.87 (12H, t, J=6.6 Hz).

MS m/z (M+H): 924.

Example 77

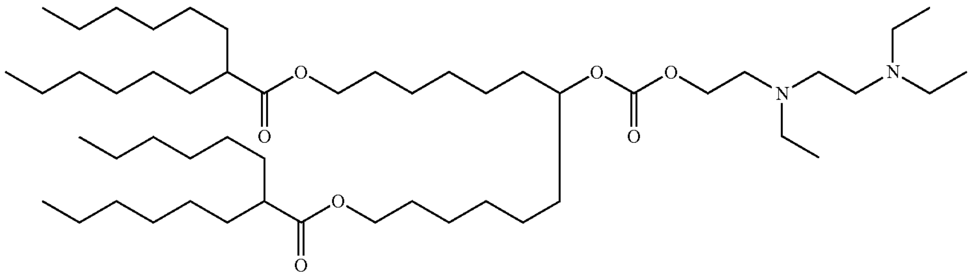 [SMILES: CCCCCCC(CCCCCC)C(=O)OCCCCCCC(CCCCCCOC(=O)C(CCCCCC)CCCCCC)OC(=O)OCCN(CC)CCN(CC)CC]

7-(((2-((2-(Diethylamino)ethyl)(ethyl)amino)ethoxy)carbonyl)oxy)tridecane-1,13-diyl bis(2-hexyloctanoate) as a colorless oily substance was obtained by the same method as that in (1) and (2) of Example 74, except that in (1) and (2) of Example 74, octanoic acid was used instead of decanoic acid, and 1-iodohexane was used instead of 1-iodooctane.

$^1$H-NMR ($CDCl_3$) δ:4.73-4.60 (1H, m), 4.17 (2H, t, J=6.6 Hz), 4.05 (4H, t, J=6.6 Hz), 2.76 (2H, t, J=6.6 Hz), 2.67-2.45 (10H, m), 2.37-2.24 (2H, m), 1.72-1.15 (60H, m), 1.12-0.96 (9H, m), 0.87 (12H, t, J=6.6 Hz).

MS m/z (M+H): 868.

Example 78

(1)

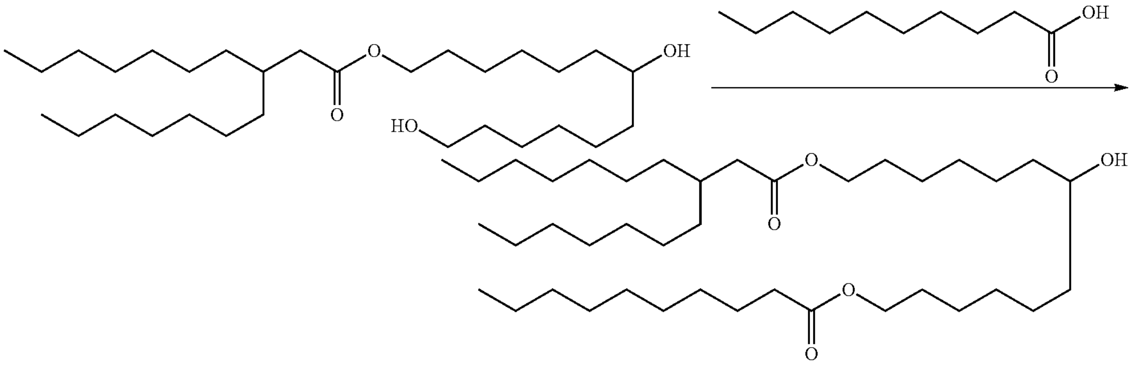

1-Ethyl-3-(3-dimethylaminopropyl)carbodiimide hydrochloride (126 mg) was added to a mixture of 7,13-dihydroxytridecyl 3-heptyldecanoate (500 mg) synthesized in (1) and (2) of Example 70, decanoic acid (195 mg), triethylamine (0.43 mL), 4-dimethylaminopyridine (38 mg), and dichloromethane (10 mL), and the mixture was stirred at room temperature for 18 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 13-(decanoyloxy)-7-hydroxytridecyl 3-heptyldecanoate (469 mg) as a colorless oily substance.

$^1$H-NMR ($CDCl_3$) δ:4.06 (4H, t, J=6.6 Hz), 3.63-3.53 (1H, m), 2.29 (2H, t, J=7.2 Hz), 2.22 (2H, d, J=7.2 Hz), 1.88-1.78 (1H, m), 1.68-1.20 (60H, m), 0.88 (9H, t, J=6.6 Hz).

(2)

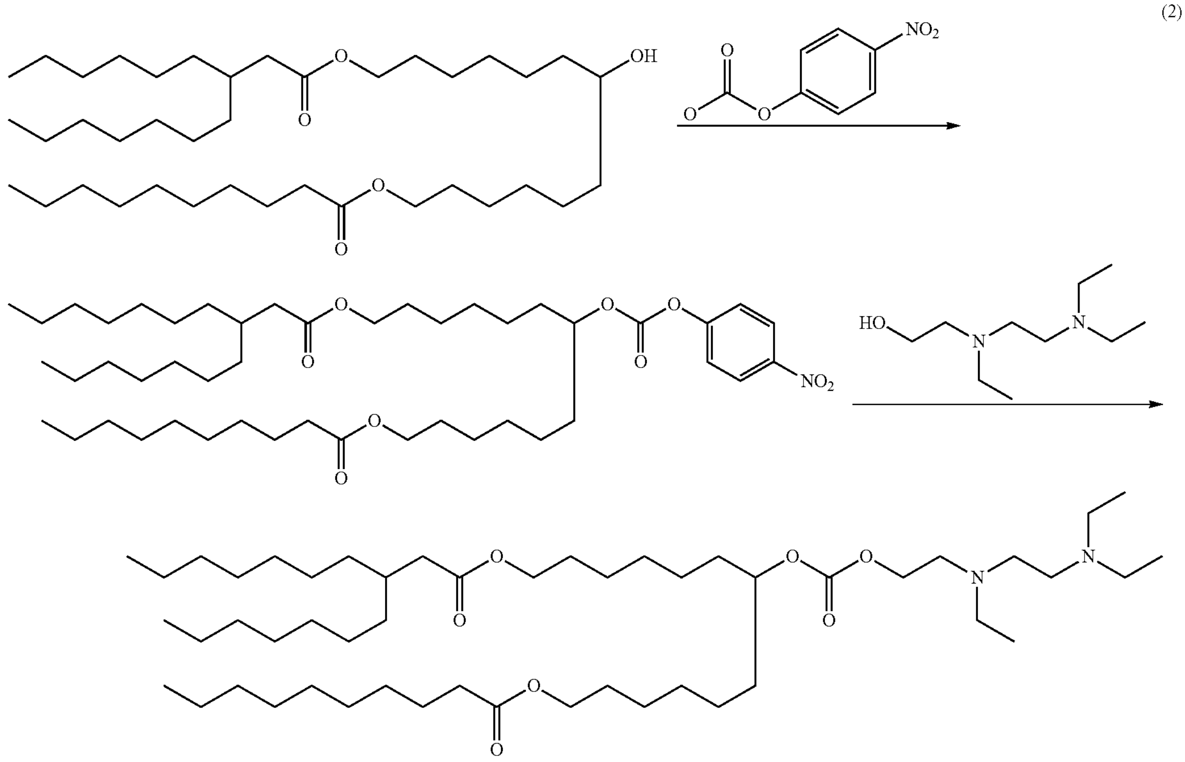

12-(6-(Decanoyloxy)hexyl)-3,6-diethyl-10-oxo-9,11-dioxa-3,6-diazooctadecan-18-yl 3-heptyldecanoate as a colorless oily substance was obtained by the same method as that in (1) and (2) of Example 20, except that in (1) and (2) of Example 20, 13-(decanoyloxy)-7-hydroxytridecyl-3-heptyldecanoate was used instead of (6Z,9Z,28Z,31Z)-heptatriaconta-6,9,28,31-tetraen-19-ol, and 2-((2-(diethylamino)ethyl)(ethyl)amino)ethan-1-ol was used instead of 2-((2-(dimethylamino)ethyl)(methyl)amino)ethan-1-ol.

$^1$H-NMR ($CDCl_3$) δ:4.72-4.61 (1H, m), 4.17 (2H, t, J=6.0 Hz), 4.04 (4H, t, J=6.6 Hz), 2.76 (2H, t, J=6.6 Hz), 2.67-2.45 (10H, m), 2.29 (2H, t, J=8.1 Hz), 2.22 (2H, d, J=7.2 Hz), 1.87-1.78 (1H, m), 1.70-1.18 (58H, m), 1.11-0.97 (9H, m), 0.93-0.82 (9H, m).

MS m/z (M+H): 854.

Example 79

(1)

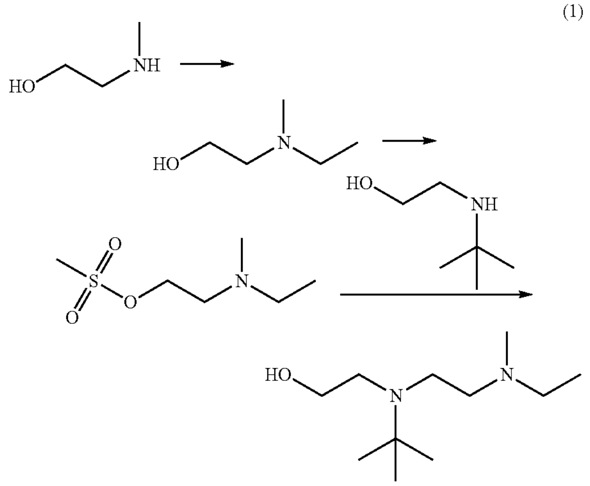

Ethyl iodide (3.4 mL) was added dropwise to an acetonitrile solution (30 mL) of 2-(methylamino)ethan-1-ol (3.0 g)

under ice cooling, and the mixture was stirred at the same temperature for 1 hour and 45 minutes and then stirred at 60° C. for 3 hours and 10 minutes. Potassium carbonate and water were added to the reaction mixture, and extraction was performed using chloroform. The organic layer was washed with saturated saline and dried over anhydrous sodium sulfate. The solvent was distilled away under reduced pressure, thereby obtaining 2-(ethyl(methyl)amino)ethan-1-ol (3.4 g) as a colorless oily substance.

MS m/z (M+H): 104.

A tetrahydrofuran solution (20 mL) of methanesulfonic anhydride (7.6 g) was added dropwise to a mixture of 2-(ethyl(methyl)amino)ethan-1-ol (3.0 g), 4-dimethylaminopyridine (0.36 g), N,N-diisopropylethylamine (9.9 mL), and tetrahydrofuran (60 mL) under ice cooling. The mixture was stirred at 0° C. for 15 minutes and then stirred at room temperature for 3 hours and 45 minutes. 2-(tert-Butylamino)ethan-1-ol (6.0 g), sodium iodide (0.45 g), and water (1 mL) were added to the reaction mixture, and the reaction mixture was stirred at 75° C. for 30 hours. The reaction mixture was cooled to room temperature, the solvent was distilled away under reduced pressure, water and a 2 mol/L aqueous sodium hydroxide solution were then added thereto, and extraction was performed using ethyl acetate. The organic layer was washed with saturated saline and dried over anhydrous sodium sulfate. The solvent was distilled away under reduced pressure, and the obtained residue was purified by silica gel column chromatography (ethyl acetate-hexane, NH silica gel), thereby obtaining 2-(tert-butyl(2-(ethyl(methyl)amino)ethyl)amino)ethan-1-ol (0.15 g) as a yellow oily substance.

MS m/z (M+H): 203.

(2)

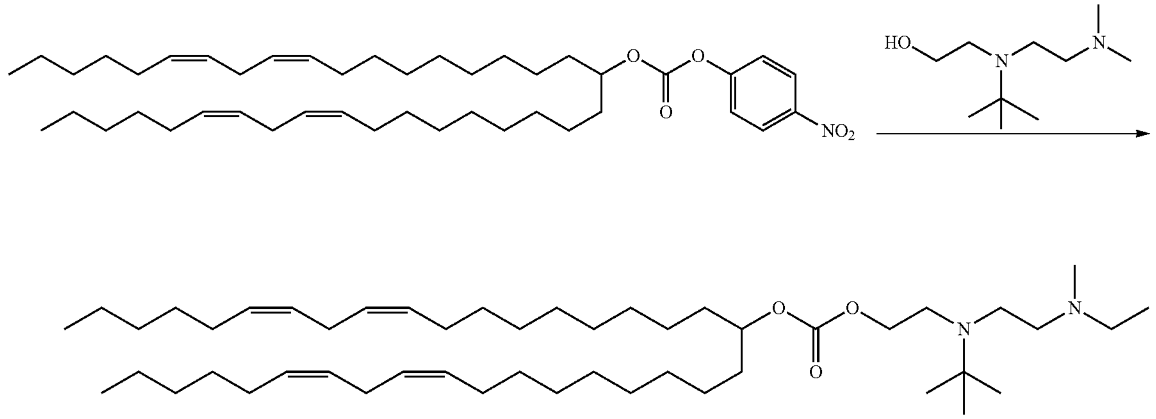

2-(tert-Butyl(2-(ethyl(methyl)amino)ethyl)amino)ethyl ((6Z,9Z,28Z,31Z)-heptatriaconta-6,9,28,31-tetraen-19-yl) carbonate as a colorless oily substance was obtained by the same method as that in (2) of Example 20, except that 2-(tert-butyl(2-(ethyl(methyl)amino)ethyl)amino)ethan-1-ol was used instead of 2-((2-(dimethylamino)ethyl)(methyl)amino)ethan-1-ol in (2) of Example 20.

$^1$H-NMR ($CDCl_3$) δ:5.44-5.25 (8H, m), 4.73-4.62 (1H, m), 4.06 (2H, t, J=7.5 Hz), 2.84-2.73 (6H, m), 2.72-2.59 (2H, m), 2.50-2.34 (4H, m), 2.25 (3H, s), 2.11-1.97 (8H, m), 1.65-1.48 (4H, m), 1.43-1.19 (36H, m), 1.12-1.01 (12H, m), 0.89 (6H, t, J=6.6 Hz).

MS m/z (M+H): 758.

Example 80

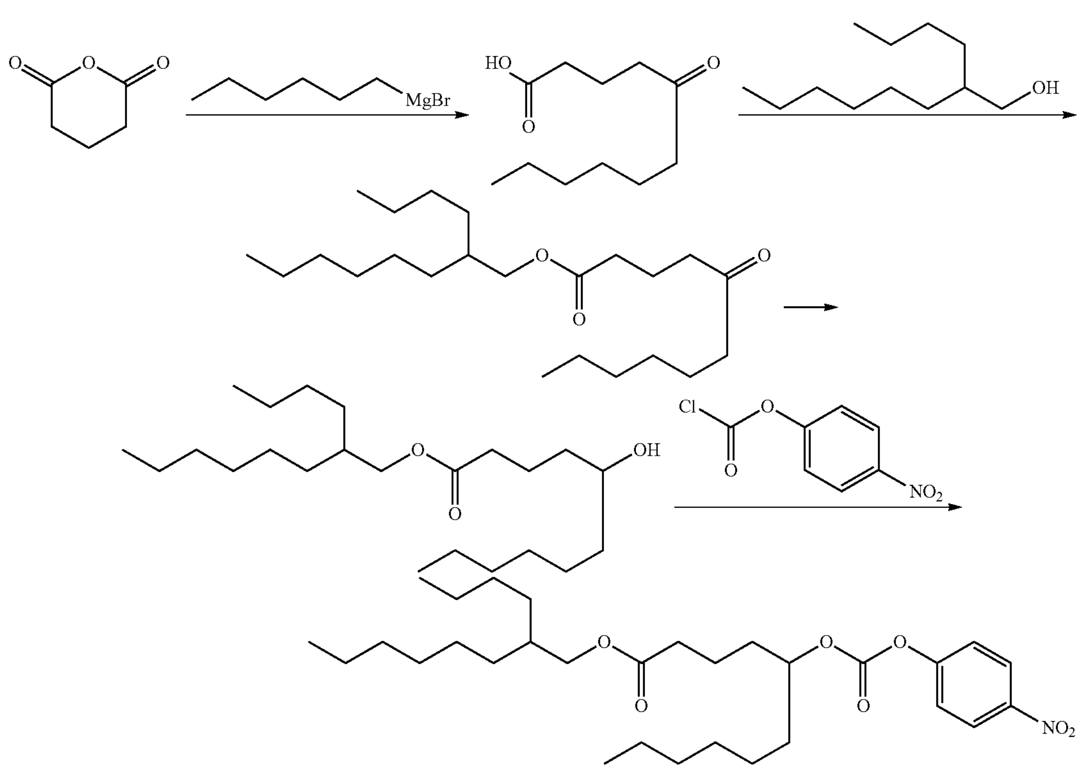

A 1 mol/L hexyl magnesium bromide-tetrahydrofuran solution (200 mL) was added dropwise to a tetrahydrofuran (273 mL) solution of glutaric anhydride (27.3 g) under ice cooling, and the mixture was stirred at the same temperature for 1 hour. A 2 mol/L aqueous hydrochloric acid solution (240 mL) was added to the reaction mixture under ice cooling, ethyl acetate (270 mL) was then added thereto, the organic layer was separated, washed with water and a saturated aqueous sodium chloride solution, and dried over anhydrous magnesium sulfate, and then the solvent was distilled away under reduced pressure. The obtained residue was purified by silica gel column chromatography (ethyl acetate-hexane), hexane (10 mL) was then added thereto, and solids were collected by filtration, washed with hexane, and then dried under reduced pressure, thereby obtaining 5-oxoundecanoic acid (16.0 g) as white solids.

$^1$H-NMR ($CDCl_3$) δ:2.50 (2H, t, J=7.2 Hz), 2.40 (4H, t, J=7.2 Hz), 2.02-1.80 (2H, m), 1.63-1.48 (2H, m), 1.37-1.20 (6H, m), 0.88 (3H, t, J=6.6 Hz).

1-Ethyl-3-(3-dimethylaminopropyl)carbodiimide hydrochloride (5.8 g) was added to a mixture of 5-oxoundecanoic acid (4.0 g), 2-butyloctan-1-ol (3.7 g), triethylamine (8.4 mL), 4-dimethylaminopyridine (1.22 g), and dichloromethane (40 mL), and the mixture was stirred at 40° C. for 3 hours. Water and ethyl acetate were added to the reaction mixture, the organic layer was separated, washed with water, and then dried over anhydrous magnesium sulfate, and the solvent was distilled away under reduced pressure. The obtained residue was purified by silica gel column chromatography (ethyl acetate-hexane), thereby obtaining 2-butyloctyl 5-oxoundecanoate (7.3 g) as a colorless oily substance.

$^1$H-NMR ($CDCl_3$) δ:3.97 (2H, d, J=5.1 Hz), 2.47 (2H, t, J=7.2 Hz), 2.39 (2H, t, J=7.2 Hz), 2.33 (2H, t, J=7.2 Hz), 1.95-1.83 (2H, m), 1.66-1.49 (3H, m), 1.36-1.20 (22H, m), 0.92-0.82 (9H, m).

Sodium borohydride (1.1 g) was added to a mixture of 2-butyloctyl 5-oxoundecanoate (7.3 g), tetrahydrofuran (35 mL), and methanol (35 mL) under ice cooling, and the mixture was stirred at the same temperature for 30 minutes. A 2.0 mol/L aqueous hydrochloric acid solution (35 mL) and hexane (35 mL) were added to the reaction mixture under ice cooling, the organic layer was separated, then washed with a saturated aqueous sodium chloride solution, and dried over anhydrous sodium sulfate, and then the solvent was distilled away under reduced pressure. The obtained residue was purified by silica gel column chromatography (ethyl acetate-hexane), thereby obtaining 2-butyloctyl 5-hydroxyundecanoate (6.3 g) as a colorless oily substance.

$^1$H-NMR ($CDCl_3$) δ:3.97 (2H, d, J=5.7 Hz), 3.65-3.53 (1H, m), 2.35 (2H, t, J=7.2 Hz), 1.87-1.20 (32H, m), 0.92-0.84 (9H, m).

4-Nitrophenyl chloroformate (1.71 g) was added to a mixture of 2-butyloctyl 5-hydroxyundecanoate (1.62 g), triethylamine (2.38 mL), and tetrahydrofuran (16 mL), and the mixture was stirred at room temperature for 4 hours. Water and ethyl acetate were added to the reaction mixture, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining 2-butyloctyl 5-(((4-nitrophenoxy)carbonyl)oxy)undecanoate (1.99 g) as a colorless oily substance.

$^1$H-NMR ($CDCl_3$) δ:8.28 (2H, d, J=9.3 Hz), 7.39 (2H, d, J=9.3 Hz), 4.88-4.77 (1H, m), 3.99 (2H, d, J=6.0 Hz), 2.41-2.31 (2H, m), 1.80-1.48 (7H, m), 1.44-1.20 (24H, m), 0.92-0.83 (9H, m).

(2)

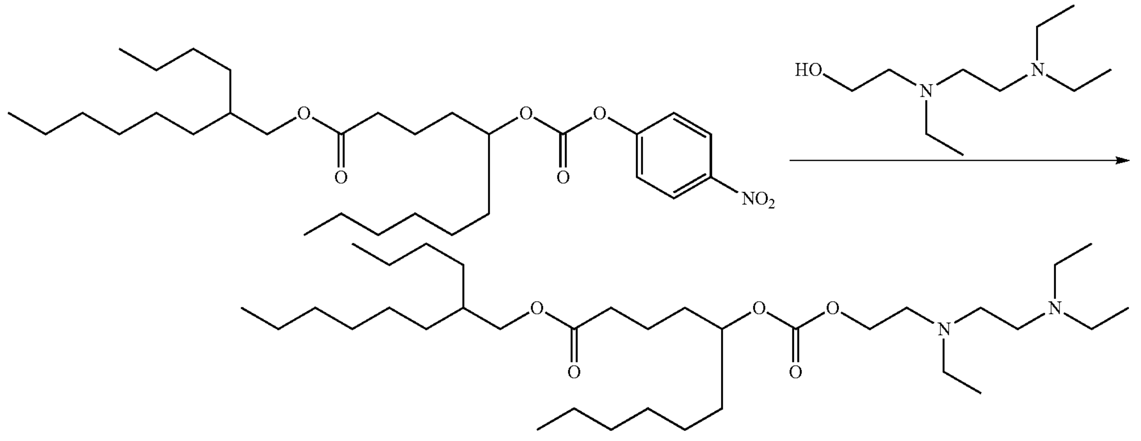

4-Dimethylaminopyridine (342 mg) was added to a mixture of 2-butyloctyl 5-(((4-nitrophenoxy)carbonyl)oxy)undecanoate (500 mg), 2-((2-(diethylamino)ethyl)(ethyl)amino)ethan-1-ol (527 mg), triethylamine (0.787 mL), and tetrahydrofuran (2.5 mL), and the mixture was stirred at 60° C. for 10 hours. The reaction mixture was cooled to room temperature, water and ethyl acetate were added thereto, the organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 2-butyloctyl 3,6-diethyl-12-hexyl-10-oxo-9,11-dioxa-3,6-diazahexadecan-16-oate (356 mg) as a colorless oily substance.

$^1$H-NMR ($CDCl_3$) δ:4.73-4.64 (1H, m), 4.22-4.12 (2H, m), 3.97 (2H, d, J=5.1 Hz), 2.76 (2H, t, J=6.6 Hz), 2.64-2.49 (10H, m), 2.32 (2H, t, J=6.6 Hz), 1.73-1.50 (7H, m), 1.36-1.20 (24H, m), 1.06-0.99 (9H, m), 0.92-0.84 (9H, m).

MS m/z (M+H): 586.

Example 81

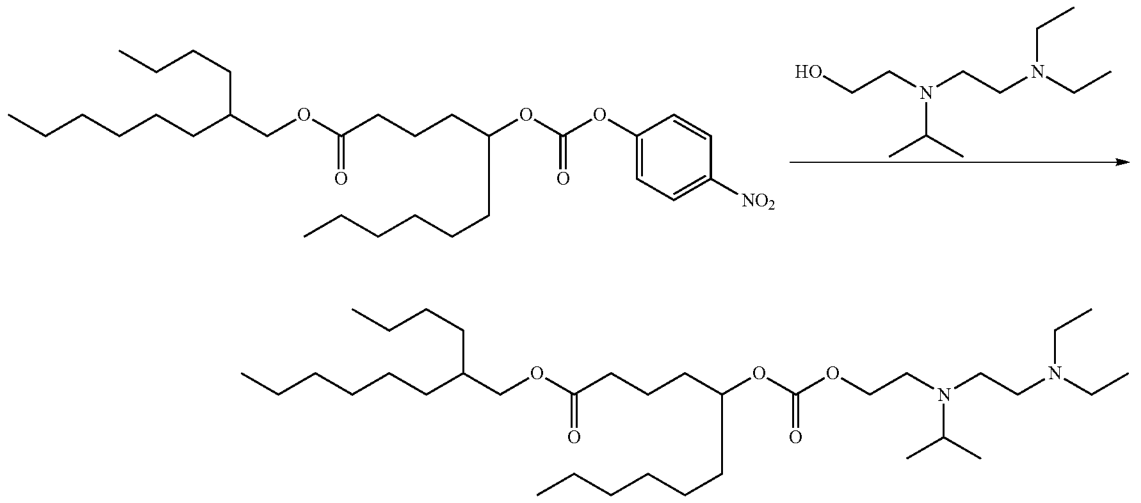

2-Butyloctyl 3-ethyl-12-hexyl-6-isopropyl-10-oxo-9,11-dioxa-3,6-diazahexadecan-16-oate as a colorless oily substance was obtained by the same method as that in (2) of Example 80, except that 2-((2-(diethylamino)ethyl)(isopropyl)amino)ethan-1-ol was used instead of 2-((2-(diethylamino)ethyl)(ethyl)amino)ethan-1-ol in (2) of Example 80.

$^1$H-NMR ($CDCl_3$) δ:4.73-4.64 (1H, m), 4.15-4.04 (2H, m), 3.97 (2H, d, J=5.4 Hz), 2.97-2.83 (1H, m), 2.68 (2H, t, 6.6 Hz), 2.58-2.43 (8H, m), 2.32 (2H, t, J=6.6 Hz), 1.73-1.50 (7H, m), 1.36-1.20 (24H, m), 1.06-0.96 (12H, m), 0.92-0.84 (9H, m).

MS m/z (M+H): 600.

Example 82

(1)

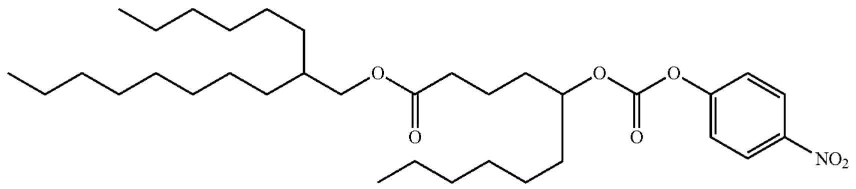

2-Hexyldecyl 5-(((4-nitrophenoxy)carbonyl)oxy)undecanoate as a colorless oily substance was obtained by the same method as that in (1) of Example 80, except that 2-hexyldecan-1-ol was used instead of 2-butyloctan-1-ol in (1) of Example 80.

$^1$H-NMR ($CDCl_3$) δ:8.27 (2H, dd, J=6.6 Hz, 1.8 Hz), 7.38 (2H, dd, J=6.6 Hz, 1.8 Hz), 4.88-4.78 (1H, m), 3.98 (2H, d, J=6.0 Hz), 2.41-2.30 (2H, m), 1.79-1.53 (7H, m), 1.42-1.20 (32H, m), 0.92-0.83 (9H, m).

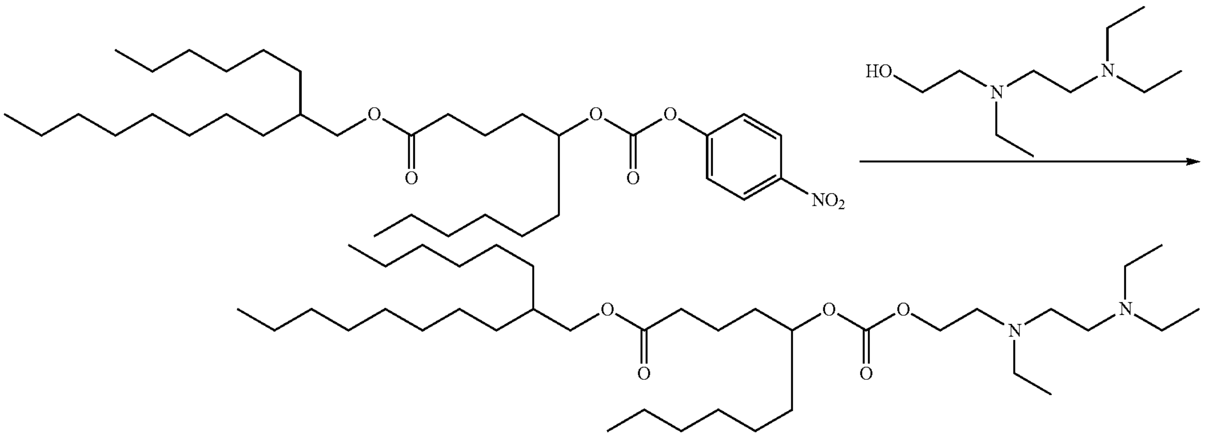

2-Hexyldecyl 3,6-diethyl-12-hexyl-10-oxo-9,11-dioxa-3,6-diazahexadecan-16-oate as a colorless oily substance was obtained by the same method as that in (2) of Example 80, except that 2-hexyldecyl 5-(((4-nitrophenoxy)carbonyl)oxy)undecanoate was used instead of 2-butyloctyl 5-(((4-nitrophenoxy)carbonyl)oxy)undecanoate in (2) of Example 80.

$^1$H-NMR ($CDCl_3$) δ:4.73-4.64 (1H, m), 4.23-4.12 (2H, m), 3.97 (2H, d, J=5.7 Hz), 2.76 (2H, t, J=6.6 Hz), 2.64-2.48 (10H, m), 2.32 (2H, t, J=6.6 Hz), 1.75-1.50 (7H, m), 1.36-1.20 (32H, m), 1.06-0.99 (9H, m), 0.92-0.84 (9H, m).

MS m/z (M+H): 642.

Example 83

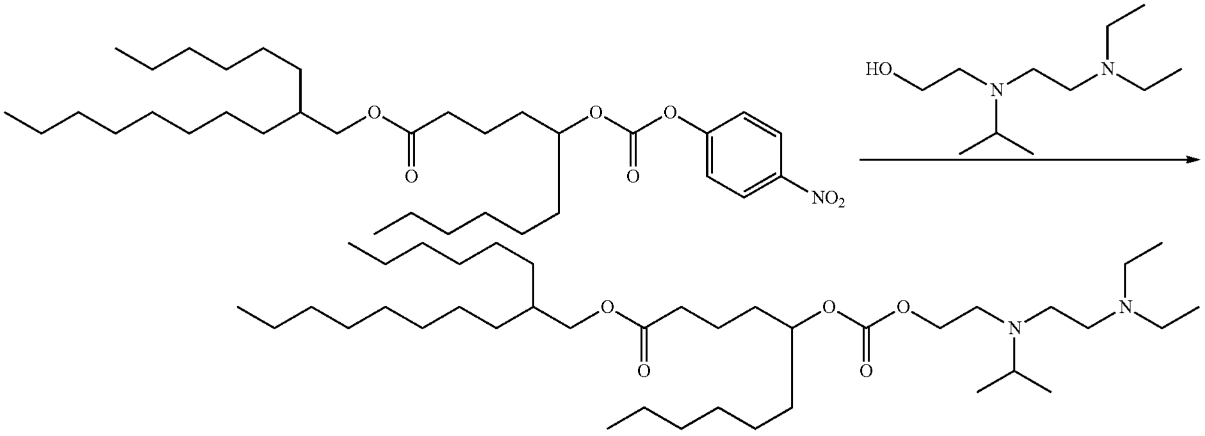

2-Hexyldecyl 3-ethyl-12-hexyl-6-isopropyl-10-oxo-9,11-dioxa-3,6-diazahexadecan-16-oate as a colorless oily substance was obtained by the same method as that in (2) of Example 82, except that 2-((2-(diethylamino)ethyl)(isopropyl)amino)ethan-1-ol was used instead of 2-((2-(diethylamino)ethyl)(ethyl)amino)ethan-1-ol in (2) of Example 82.

$^1$H-NMR ($CDCl_3$) δ:4.73-4.64 (1H, m), 4.17-4.03 (2H, m), 3.97 (2H, d, J=6.0 Hz), 2.97-2.84 (1H, m), 2.68 (2H, t, J=6.6 Hz), 2.57-2.42 (8H, m), 2.32 (2H, t, J=6.6 Hz), 1.73-1.50 (7H, m), 1.38-1.19 (32H, m), 1.06-0.96 (12H, m), 0.92-0.84 (9H, m).

MS m/z (M+H): 656.

Example 84

(1)

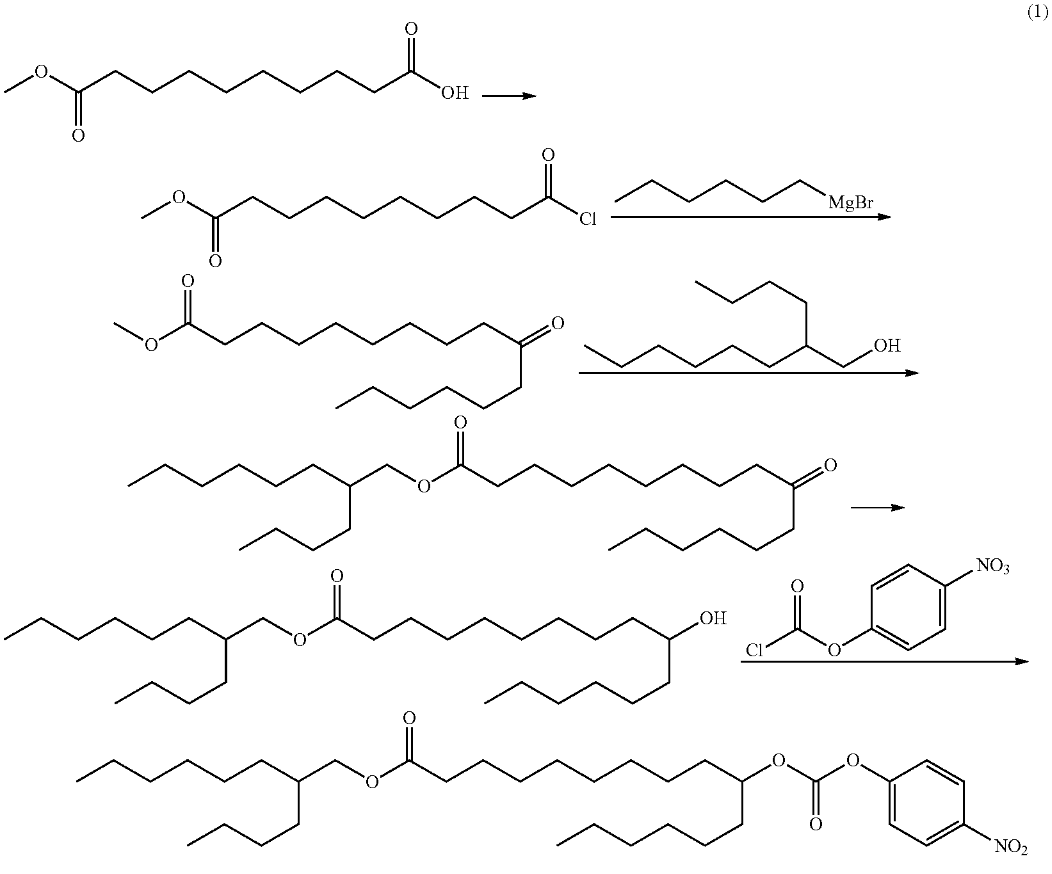

A mixture of 10-methoxy-10-oxodecanoic acid (47.6 g), thionyl chloride (47.6 mL), and N,N-dimethylformamide (0.1 mL) was stirred and heated under reflux for 1 hour. The solvent was distilled away under reduced pressure, thereby obtaining methyl 10-chloro-10-oxodecanoate (59.7 g) as a brown oily substance.

$^1$H-NMR ($CDCl_3$) δ:3.67 (3H, s), 2.88 (2H, t, J=7.2 Hz), 2.30 (2H, t, J=7.2 Hz), 1.75-1.57 (4H, m), 1.38-1.25 (8H, m).

A 1.0 mol/L hexyl magnesium bromide-diethyl ether solution (440 mL) was added dropwise to a tetrahydrofuran (500 mL) suspension of zinc (II) chloride (30.0 g) at −78° C., and the mixture was heated to 0° and then stirred at the same temperature for 30 minutes. Tetrakis(triphenylphosphine) palladium(0) (6.4 g) was added to the reaction mixture under ice cooling, methyl 10-chloro-10-oxodecanoate (59.7 g) was then added dropwise thereto at the same temperature, and the reaction mixture was stirred at the same temperature for 1 hour. A 1.0 mol/L aqueous hydrochloric acid solution (200 mL) and ethyl acetate (600 mL) were added to the reaction mixture, the organic layer was separated, washed with a saturated aqueous sodium chloride solution (560 mL), and then dried over anhydrous sodium sulfate, and the solvent was distilled away under reduced pressure. The obtained residue was purified by silica gel column chromatography (ethyl acetate-hexane), thereby obtaining methyl 10-oxohexadecanoate (50.6 g) as white solids.

$^1$H-NMR ($CDCl_3$) δ:3.67 (3H, s), 2.38 (4H, t, J=7.2 Hz), 2.30 (2H, t, 7.2 Hz), 1.65-1.49 (6H, m), 1.35-1.20 (14H, m), 0.88 (3H, t, J=7.2 Hz).

Tetraisopropyl orthotitanate (1.5 g) was added to a mixture of methyl 10-oxohexadecanoate (15.0 g) and 2-butyloctan-1-ol (14.7 g), and the mixture was stirred at 110° C. for 1 hour. Water (1 mL) was added to the reaction mixture, and the reaction mixture was stirred at room temperature for 15 minutes and then purified by silica gel column chromatography (ethyl acetate-hexane), thereby obtaining 2-butyloctyl 10-oxohexadecanoate (21.6 g) as a colorless oily substance.

$^1$H-NMR ($CDCl_3$) δ:3.97 (2H, d, J=5.6 Hz), 2.38 (4H, t, J=7.6 Hz), 2.29 (2H, t, J=7.6 Hz), 1.65-1.50 (7H, m), 1.35-1.20 (30H, m), 0.92-0.83 (9H, m).

Sodium borohydride (2.8 g) was added to a mixture of 2-butyloctyl 10-oxohexadecanoate (21.6 g), methanol (86 mL), and tetrahydrofuran (86 mL) under ice cooling, and the mixture was stirred at the same temperature for 30 minutes. The reaction mixture was poured into a mixture of ice (80 g) and water (80 g), a 1.0 mol/L aqueous hydrochloric acid solution (110 mL) and ethyl acetate (200 mL) were added thereto, the organic layer was separated, then washed with a saturated aqueous sodium chloride solution (200 mL), and dried over anhydrous sodium sulfate, and then the solvent was distilled away under reduced pressure. The obtained residue was purified by silica gel column chromatography (ethyl acetate-hexane), thereby obtaining 2-butyloctyl 10-hydroxyhexadecanoate (18.0 g) as a colorless oily substance.

$^1$H-NMR ($CDCl_3$) δ:3.97 (2H, d, J=6.0 Hz), 3.61-3.54 (1H, m), 2.30 (2H, t, J=7.6 Hz), 1.65-1.56 (3H, m), 1.48-1.22 (38H, m), 0.92-0.83 (9H, m).

4-Nitrophenyl chloroformate (1.03 g) was added to a mixture of 2-butyloctyl 10-hydroxyhexadecanoate (1.50 g), triethylamine (1.43 mL), and tetrahydrofuran (15 mL), and the mixture was stirred at room temperature for 4 hours. Water and ethyl acetate were added to the reaction mixture, the organic layer was separated, washed with water, and then dried over anhydrous sodium sulfate, and the solvent was distilled away under reduced pressure. The obtained residue was purified by silica gel column chromatography (ethyl acetate-hexane), thereby obtaining 2-butyloctyl 10-(((4-nitrophenoxy)carbonyl)oxy)hexadecanoate (2.07 g) as a colorless oily substance.

$^1$H-NMR ($CDCl_3$) δ:8.28 (2H, dd, J=7.2 Hz, 2.1 Hz), 7.39 (2H, dd, J=7.2 Hz, 2.1 Hz), 4.86-4.76 (1H, m), 3.97 (2H, d, J=5.7 Hz), 2.30 (2H, t, J=7.2 Hz), 1.74-1.20 (41H, m), 0.92-0.85 (9H, m).

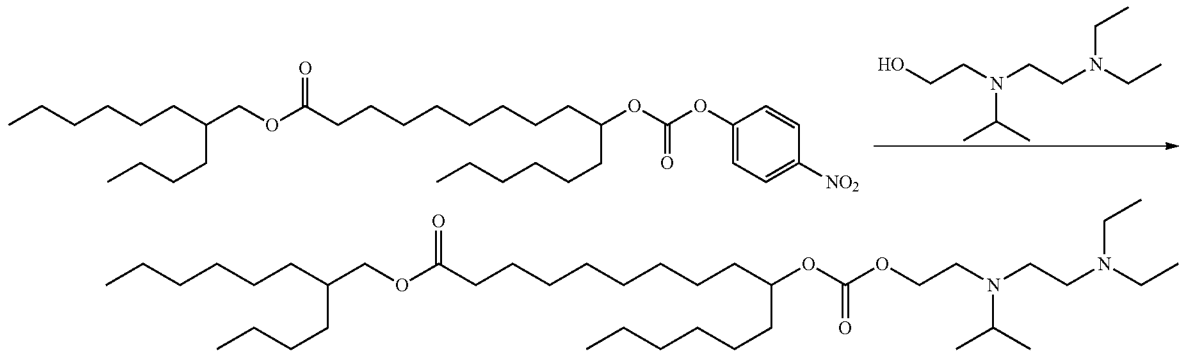

4-Dimethylaminopyridine (183 mg) was added to a mixture of 2-butyloctyl 10-(((4-nitrophenoxy)carbonyl)oxy)hexadecanoate (300 mg), 2-((2-(diethylamino)ethyl)(isopropyl)amino)ethan-1-ol (304 mg), triethylamine (0.211 mL), and tetrahydrofuran (6 mL), and the mixture was stirred at 80° C. for 8 hours. The reaction mixture was cooled to room temperature, water and ethyl acetate were added thereto, the organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 2-butyloctyl 3-ethyl-12-hexyl-6-isopropyl-10-oxo-9,11-dioxa-3,6-diazahenicosan-21-oate (296 mg) as a colorless oily substance.

$^1$H-NMR ($CDCl_3$) δ:4.73-4.61 (1H, m), 4.10 (2H, t, J=6.6 Hz), 3.97 (2H, d, J=6.0 Hz), 2.97-2.85 (1H, m), 2.68 (2H, t, J=7.2 Hz), 2.63-2.40 (8H, m), 2.29 (2H, t, J=7.2 Hz), 1.68-1.47 (7H, m), 1.40-1.19 (34H, m), 1.10-0.96 (12H, m), 0.95-0.79 (9H, m).

MS m/z (M+H): 670.

Example 85

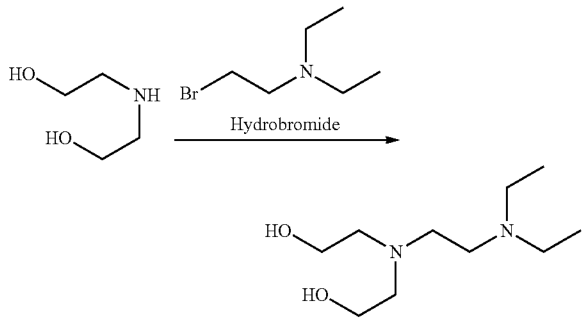

Potassium carbonate (7.9 g) was added to a mixture of 2,2'-azanediylbis(ethan-1-ol) (2.0 g), 2-bromo-N,N-diethylethan-1-amine hydrobromide (7.4 g), and ethanol (40 mL), and the mixture was stirred and heated under reflux for 8 hours. The reaction mixture was cooled to room temperature, the insoluble matters were filtered off, and the solvent was distilled away under reduced pressure. The obtained residue was purified by silica gel column chromatography (ethyl acetate-hexane, NH silica gel), thereby obtaining 2,2'-((2-(diethylamino)ethyl)azanediyl)bis(ethan-1-ol) (2.3 g) as a light yellow oily substance.

MS m/z (M+H): 205.

(2)

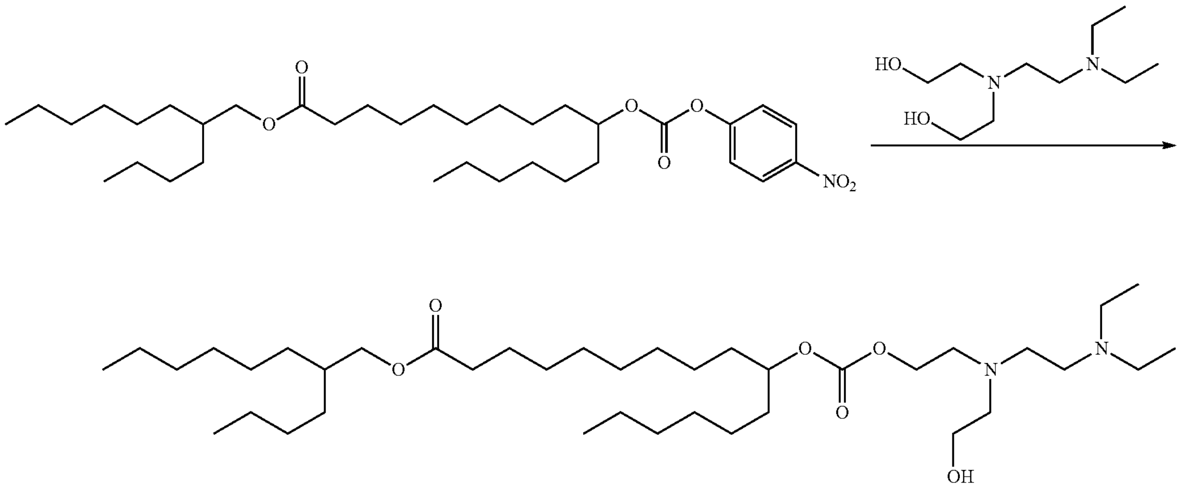

2-Butyloctyl 3-ethyl-12-hexyl-6-(2-hydroxyethyl)-10-oxo-9,11-dioxa-3,6-diazahenicosan-21-oate as a colorless oily substance was obtained by the same method as that in (2) of Example 84, except that 2,2'-((2-(diethylamino)ethyl)azanediyl)bis(ethan-1-ol) was used instead of 2-((2-(diethylamino)ethyl)(isopropyl)amino)ethan-1-ol in (2) of Example 84.

$^1$H-NMR ($CDCl_3$) δ:4.75-4.61 (1H, m), 4.21 (2H, t, J=6.6 Hz), 3.97 (2H, d, J=5.7 Hz), 3.55 (2H, t, J=5.1 Hz), 2.89 (2H, t, J=6.6 Hz), 2.76-2.65 (4H, m), 2.64-2.41 (6H, m), 2.30 (2H, t, J=8.1 Hz), 1.72-1.45 (7H, m), 1.40-1.20 (34H, m), 1.13-0.98 (6H, m), 0.96-0.81 (9H, m).

MS m/z (M+H): 672.

Example 86

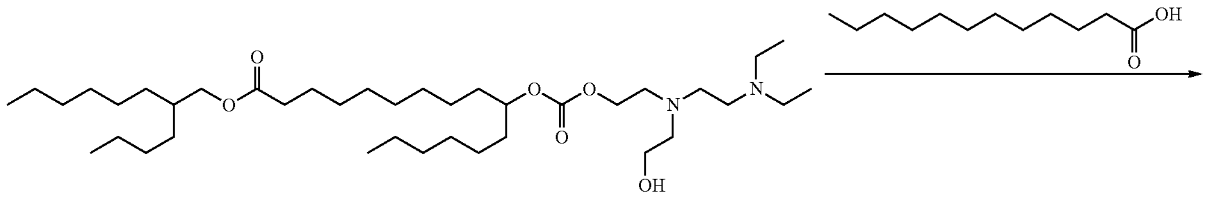

-continued

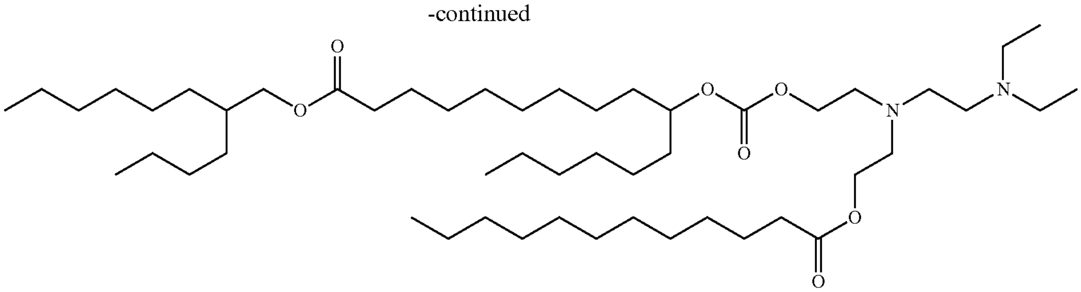

1-Ethyl-3-(3-dimethylaminopropyl)carbodiimide hydrochloride (142 mg) was added to a mixture of 2-butyloctyl 3-ethyl-12-hexyl-6-(2-hydroxyethyl)-10-oxo-9,11-dioxa-3,6-diazahenicosan-21-oate (250 mg) synthesized in (2) of Example 85, dodecanoic acid (112 mg), triethylamine (0.31 mL), 4-dimethylaminopyridine (136 mg), and dichloromethane (5 mL), and the mixture was stirred at room temperature for 6 hours. Water and ethyl acetate were added to the reaction mixture, the organic layer was separated, washed with water, and then dried over anhydrous magnesium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 2-butyloctyl 6-(2-(dodecanoyloxy)ethyl)-3-ethyl-12-hexyl-10-oxo-9,11-dioxa-3,6-diazahenicosan-21-oate (177 mg) as a colorless oily substance.

$^1$H-NMR ($CDCl_3$) δ:4.72-4.60 (1H, m), 4.21-4.08 (4H, m), 3.97 (2H, d, J=6.0 Hz), 2.88-2.75 (4H, m), 2.73-2.43 (8H, m), 2.29 (4H, t, J=7.5 Hz), 1.70-1.46 (9H, m), 1.39-1.18 (50H, m), 1.12-0.97 (6H, m), 0.95-0.81 (12H, m).

MS m/z (M+H): 854.

Example 87

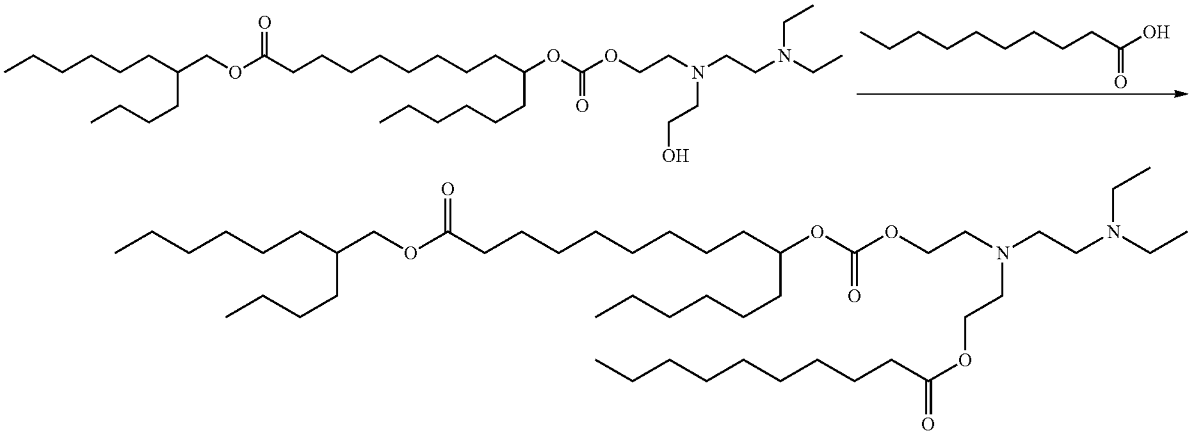

6-(2-(decanoyloxy)ethyl)-3-ethyl-12-hexyl-10-oxo-9,11-dioxa-3,6-diazahenicosan-21-oate as a colorless oily substance was obtained by the same method as that in Example 86, except that decanoic acid was used instead of dodecanoic acid in Example 86.

$^1$H-NMR ($CDCl_3$) δ:4.72-4.61 (1H, m), 4.22-4.07 (4H, m), 3.97 (2H, d, J=6.0 Hz), 2.89-2.77 (4H, m), 2.74-2.43 (8H, m), 2.30 (4H, t, J=8.1 Hz), 1.68-1.46 (9H, m), 1.40-1.18 (46H, m), 1.13-0.97 (6H, m), 0.95-0.80 (12H, m).

MS m/z (M+H): 826.

Example 88

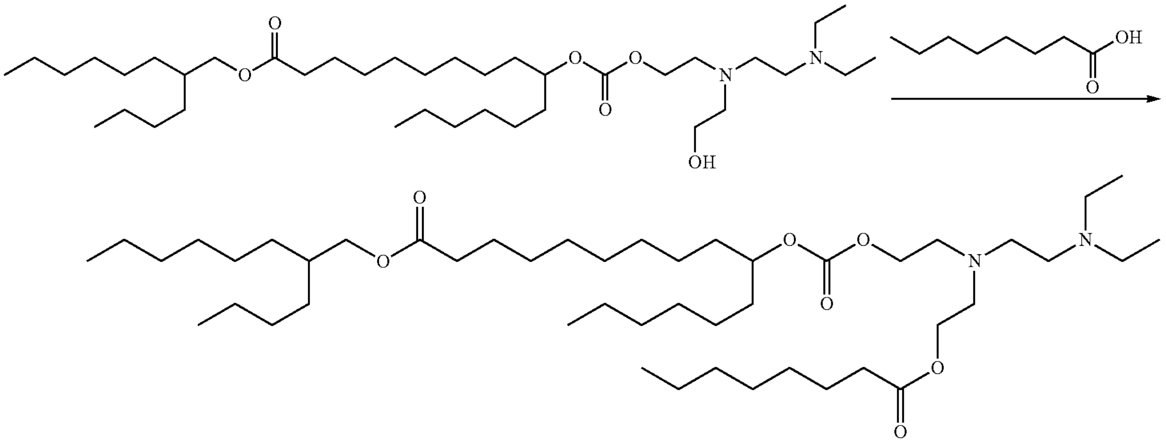

2-Butyloctyl 3-ethyl-12-hexyl-6-(2-(octanoyloxy)ethyl)-10-oxo-9,11-dioxa-3,6-diazahenicosan-21-oate as a colorless oily substance was obtained by the same method as that in Example 86, except that octanoic acid was used instead of dodecanoic acid in Example 86.

$^1$H-NMR ($CDCl_3$) δ:4.71-4.62 (1H, m), 4.20-4.08 (4H, m), 3.97 (2H, d, J=5.6 Hz), 2.89-2.77 (4H, m), 2.73-2.42 (8H, m), 2.29 (4H, t, J=7.6 Hz), 1.68-1.48 (9H, m), 1.39-1.18 (42H, m), 1.10-0.98 (6H, m), 0.94-0.81 (12H, m).

MS m/z (M+H): 798.

Example 89

(1)

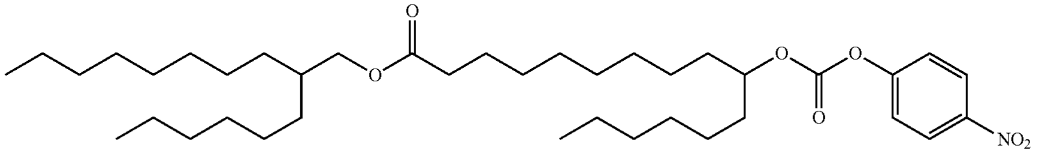

2-Hexyldecyl 10-(((4-nitrophenoxy)carbonyl)oxy)hexadecanoate as a colorless oily substance was obtained by the same method as that in (1) of Example 84, except that 2-hexyldecan-1-ol was used instead of 2-butyloctan-1-ol in (1) of Example 84.

$^1$H-NMR ($CDCl_3$) δ:8.28 (2H, dd, J=7.2 Hz, 2.4 Hz), 7.39 (2H, dd, J=7.2 Hz, 2.4 Hz), 4.85-4.77 (1H, m), 3.97 (2H, d, J=5.6 Hz), 2.30 (2H, t, J=7.6 Hz), 1.72-1.20 (49H, m), 0.92-0.85 (9H, m).

(2)

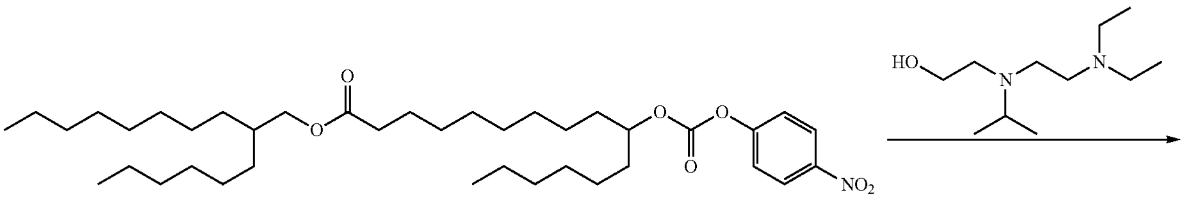

-continued

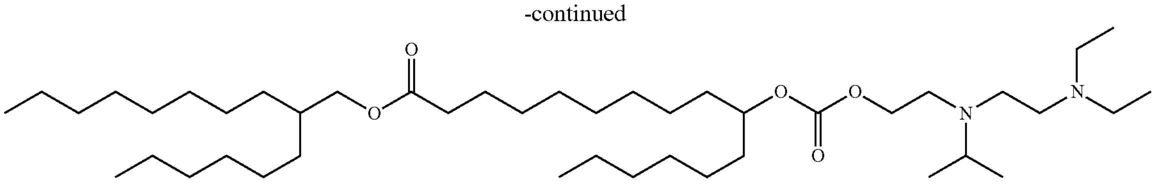

2-Hexyldecyl 3-ethyl-12-hexyl-6-isopropyl-10-oxo-9,11-dioxa-3,6-diazahenicosan-21-oate as a colorless oily substance was obtained by the same method as that in (2) of Example 84, except that 2-hexyldecyl 10-(((4-nitrophenoxy)carbonyl)oxy)hexadecanoate was used instead of 2-butyloctyl 10-(((4-nitrophenoxy)carbonyl)oxy)hexadecanoate in (2) of Example 84.

$^1$H-NMR ($CDCl_3$) δ:4.72-4.61 (1H, m), 4.10 (2H, t, J=6.6 Hz), 3.97 (2H, d, J=5.7 Hz), 2.97-2.87 (1H, m), 2.68 (2H, t, J=6.6 Hz), 2.62-2.40 (8H, m), 2.29 (2H, t, J=7.2 Hz), 1.69-1.49 (7H, m), 1.40-1.19 (42H, m), 1.12-0.95 (12H, m), 0.93-0.82 (9H, m).

MS m/z (M+H): 726.

Example 90

(1)

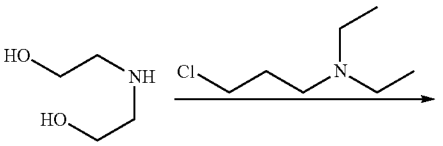

-continued

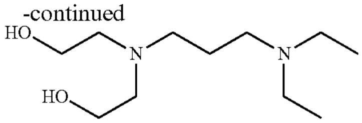

2,2'-((3-(Diethylamino)propyl)azanediyl)bis(ethan-1-ol) as a colorless oily substance was obtained by the same method as that in (1) of Example 85, except that 3-chloro-N,N-diethylpropan-1-amine was used instead of 2-bromo-N,N-diethylethan-1-amine hydrobromide in (1) of Example 85.

MS m/z (M+H): 219.

(2)

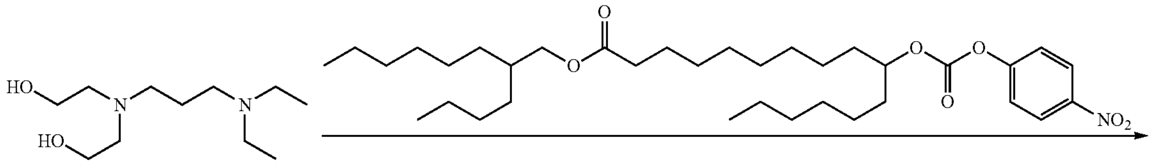

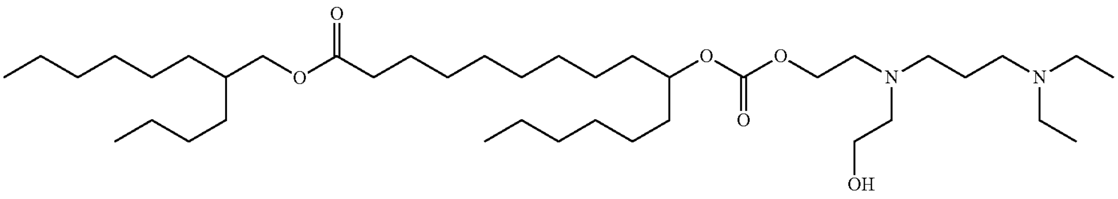

2-Butyloctyl 3-ethyl-13-hexyl-7-(2-hydroxyethyl)-11-oxo-10,12-dioxa-3,7-diazadocosan-22-oate as a colorless oily substance was obtained by the same method as that in (2) of Example 85, except that 2,2'-((3-(diethylamino)propyl)azanediyl)bis(ethan-1-ol) was used instead of 2,2'-((2-(diethylamino)ethyl)azanediyl)bis(ethan-1-ol) in (2) of Example 85.

$^1$H-NMR ($CDCl_3$) δ:4.73-4.61 (1H, m), 4.17 (2H, t, J=6.0 Hz), 3.97 (2H, d, J=6.0 Hz), 3.58 (2H, t, J=5.4 Hz), 2.76 (2H, t, J=5.7 Hz), 2.67-2.40 (10H, m), 2.30 (2H, t, J=8.1 Hz), 1.76-1.46 (9H, m), 1.38-1.19 (34H, m), 1.12-0.98 (6H, m), 0.94-0.82 (9H, m).

MS m/z (M+H): 686.

Example 91

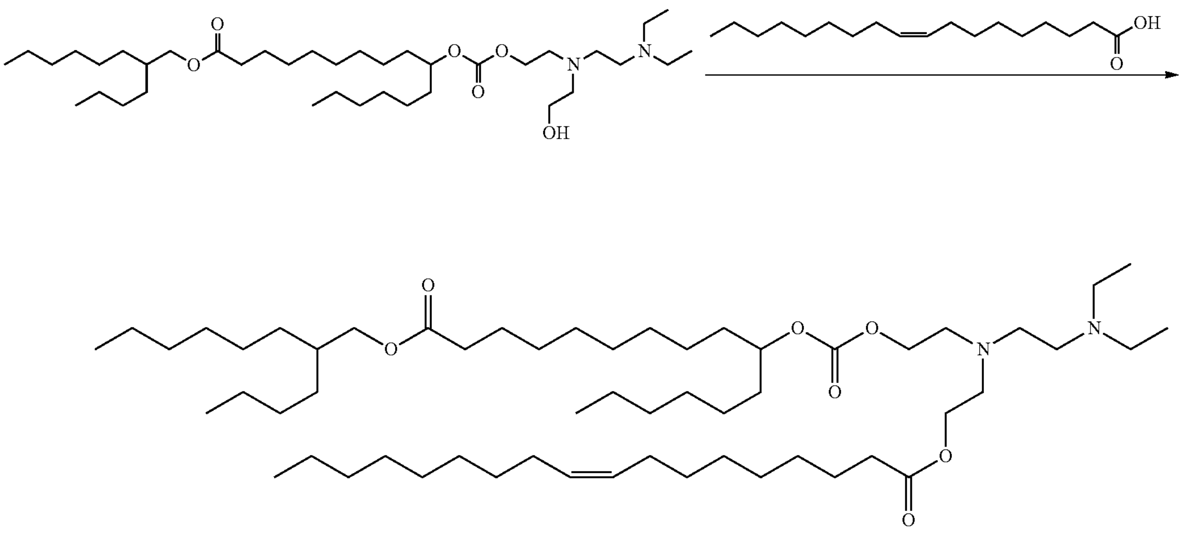

2-Butyloctyl 3-ethyl-12-hexyl-6-(2-(oleoyloxy)ethyl)-10-oxo-9,11-dioxa-3,6-diazahenicosan-21-oate as a colorless oily substance was obtained by the same method as that in Example 86, except that oleic acid was used instead of dodecanoic acid in Example 86.

$^1$H-NMR ($CDCl_3$) δ:5.38-5.28 (2H, m), 4.72-4.63 (1H, m), 4.21-4.06 (4H, m), 3.97 (2H, d, J=6.0 Hz), 2.90-2.76 (4H, m), 2.74-2.44 (8H, m), 2.29 (4H, t, J=7.8 Hz), 2.07-1.93 (4H, m), 1.68-1.45 (9H, m), 1.38-1.17 (54H, m), 1.11-0.96 (6H, m), 0.94-0.81 (12H, m).

MS m/z (M+H): 936.

Example 92

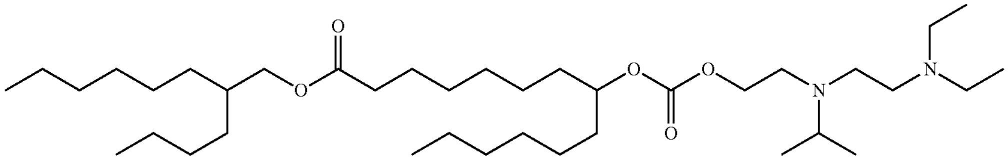 [SMILES: CCCCCCC(CCCC)COC(=O)CCCCCCC(CCCCCC)OC(=O)OCCN(CCN(CC)CC)C(C)C]

2-Butyloctyl 3-ethyl-12-hexyl-6-isopropyl-10-oxo-9,11-dioxa-3,6-diazanonadecan-19-oate as a colorless oily substance was obtained by the same method as that in (1) and (2) of Examples 84, except that 8-methoxy-8-oxooctanoic acid was used instead of 10-methoxy-10-oxodecanoic acid in (1) and (2) of Example 84.

$^1$H-NMR ($CDCl_3$) δ:4.72-4.59 (1H, m), 4.17-4.04 (2H, m), 3.97 (2H, d, J=5.4 Hz), 2.97-2.84 (1H, m), 2.69 (2H, t, J=6.6 Hz), 2.64-2.42 (8H, m), 2.29 (2H, t, J=7.2 Hz), 1.68-1.46 (7H, m), 1.40-1.18 (30H, m), 1.14-0.94 (12H, m), 0.93-0.82 (9H, m).

MS m/z (M+H): 642.

Example 93

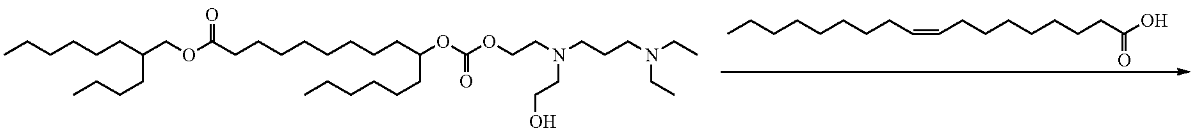

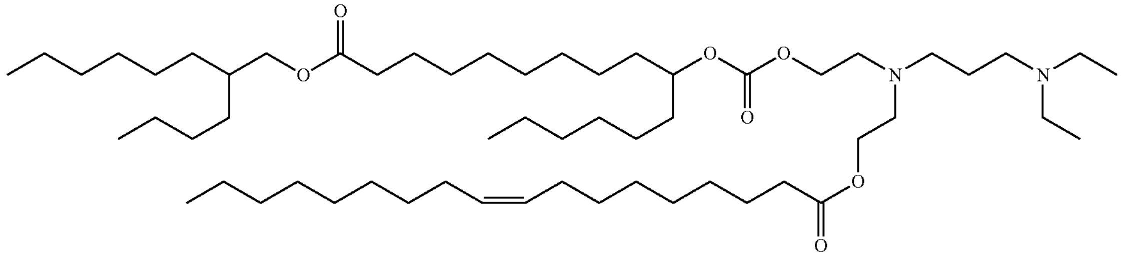

2-Butyloctyl 3-ethyl-13-hexyl-7-(2-(oleoyloxy)ethyl)-11-oxo-10,12-dioxa-3,7-diazadocosan-22-oate as a colorless oily substance was obtained by the same method as that in Example 86, except that in Example 86, 2-butyloctyl 3-ethyl-13-hexyl-7-(2-hydroxyethyl)-11-oxo-10,12-dioxa-3,7-diazadocosan-22-oate was used instead of 2-butyloctyl 3-ethyl-12-hexyl-6-(2-hydroxyethyl)-10-oxo-9,11-dioxa-3,6-diazahenicosan-21-oate, and oleic acid was used instead of dodecanoic acid.

$^{1}$H-NMR ($CDCl_3$) δ:5.42-5.27 (2H, m), 4.72-4.59 (1H, m), 4.21-4.07 (4H, m), 3.97 (2H, d, J=6.0 Hz), 2.86-2.71 (4H, m), 2.65-2.35 (8H, m), 2.29 (4H, t, J=7.2H), 2.07-1.94 (4H, m), 1.70-1.48 (11H, m), 1.41-1.19 (54H, m), 1.11-0.97 (6H, m), 0.96-0.82 (12H, m).

MS m/z (M+H): 950.

Example 94

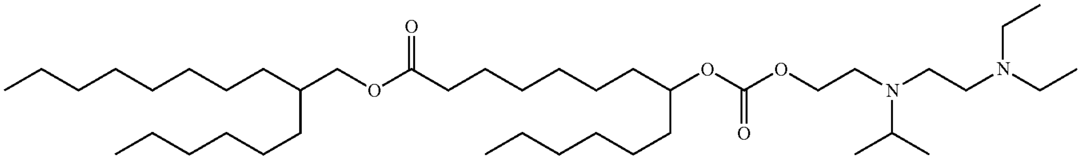 [SMILES: CCCCCCCCC(CCCCCC)COC(=O)CCCCCCC(CCCCCC)OC(=O)OCCN(CCN(CC)CC)C(C)C]

2-Hexyldecyl 3-ethyl-12-hexyl-6-isopropyl-10-oxo-9,11-dioxa-3,6-diazanonadecan-19-oate as a colorless oily substance was obtained by the same method as that in Example 92, except that 2-hexyldecan-1-ol was used instead of 2-butyloctan-1-ol in Example 92.

$^{1}$H-NMR ($CDCl_3$) δ:4.71-4.62 (1H, m), 4.16-4.04 (2H, m), 3.96 (2H, d, J=6.0 Hz), 2.97-2.85 (1H, m), 2.68 (2H, t, J=6.6 Hz), 2.64-2.41 (8H, m), 2.29 (2H, t, J=7.5 Hz), 1.70-1.47 (7H, m), 1.41-1.19 (38H, m), 1.11-0.95 (12H, m), 0.93-0.83 (9H, m).

MS m/z (M+H): 698.

Example 95

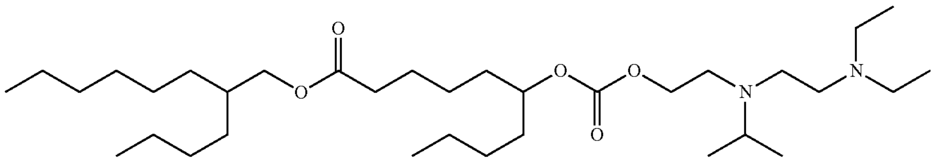 [SMILES: CCCCCCC(CCCC)COC(=O)CCCCC(CCCC)OC(=O)OCCN(CCN(CC)CC)C(C)C]

2-Butyloctyl 3-ethyl-12-hexyl-6-isopropyl-10-oxo-9,11-dioxa-3,6-diazaheptadecan-17-oate as a colorless oily substance was obtained by the same method as that in (1) and (2) of Examples 84, except that 6-methoxy-6-oxohexanoic acid was used instead of 10-methoxy-10-oxodecanoic acid in (1) and (2) of Example 84.

$^1$H-NMR ($CDCl_3$) δ:4.73-4.61 (1H, m), 4.16-4.04 (2H, m), 3.96 (2H, d, J=5.7 Hz), 2.97-2.85 (1H, m), 2.68 (2H, t, J=6.6 Hz), 2.63-2.42 (8H, m), 2.30 (2H, t, J=8.1 Hz), 1.69-1.49 (7H, m), 1.44-1.20 (26H, m), 1.12-0.95 (12H, m), 0.94-0.82 (9H, m).

MS m/z (M+H): 614.

Example 96

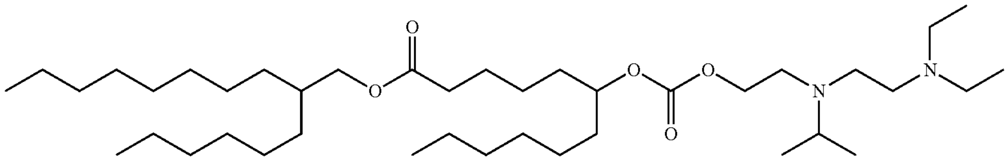 [SMILES: CCCCCCCCC(CCCCCC)COC(=O)CCCCC(CCCCCC)OC(=O)OCCN(CCN(CC)CC)C(C)C]

2-Hexyldecyl 3-ethyl-12-hexyl-6-isopropyl-10-oxo-9,11-dioxa-3,6-diazaheptadecan-17-oate as a colorless oily substance was obtained by the same method as that in Example 95, except that 2-hexyldecan-1-ol was used instead of 2-butyloctan-1-ol in Example 95.

$^1$H-NMR ($CDCl_3$) δ:4.73-4.62 (1H, m), 4.17-4.04 (2H, m), 3.96 (2H, d, J=5.7 Hz), 2.98-2.83 (1H, m), 2.68 (2H, t, J=6.6 Hz), 2.62-2.41 (8H, m), 2.30 (2H, t, J=7.8 Hz), 1.69-1.49 (7H, m), 1.42-1.18 (34H, m), 1.12-0.96 (12H, m), 0.93-0.81 (9H, m).

MS m/z (M+H): 670.

Example 97

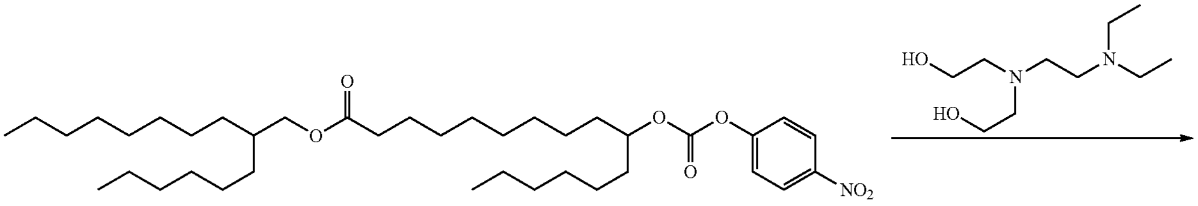

-continued

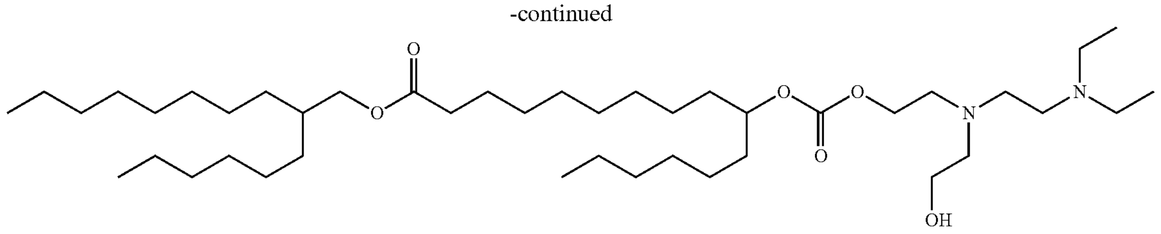

2-Hexyldecyl 3-ethyl-12-hexyl-6-(2-hydroxyethyl)-10-oxo-9,11-dioxa-3,6-diazahenicosan-21-oate as a colorless oily substance was obtained by the same method as that in Example 85, except that 2-hexyldecyl 10-((((4-nitrophenoxy)carbonyl)oxy)hexadecanoate was used instead of 2-butyloctyl 10-(((4-nitrophenoxy)carbonyl)oxy)hexadecanoate in Example 85.

$^1$H-NMR ($CDCl_3$) δ:4.73-4.61 (1H, m), 4.20 (2H, t, J=6.6 Hz), 3.96 (2H, d, J=5.4 Hz), 3.54 (2H, t, J=5.4 Hz), 2.89 (2H, t, J=6.0 Hz), 2.76-2.63 (4H, m), 2.62-2.42 (6H, m), 2.29 (2H, t, J=7.5 Hz), 1.72-1.46 (7H, m), 1.39-1.18 (42H, m), 1.04 (6H, t, J=7.2 Hz), 0.94-0.80 (9H, m).

MS m/z (M+H): 728.

Example 98

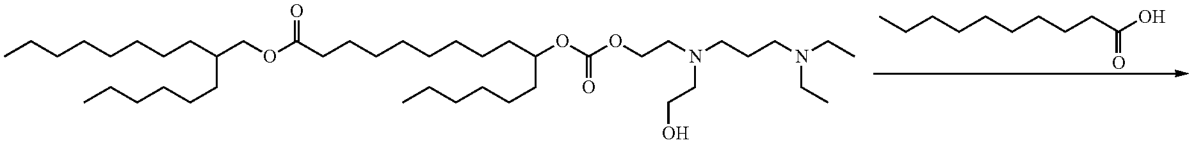

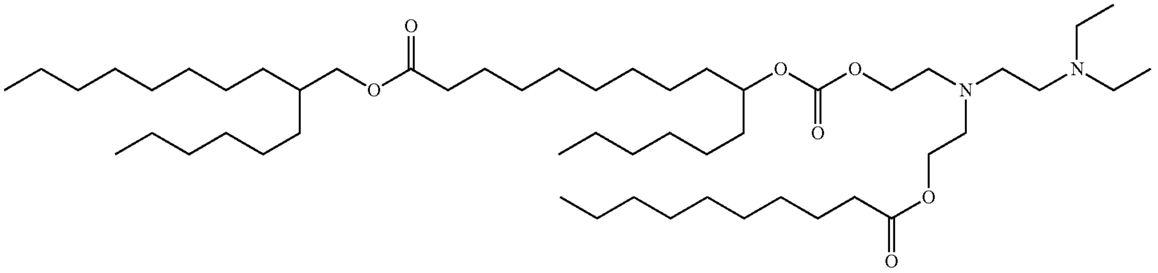

2-Hexyldecyl 6-(2-(decanoyloxy)ethyl)-3-ethyl-12-hexyl-10-oxo-9,11-dioxa-3,6-diazahenicosan-21-oate as a colorless oily substance was obtained by the same method as that in Example 86, except that in Example 86, 2-hexyldecyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and decanoic acid was used instead of dodecanoic acid.

$^1$H-NMR ($CDCl_3$) δ:4.72-4.63 (1H, m), 4.22-4.08 (4H, m), 3.96 (2H, d, J=5.4 Hz), 2.88-2.76 (4H, m), 2.75-2.43 (8H, m), 2.29 (4H, t, J=7.2 Hz), 1.68-1.50 (9H, m), 1.39-1.16 (54H, m), 1.03 (6H, t, J=6.6 Hz), 0.95-0.82 (12H, m).

MS m/z (M+H): 882.

Example 99

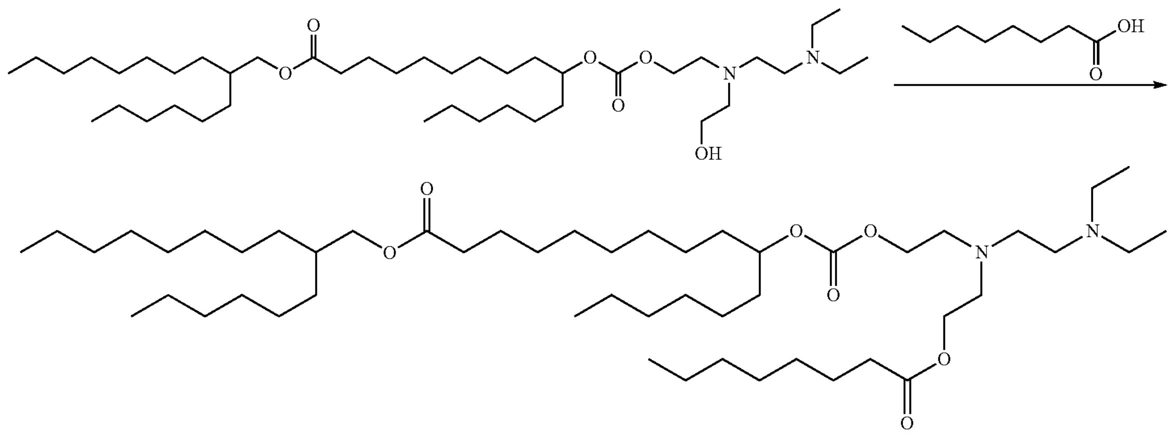

2-Hexyldecyl 3-ethyl-12-hexyl-6-(2-(octanoyloxy)ethyl)-10-oxo-9,11-dioxa-3,6-diazahenicosan-21-oate as a colorless oily substance was obtained by the same method as that in Example 98, except that octanoic acid was used instead of decanoic acid in Example 98.

$^1$H-NMR ($CDCl_3$) δ:4.72-4.61 (1H, m), 4.21-4.07 (4H, m), 3.96 (2H, d, J=5.1 Hz), 2.90-2.76 (4H, m), 2.76-2.42 (8H, m), 2.29 (4H, t, J=7.8 Hz), 1.68-1.47 (9H, m), 1.39-1.19 (50H, m), 1.12-0.96 (6H, m), 0.95-0.82 (12H, m).

MS m/z (M+H): 854.

Example 100

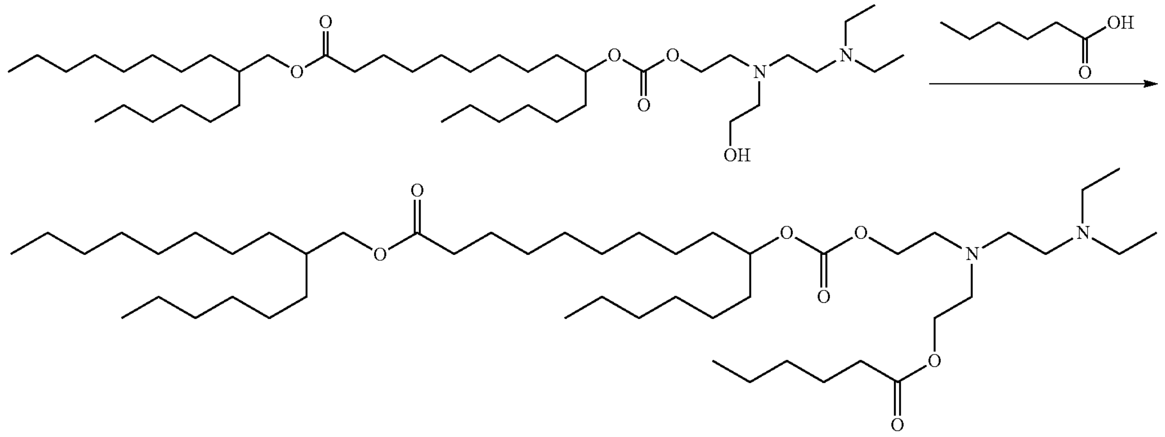

2-Hexyldecyl 3-ethyl-6-(2-(hexanoyloxy)ethyl)-12-hexyl-10-oxo-9,11-dioxa-3,6-diazahenicosan-21-oate as a colorless oily substance was obtained by the same method as that in Example 98, except that hexanoic acid was used instead of decanoic acid in Example 98.

$^1$H-NMR ($CDCl_3$) δ:4.72-4.61 (1H, m), 4.21-4.07 (4H, m), 3.96 (2H, d, J=5.7 Hz), 2.90-2.77 (4H, m), 2.73-2.41 (8H, m), 2.29 (4H, t, J=7.2 Hz), 1.70-1.46 (9H, m), 1.42-1.18 (46H, m), 1.13-0.97 (6H, m), 0.95-0.81 (12H, m).

MS m/z (M+H): 826.

Example 101

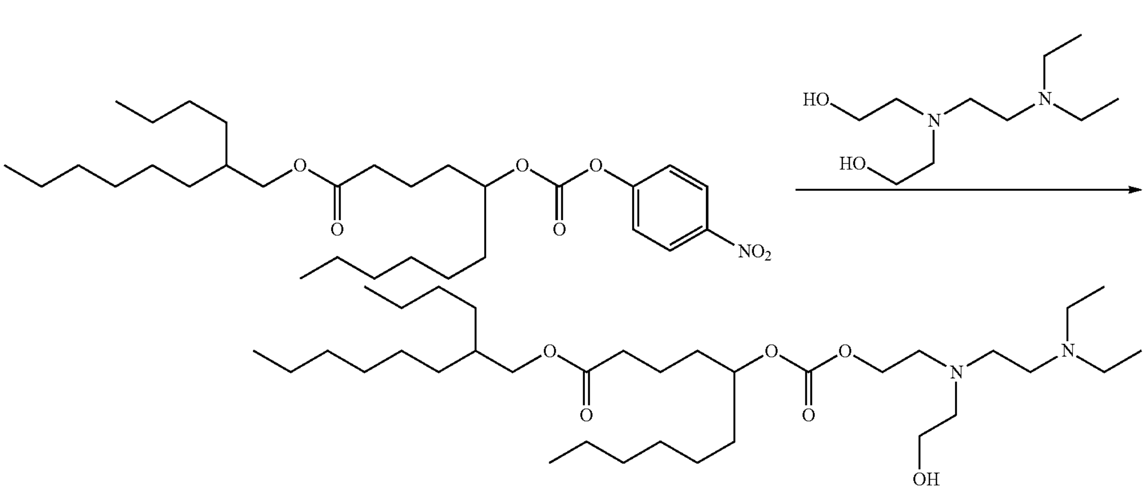

2-Butyloctyl 3-ethyl-12-hexyl-6-(2-hydroxyethyl)-10-oxo-9,11-dioxa-3,6-diazahexadecan-16-oate as a colorless oily substance was obtained by the same method as that in (2) of Example 80, except that 2,2'-((2-(diethylamino)ethyl)azanediyl)bis(ethan-1-ol) was used instead of 2-((2-(diethylamino)ethyl)(ethyl)amino)ethan-1-ol in (2) of Example 80.

$^1$H-NMR ($CDCl_3$) δ:4.75-4.64 (1H, m), 4.25-4.15 (2H, m), 3.97 (2H, d, J=6.0 Hz), 3.54 (2H, t, J=5.4 Hz), 2.89 (2H, t, J=6.6 Hz), 2.75-2.63 (4H, m), 2.60-2.42 (6H, m), 2.33 (2H, t, J=6.6 Hz), 1.73-1.50 (7H, m), 1.39-1.20 (24H, m), 1.03 (6H, t, J=7.2 Hz), 0.95-0.81 (9H, m).

MS m/z (M+H): 602.

Example 102

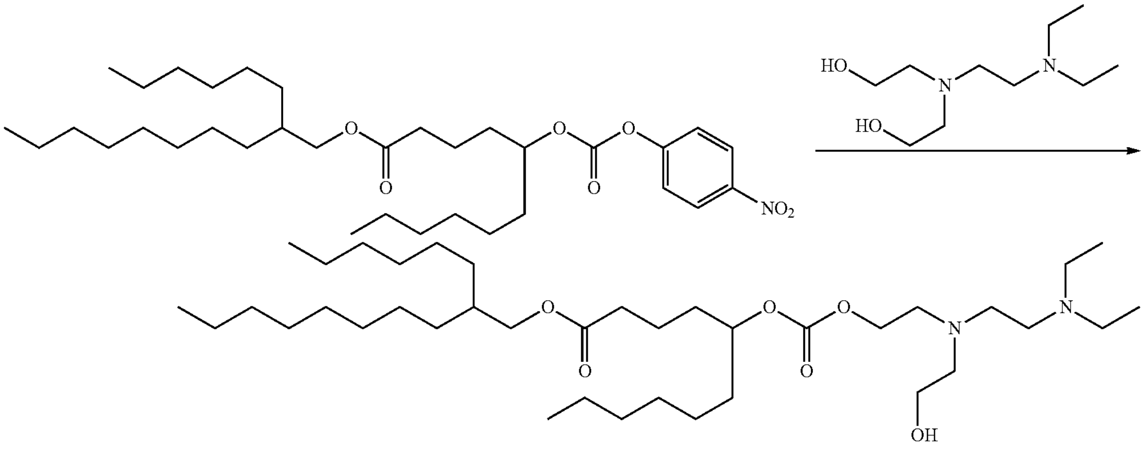

2-Hexyldecyl 3-ethyl-12-hexyl-6-(2-hydroxyethyl)-10-oxo-9,11-dioxa-3,6-diazahexadecan-16-oate as a colorless oily substance was obtained by the same method as that in (2) of Example 85, except that 2-hexyldecyl 5-(((4-nitrophenoxy)carbonyl)oxy)undecanoate was used instead of 2-butyloctyl 10-(((4-nitrophenoxy)carbonyl)oxy)hexadecanoate in (2) of Example 85.

$^1$H-NMR ($CDCl_3$) δ:4.75-4.63 (1H, m) 4.25-4.14 (2H, m), 3.97 (2H, d, J=6.0 Hz), 3.54 (2H, t, J=4.8 Hz), 2.89 (2H, t, J=6.0 Hz), 2.76-2.63 (4H, m), 2.60-2.43 (6H, m), 2.33 (2H, t, J=7.5 Hz), 1.73-1.48 (7H, m), 1.40-1.17 (32H, m), 1.03 (6H, t, J=7.2 Hz), 0.96-0.78 (9H, m).

MS m/z (M+H): 658.

Example 103

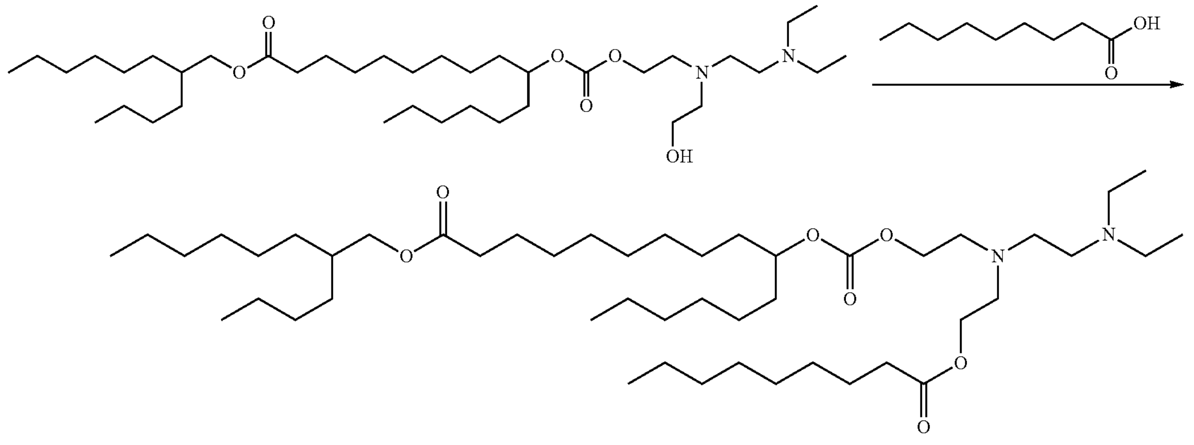

2-Butyloctyl 3-ethyl-12-hexyl-6-(2-(nonanoyloxy)ethyl)-10-oxo-9,11-dioxa-3,6-diazahenicosan-21-oate as a colorless oily substance was obtained by the same method as that in Example 86, except that nonanoic acid was used instead of dodecanoic acid in Example 86.

$^1$H-NMR ($CDCl_3$) δ:4.72-4.61 (1H, m), 4.21-4.09 (4H, m), 3.97 (2H, d, J=6.0 Hz), 2.88-2.47 (4H, m), 2.72-2.62 (2H, m), 2.58-2.46 (6H, m), 2.29 (4H, t, J=7.8 Hz), 1.69-1.50 (9H, m), 1.40-1.19 (44H, m), 1.01 (6H, t, J=7.2 Hz), 0.95-0.82 (12H, m).

MS m/z (M+H): 812.

Example 104

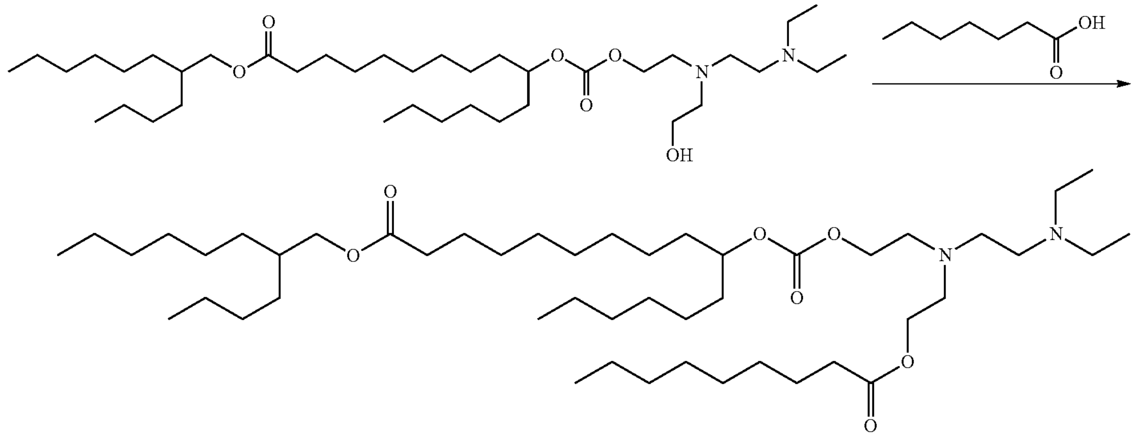

2-Butyloctyl 3-ethyl-6-(2-(heptanoyloxy)ethyl)-12-hexyl-10-oxo-9,11-dioxa-3,6-diazahenicosan-21-oate as a colorless oily substance was obtained by the same method as that in Example 86, except that heptanoic acid was used instead of dodecanoic acid in Example 86.

$^1$H-NMR ($CDCl_3$) δ:4.72-4.60 (1H, m), 4.20-4.06 (4H, m), 3.97 (2H, d, J=5.1 Hz), 2.89-2.76 (4H, m), 2.71-2.62 (2H, m), 2.58-2.46 (6H, m), 2.30 (4H, t, J=8.1 Hz), 1.68-1.47 (9H, m), 1.39-1.19 (40H, m), 1.02 (6H, t, J=6.6 Hz), 0.95-0.83 (12H, m).

MS m/z (M+H): 784.

Example 105

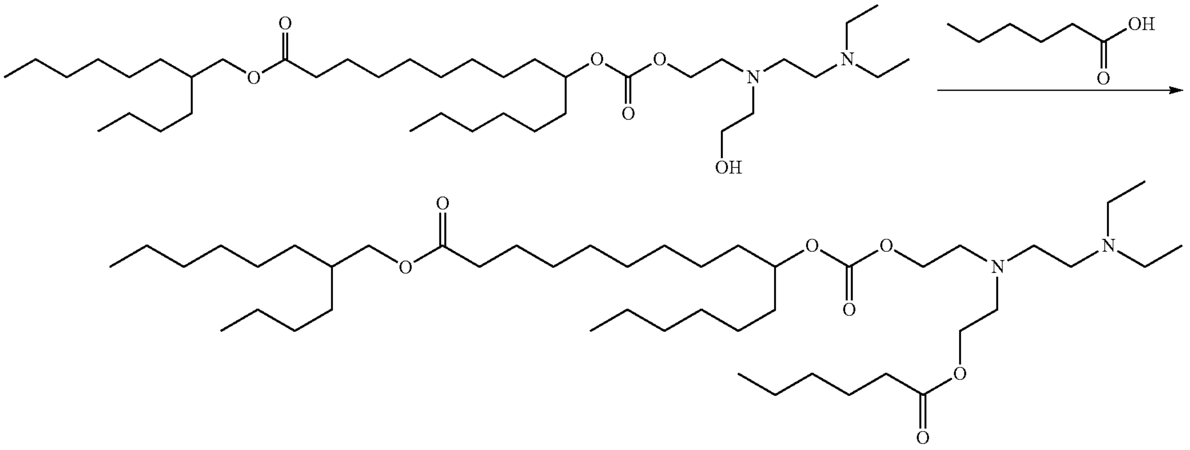

2-Butyloctyl 3-ethyl-6-(2-(hexanoyloxy)ethyl)-12-hexyl-10-oxo-9,11-dioxa-3,6-diazahenicosan-21-oate as a colorless oily substance was obtained by the same method as that in Example 86, except that hexanoic acid was used instead of dodecanoic acid in Example 86.

$^1$H-NMR ($CDCl_3$) δ:4.73-4.61 (1H, m), 4.21-4.08 (4H, m), 3.97 (2H, d, J=5.4 Hz), 2.89-2.76 (4H, m), 2.72-2.62 (2H, m), 2.59-2.45 (6H, m), 2.30 (4H, t, J=8.1 Hz), 1.71-1.47 (9H, m), 1.40-1.19 (38H, m), 1.02 (6H, t, J=6.6 Hz), 0.94-0.82 (12H, m).

MS m/z (M+H): 770.

Example 106

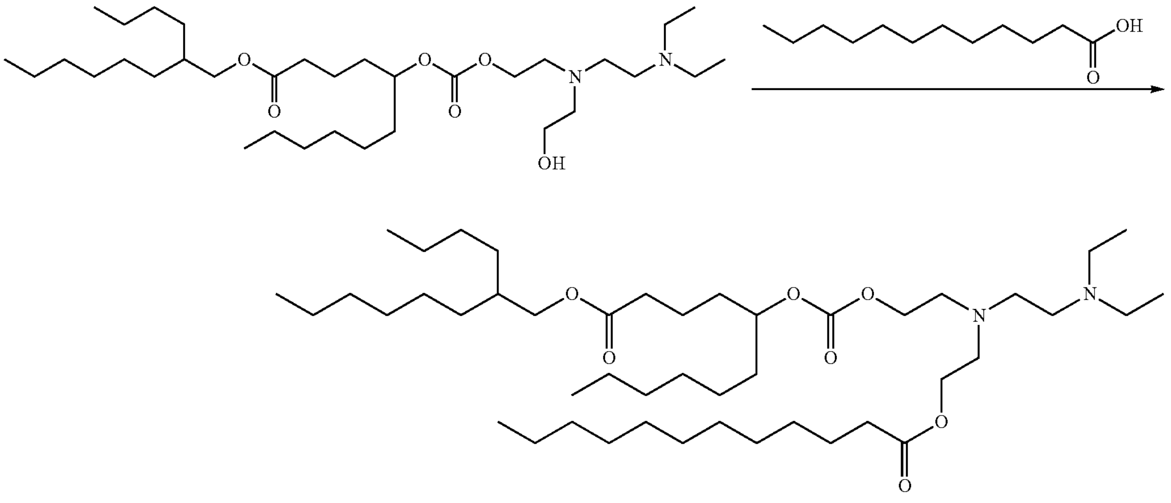

2-Butyloctyl 6-(2-(dodecanoyloxy)ethyl)-3-ethyl-12-hexyl-10-oxo-9,11-dioxa-3,6-diazahexadecan-16-oate as a colorless oily substance was obtained by the same method as that in Example 86, except that 2-butyloctyl 3-ethyl-12-hexyl-6-(2-hydroxyethyl)-10-oxo-9,11-dioxa-3,6-diazahexadecan-16-oate was used instead of 2-butyloctyl 3-ethyl-12-hexyl-6-(2-hydroxyethyl)-10-oxo-9,11-dioxa-3,6-diazahenicosan-21-oate in Example 86.

$^1$H-NMR ($CDCl_3$) δ:4.74-4.64 (1H, m), 4.21-4.07 (4H, m), 3.97 (2H, d, J=6.0 Hz), 2.89-2.76 (4H, m), 2.72-2.63 (2H, m), 2.58-2.46 (6H, m), 2.37-2.25 (4H, m), 1.74-1.50 (9H, m), 1.39-1.19 (40H, m), 1.02 (6H, t, J=6.6 Hz), 0.95-0.83 (12H, m).

MS m/z (M+H): 784.

Example 107

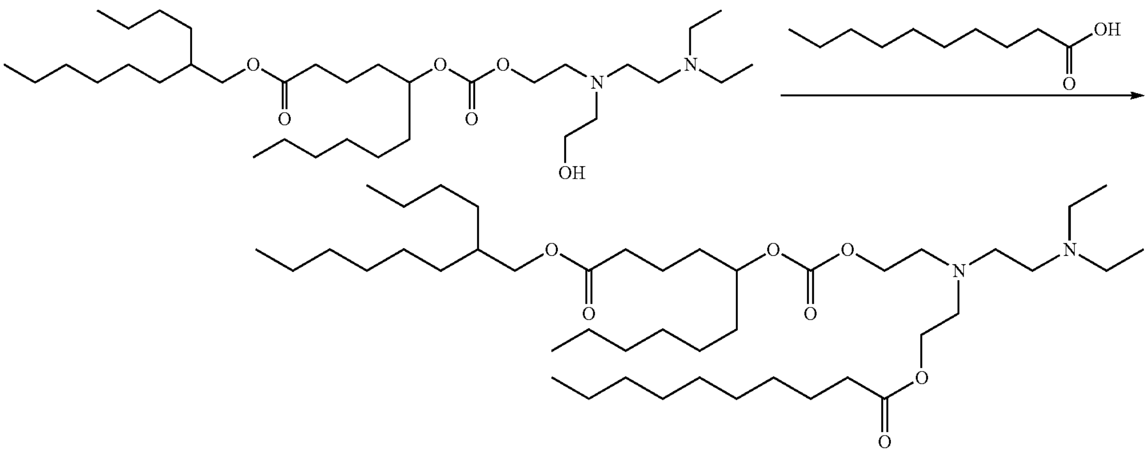

2-Butyloctyl 6-(2-(decanoyloxy)ethyl)-3-ethyl-12-hexyl-10-oxo-9,11-dioxa-3,6-diazahexadecan-16-oate as a colorless oily substance was obtained by the same method as that in Example 106, except that decanoic acid was used instead of dodecanoic acid in Example 106.

$^1$H-NMR ($CDCl_3$) δ:4.74-4.64 (1H, m), 4.22-4.07 (4H, m), 3.97 (2H, d, J=6.0 Hz), 2.88-2.75 (4H, m), 2.72-2.62 (2H, m), 2.58-2.46 (6H, m), 2.37-2.25 (4H, m), 1.74-1.52 (9H, m), 1.40-1.19 (36H, m), 1.02 (6H, t, J=7.2 Hz), 0.94-0.82 (12H, m).

MS m/z (M+H): 756.

Example 108

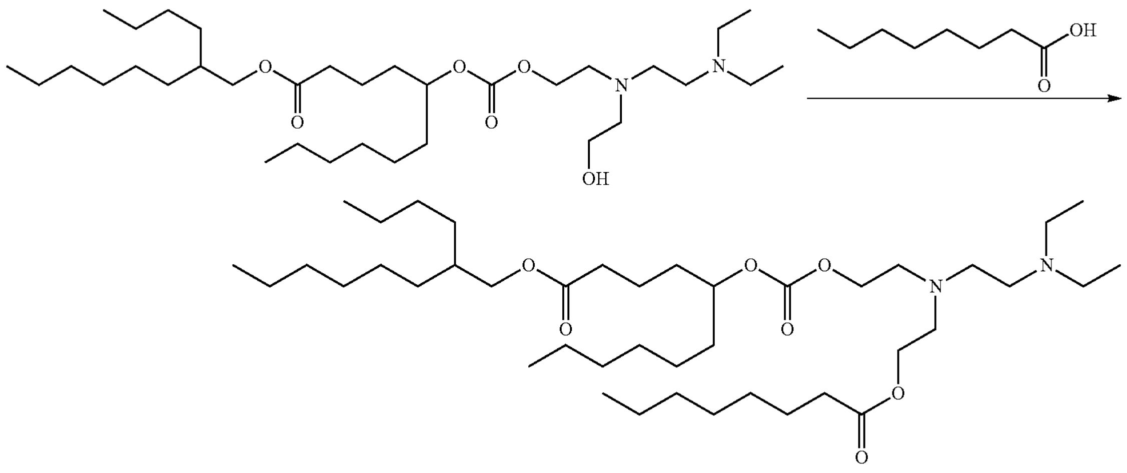

2-Butyloctyl 3-ethyl-12-hexyl-6-(2-(octanoyloxy)ethyl)-10-oxo-9,11-dioxa-3,6-diazahexadecan-16-oate as a colorless oily substance was obtained by the same method as that in Example 106, except that octanoic acid was used instead of dodecanoic acid in Example 106.

$^1$H-NMR ($CDCl_3$) δ:4.74-4.64 (1H, m), 4.21-4.08 (4H, m), 3.97 (2H, d, J=6.0 Hz), 2.88-2.76 (4H, m), 2.72-2.62 (2H, m), 2.58-2.46 (6H, m), 2.37-2.27 (4H, m), 1.74-1.50 (9H, m), 1.40-1.19 (32H, m), 1.02 (6H, t, J=7.2 Hz), 0.95-0.83 (12H, m).

MS m/z (M+H): 728.

Example 109

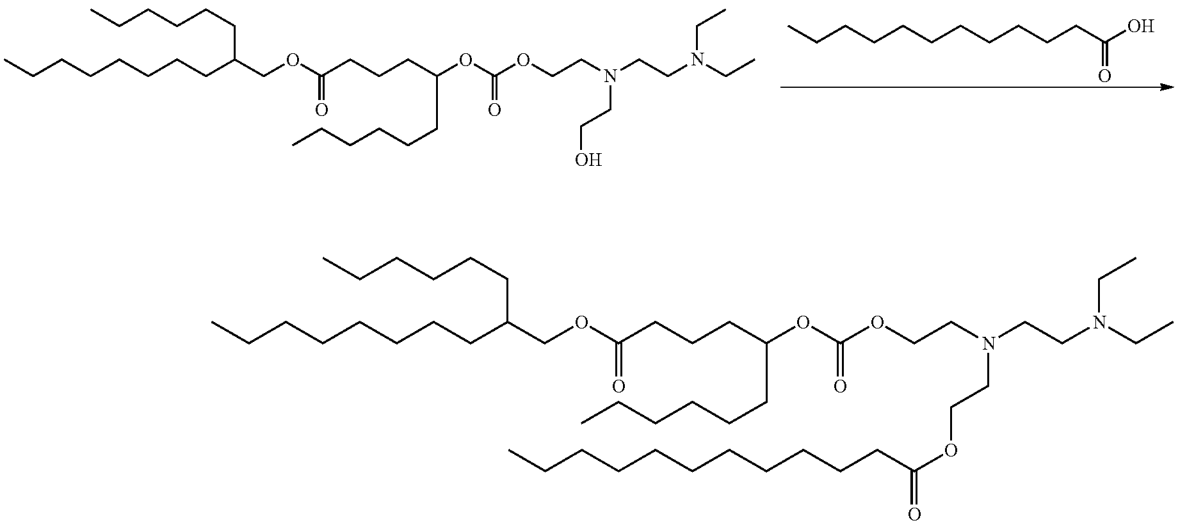

2-Hexyldecyl 6-(2-(dodecanoyloxy)ethyl)-3-ethyl-12-hexyl-10-oxo-9,11-dioxa-3,6-diazahexadecan-16-oate as a colorless oily substance was obtained by the same method as that in Example 86, except that 2-hexyldecyl 3-ethyl-12-hexyl-6-(2-hydroxyethyl)-10-oxo-9,11-dioxa-3,6-diazahexadecan-16-oate was used instead of 2-butyloctyl 3-ethyl-12-hexyl-6-(2-hydroxyethyl)-10-oxo-9,11-dioxa-3,6-diazahenicosan-21-oate in Example 86.

$^1$H-NMR ($CDCl_3$) δ:4.74-4.64 (1H, m), 4.21-4.06 (4H, m), 3.97 (2H, d, J=5.4 Hz), 2.88-2.76 (4H, m), 2.71-2.63 (2H, m), 2.57-2.46 (6H, m), 2.36-2.25 (4H, m), 1.72-1.52 (9H, m), 1.39-1.20 (48H, m), 1.02 (6H, t, J=7.5 Hz), 0.95-0.81 (12H, m).

MS m/z (M+H): 840.

Example 110

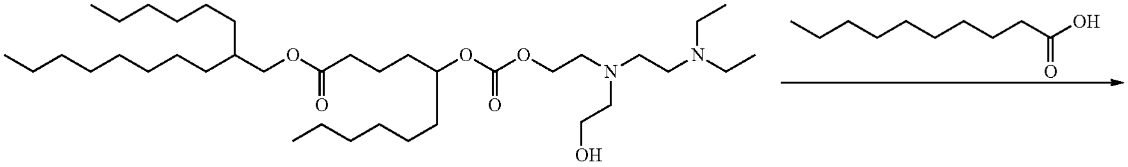

-continued

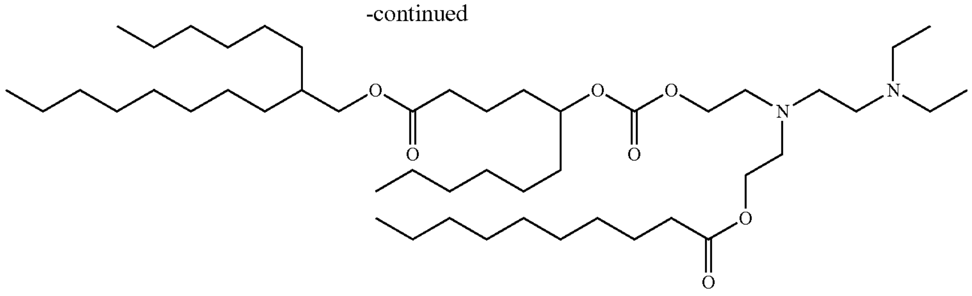

2-Hexyldecyl 6-(2-(decanoyloxy)ethyl)-3-ethyl-12-hexyl-10-oxo-9,11-dioxa-3,6-diazahexadecan-16-oate as a colorless oily substance was obtained by the same method as that in Example 109, except that decanoic acid was used instead of dodecanoic acid in Example 109.

$^1$H-NMR ($CDCl_3$) δ:4.75-4.63 (1H, m), 4.21-4.07 (4H, m), 3.97 (2H, d, J=5.7 Hz), 2.88-2.76 (4H, m), 2.71-2.62 (2H, m), 2.58-2.45 (6H, m), 2.36-2.26 (4H, m), 1.73-1.52 (9H, m), 1.38-1.19 (44H, m), 1.02 (6H, t, J=7.2 Hz), 0.95-0.81 (12H, m).

MS m/z (M+H): 812.

Example 111

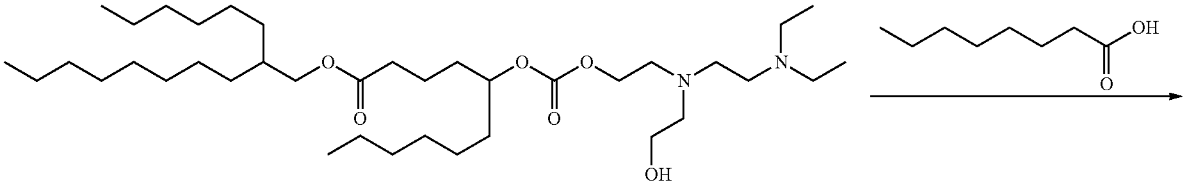

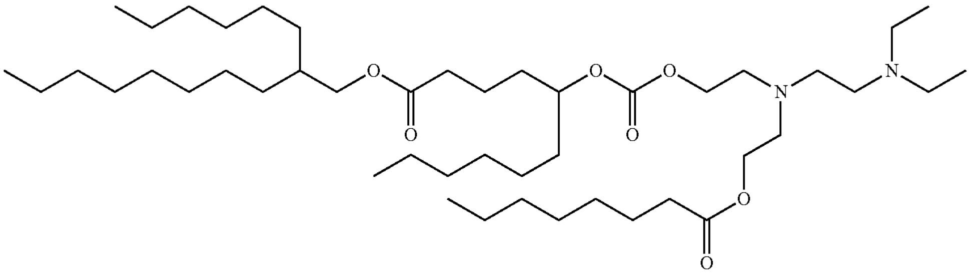

2-Hexyldecyl 3-ethyl-12-hexyl-6-(2-(octanoyloxy)ethyl)-10-oxo-9,11-dioxa-3,6-diazahexadecan-16-oate as a colorless oily substance was obtained by the same method as that in Example 109, except that octanoic acid was used instead of dodecanoic acid in Example 109.

$^1$H-NMR ($CDCl_3$) δ:4.75-4.63 (1H, m), 4.22-4.07 (4H, m), 3.96 (2H, d, J=5.1 Hz), 2.88-2.76 (4H, m), 2.71-2.63 (2H, m), 2.58-2.45 (6H, m), 2.37-2.24 (4H, m), 1.74-1.52 (9H, m), 1.39-1.19 (40H, m), 1.02 (6H, t, J=6.6 Hz), 0.96-0.83 (12H, m).

MS m/z (M+H): 784.

Example 112

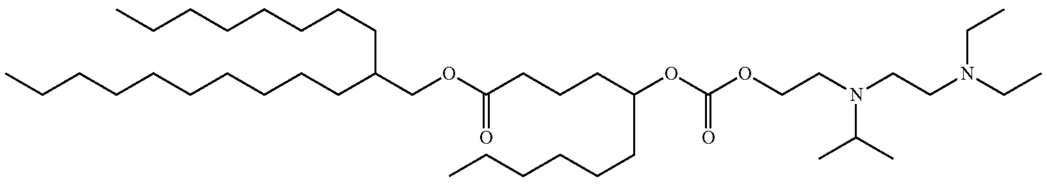 [SMILES: CCCCCCCCCCC(CCCCCCCC)COC(=O)CCCC(CCCCCC)OC(=O)OCCN(CCN(CC)CC)C(C)C]

2-Octyldodecyl 3-ethyl-12-hexyl-6-isopropyl-10-oxo-9,11-dioxa-3,6-diazahexadecan-16-oate as a colorless oily substance was obtained by the same method as that in (1) and (2) of Example 80, except that in (1) and (2) of Example 80, 2-octyldodecan-1-ol was used instead of 2-butyloctan-1-ol, and 2-((2-(diethylamino)ethyl)(isopropyl)amino)ethan-1-ol was used instead of 2-((2-(diethylamino)ethyl)(ethyl)amino)ethan-1-ol.

$^1$H-NMR ($CDCl_3$) δ:4.75-4.63 (1H, m), 4.18-4.02 (2H, m), 3.96 (2H, d, J=6.0 Hz), 2.97-2.83 (1H, m), 2.68 (2H, t, J=7.2 Hz), 2.60-2.41 (8H, m), 2.32 (2H, t, J=6.6 Hz), 1.74-1.50 (7H, m), 1.39-1.16 (40H, m), 1.09-0.95 (12H, m), 0.93-0.80 (9H, m).

MS m/z (M+H): 712.

Example 113

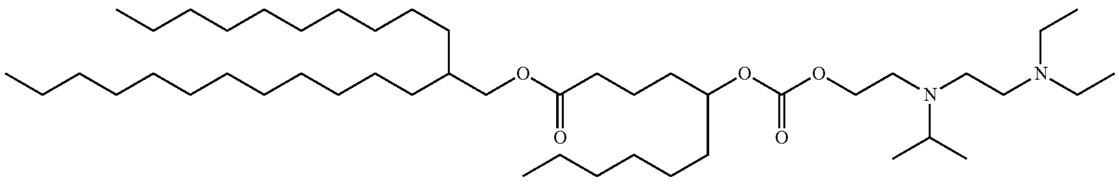 [SMILES: CCCCCCCCCCCCC(CCCCCCCCCC)COC(=O)CCCC(CCCCCC)OC(=O)OCCN(CCN(CC)CC)C(C)C]

2-Decyltetradecyl 3-ethyl-12-hexyl-6-isopropyl-10-oxo-9,11-dioxa-3,6-diazahexadecan-16-oate as a colorless oily substance was obtained by the same method as that in (1) and (2) of Example 80, except that in (1) and (2) of Example 80, 2-decyltetradecan-1-ol was used instead of 2-butyloctan-1-ol, and 2-((2-(diethylamino)ethyl)(isopropyl)amino)ethan-1-ol was used instead of 2-((2-(diethylamino)ethyl)(ethyl)amino)ethan-1-ol.

$^1$H-NMR ($CDCl_3$) δ:4.75-4.63 (1H, m), 4.17-4.02 (2H, m), 3.96 (2H, d, J=5.4 Hz), 2.97-2.85 (1H, m), 2.68 (2H, t, J=6.6 Hz), 2.60-2.42 (8H, m), 2.32 (2H, t, J=7.2 Hz), 1.74-1.49 (7H, m), 1.39-1.17 (48H, m), 1.09-0.95 (12H, m), 0.94-0.81 (9H, m).

MS m/z (M+H): 768.

Example 114

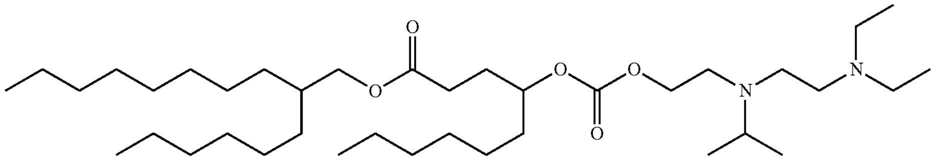 [SMILES: CCCCCCCCC(CCCCCC)COC(=O)CCC(CCCCCC)OC(=O)OCCN(CCN(CC)CC)C(C)C]

2-Hexyldecyl 3-ethyl-12-hexyl-6-isopropyl-10-oxo-9,11-dioxa-3,6-diazapentadecan-15-oate as a colorless oily substance was obtained by the same method as that in (1) and (2) of Example 84, except that in (1) and (2) of Example 84, 4-ethoxy-4-oxobutanoic acid was used instead of 10-methoxy-10-oxodecanoic acid, and 2-hexyldecan-1-ol was used instead of 2-butyloctan-1-ol.

$^1$H-NMR ($CDCl_3$) δ:4.77-4.67 (1H, m), 4.18-4.04 (2H, m), 3.97 (2H, d, J=5.4 Hz), 2.97-2.84 (1H, m), 2.68 (2H, t, J=7.5 Hz), 2.61-2.30 (10H, m), 2.02-1.78 (2H, m), 1.70-1.48 (3H, m), 1.41-1.17 (32H, m), 1.11-0.95 (12H, m), 0.94-0.81 (9H, m).

MS m/z (M+H): 642.

Example 115

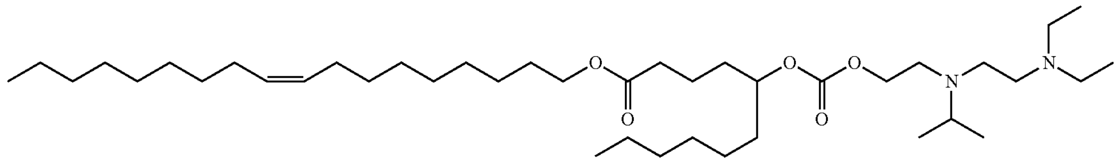 [SMILES: CCCCCCCC/C=C\CCCCCCCCOC(=O)CCCC(CCCCCC)OC(=O)OCCN(CCN(CC)CC)C(C)C]

(Z)-octadec-9-en-1-yl 3-ethyl-12-hexyl-6-isopropyl-10-oxo-9,11-dioxa-3,6-diazahexadecan-16-oate as a colorless oily substance was obtained by the same method as that in (1) and (2) of Example 80, except that in (1) and (2) of Example 80, (Z)-octadec-9-en-1-ol was used instead of 2-butyloctan-1-ol, and 2-((2-(diethylamino)ethyl)(isopropyl)amino)ethan-1-ol was used instead of 2-((2-(diethylamino)ethyl)(ethyl)amino)ethan-1-ol.

$^1$H-NMR ($CDCl_3$) δ:5.41-5.26 (2H, m), 4.74-4.64 (1H, m), 4.15-4.01 (4H, m), 2.97-2.85 (1H, m), 2.68 (2H, t, J=6.6 Hz), 2.60-2.42 (8H, m), 2.31 (2H, t, J=7.2 Hz), 2.08-1.94 (4H, m), 1.74-1.50 (10H, m), 1.41-1.19 (28H, m), 1.07-0.95 (12H, m), 0.92-0.82 (6H, m).

MS m/z (M+H): 682.

Example 116

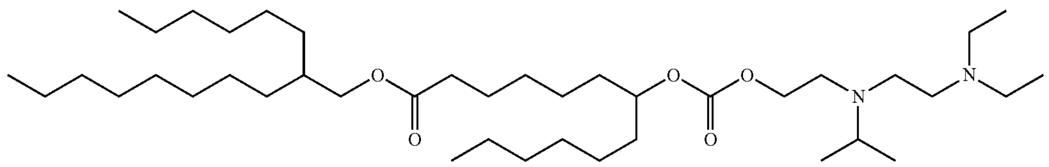 [SMILES: CCCCCCCCC(CCCCCC)COC(=O)CCCCCC(CCCCCC)OC(=O)OCCN(CCN(CC)CC)C(C)C]

2-Hexyldecyl 3-ethyl-12-hexyl-6-isopropyl-10-oxo-9,11-dioxa-3,6-diazoctadecan-18-oate as a colorless oily substance was obtained by the same method as that in (1) and (2) of Example 84, except that in (1) and (2) of Example 84, 7-ethoxy-7-oxoheptanoic acid was used instead of 10-methoxy-10-oxodecanoic acid, and 2-hexyldecan-1-ol was used instead of 2-butyloctan-1-ol.

$^1$H-NMR ($CDCl_3$) δ:4.72-4.62 (1H, m), 4.17-4.03 (2H, m), 3.96 (2H, d, J=6.0 Hz), 2.97-2.85 (1H, m), 2.68 (2H, t, J=7.5 Hz), 2.60-2.41 (8H, m), 2.29 (2H, t, J=7.8 Hz), 1.68-1.48 (7H, m), 1.41-1.18 (36H, m), 1.08-0.95 (12H, m), 0.93-0.81 (9H, m).

MS m/z (M+H): 684.

Example 117

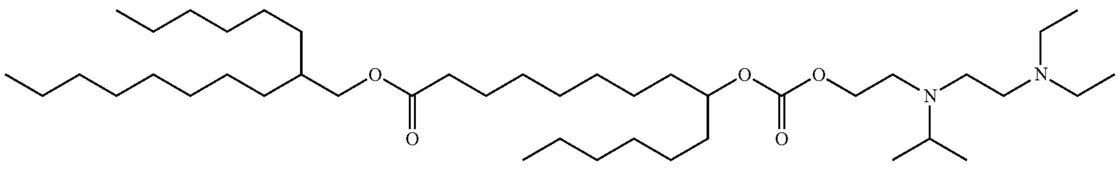 [SMILES: CCCCCCCCC(CCCCCC)COC(=O)CCCCCCCC(CCCCCC)OC(=O)OCCN(CCN(CC)CC)C(C)C]

2-Hexyldecyl 3-ethyl-12-hexyl-6-isopropyl-10-oxo-9,11-dioxa-3,6-diazaicosan-20-oate as a colorless oily substance was obtained by the same method as that in (1) and (2) of Example 84, except that in (1) and (2) of Example 84, 9-methoxy-9-oxononanoic acid was used instead of 10-methoxy-10-oxodecanoic acid, and 2-hexyldecan-1-ol was used instead of 2-butyloctan-1-ol.

$^1$H-NMR ($CDCl_3$) δ:4.73-4.61 (1H, m), 4.15-4.03 (2H, m), 3.96 (2H, d, J=5.1 Hz), 2.98-2.84 (1H, m), 2.68 (2H, t, J=6.6 Hz), 2.60-2.42 (8H, m), 2.29 (2H, t, J=7.2 Hz), 1.68-1.47 (7H, m), 1.40-1.19 (40H, m), 1.08-0.95 (12H, m), 0.93-0.81 (9H, m).

MS m/z (M+H): 712.

Example 118

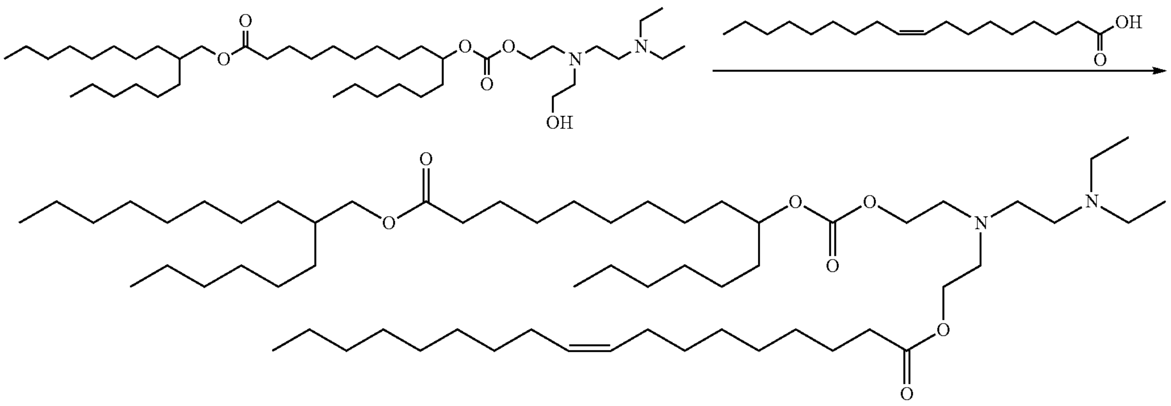

2-Hexyldecyl 3-ethyl-12-hexyl-6-(2-(oleoyloxy)ethyl)-10-oxo-9,11-dioxa-3,6-diazahenicosan-21-oate as a colorless oily substance was obtained by the same method as that in Example 98, except that oleic acid was used instead of decanoic acid in Example 98.

$^1$H-NMR ($CDCl_3$) δ:5.38-5.28 (2H, m), 4.71-4.61 (1H, m), 4.21-4.08 (4H, m), 3.96 (2H, d, J=6.0 Hz), 2.87-2.76 (4H, m), 2.71-2.63 (2H, m), 2.57-2.45 (6H, m), 2.29 (4H, t, J=7.2 Hz), 2.06-1.94 (4H, m), 1.67-1.49 (9H, m), 1.39-1.18 (62H, m), 1.02 (6H, t, J=7.2 Hz), 0.95-0.82 (12H, m).

MS m/z (M+H): 992.

Example 119

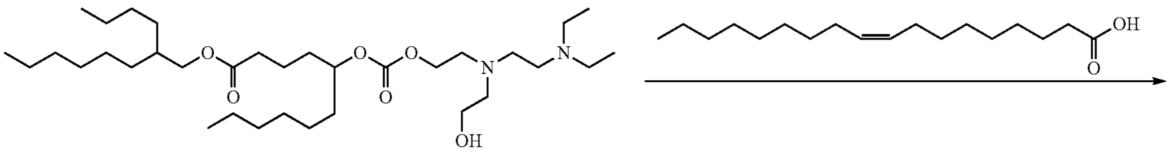

-continued

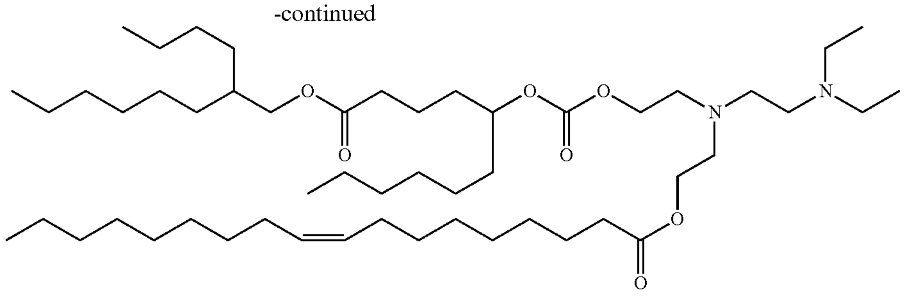

2-Butyloctyl 3-ethyl-12-hexyl-6-(2-(oleoyloxy)ethyl)-10-oxo-9,11-dioxa-3,6-diazahexadecan-16-oate as a colorless oily substance was obtained by the same method as that in Example 106, except that oleic acid was used instead of dodecanoic acid in Example 106.

$^1$H-NMR ($CDCl_3$) δ:5.40-5.28 (2H, m), 4.74-4.63 (1H, m), 4.22-4.07 (4H, m), 3.97 (2H, d, J=6.0 Hz), 2.88-2.76 (4H, m), 2.73-2.62 (2H, m), 2.59-2.45 (6H, m), 2.37-2.25 (4H, m), 2.08-1.94 (4H, m), 1.73-1.50 (9H, m), 1.41-1.18 (44H, m), 1.02 (6H, t, J=6.6 Hz), 0.96-0.82 (12H, m).

MS m/z (M+H): 866.

Example 120

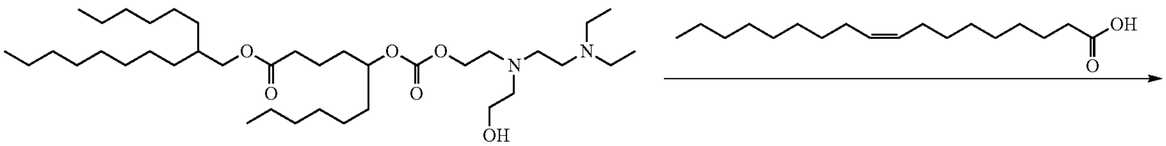

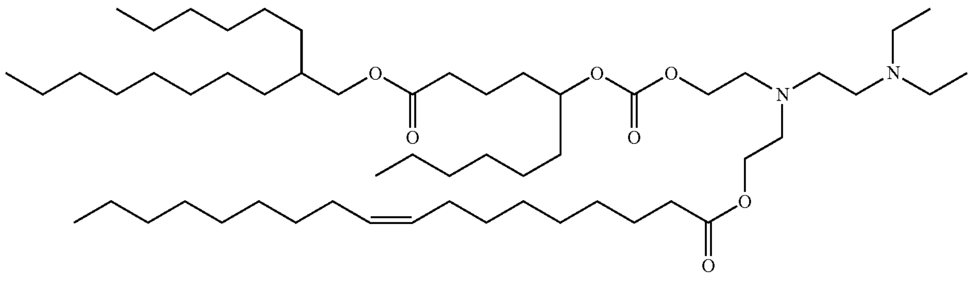

2-Hexyldecyl 3-ethyl-12-hexyl-6-(2-(oleoyloxy)ethyl)-10-oxo-9,11-dioxa-3,6-diazahexadecan-16-oate as a colorless oily substance was obtained by the same method as that in Example 109, except that oleic acid was used instead of dodecanoic acid in Example 109.

$^1$H-NMR ($CDCl_3$) δ:5.40-5.28 (2H, m), 4.73-4.64 (1H, m), 4.21-4.07 (4H, m), 3.96 (2H, d, J=5.1 Hz), 2.88-2.76 (4H, m), 2.72-2.62 (2H, m), 2.58-2.45 (6H, m), 2.37-2.24 (4H, m), 2.07-1.94 (4H, m), 1.73-1.51 (9H, m), 1.39-1.19 (52H, m), 1.02 (6H, t, J=6.6 Hz), 0.94-0.81 (12H, m).

MS m/z (M+H): 922.

Example 121

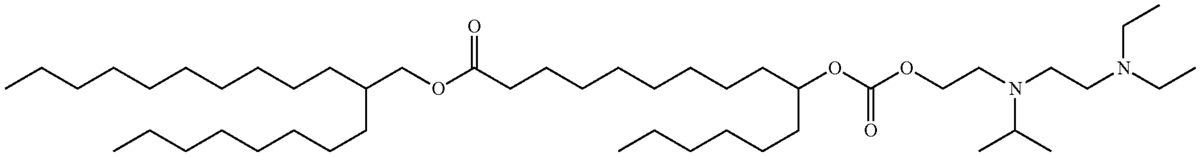 [SMILES: CCCCCCCCCCC(CCCCCCCC)COC(=O)CCCCCCCCC(CCCCCC)OC(=O)OCCN(CCN(CC)CC)C(C)C]

2-Octyldodecyl 3-ethyl-12-hexyl-6-isopropyl-10-oxo-9, 11-dioxa-3,6-diazahenicosan-21-oate as a colorless oily substance was obtained by the same method as that in (1) and (2) of Example 84, except that 2-octyldodecan-1-ol was used instead of 2-butyloctan-1-ol in (1) and (2) of Example 84.

$^1$H-NMR ($CDCl_3$) δ:4.73-4.61 (1H, m), 4.15-4.06 (2H, m), 3.96 (2H, d, J=6.0 Hz), 2.97-2.84 (1H, m), 2.68 (2H, t, J=6.6 Hz), 2.59-2.42 (8H, m), 2.29 (2H, t, J=8.1 Hz), 1.68-1.48 (7H, m), 1.38-1.19 (50H, m), 1.09-0.96 (12H, m), 0.93-0.82 (9H, m).

MS m/z (M+H): 782.

Example 122

(1)

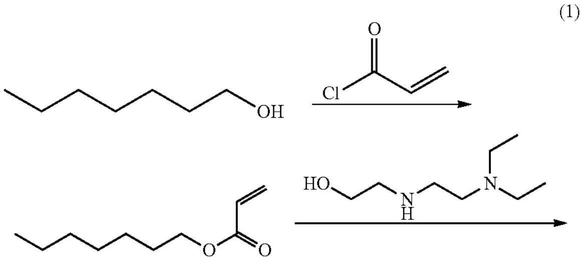

-continued

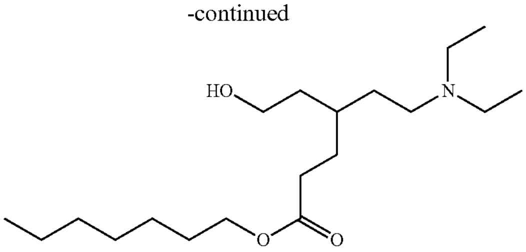

Acrylic acid chloride (0.45 mL) was added to a mixture of heptan-1-ol (0.86 mL), triethylamine (1.55 mL), and tetrahydrofuran (5.00 mL) under ice cooling, and the mixture was stirred at room temperature for 2 hours. Water and ethyl acetate were added to the reaction mixture, the organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining heptyl acrylate (0.57 g) as a colorless oily substance.

Triethylamine (1.24 mL) was added to a mixture of the obtained heptyl acrylate (0.57 g), 2-((2-(diethylamino)ethyl) amino)ethan-1-ol dihydrochloride (0.52 g), and tetrahydrofuran (10 mL), and the mixture was stirred and heated under reflux for 8 hours. The reaction mixture was cooled to room temperature, and the solvent was distilled away under reduced pressure. The obtained residue was purified by silica gel column chromatography (ethyl acetate-hexane, NH silica gel), thereby obtaining heptyl 3-((2-(diethylamino) ethyl)(2-hydroxyethyl)amino)propanoate (0.21 g) as a colorless oily substance.

MS m/z (M+H): 331.

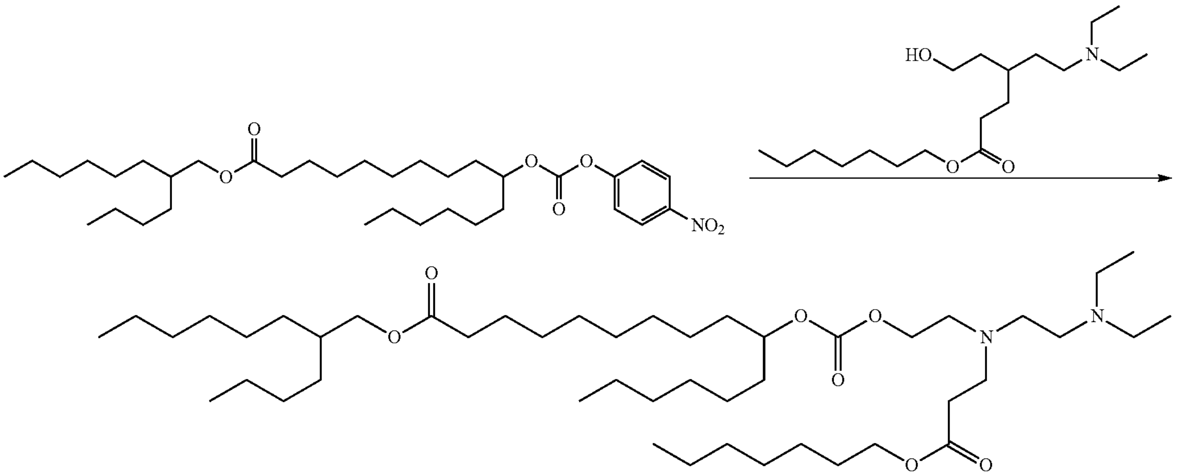

2-Butyloctyl 3-ethyl-6-(3-(heptyloxy)-3-oxopropyl)-12-hexyl-10-oxo-9,11-dioxa-3,6-diazahenicosan-21-oat e as a colorless oily substance was obtained by the same method as that in (2) of Example 84, except that heptyl 3-((2-(diethylamino)ethyl)(2-hydroxyethyl)amino)propanoate was used instead of 2-((2-(diethylamino)ethyl)(isopropyl)amino)ethan-1-ol in (2) of Example 84.

$^1$H-NMR ($CDCl_3$) δ:4.72-4.61 (1H, m), 4.20-4.11 (2H, m), 4.06 (2H, t, J=6.6 Hz), 3.96 (2H, d, J=6.0 Hz), 2.87 (2H, t, J=6.6 Hz), 2.77 (2H, d, J=6.0 Hz), 2.64-2.41 (10H, m), 2.29 (2H, t, J=7.2 Hz), 1.66-1.50 (9H, m), 1.37-1.22 (42H, m), 1.02 (6H, t, J=6.6 Hz), 0.92-0.84 (12H, m).

MS m/z (M+H): 798.

Example 123

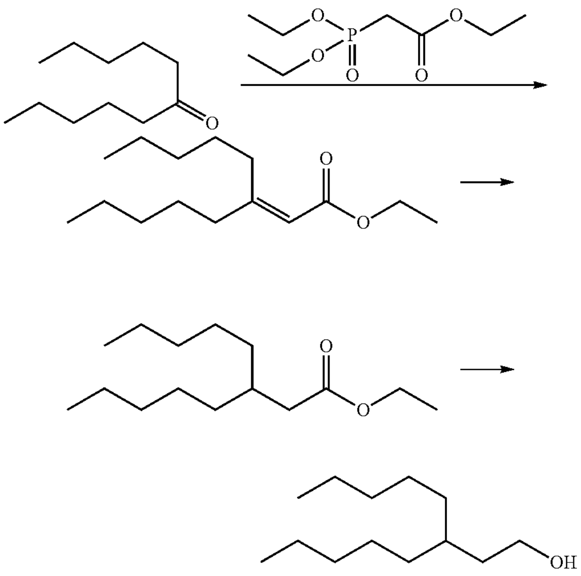

Ethyl 2-(diethoxyphosphoryl)acetate (18.8 mL) was added dropwise to a tetrahydrofuran (80 mL) suspension of 60 wt % sodium hydride (3.3 g) under ice cooling, and the mixture was stirred at the same temperature for 30 minutes. Undecan-6-one (2.0 g) was added to the reaction mixture, and the reaction mixture was stirred and heated under reflux for 5 hours. The reaction mixture was cooled to room temperature and poured into ice water, and then ethyl acetate was added thereto. The organic layer was separated and washed with a saturated aqueous sodium chloride solution, the solvent was then distilled away under reduced pressure, and the obtained residue was purified by silica gel column chromatography (ethyl acetate-hexane), thereby obtaining ethyl 3-pentyloct-2-enoate (2.8 g) as a colorless oily substance.

$^1$H-NMR ($CDCl_3$) δ:5.61 (1H, s), 4.14 (2H, q, J=6.6 Hz), 2.58 (2H, t, J=7.2 Hz), 2.12 (2H, t, J=7.2 Hz), 1.50-1.20 (15H, m), 0.89 (6H, t, J=6.6 Hz).

Ammonium formate (4.4 g) was added to a mixture of ethyl 3-pentyloct-2-enoate (2.8 g), 10% palladium-carbon (0.84 g), and methanol (56 mL), and the mixture was stirred and heated under reflux for 3 hours. The reaction mixture was cooled to room temperature, the insoluble matters were filtered off using celite, and then the solvent was distilled away under reduced pressure. The obtained residue was purified by silica gel column chromatography (ethyl acetate-hexane), thereby obtaining ethyl 3-pentyloctanoate (2.8 g) as a colorless oily substance.

$^1$H-NMR ($CDCl_3$) δ:4.12 (2H, q, J=7.2 Hz), 2.22 (2H, t, J=6.6 Hz), 2.05-2.04 (1H, m), 1.34-1.20 (19H, m), 0.88 (6H, t, J=6.6 Hz).

A tetrahydrofuran (10 mL) solution of ethyl 3-pentyloctanoate (2.8 g) was added dropwise to a mixture of a 2.5 mol/L lithium aluminum hydride-tetrahydrofuran solution (9.3 mL) and tetrahydrofuran (50 mL) under ice cooling, and the mixture was stirred at the same temperature for 30 minutes and then stirred at room temperature for 2 hours. Ethyl acetate was added to the reaction mixture, the reaction mixture was poured into ice water under ice cooling, and then the insoluble matters were filtered off using celite. The organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 3-pentyloctan-1-ol (2.2 g) as a colorless oily substance.

$^1$H-NMR ($CDCl_3$) δ:3.71-3.62 (2H, m), 1.57-1.49 (2H, m), 1.35-1.20 (17H, m), 0.88 (6H, t, J=6.6 Hz).

(2)

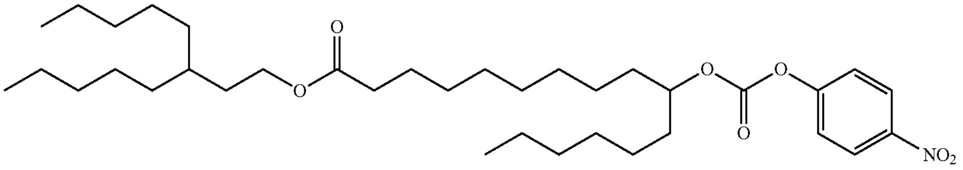

3-Pentyloctyl 10-(((4-nitrophenoxy)carbonyl)oxy)hexadecanoate as a colorless oily substance was obtained by the same method as that in (1) of Example 84, except that 3-pentyloctan-1-ol was used instead of 2-butyloctan-1-ol in (1) of Example 84.

$^1$H-NMR ($CDCl_3$) δ: 8.31-8.25 (2H, m), 7.41-7.36 (2H, m), 4.86-4.77 (1H, m), 3.97 (2H, d, J=5.4 Hz), 2.30 (2H, t, J=7.5 Hz), 1.72-1.20 (43H, m), 0.92-0.85 (9H, m).

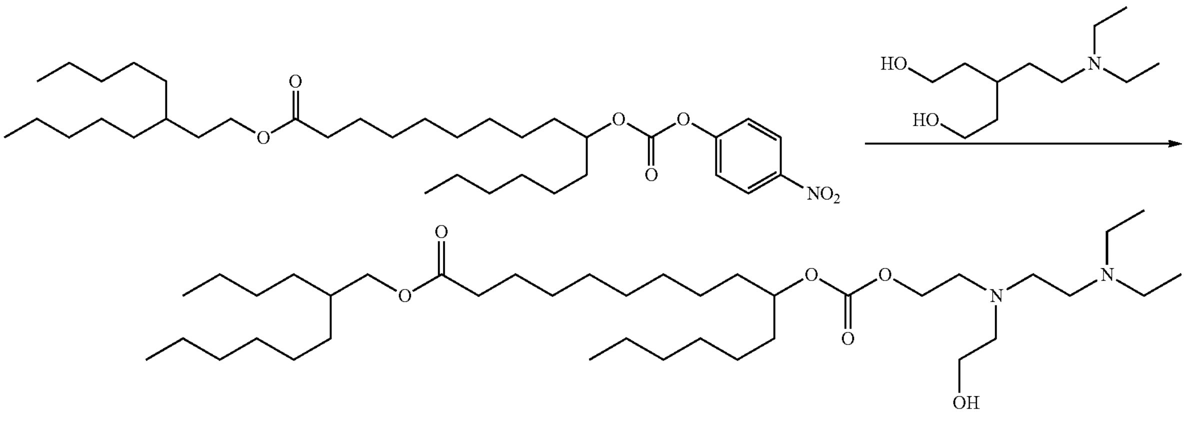

3-Pentyloctyl 3-ethyl-12-hexyl-6-(2-hydroxyethyl)-10-oxo-9,11-dioxa-3,6-diazahenicosan-21-oate as a colorless oily substance was obtained by the same method as that in (2) of Example 85, except that 3-pentyloctyl 10-(((4-nitrophenoxy)carbonyl)oxy)hexadecanoate was used instead of 2-butyloctyl 10-(((4-nitrophenoxy)carbonyl)oxy)hexadecanoate in (2) of Example 85.

$^1$H-NMR ($CDCl_3$) δ:4.74-4.06 (1H, m), 4.20 (2H, t, J=6.0 Hz), 4.08 (2H, t, J=6.6 Hz), 3.54 (2H, t, J=4.5 Hz), 2.88 (2H, t, J=5.7 Hz), 2.75-2.63 (4H, m), 2.60-2.41 (6H, m), 2.28 (2H, t, J=7.8 Hz), 1.72-1.47 (8H, m), 1.44-1.14 (35H, m), 1.03 (6H, t, J=7.2 Hz), 0.94-0.81 (9H, m).

MS m/z (M+H): 686.

Example 124

(1)

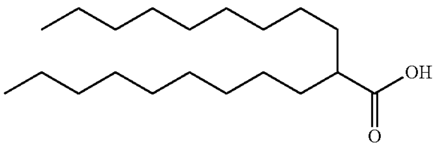

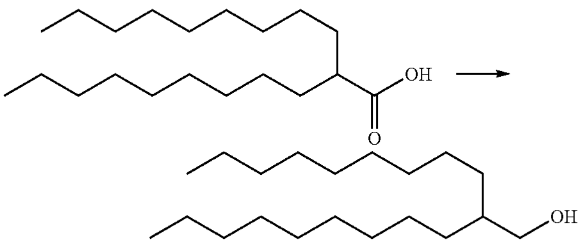

A tetrahydrofuran (10 mL) solution of 2-nonylundecanoate (3.0 g) was added dropwise to a mixture of a 2.5 mol/L lithium aluminum hydride-tetrahydrofuran solution (7.6 mL) and tetrahydrofuran (60 mL) under ice cooling, and the mixture was stirred at the same temperature for 30 minutes and then stirred at room temperature for 6 hours. Ethyl acetate was added to the reaction mixture, the reaction mixture was poured into ice water under ice cooling, and then the insoluble matters were filtered off using celite. The organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 2-nonylundecan-1-ol (2.8 g) as a colorless oily substance.

$^1$H-NMR ($CDCl_3$) δ:3.57-3.51 (2H, m), 1.50-1.20 (33H, m), 0.88 (6H, t, J=6.6 Hz).

(3)

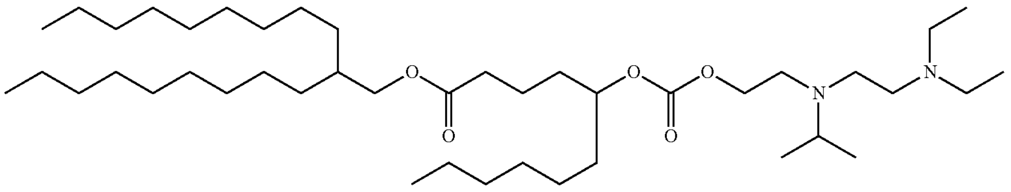

2-Nonylundecanoate as a colorless oily substance was obtained by the same method as that in (1) of Example 74, except that in (1) of Example 74, undecanoic acid was used instead of decanoic acid, and 1-iodononane was used instead of 1-iodooctane.

$^1$H-NMR ($CDCl_3$) δ:2.29-2.41 (1H, m), 1.68-1.20 (32H, m), 0.88 (6H, t, J=6.6 Hz).

2-Nonylundecyl 3-ethyl-12-hexyl-6-isopropyl-10-oxo-9,11-dioxa-3,6-diazahexadecan-16-oate as a colorless oily substance was obtained by the same method as that in (1) and (2) of Example 84, except that 2-nonylundecan-1-ol was used instead of 2-butyloctan-1-ol in (1) and (2) of Example 84.

$^1$H-NMR ($CDCl_3$) δ:4.76-4.62 (1H, m), 4.18-4.02 (2H, m), 3.96 (2H, d, J=5.7 Hz), 2.97-2.84 (1H, m), 2.68 (2H, t,

J=7.2 Hz), 2.60-2.42 (8H, m), 2.36-2.27 (2H, m), 1.76-1.49 (7H, m), 1.39-1.19 (40H, m), 1.09-0.94 (12H, m), 0.93-0.83 (9H, m).

MS m/z (M+H): 712.

Example 125

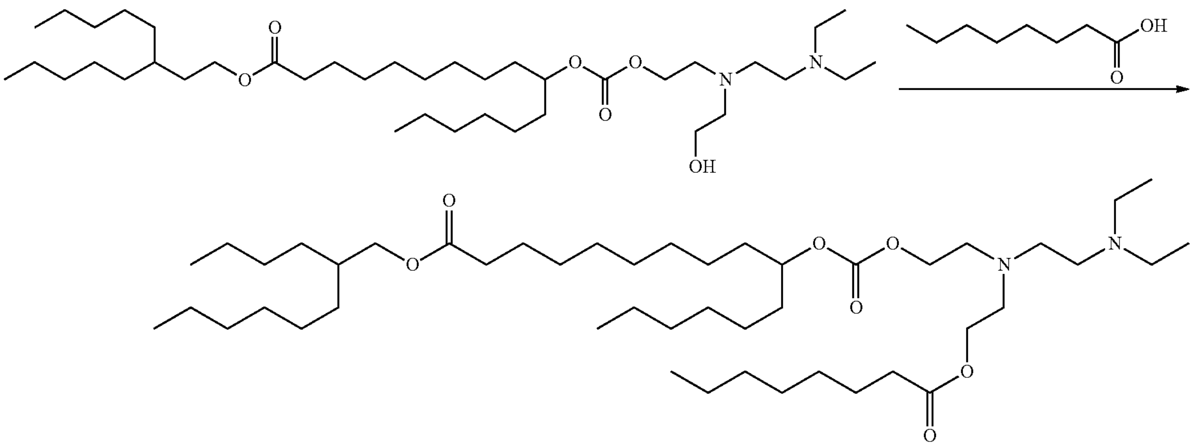

3-Pentyloctyl 3-ethyl-12-hexyl-6-(2-(octanoyloxy)ethyl)-10-oxo-9,11-dioxa-3,6-diazahenicosan-21-oate as a colorless oily substance was obtained by the same method as that in Example 86, except that in Example 86, 3-pentyloctyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and octanoic acid was used instead of dodecanoic acid.

$^1$H-NMR ($CDCl_3$) δ:4.72-4.61 (1H, m), 4.21-4.02 (6H, m), 2.88-2.75 (4H, m), 2.71-2.62 (2H, m), 2.58-2.45 (6H, m), 2.34-2.22 (4H, m), 1.68-1.48 (10H, m), 1.44-1.17 (43H, m), 1.02 (6H, t, J=6.6 Hz), 0.94-0.81 (12H, m).

MS m/z (M+H): 812.

Example 126

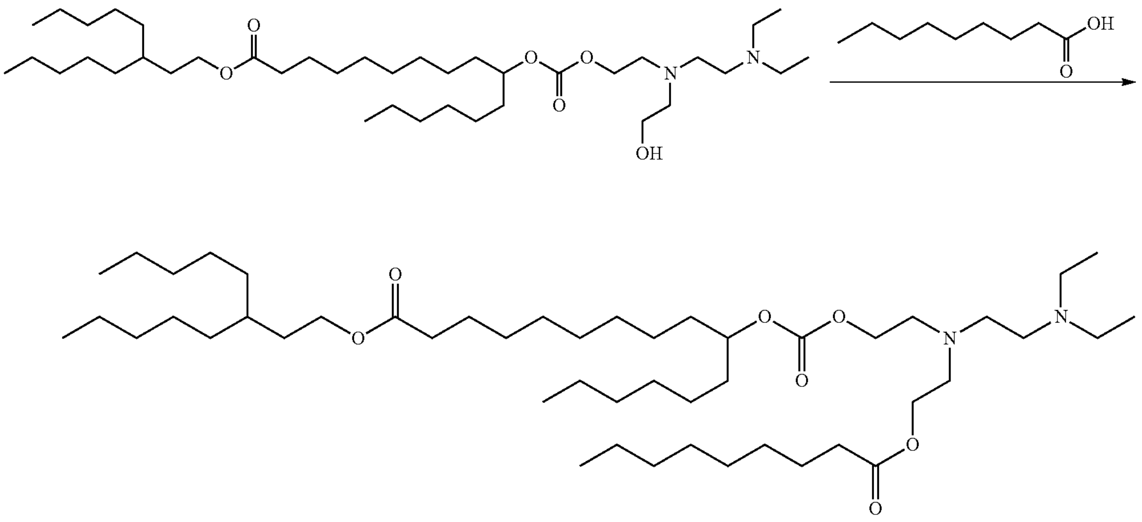

3-Pentyloctyl 3-ethyl-12-hexyl-6-(2-(nonanoyloxy)ethyl)-10-oxo-9,11-dioxa-3,6-diazahenicosan-21-oate as a colorless oily substance was obtained by the same method as that in Example 86, except that in Example 86, 3-pentyloctyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and nonanoic acid was used instead of dodecanoic acid.

$^1$H-NMR ($CDCl_3$) δ:4.73-4.59 (1H, m), 4.23-4.01 (6H, m), 2.90-2.76 (4H, m), 2.72-2.62 (2H, m), 2.58-2.45 (6H, m), 2.35-2.22 (4H, m), 1.69-1.47 (10H, m), 1.44-1.18 (45H, m), 1.02 (6H, t, J=7.5 Hz), 0.96-0.80 (12H, m).

MS m/z (M+H): 826.

Example 127

(1)

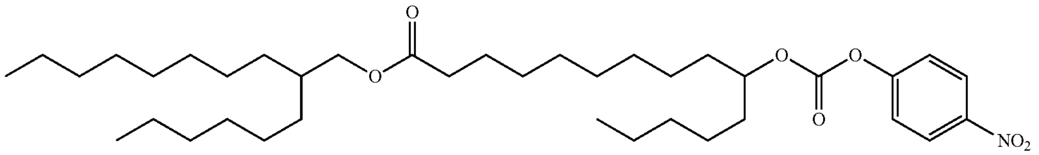

2-Hexyldecyl 10-(((4-nitrophenoxy)carbonyl)oxy)pentadecanoate as a colorless oily substance was obtained by the same method as that in (1) of Example 84, except that in (1) of Example 84, a 1.0 mol/L pentyl magnesium bromide-tetrahydrofuran solution was used instead of a 1.0 mol/L hexyl magnesium bromide-diethyl ether solution, and 2-hexyldecan-1-ol was used instead of 2-butyloctan-1-ol.

$^1$H-NMR ($CDCl_3$) δ:8.31-8.25 (2H, m), 7.41-7.35 (2H, m), 4.87-4.75 (1H, m), 3.96 (2H, d, J=6.0 Hz), 2.30 (2H, t, J=7.2 Hz), 1.72-1.20 (47H, m), 0.93-0.83 (9H, m).

(2)

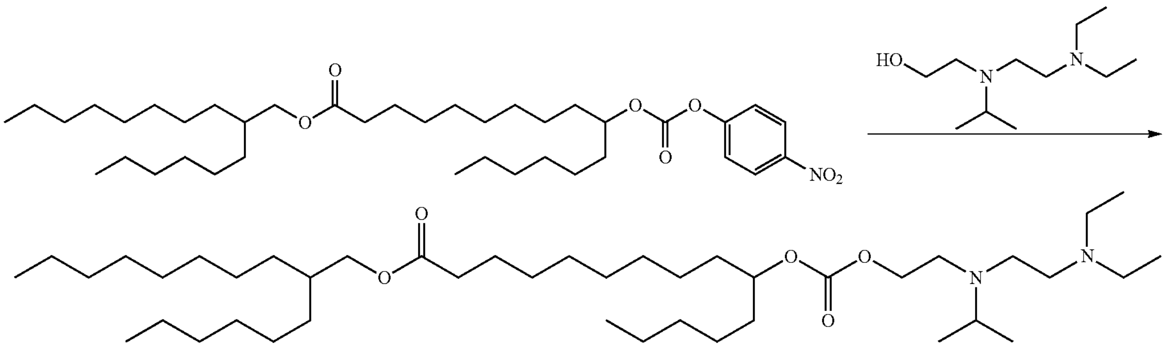

2-Hexyldecyl 3-ethyl-6-isopropyl-10-oxo-12-pentyl-9,11-dioxa-3,6-diazahenicosan-21-oate as a colorless oily substance was obtained by the same method as that in (2) of Example 84, except that 2-hexyldecyl 10-(((4-nitrophenoxy)carbonyl)oxy)pentadecanoate was used instead of 2-butyloctyl 10-(((4-nitrophenoxy)carbonyl)oxy)hexadecanoate in (2) of Example 84.

$^1$H-NMR ($CDCl_3$) δ:4.72-4.62 (1H, m), 4.10 (2H, t, J=6.6 Hz), 3.96 (2H, d, J=6.0 Hz), 2.98-2.82 (1H, m), 2.68 (2H, t, J=6.6 Hz), 2.59-2.42 (8H, m), 2.29 (2H, t, J=7.2 Hz), 1.66-1.47 (7H, m), 1.40-1.18 (40H, m), 1.06-0.96 (12H, m), 0.92-0.84 (9H, m).

MS m/z (M+H): 712.

Example 128

(1)

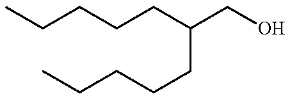

2-Pentylheptan-1-ol as a colorless oily substance was obtained by the same method as that in (2) of Example 124, except that 2-pentylheptanoate was used instead of 2-nonylundecanoate in (2) of Example 124.

$^1$H-NMR ($CDCl_3$) δ:3.57-3.51 (2H, m), 1.50-1.20 (17H, m), 0.88 (6H, t, J=6.6 Hz).

(2)

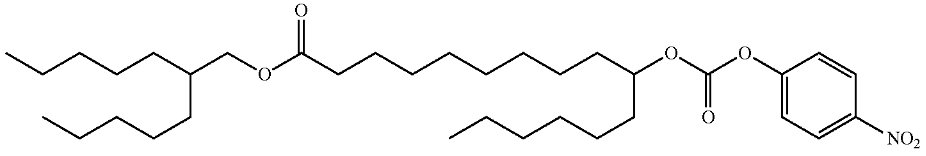

2-Pentylheptyl 10-(((4-nitrophenoxy)carbonyl)oxy)hexadecanoate as a colorless oily substance was obtained by the same method as that in (1) of Example 84, except that 2-pentylheptan-1-ol was used instead of 2-butyloctan-1-ol in (1) of Example 84.

$^1$H-NMR ($CDCl_3$) δ:8.28 (2H, dd, J=7.2 Hz, 2.1 Hz), 7.39 (2H, dd, J=7.2 Hz, 2.1 Hz), 4.86-4.76 (1H, m), 3.97 (2H, d, J=6.0 Hz), 2.30 (2H, t, J=7.2 Hz), 1.74-1.20 (41H, m), 0.92-0.85 (9H, m).

(3)

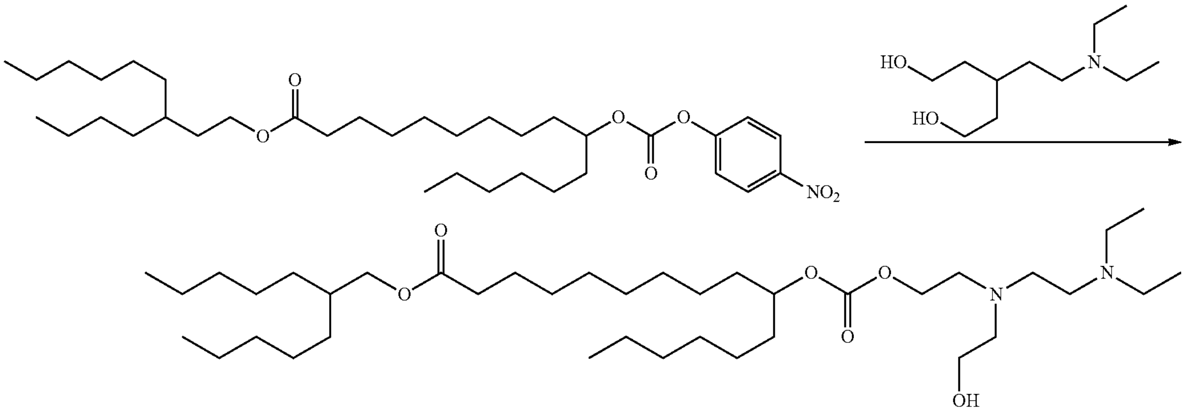

2-Pentylheptyl 3-ethyl-12-hexyl-6-(2-hydroxyethyl)-10-oxo-9,11-dioxa-3,6-diazahenicosan-21-oate as a colorless oily substance was obtained by the same method as that in (2) of Example 85, except that 2-pentylheptyl 10-(((4-nitrophenoxy)carbonyl)oxy)hexadecanoate was used instead of 2-butyloctyl 10-(((4-nitrophenoxy)carbonyl)oxy)hexadecanoate in (2) of Example 85.

$^1$H-NMR ($CDCl_3$) δ:4.73-4.61 (1H, m), 4.20 (2H, t, J=6.0 Hz), 3.97 (2H, d, J=5.4 Hz), 3.54 (2H, t, J=4.5 Hz), 2.88 (2H, t, J=6.6 Hz), 2.74-2.64 (4H, m), 2.59-2.44 (6H, m), 2.29 (2H, t, J=7.2 Hz), 1.75-1.45 (7H, m), 1.40-1.19 (34H, m), 1.02 (6H, t, J=7.2 Hz), 0.92-0.84 (9H, m).

MS m/z (M+H): 672.

Example 129

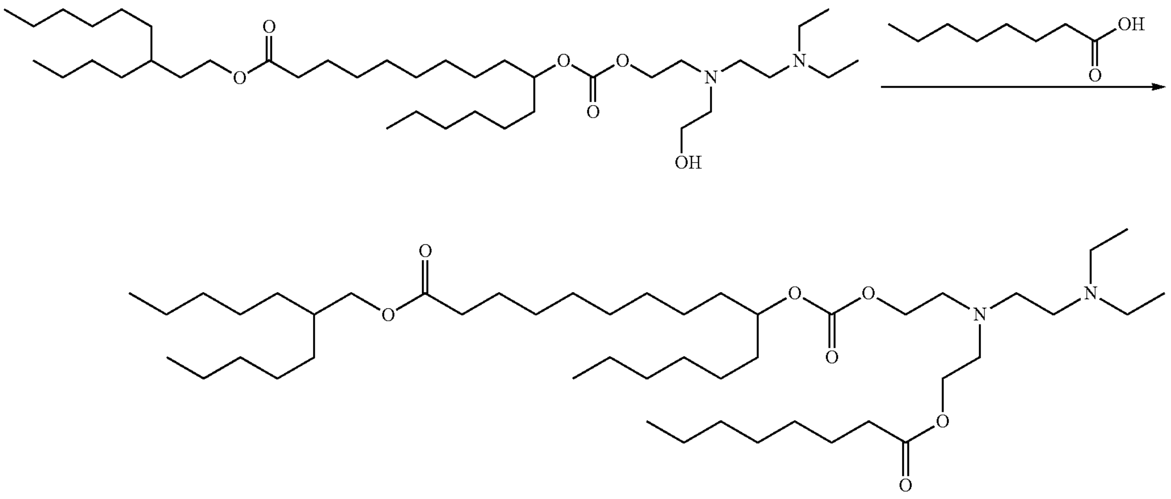

2-Pentylheptyl 3-ethyl-12-hexyl-6-(2-(octanoyloxy)ethyl)-10-oxo-9,11-dioxa-3,6-diazahenicosan-21-oate as a colorless oily substance was obtained by the same method as that in Example 86, except that in Example 86, 2-pentylheptyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and octanoic acid was used instead of dodecanoic acid.

$^{1}$H-NMR ($CDCl_3$) δ:4.73-4.61 (1H, m), 4.21-4.07 (4H, m), 3.97 (2H, d, J=5.4 Hz), 2.88-2.77 (4H, m), 2.72-2.62 (2H, m), 2.58-2.45 (6H, m), 2.29 (4H, t, J=7.2 Hz), 1.69-1.48 (9H, m), 1.41-1.18 (42H, m), 1.02 (6H, t, J=7.2 Hz), 0.94-0.82 (12H, m).

MS m/z (M+H): 798.

Example 130

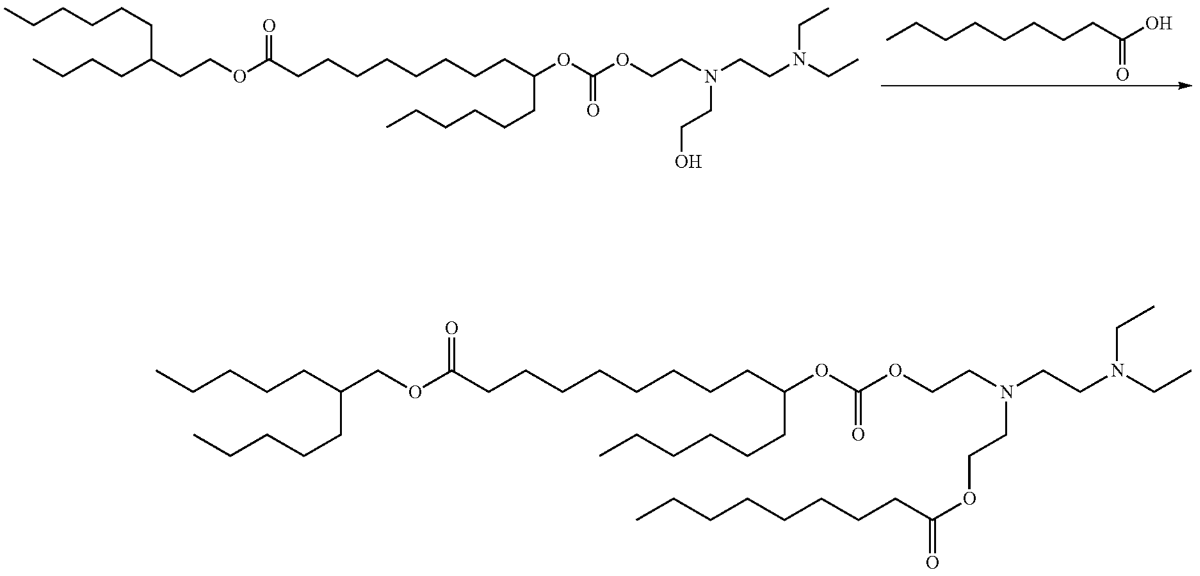

2-Pentylheptyl 3-ethyl-12-hexyl-6-(2-(nonanoyloxy)ethyl)-10-oxo-9,11-dioxa-3,6-diazahenicosan-21-oate as a colorless oily substance was obtained by the same method as that in Example 86, except that in Example 86, 2-pentylheptyl 3-ethyl-12-hexyl-6-(2-hydroxyethyl)-10-oxo-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and nonanoic acid was used instead of dodecanoic acid.

$^1$H-NMR ($CDCl_3$) δ:4.72-4.61 (1H, m), 4.22-4.08 (4H, m), 3.97 (2H, d, J=6.0 Hz), 2.88-2.75 (4H, m), 2.72-2.62 (2H, m), 2.60-2.46 (6H, m), 2.29 (4H, t, J=7.5 Hz), 1.70-1.47 (9H, m), 1.41-1.18 (44H, m), 1.02 (6H, t, J=6.6 Hz), 0.95-0.81 (12H, m).

MS m/z (M+H): 812.

Example 131

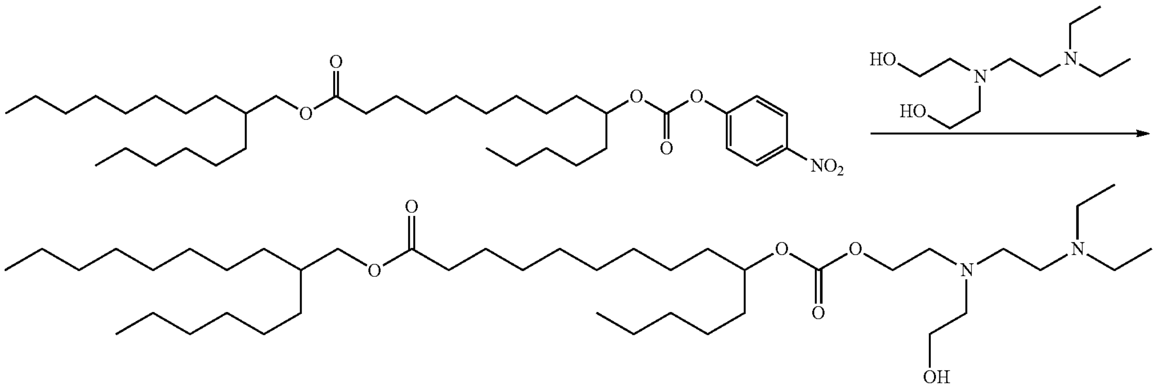

2-Hexyldecyl 3-ethyl-6-(2-hydroxyethyl)-10-oxo-12-pentyl-9,11-dioxa-3,6-diazahenicosan-21-oate as a colorless oily substance was obtained by the same method as that in (2) of Example 85, except that 2-hexyldecyl 10-(((4-nitrophenoxy)carbonyl)oxy)pentadecanoate was used instead of 2-butyloctyl 10-(((4-nitrophenoxy)carbonyl)oxy)hexadecanoate in (2) of Example 85.

$^1$H-NMR ($CDCl_3$) δ:4.74-4.62 (1H, m), 4.20 (2H, t, J=6.0 Hz), 3.96 (2H, d, J=5.7 Hz), 3.54 (2H, t, J=4.5 Hz), 2.89 (2H, t, J=6.0 Hz), 2.75-2.64 (4H, m), 2.60-2.43 (6H, m), 2.29 (2H, t, J=7.8 Hz), 1.67-1.49 (7H, m), 1.41-1.19 (40H, m), 1.02 (6H, t, J=7.2 Hz), 0.94-0.82 (9H, m).

MS m/z (M+H): 714.

Example 132

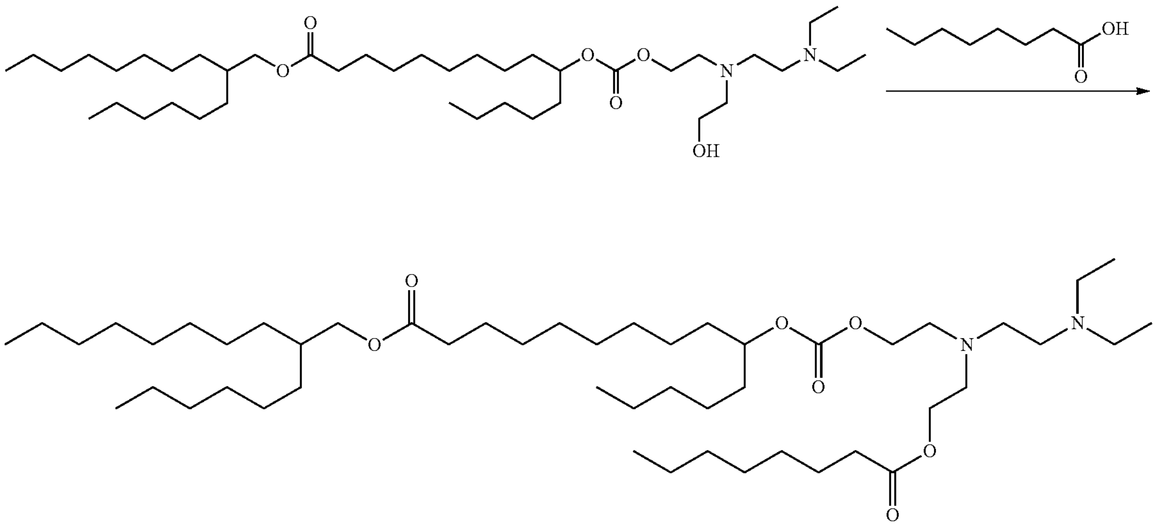

2-Hexyldecyl 3-ethyl-6-(2-(octanoyloxy)ethyl)-10-oxo-12-pentyl-9,11-dioxa-3,6-diazahenicosan-21-oate as a colorless oily substance was obtained by the same method as that in Example 86, except that in Example 86, 2-hexyldecyl 3-ethyl-6-(2-hydroxyethyl)-10-oxo-12-pentyl-9,11-dioxa-3,6-diazahenicosan-21-oate was used instead of 2-butyloctyl 3-ethyl-12-hexyl-6-(2-hydroxyethyl)-10-oxo-9,11-dioxa-3,6-diazahenicosan-21-oate, and octanoic acid was used instead of dodecanoic acid.

$^1$H-NMR ($CDCl_3$) δ:4.72-4.61 (1H, m), 4.22-4.06 (4H, m), 3.96 (2H, d, J=6.0 Hz), 2.88-2.76 (4H, m), 2.72-2.62 (2H, m), 2.58-2.45 (6H, m), 2.29 (4H, t, J=7.2 Hz), 1.68-1.48 (9H, m), 1.39-1.18 (48H, m), 1.02 (6H, t, J=6.6 Hz), 0.94-0.82 (12H, m).

MS m/z (M+H): 840.

Example 133

(1)

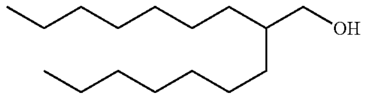

2-Heptylnonan-1-ol as a colorless oily substance was obtained by the same method as that in (1) and (2) of Example 124, except that in (1) and (2) of Example 124, nonanoic acid was used instead of undecanoic acid, and 1-iodoheptane was used instead of 1-iodononane.

$^1$H-NMR ($CDCl_3$) δ:3.57-3.51 (2H, m), 1.50-1.20 (25H, m), 0.88 (6H, t, J=6.6 Hz).

(2)

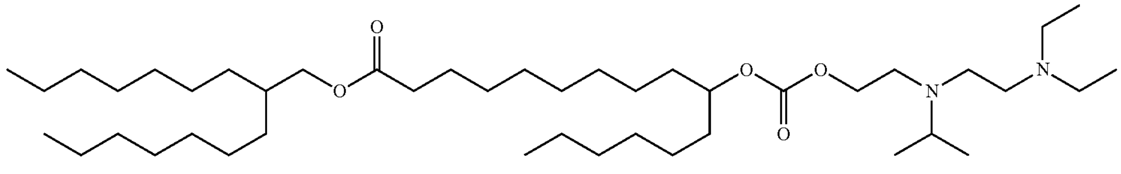

2-Heptylnonyl 3-ethyl-12-hexyl-6-isopropyl-10-oxo-9,11-dioxa-3,6-diazahenicosan-21-oate as a colorless oily substance was obtained by the same method as that in (1) and (2) of Example 84, except that 2-heptylnonan-1-ol was used instead of 2-butyloctan-1-ol in (1) and (2) of Example 84.

$^1$H-NMR ($CDCl_3$) δ:4.72-4.62 (1H, m), 4.10 (2H, t, J=6.6 Hz), 3.96 (2H, d, J=6.0 Hz), 2.97-2.85 (1H, m), 2.68 (2H, t, J=6.9 Hz), 2.60-2.41 (8H, m), 2.29 (2H, t, J=7.2 Hz), 1.67-1.47 (7H, m), 1.39-1.19 (42H, m), 1.08-0.95 (12H, m), 0.94-0.82 (9H, m).

MS m/z (M+H): 726.

Example 134

(1)

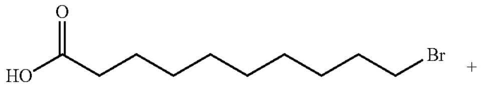

-continued

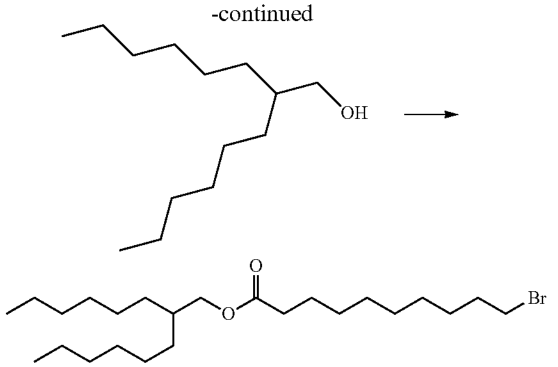

2-Hexyl-1-octanol (4.4 g), 1-(3-dimethylaminopropyl)-3-ethylcarbodiimide hydrochloride (3.9 g), 4-dimethylaminopyridine (0.9 g), and triethylamine (8.6 mL) were added to a dichloromethane (80 mL) solution of 10-bromodecanoic acid (4.0 g) at room temperature, and the mixture was stirred overnight at the same temperature. Ethyl acetate and water were added to the reaction mixture. The organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane), thereby obtaining 2-hexyloctyl 10-bromodecanoate (3.4 g) as a colorless oily substance.

$^1$H-NMR ($CDCl_3$) δ:3.97 (2H, d, J=6.0 Hz), 3.41 (2H, t, J=6.6 Hz), 2.30 (2H, t, J=7.5 Hz), 1.91-1.78 (2H, m), 1.69-1.19 (33H, m), 0.89 (6H, t, J=7.5 Hz).

(2)

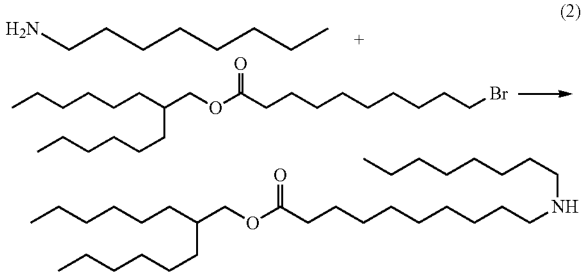

N-octylamine (1.1 mL) and potassium carbonate (1.9 g) were added to a N,N-dimethylformamide (5 mL) solution of 2-hexyloctyl 10-bromodecanoate (1.0 g) at room temperature, and the mixture was stirred for 4 hours at 60° C. The reaction mixture was cooled to room temperature, and then ethyl acetate and water were added thereto. The organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate), thereby obtaining 2-hexyloctyl 10-(octylamino)decanoate (806 mg) as a light yellow oily substance.

$^1$H-NMR ($CDCl_3$) δ: 3.97 (2H, d, J=6.0 Hz), 2.58 (4H, t, J=7.2 Hz), 2.29 (2H, t, J=7.2 Hz), 1.68-1.20 (47H, m), 0.92-0.84 (9H, m).

(3)

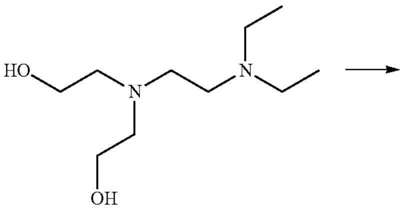

-continued

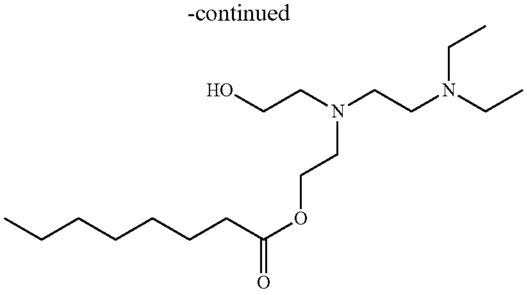

Octanoic acid (0.79 mL), 1-(3-dimethylaminopropyl)-3-ethylcarbodiimide hydrochloride (1.4 g), 4-dimethylamino-pyridine (1.2 g), and triethylamine (2.1 mL) were added to a dichloromethane (20 mL) solution of 2,2'-((2-(diethyl-amino)ethyl)azanediyl)bis(ethan-1-ol) (1.0 g) at room temperature, and the mixture was stirred at the same temperature for 12 hours. Ethyl acetate and water were added to the reaction mixture. The organic layer was separated, washed with a saturated aqueous sodium chloride solution, and then dried over anhydrous sodium sulfate, and the solvent was distilled away under reduced pressure. The obtained residue was purified by silica gel column chromatography (ethyl acetate-hexane, NH silica gel), thereby obtaining 2-((2-(diethylamino)ethyl)(2-hydroxyethyl)amino)ethyl octanoate (541 mg) as a colorless oily substance.

$^1$H-NMR ($CDCl_3$) δ: 4.15 (2H, t, J=5.4 Hz), 3.54 (2H, t, J=5.4 Hz), 2.84 (2H, t, J=6.0 Hz), 2.72-2.63 (4H, m), 2.59-2.44 (6H, m), 2.30 (2H, t, J=7.2 Hz), 1.78-1.19 (10H, m), 1.03 (6H, t, J=7.2 Hz), 0.88 (3H, t, J=6.6 Hz).

(4)

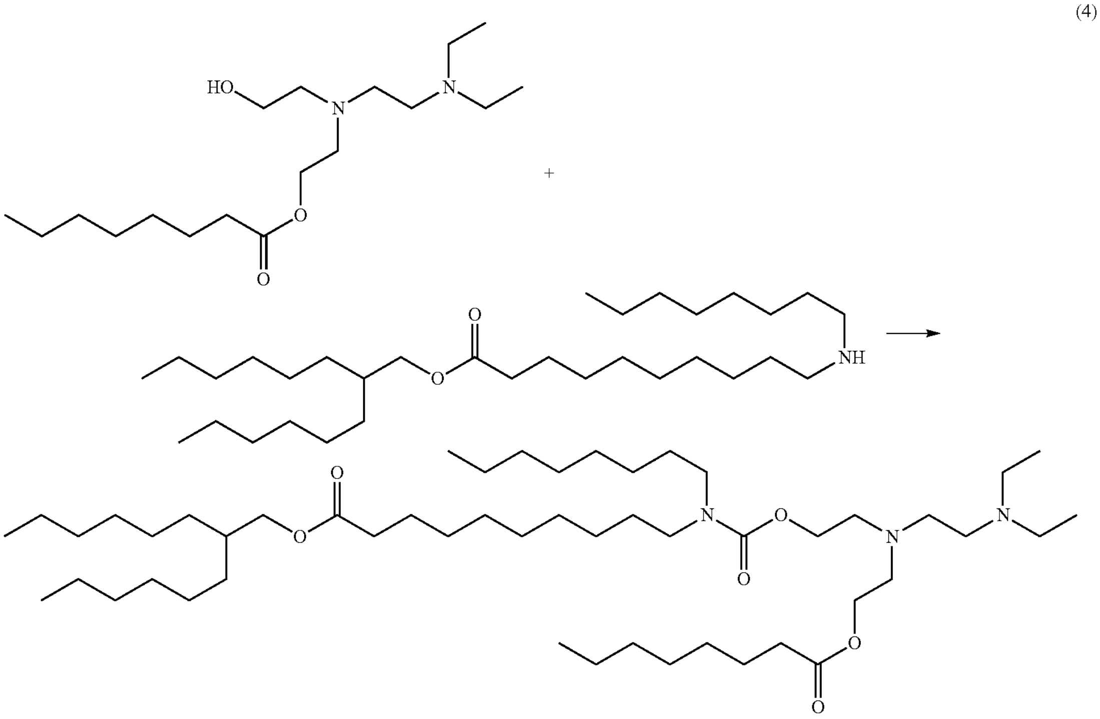

4-Nitrophenylchloroformate (311 mg) was added to a tetrahydrofuran (6 mL) solution of 2-((2-(diethylamino) ethyl)(2-hydroxyethyl)amino)ethyl octanoate (500 mg) at room temperature, and the mixture was stirred at the same temperature for 1 hour. 2-Hexyloctyl 10-(octylamino)decanoate (300 mg) and triethylamine (0.34 mL) were added to the reaction mixture at room temperature, and the mixture was stirred at 60° C. for 3 hours. The reaction mixture was cooled to room temperature, and then ethyl acetate and water were added thereto. The organic layer was separated, washed with a saturated aqueous sodium chloride solution, and then dried over anhydrous sodium sulfate, and the solvent was distilled away under reduced pressure. The obtained residue was purified by silica gel column chromatography (methanol-ethyl acetate) and silica gel column chromatography (ethyl acetate-hexane, NH silica gel), thereby obtaining 2-hexyloctyl 3-ethyl-6-(2-(octanoyloxy)

ethyl)-11-octyl-10-oxo-9-oxa-3,6,11-triazahenicosan-21-oate (117 mg) as a colorless oily substance.

$^1$H-NMR ($CDCl_3$) δ:4.16-4.07 (4H, m), 3.97 (2H, d, J=6.0 Hz), 3.24-3.09 (4H, m), 2.84-2.75 (4H, m), 2.71-2.61 (2H, m), 2.58-2.46 (6H, m), 2.34-2.23 (4H, m) 1.68-1.42 (5H, m), 1.36-1.18 (52H, m), 1.02 (6H, t, J=7.5 Hz), 0.93-0.83 (12H, m).

MS m/z (M+H): 853.

Example 135

(1)

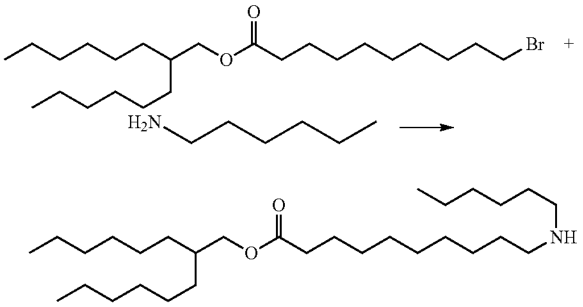

2-Hexyloctyl 10-(hexylamino)decanoate as a light yellow oily substance was obtained by the same method as that in (2) of Example 134, except that in (2) of Example 134, N-hexylamine was used instead of N-octylamine.

$^1$H-NMR ($CDCl_3$) δ: 3.96 (2H, d, J=6.0 Hz), 2.58 (4H, t, J=7.2 Hz), 2.30 (2H, t, J=8.1 Hz), 1.67-1.21 (43H, m), 0.93-0.84 (9H, m).

2-Hexyloctyl 3-ethyl-11-hexyl-6-(2-(octanoyloxy)ethyl)-10-oxo-9-oxa-3,6,11-triazahenicosan-21-oate as a colorless oily substance was obtained by the same method as that in (4) of Example 134, except that in (4) of Example 134, 2-hexyloctyl 10-(hexylamino)decanoate was used instead of 2-hexyloctyl 10-(octylamino)decanoate.

$^1$H-NMR ($CDCl_3$) δ:4.15-4.08 (4H, m), 3.97 (2H, d, J=6.0 Hz), 3.24-3.08 (4H, m), 2.85-2.75 (4H, m), 2.71-2.62 (2H, m), 2.57-2.46 (6H, m), 2.34-2.24 (4H, m), 1.67-1.44 (5H, m), 1.37-1.18 (48H, m), 1.02 (6H, t, J=7.5 Hz), 0.93-0.81 (12H, m).

MS m/z (M+H): 825.

Example 136

(1)

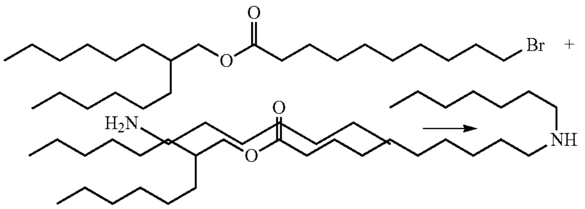

2-Hexyloctyl 10-(heptylamino)decanoate as a light yellow oily substance was obtained by the same method as that in (2) of Example 134, except that in (2) of Example 134, N-heptylamine was used instead of N-octylamine.

$^1$H-NMR ($CDCl_3$) δ: 3.97 (2H, d, J=6.0 Hz), 2.58 (4H, t, J=7.5 Hz), 2.29 (2H, t, J=7.2 Hz), 1.70-1.20 (45H, m), 0.95-0.83 (9H, m).

(2)

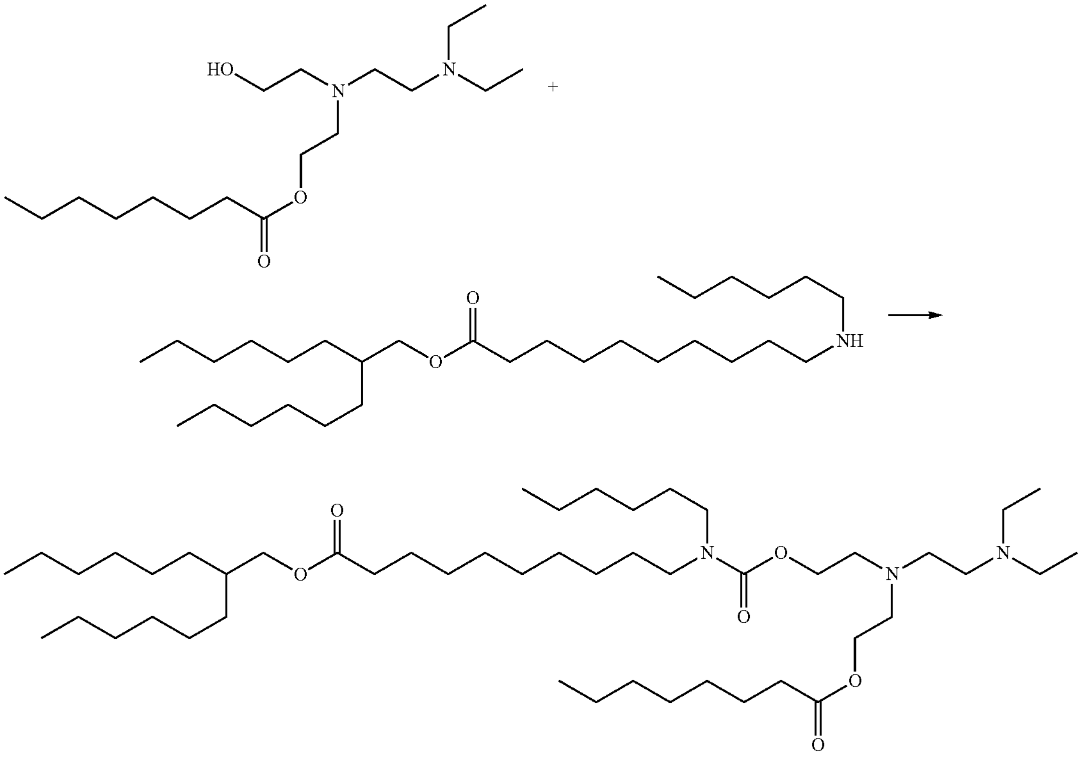

(2)

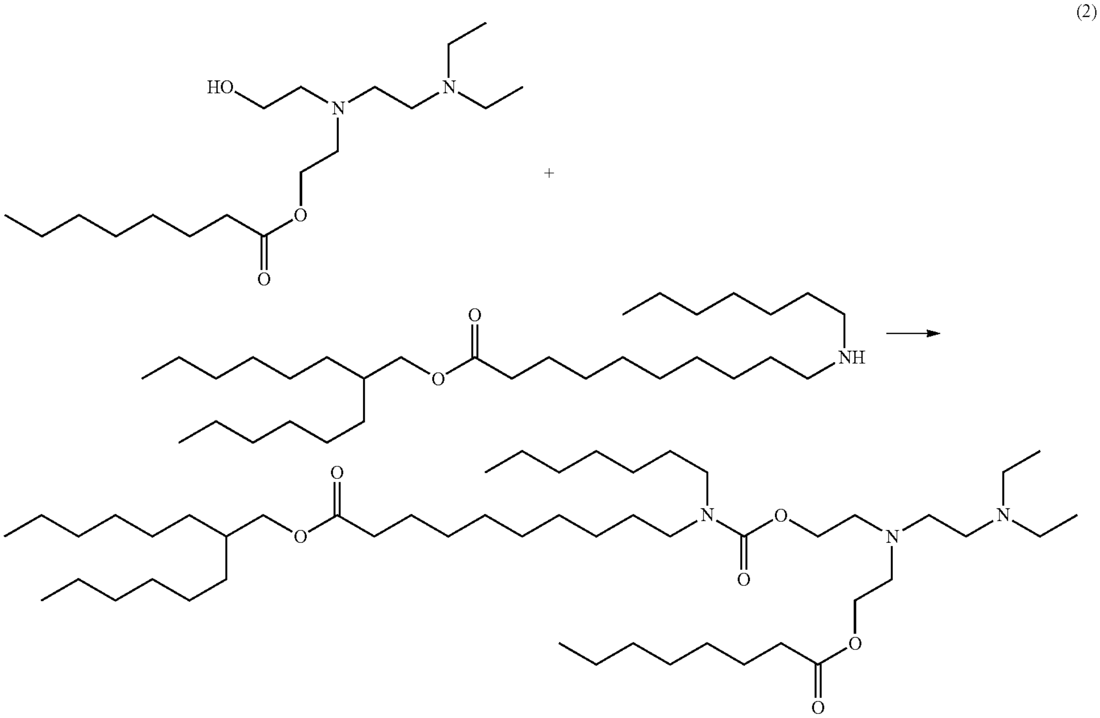

2-Hexyloctyl 3-ethyl-11-heptyl-6-(2-(octanoyloxy)ethyl)-10-oxo-9-oxa-3,6,11-triazahenicosan-21-oate as a colorless oily substance was obtained by the same method as that in (4) of Example 134, except that in (4) of Example 134, 2-hexyloctyl 10-(heptylamino)decanoate was used instead of 2-hexyloctyl 10-(octylamino)decanoate.

$^1$H-NMR ($CDCl_3$) δ:4.16-4.07 (4H, m), 3.97 (2H, d, J=6.0 Hz), 3.24-3.08 (4H, m), 2.85-2.74 (4H, m), 2.71-2.61 (2H, m), 2.58-2.46 (6H, m), 2.35-2.24 (4H, m), 1.66-1.44 (5H, m), 1.38-1.17 (50H, m), 1.02 (6H, t, J=7.2 Hz), 0.93-0.82 (12H, m).

MS m/z (M+H): 839.

Example 137

(1)

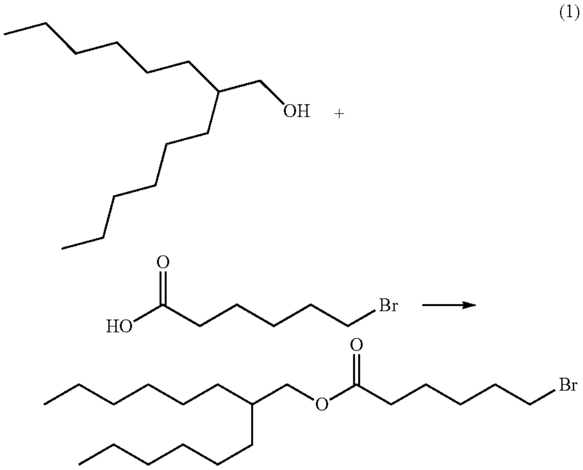

2-Hexyloctyl 6-bromohexanoate as a colorless oily substance was obtained by the same method as that in (1) of Example 134, except that in (1) of Example 134, 6-bromohexanoic acid was used instead of 10-bromodecanoic acid.

$^1$H-NMR ($CDCl_3$) δ: 3.98 (2H, d, J=5.4 Hz), 3.41 (2H, t, J=6.6 Hz), 2.33 (2H, t, J=8.1 Hz), 1.95-1.81 (2H, m), 1.72-1.20 (25H, m), 0.89 (6H, t, J=6.6 Hz).

(2)

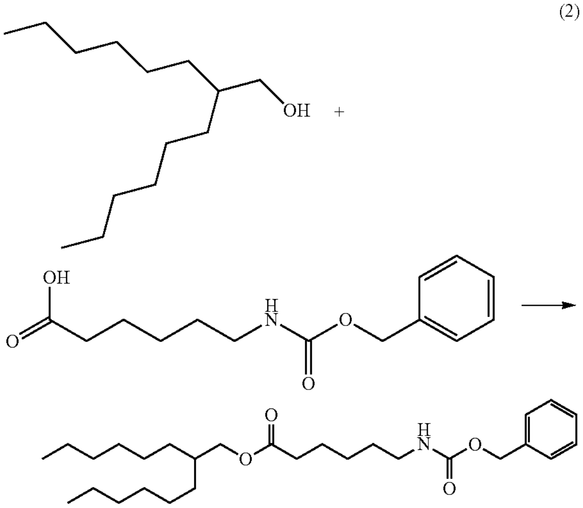

2-Hexyloctyl 6-(((benzyloxy)carbonyl)amino)hexanoate as a colorless oily substance was obtained by the same method as that in (1) of Example 134, except that in (1) of Example 134, 6-(((benzyloxy)carbonyl)amino)hexanoate was used instead of 10-bromodecanoic acid.

$^1$H-NMR ($CDCl_3$) δ: 7.42-7.22 (5H, m), 5.09 (2H, s), 4.86-4.66 (1H, m), 3.96 (2H, d, J=6.0 Hz), 3.26-3.13 (2H, m), 2.30 (2H, t, J=7.2 Hz), 1.71-1.20 (27H, m), 0.88 (6H, t, J=6.6 Hz).

(3)

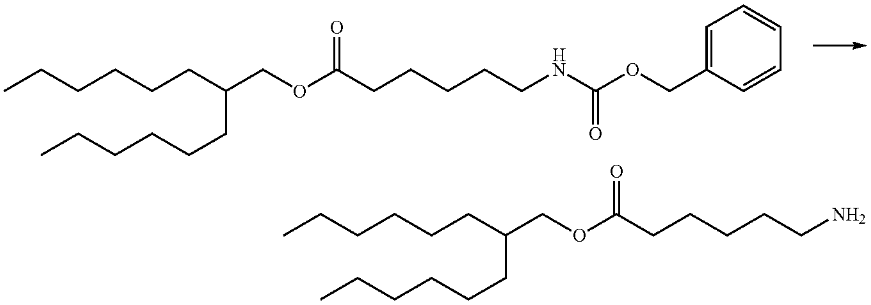

Palladium-carbon (10%, 1.1 g) and ammonium formate (3.1 g) were added to a methanol (38 mL) solution of 2-hexyloctyl 6-(((benzyloxy)carbonyl)amino)hexanoate (3.8 g), and stirred under reflux for 2 hours. The reaction mixture was cooled to room temperature, the insoluble matters were filtered off using celite, and then the solvent was distilled away under reduced pressure. The obtained residue was purified by silica gel column chromatography (ethyl acetate-hexane), thereby obtaining 2-hexyloctyl 6-aminohexanoate (1.5 g) as a colorless oily substance.

$^1$H-NMR ($CDCl_3$) δ: 3.97 (2H, d, J=5.1 Hz), 2.69 (2H, t, J=7.2 Hz), 2.32 (2H, t, J=7.2 Hz), 1.71-1.20 (27H, m), 0.88 (6H, t, J=6.6 Hz).

(4)

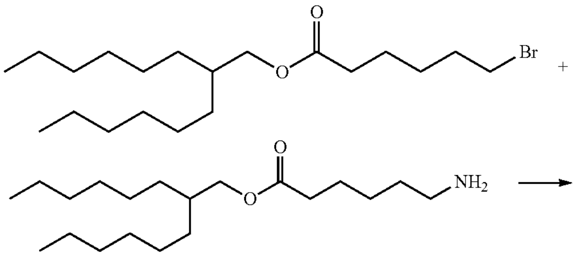

-continued

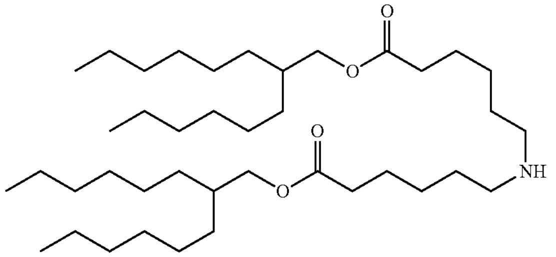

Bis(2-hexyloctyl) 6,6'-azanediyldihexanoate as a light yellow oily substance was obtained by the same method as that in (2) of Example 134, except that in (2) of Example 134, 2-hexyloctyl 6-aminohexanoate was used instead of N-octylamine, and 2-hexyloctyl 6-bromohexanoate was used instead of 2-hexyloctyl 10-bromodecanoate.

$^1$H-NMR ($CDCl_3$) δ: 3.97 (4H, d, J=6.0 Hz), 2.59 (4H, t, J=7.5 Hz), 2.31 (4H, t, J=7.5 Hz), 1.70-1.20 (54H, m), 0.88 (12H, t, J=6.6 Hz).

(5)

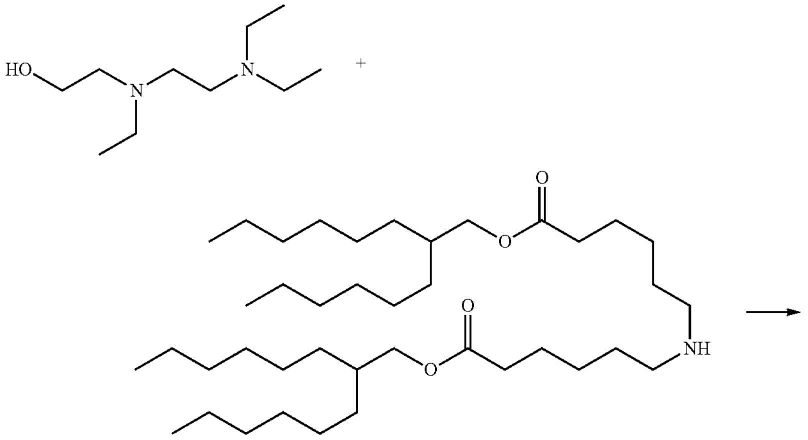

-continued

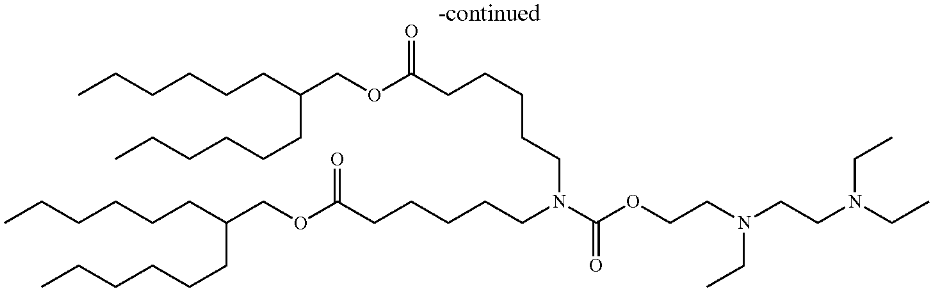

2-Hexyloctyl 3,6-diethyl-1 1-(6-((2-hexyloctyl)oxy)-6-oxohexyl)-10-oxo-9-oxa-3,6,11-triazaheptadecan-17-oate as a colorless oily substance was obtained by the same method as that in (4) of Example 134, except that in (4) of Example 134, bis(2-hexyloctyl) 6,6'-azanediyldihexanoate was used instead of 2-hexyloctyl 10-(octylamino)decanoate, and 2-((2-(diethylamino)ethyl)(ethyl)amino)ethan-1-ol was used instead of 2-((2-(diethylamino)ethyl)(2-hydroxyethyl)amino)ethyl octanoate.

$^1$H-NMR ($CDCl_3$) δ: 4.12 (2H, t, J=6.6 Hz), 3.97 (4H, d, J=6.0 Hz), 3.25-3.10 (4H, m), 2.72 (2H, t, J=6.0 Hz), 2.64-2.47 (10H, m), 2.30 (4H, t, J=7.8 Hz), 1.71-1.20 (54H, m), 1.09-0.98 (9H, m), 0.94-0.83 (12H, m).

MS m/z (M+H): 853.

Example 138

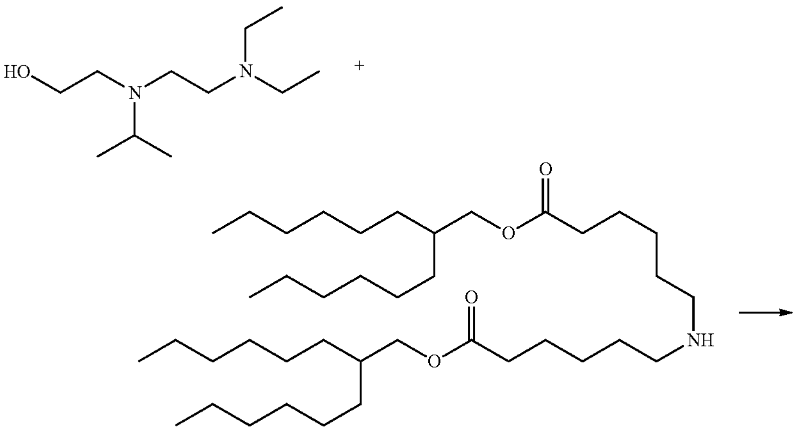

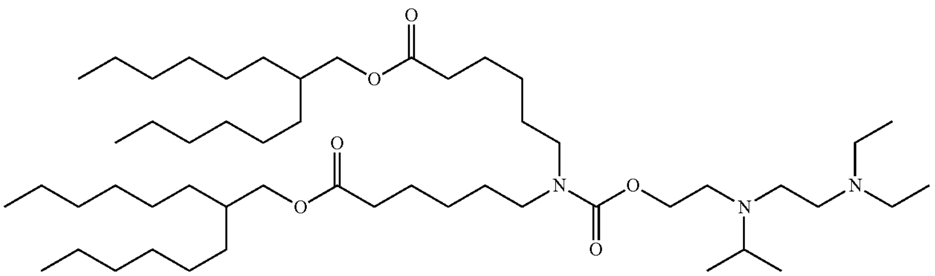

2-Hexyloctyl 3-ethyl-11-(6-((2-hexyloctyl)oxy)-6-oxo-hexyl)-6-isopropyl-10-oxo-9-oxa-3,6,11-triazaheptade can-17-oate as a colorless oily substance was obtained by the same method as that in (4) of Example 134, except that in (4) of Example 134, bis(2-hexyloctyl) 6,6'-azanediyldihexanoate was used instead of 2-hexyloctyl 10-(octylamino)decanoate, and 2-((2-(diethylamino)ethyl)(isopropyl)amino)ethan-1-ol was used instead of 2-((2-(diethylamino)ethyl)(2-hydroxyethyl)amino)ethyl octanoate.

$^1$H-NMR ($CDCl_3$) δ: 4.04 (2H, t, J=6.6 Hz), 3.97 (4H, d, J=6.0 Hz), 3.24-3.11 (4H, m), 2.98-2.85 (1H, m), 2.64 (2H, t, J=6.6 Hz), 2.59-2.42 (8H, m), 2.30 (4H, t, J=7.8 Hz), 1.72-1.19 (54H, m), 1.08-0.95 (12H, m), 0.94-0.82 (12H, m).

MS m/z (M+H): 867.

[Preparation of Nucleic Acid Lipid Particles and Measurement of Reporter Protein Knockdown Rate in Mice]

<Preparation of Nucleic Acid Lipid Particles>

The compounds 56, 62, 70, 76, 77, 88, 89, 94, 100, 112, 124, 133, 134, 135, 136, 137, and 138 synthesized in the above examples were used as the lipid represented by Formula (1).

For comparison, a lipid having the following structure (comparative compound C) synthesized by the method described in WO2010/144740A was used.

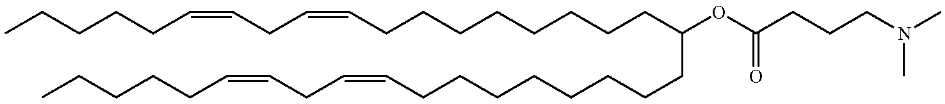 [SMILES: CCCCC/C=C\C/C=C\CCCCCCCCC(CCCCCCCC/C=C\C/C=C\CCCCC)OC(=O)CCCN(C)C]

The lipid represented by Formula (1), 1,2-distearoyl-sn-glycero-3-phosphocholine (DSPC, trade name: COATSOME MC-8080; NOF corporation), cholesterol (trade name: Cholesterol HP; NIPPON FINE CHEMICAF CO., LTD.), DMG-PEG2000, (trade name: SUNBRIGHT® GM-020; NOF corporation) were dissolved in ethanol at the molar ratio shown in Tables 1 to 3 so that the total lipid concentration was 20 mmol/L, thereby obtaining an oil phase.

siFVII (5 mg) having the sequence on p. 878 of Molecular Therapy (2009) 17 was dissolved in 1 mL of sterile water, and diluted with 10 mmol/L acetate buffer having a pH 4 so that the nucleic acid concentration was 19.7 μmol/L, thereby obtaining a water phase. Then, the water phase and the oil phase were mixed together with a micromixer (see JP5288254B) using a syringe pump so that the volume ratio of water phase:oil phase was 3:1. The mixed solution was diluted 2× with a phosphate buffered saline (PBS), thereby obtaining a nucleic acid lipid particle dispersion.

Tables 1 to 3 show the values of "(A)-(B)" obtained in a case where (A) represents the molar ratio in percentage of the lipid represented by Formula (1) to the total lipids constituting the lipid composition, and (B) represents the molar ratio in percentage of the zwitterionic lipid to the total lipids constituting the lipid composition.

Tables 1 to 3 also show the weight ratio of the nucleic acid to the total weight of lipids at the time of mixing.

In Tables 1 to 3, "Lipid *" is the lipid represented by Formula (1) or a comparative lipid.

TABLE 1

| | | Compositional ratio of lipid (mol %) | | | | | Mass ratio of |
|---|---|---|---|---|---|---|---|
| | Lipid* | Lipid* | phospholipid DSPC | Cholesterol | PEG lipid DME-PEG2000 | (A) − (B) | nucleic acid to total lipids |
| Comparative Example 301 | Comparative compound C | 50 | 10 | 38.5 | 1.5 | 40 | 6.7% |
| Comparative Example 302 | Compound 89 | 50 | 10 | 38.5 | 1.5 | 40 | 5.9% |
| Example 301 | Compound 89 | 60 | 10 | 28.5 | 1.5 | 50 | 5.6% |
| Example 302 | Compound 89 | 55 | 5 | 38.5 | 1.5 | 50 | 5.9% |
| Example 303 | Compound 89 | 55 | 2 | 41.5 | 1.5 | 53 | 6.0% |
| Example 304 | Compound 88 | 50 | | 48.5 | 1.5 | 50 | 6.3% |
| Example 305 | Compound 88 | 60 | | 38.5 | 1.5 | 60 | 5.9% |
| Example 306 | Compound 88 | 65 | | 33.5 | 1.5 | 65 | 5.7% |
| Example 307 | Compound 88 | 60 | | 38 | 2 | 60 | 5.8% |
| Example 308 | Compound 88 | 50 | | 48 | 2 | 50 | 6.2% |
| Example 309 | Compound 89 | 55 | | 43.5 | 1.5 | 55 | 6.5% |
| Example 310 | Compound 89 | 55 | | 43 | 2 | 55 | 6.4% |
| Example 311 | Compound 56 | 50 | | 48.5 | 1.5 | 50 | 5.7% |

TABLE 2

| | | Compositional ratio of lipid (mol %) | | | | | Mass ratio of |
|---|---|---|---|---|---|---|---|
| | Lipid* | Lipid* | phospholipid DSPC | Cholesterol | PEG lipid DME-PEG2000 | (A) − (B) | nucleic acid to total lipids |
| Comparative Example 401 | Comparative compound C | 50 | 10 | 38.5 | 1.5 | 40 | 6.7% |
| Example 401 | Compound 135 | 50 | | 48.5 | 1.5 | 50 | 6.2% |
| Example 402 | Compound 135 | 50 | 5 | 43.5 | 1.5 | 45 | 6.0% |
| Example 403 | Compound 136 | 50 | | 48.5 | 1.5 | 50 | 6.1% |
| Example 404 | Compound 136 | 50 | 5 | 43.5 | 1.5 | 45 | 5.9% |
| Example 405 | Compound 134 | 50 | | 48.5 | 1.5 | 50 | 6.0% |
| Example 406 | Compound 134 | 50 | 5 | 43.5 | 1.5 | 45 | 5.9% |
| Example 407 | Compound 137 | 50 | | 48.5 | 1.5 | 50 | 6.0% |
| Example 408 | Compound 137 | 50 | 5 | 43.5 | 1.5 | 45 | 5.9% |
| Example 409 | Compound 138 | 50 | | 48.5 | 1.5 | 50 | 6.0% |
| Example 410 | Compound 138 | 50 | 5 | 43.5 | 1.5 | 45 | 5.8% |

TABLE 3

| | | Compositional ratio of lipid (mol %) | | | | | Mass ratio of |
|---|---|---|---|---|---|---|---|
| | Lipid* | Lipid* | phospholipid | Cholesterol | PEG lipid DME-PEG2000 | (A) − (B) | nucleic acid to total lipids |
| Comparative Example 501 | Comparative compound C | 50 | DSPC: 10 | 38.5 | 1.5 | 40 | 6.7% |
| Example 501 | Compound 62 | 50 | | 48.5 | 1.5 | 50 | 5.7% |
| Example 502 | Compound 62 | 50 | DSPC: 5 | 43.5 | 1.5 | 45 | 5.5% |
| Example 503 | Compound 70 | 50 | | 48.5 | 1.5 | 50 | 5.6% |
| Example 504 | Compound 76 | 50 | | 48.5 | 1.5 | 50 | 5.7% |
| Example 505 | Compound 77 | 50 | | 48.5 | 1.5 | 50 | 6.0% |
| Example 506 | Compound 124 | 50 | | 48.5 | 1.5 | 50 | 6.8% |
| Example 507 | Compound 133 | 50 | | 48.5 | 1.5 | 50 | 6.7% |
| Example 508 | Compound 94 | 50 | | 48.5 | 1.5 | 50 | 6.9% |
| Example 509 | Compound 100 | 50 | | 48.5 | 1.5 | 50 | 6.2% |
| Example 510 | Compound 88 | 55 | DSPC: 5 | 38.5 | 1.5 | 50 | 5.9% |
| Example 511 | Compound 88 | 55 | DOPE: 5 | 38.5 | 1.5 | 50 | 5.9% |
| Example 512 | Compound 88 | 55 | DPPC: 5 | 38.5 | 1.5 | 50 | 6.0% |
| Example 513 | Compound 112 | 55 | DSPC: 10 | 33.5 | 1.5 | 45 | 6.2% |
| Example 514 | Compound 112 | 70 | | 28.5 | 1.5 | 70 | 6.1% |

<Measurement of Particle Size>

By using the dispersion liquid of lipid particle as it was, the particle size of the lipid particles was measured.

The measurement results are shown in Tables 4 to 6.

<Evaluation of Encapsulation Rate of siRNA>

(Quantification of Total Nucleic Acid Concentration)

A 3 mol/L aqueous sodium acetate solution (30 μL) and 9 μL of glycogen were added to 60 μL of the lipid particles retaining nucleic acids, and then 1.5 mL of ethanol was added thereto so that only the nucleic acids were precipitated while the lipid was dissolved. Then, the supernatant was removed by centrifugation. After the precipitates were air-dried for 15 minutes or longer, water was added thereto so that the precipitates were redissolved, and the concentration thereof was measured using Nanodrop NF1000 (Thermo Fisher Scientific), thereby quantifying the total nucleic acid concentration.

(Quantification of Nucleic Acid Concentration in Outer Water Phase)

The nucleic acid concentration was quantified using a Quant-iT RiboGreen RNA Assay Kit (Thermo Fisher Scientific) according to the protocol. First, a 20×TE buffer included in the above kit was diluted with water, thereby obtaining a 1×TE buffer. TE represents Tris/EDTA (ethylenediaminetetraacetic acid). In order to quantify only the nucleic acid in the outer water phase, the dispersion liquid of lipid particles retaining nucleic acids was diluted 10,000× with the 1×TE buffer.

The 10,000× diluted dispersion liquid of lipid particles (100 μL) was put in a 96-well plate, then 100 μL of a RiboGreen reagent (reagent included in the Quanti-iT Ribogreen RNA Assay Kit described above) diluted 2000× with the 1×TE buffer was added to a sample, and fluorescence (excitation wavelength: 485 nm, fluorescence wavelength: 535 nm) was measured using a plate reader Infinit EF200 (TECAN), thereby quantifying the nucleic acid concentration in the outer water phase.

(Calculation of Encapsulation Rate)

By using the total nucleic acid concentration obtained through the above steps and the quantified nucleic acid concentration in the outer water phase, the nucleic acid encapsulation rate of the nucleic acid lipid particles was calculated according to the following Equation. Nucleic acid encapsulation rate (%)=(total nucleic acid concentration−nucleic acid concentration in outer water phase)/total nucleic acid concentration×100 The calculation results are shown in Tables 4 to 6.

<Measurement of Factor VII (FVII) Protein>

The Factor VII (FVII) protein was measured according to the method described in Nature Biotechnology (2010) 28, 172-176. C57BL6/J mice were randomly grouped (n=3). The dispersion liquid of nucleic acid lipid particles prepared in Preparation of Nucleic Acid Lipid Particles> was administered to the caudal vein of the mice at a dosage of 0.1 mg/kg. For comparison, PBS at the same volume was administered to the caudal vein of the mice. Twenty four hours after the administration, blood was collected from the caudal vena cava, thereby obtaining plasma. The amount of FVII protein was quantified using the obtained plasma and a Biophen FVII assay kit (Aniara).

The FVII amount in the plasma sample of each individual in the PBS administration group was regarded as 100%, and the ratio of the FVII amount in the plasma sample of each individual to 100% was adopted as a measurement value. The results are shown in Tables 4 to 6.

TABLE 4

| | Particle size (nm) | Encapsulation rate (%) | Dosage (mg/kg) | Relative FVII protein amount (%) |
|---|---|---|---|---|
| Comparative Example 301 | 87 | 92 | 0.1 | 7.3 |
| Comparative Example 302 | 88 | 61 | 0.1 | 9.8 |
| Example 301 | 86 | 67 | 0.1 | 5.4 |
| Example 302 | 81 | 83 | 0.1 | 3.2 |
| Example 303 | 78 | 81 | 0.1 | 2.3 |
| Example 304 | 81 | 90 | 0.1 | 2.5 |
| Example 305 | 85 | 68 | 0.1 | 2.2 |
| Example 306 | 82 | 59 | 0.1 | 3.0 |
| Example 307 | 87 | 70 | 0.1 | 3.4 |
| Example 308 | 70 | 89 | 0.1 | 2.6 |
| Example 309 | 82 | 93 | 0.1 | 1.6 |
| Example 310 | 68 | 93 | 0.1 | 3.7 |
| Example 311 | 82 | 94 | 0.1 | 1.3 |

TABLE 5

| | Particle size (nm) | Encapsulation rate (%) | Dosage (mg/kg) | Relative FVII protein amount (%) |
|---|---|---|---|---|
| Comparative Example 401 | 63 | 94 | 0.1 | 19.2 |
| Example 401 | 80 | 90 | 0.1 | 2.0 |
| Example 402 | 81 | 93 | 0.1 | 4.3 |
| Example 403 | 80 | 94 | 0.1 | 2.7 |
| Example 404 | 78 | 93 | 0.1 | 3.1 |
| Example 405 | 81 | 94 | 0.1 | 1.6 |
| Example 406 | 75 | 94 | 0.1 | 2.9 |
| Example 407 | 91 | 95 | 0.1 | 4.3 |
| Example 408 | 81 | 93 | 0.1 | 12.7 |
| Example 409 | 83 | 95 | 0.1 | 2.6 |
| Example 410 | 81 | 94 | 0.1 | 6.1 |

TABLE 6

| | Particle size (nm) | Encapsulation rate (%) | Dosage (mg/kg) | Relative FVII protein amount (%) |
|---|---|---|---|---|
| Comparative Example 501 | 67 | 90 | 0.1 | 14.6 |
| Example 501 | 73 | 92 | 0.1 | 6.7 |
| Example 502 | 74 | 91 | 0.1 | 6.8 |
| Example 503 | 77 | 91 | 0.1 | 5.9 |
| Example 504 | 76 | 93 | 0.1 | 5.8 |
| Example 505 | 76 | 92 | 0.1 | 2.6 |
| Example 506 | 75 | 93 | 0.1 | 7.8 |
| Example 507 | 77 | 93 | 0.1 | 8.9 |
| Example 508 | 85 | 91 | 0.1 | 8.7 |
| Example 509 | 78 | 92 | 0.1 | 6.8 |
| Example 510 | 76 | 83 | 0.1 | 5.2 |
| Example 511 | 75 | 92 | 0.1 | 7.5 |
| Example 512 | 75 | 85 | 0.1 | 5.2 |

TABLE 6-continued

| | Particle size (nm) | Encapsulation rate (%) | Dosage (mg/kg) | Relative FVII protein amount (%) |
|---|---|---|---|---|
| Example 513 | 74 | 91 | 0.1 | 4.6 |
| Example 514 | 91 | 86 | 0.1 | 7.5 |

In the comparative examples, the FVII inhibitory activity was not preferable. On the other hand, the nucleic acid lipid composition according to the embodiment of the present invention showed a strong FVII inhibitory activity and an excellent nucleic acid delivery effect.

[Preparation of Nucleic Acid Lipid Particles and Evaluation of Hepatotoxicity Markers in Mice]

<Preparation of Nucleic Acid Lipid Particles>

The compounds 88 and 89 synthesized in the above examples were used as the lipid represented by Formula (1).

The lipid represented by Formula (1), 1,2-distearoyl-sn-glycero-3-phosphocholine (DSPC, trade name: COATSOME MC-8080; NOF corporation), cholesterol (trade name: Cholesterol HP; NIPPON FINE CHEMICAL CO., LTD.), DMG-PEG2000, (trade name: SUNBRIGHT® GM-020; NOF corporation) were dissolved in ethanol at the molar ratio shown in Tables 1 to 3 so that the total lipid concentration was 20 mmol/L, thereby obtaining an oil phase.

gp46 mouse siRNA (prepared with reference to JP2014-529328A, 5 mg) was dissolved in 1 mL of sterile water. This solution was diluted with a 10 mmol/L citrate buffer having a pH 4 in Example 601 and with a 50 mmol/L citrate buffer having a pH 4 in Example 602 so that the concentration of nucleic acid was 19.7 μmol/L, thereby obtaining a water phase. Then, the water phase and the oil phase were mixed together with a micromixer (see JP5288254B) using a syringe pump so that the volume ratio of water phase:oil phase was 3:1. The mixed solution was diluted 2× with a phosphate buffered saline (PBS), thereby obtaining a nucleic acid lipid particle dispersion. The dispersion liquid was dialyzed using a dialysis cassette (Slide-A-Lyzer G2, MWCO: 10 kD, Thermo Fisher Scientific) including PBS so that ethanol was removed, and sterilized by being filtered with a filter (Sartorius AG Minisart 16534-K) having a pore size of 0.22 μm. Table 7 shows the mass ratio of siRNA to the total mass of lipids at the time of mixing.

```
gp46 mouse siRNA sequence
5'-GGACAGGCCUGUACAACUATT-3'

3'-TTCCUGUCCGGACAUGUUGAU-5'
```

TABLE 7

| | Type of cationic lipid | Composition ratio of lipid (mol %) | | | | Mass ratio of siRNA to total lipids |
|---|---|---|---|---|---|---|
| | | Cationic lipid | Phospholipid | Cholesterol | PEG lipid | |
| Example 601 | Compound 88 | 50 | 0 | 48.5 | 1.5 | 6.29% |
| Example 602 | Compound 89 | 50 | 0 | 48.5 | 1.5 | 6.68% |

<Measurement of Particle Size and siRNA Encapsulation Rate>

By using the dispersion liquid of lipid particle as it was, the particle size of the lipid particles was measured.

<Measurement of Particle Size>

By using the dispersion liquid of lipid particles as it was, the particle size of the lipid particles encapsulating gp46 mouse siRNA was measured using a particle size measurement system ELS-Z2 (Otsuka Electronics Co., Ltd.).

<Evaluation of Encapsulation Rate of siRNA>

(Quantification of Total Nucleic Acid Concentration)

A 3 mol/L aqueous sodium acetate solution (30 μL) and 9 μL of glycogen were added to 60 μL of the lipid particles retaining nucleic acids, and then 1.5 mL of ethanol was added thereto so that only the nucleic acids were precipitated while the lipid was dissolved. Then, the supernatant was removed by centrifugation. After the precipitates were air-dried for 15 minutes or longer, water was added thereto so that the precipitates were redissolved, and the concentration thereof was measured using Nanodrop NF1000 (Thermo Fisher Scientific), thereby quantifying the total nucleic acid concentration.

(Quantification of Nucleic Acid Concentration in Outer Water Phase)

The nucleic acid concentration was quantified using a Quant-iT RiboGreen RNA Assay Kit (Thermo Fisher Scientific) according to the protocol. First, a 20×TE buffer included in the above kit was diluted with water, thereby obtaining a 1×TE buffer. TE represents Tris/EDTA (ethylenediaminetetraacetic acid). In order to quantify only the nucleic acid in the outer water phase, the dispersion liquid of lipid particles retaining nucleic acids was diluted 10,000× with the 1×TE buffer.

The 10,000× diluted dispersion liquid of lipid particles (100 μL) was put in a 96-well plate, then 100 μL of a RiboGreen reagent (reagent included in the Quanti-iT Ribogreen RNA Assay Kit described above) diluted 2000× with the 1×TE buffer was added to a sample, and fluorescence (excitation wavelength: 485 nm, fluorescence wavelength: 535 nm) was measured using a plate reader Infinit EF200 (TECAN), thereby quantifying the nucleic acid concentration in the outer water phase.

(Calculation of Encapsulation Rate)

By using the total nucleic acid concentration obtained through the above steps and the quantified nucleic acid concentration in the outer water phase, the nucleic acid encapsulation rate of the nucleic acid lipid particles was calculated according to the following Equation. Nucleic acid encapsulation rate (%)=(total nucleic acid concentration−nucleic acid concentration in outer water phase)/total nucleic acid concentration×100 The results are shown in Table 8.

TABLE 8

| | Particle size (nm) | Encapsulation rate (%) |
|---|---|---|
| Example 601 | 84.9 | 78% |
| Example 602 | 93.9 | 63% |

<Preparation of Dosing Preparation>

The dispersion liquid of lipid particles obtained in Examples 601 and 602 were concentrated by an ultrafiltration membrane using an AMICON ultracentrifugal filter unit (manufactured by Merck Millipore), and then diluted with PBS to a desired concentration, thereby obtaining a dosing preparation.

<Evaluation of Hepatotoxicity Marker in Mice>

The nucleic acid lipid particles prepared in Examples 601 and 602 having concentration adjusted as above or PBS as negative control was administered to the caudal vein of C57BL/6J mice (male, 6 weeks old) (3 mg/kg, for 2 weeks at 3 times/week, n=5 in each group). Twenty four hours after the final administration, blood was collected using a heparinized syringe, and plasma was collected by centrifugation (1800×g, for 10 minutes, 4° C.). By using Hitachi 7180 automatic analyzer, aspartate aminotransferase (AST) and alanine aminotransferase (ALT) in the plasma were quantified according to the JSCC reference standard method established by Japanese Committee for Clinical Laboratory Standards. The measurement results are shown in Table 9.

TABLE 9

| | AST(IU/L) | ALT(IU/L) |
|---|---|---|
| Negative control | 32 | 22 |
| (PBS) | 29 | 19 |
| | 29 | 19 |
| | 29 | 18 |
| | 33 | 20 |
| Example 601 | 49 | 34 |
| | 51 | 33 |
| | 48 | 27 |
| | 70 | 39 |
| | 79 | 43 |
| Example 602 | 125 | 82 |
| | 72 | 35 |
| | 83 | 65 |
| | 85 | 53 |
| | 69 | 36 |

It has been found that the AST level and ALT level increase less in a case where the nucleic acid lipid composition according to the embodiment of the present invention is administered, than in a case where the negative control is administered.

SEQUENCE LIST

International Application 19F00987W1JP20022279_243.app under the Patent Cooperation Treaty

What is claimed is:

1. A lipid composition comprising:

a lipid represented by Formula (1) or a salt thereof;

a nonionic lipid;

a lipid having a nonionic hydrophilic polymer structure; and a nucleic acid, wherein the lipid composition contains or does not contain a zwitterionic lipid, and in a case where (A) represents a molar ratio in percentage of the lipid represented by Formula (1) or a salt thereof to total lipids constituting the lipid composition, and (B) represents a molar ratio in percentage of the zwitterionic lipid to the total lipids constituting the lipid composition, (A) and (B) satisfy $40<(A)-(B)\leq 90$, (1)

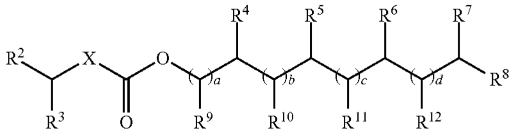

in the formula, X represents —$NR^1$— or —O—, $R^1$ represents a hydrogen atom, a hydrocarbon group having 6 to 24 carbon atoms, or a group represented by $R^{21}$-$L^1$-$R^{22}$—, $R^{21}$ represents a hydrocarbon group having 1 to 24 carbon atoms, $L^1$ represents —O(CO)O—, —O(CO)—, —(CO)O—, —O—, or a group represented by the following formula,

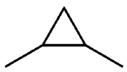

$R^{22}$ represents a divalent hydrocarbon linking group having 1 to 18 carbon atoms, $R^2$ and $R^3$ each independently represent a hydrogen atom, a hydrocarbon group having 3 to 24 carbon atoms, or a group represented by $R^{31}$-$L^2$-$R^{32}$—, $R^{31}$ represents a hydrocarbon group having 1 to 24 carbon atoms, $L^2$ represents —O(CO)O—, —O(CO)—, —(CO)O—, —O—, or a group represented by the following formula,

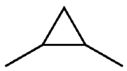

$R^{32}$ represents a divalent hydrocarbon linking group having 1 to 18 carbon atoms, $R^4$, $R^5$, $R^6$, $R^7$, $R^8$, $R^9$, $R^{10}$, $R^{11}$, and $R^{12}$ each independently represent a hydrogen atom or an alkyl group having 1 to 18 carbon atoms that may be substituted, groups in any one or more pairs among $R^4$ and $R^5$, $R^{10}$ and $R^5$, $R^5$ and $R^{12}$, $R^4$ and $R^6$, $R^5$ and $R^6$, $R^6$ and $R^7$, $R^6$ and $R^{10}$, $R^{12}$ and $R^7$, and $R^7$ and $R^8$ may be linked to each other to form a 4- to 7-membered ring which may contain an O atom, a substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$, and $R^{46}$ each independently represent a hydrocarbon group having 1 to 18 carbon atoms, and a, b, c, and d each independently represent an integer of 0 to 3, a+b is 1 or more, and c+d is 1 or more.

2. The lipid composition according to claim 1, wherein the nonionic lipid is sterols.

3. The lipid composition according to claim 2, wherein the sterols are cholesterol.

4. The lipid composition according to claim 1, wherein the zwitterionic lipid is phospholipid.

5. The lipid composition according to claim 1, wherein the lipid having a nonionic hydrophilic polymer structure is a lipid having a polyethylene glycol structure.

6. The lipid composition according to claim 5, wherein the lipid having a polyethylene glycol structure is a lipid having a diacylglycerol structure and a polyethylene glycol structure.

7. The lipid composition according to claim 1, wherein a content of the lipid represented by Formula (1) or a salt thereof is more than 40 mol % and 90 mol % or less, a content of the nonionic lipid is 20 to 60 mol %, a content of the lipid having a nonionic hydrophilic polymer structure is 0.5 to 10 mol %, and a content of the zwitterionic lipid is 0 to 30 mol %.

8. The lipid composition according to claim 1, wherein the compound represented by Formula (1) is a compound represented by Formula (2), (2)

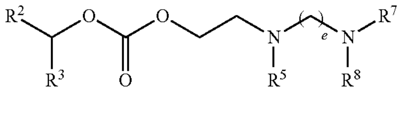

in the formula, $R^2$ and $R^3$ each independently represent a hydrogen atom, a hydrocarbon group having 3 to 24 carbon atoms, or a group represented by $R^{31}$-$L^2$-$R^{32}$—, $R^{31}$ represents a hydrocarbon group having 1 to 24 carbon atoms, $L^2$ represents —O(CO)O—, —O(CO)—, —(CO)O—, —O—, or a group represented by the following formula,

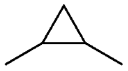

$R^{32}$ represents a divalent hydrocarbon linking group having 1 to 18 carbon atoms, $R^5$ represents a hydrogen atom or an alkyl group having 1 to 18 carbon atoms that may be substituted, $R^7$ and $R^8$ each independently represent a hydrogen atom or an alkyl group having 1 to 18 carbon atoms that may be substituted, a substituent on the alkyl group having 1 to 18 carbon atoms that may be substituted is a hydroxyl group, a carboxyl group, an amino group represented by —$NR^{45}R^{46}$, a substituted or unsubstituted aryl group, a substituted or unsubstituted heteroaryl group, or a group represented by —O(CO)O—$R^{41}$, —O(CO)—$R^{42}$, —(CO)O—$R^{43}$, or —O—$R^{44}$, $R^{41}$, $R^{42}$, $R^{43}$, $R^{44}$, $R^{45}$, and $R^{46}$ each independently represent a hydrocarbon group having 1 to 18 carbon atoms, a substituent on the substituted or unsubstituted aryl group and on the substituted or unsubstituted heteroaryl group is an alkyl group having 1 to 18 carbon atoms, a hydroxyl group, a carboxyl group, an amino group represented by —$NR^{45}R^{46}$, or a group represented by —O(CO)O—$R^{41}$, —O(CO)—$R^{42}$, —(CO)O—$R^{43}$, or —O—$R^{44}$, and $R^{41}$, $R^{42}$, $R^{43}$, $R^{44}$, $R^{45}$, and $R^{46}$ each independently represent a hydrocarbon group having 1 to 18 carbon atoms, and e represents 2 or 3.

9. The lipid composition according to claim 8, wherein in Formula (2), at least one of $R^2$ or $R^3$ represents a hydrocarbon group having 3 to 24 carbon atoms containing one or more unsaturated bonds; $R^2$ and $R^3$ each independently represent a group represented by $R^{31}$-$L^2$-$R^{32}$—: or one of $R^2$ and $R^3$ represents a group represented by $R^{31}$-$L^2$-$R^{32}$- and the other represents a hydrocarbon group having 3 to 24 carbon atoms, $R^5$ represents an unsubstituted alkyl group having 1 to 18 carbon atoms or an alkyl group having 1 to 18 carbon atoms substituted with —O(CO)—$R^{42}$ or —(CO)O—$R^{43}$, $R^7$ and $R^8$ each independently represent an alkyl group having 1 to 4 carbon atoms, and $R^{31}$, $L^2$, $R^{32}$, $R^{42}$, and $R^{43}$ have the same definitions as $R^{31}$, $L^2$, $R^{32}$, $R^{42}$, and $R^{43}$ in claim 8.

10. The lipid composition according to claim 1, wherein a content of the nucleic acid with respect to the total lipids is 1% to 25% by mass.

11. The lipid composition according to claim 1, further comprising:

a pharmaceutically acceptable carrier.

12. The lipid composition according to claim 1, which is a composition for introducing nucleic acids into cells.

13. The lipid composition according to claim 1, which is a composition for in vivo delivery of nucleic acids.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic siRNA sequence

<400> SEQUENCE: 1

ggacaggccu guacaacuat t                                                21


<210> SEQ ID NO 2
<211> LENGTH: 21
<212> TYPE: DNA
<213> ORGANISM: Artificial Sequence
<220> FEATURE:
```

-continued

<223> OTHER INFORMATION: Synthetic siRNA sequence

<400> SEQUENCE: 2
ttccuguccg gacauguuga u 21